(12) United States Patent
Reiserer et al.

(10) Patent No.: US 11,939,563 B2
(45) Date of Patent: *Mar. 26, 2024

(54) CONTINUOUS AUTOMATED PERFUSION CULTURE ANALYSIS SYSTEM (CAPCAS) AND APPLICATIONS OF SAME

(71) Applicant: VANDERBILT UNIVERSITY, Nashville, TN (US)

(72) Inventors: Ronald S. Reiserer, Nashville, TN (US); Gregory B. Gerken, Nashville, TN (US); David K. Schaffer, Nashville, TN (US); John P. Wikswo, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,302

(22) Filed: Sep. 19, 2022

(65) Prior Publication Data
US 2023/0019924 A1    Jan. 19, 2023

Related U.S. Application Data

(63) Continuation of application No. 17/578,966, filed on Jan. 19, 2022, now Pat. No. 11,447,734, which is a
(Continued)

(51) Int. Cl.
*C12M 1/00* (2006.01)
*C12M 1/06* (2006.01)
(Continued)

(52) U.S. Cl.
CPC ............ *C12M 29/10* (2013.01); *C12M 23/08* (2013.01); *C12M 23/10* (2013.01); *C12M 23/12* (2013.01);
(Continued)

(58) Field of Classification Search
CPC ...... C12M 29/10; C12M 23/08; C12M 23/10; C12M 23/12; C12M 23/16; C12M 23/50;
(Continued)

(56) References Cited

U.S. PATENT DOCUMENTS

| | | | |
|---|---|---|---|
| 11,447,734 B2 * | 9/2022 | Reiserer | C12M 23/08 |
| 2011/0003323 A1 * | 1/2011 | Bargh | C12M 23/42 |
| | | | 435/29 |

(Continued)

*Primary Examiner* — Michael L Hobbs
(74) *Attorney, Agent, or Firm* — Locke Lord LLP; Tim Tingkang Xia, Esq.

(57) ABSTRACT

A continuous automated perfusion culture analysis system (CAPCAS) comprises one or more fluidic systems configured to operate large numbers of biodevices in parallel. Each fluidic system comprises an input reservoir plate for receiving media; a biodevice plate comprising an array of biodevices fluidically coupled to the input reservoir plate, configured such that each biodevice has independent media delivery, fluid removal, stirring, and gas control, and each biodevice is capable of continuously receiving the media from the input reservoir plate; and an output plate fluidically coupled to the biodevice plate for real-time analysis and sampling. The operations of the CAPCAS are automated and computer-controlled wirelessly. The CAPCAS can also be used for abiotic and biotic chemical synthesis processes.

8 Claims, 69 Drawing Sheets

Related U.S. Application Data continuation-in-part of application No. PCT/US2021/042179, filed on Jul. 19, 2021, and a continuation-in-part of application No. PCT/US2020/040061, filed on Jun. 29, 2020.

(60) Provisional application No. 63/300,321, filed on Jan. 18, 2022, provisional application No. 63/277,329, filed on Nov. 9, 2021, provisional application No. 63/257,149, filed on Oct. 19, 2021, provisional application No. 63/163,160, filed on Mar. 19, 2021, provisional application No. 63/139,138, filed on Jan. 19, 2021, provisional application No. 63/053,388, filed on Jul. 17, 2020, provisional application No. 62/868,303, filed on Jun. 28, 2019.

(51) Int. Cl.
*C12M 1/22* (2006.01)
*C12M 1/24* (2006.01)
*C12M 1/32* (2006.01)
*C12M 1/36* (2006.01)
*C12M 1/42* (2006.01)
*C12M 3/04* (2006.01)
*C12M 3/06* (2006.01)

(52) U.S. Cl.
CPC ............ *C12M 23/16* (2013.01); *C12M 23/50* (2013.01); *C12M 23/58* (2013.01); *C12M 27/02* (2013.01); *C12M 27/12* (2013.01); *C12M 35/02* (2013.01); *C12M 35/04* (2013.01); *C12M 41/48* (2013.01)

(58) Field of Classification Search
CPC ...... C12M 23/58; C12M 27/02; C12M 27/12; C12M 35/02; C12M 35/04; C12M 41/48
See application file for complete search history.

(56) References Cited

U.S. PATENT DOCUMENTS

2015/0298123 A1* 10/2015 Block, III ........... F04B 43/0054
　　　　　　　　　　　　　　　　　　　　　　435/284.1
2017/0081625 A1* 3/2017 Wikswo .............. F04B 43/0045

* cited by examiner

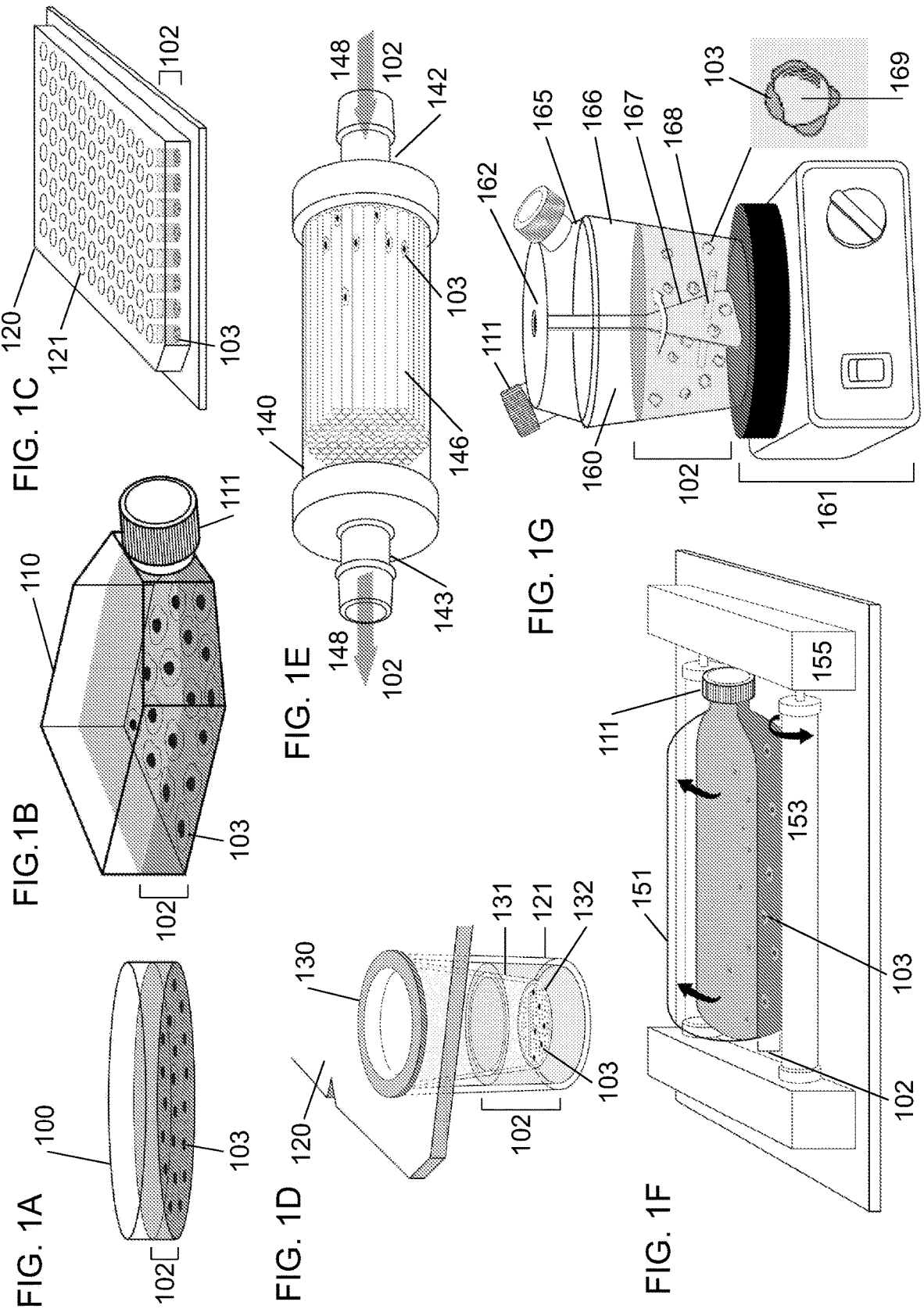

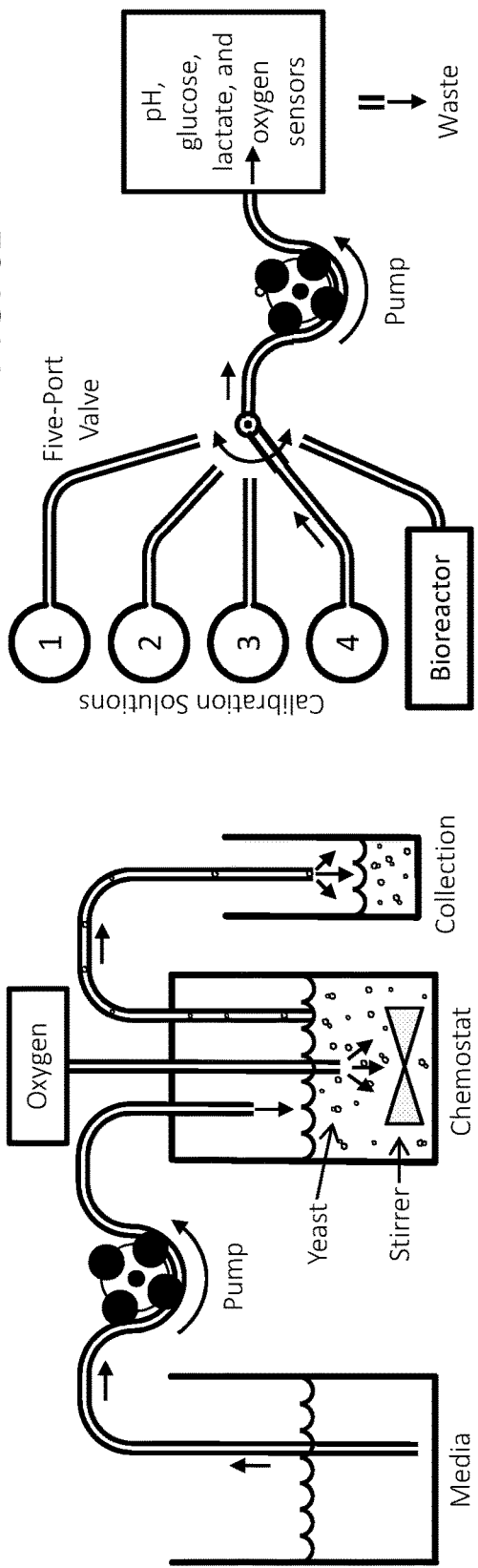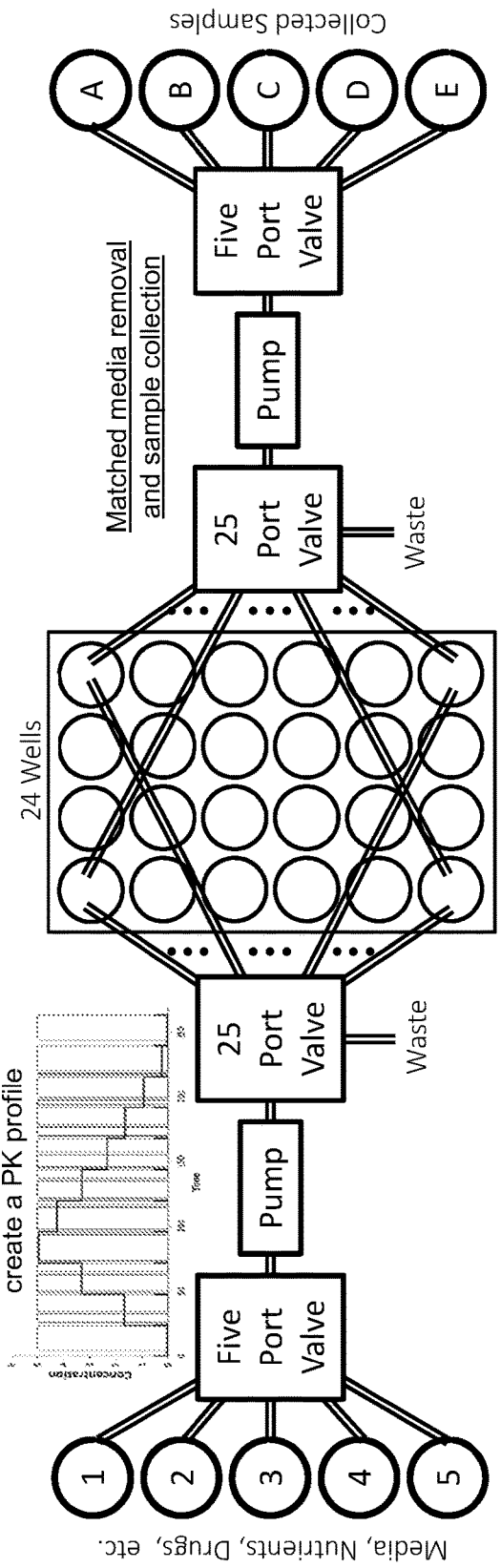

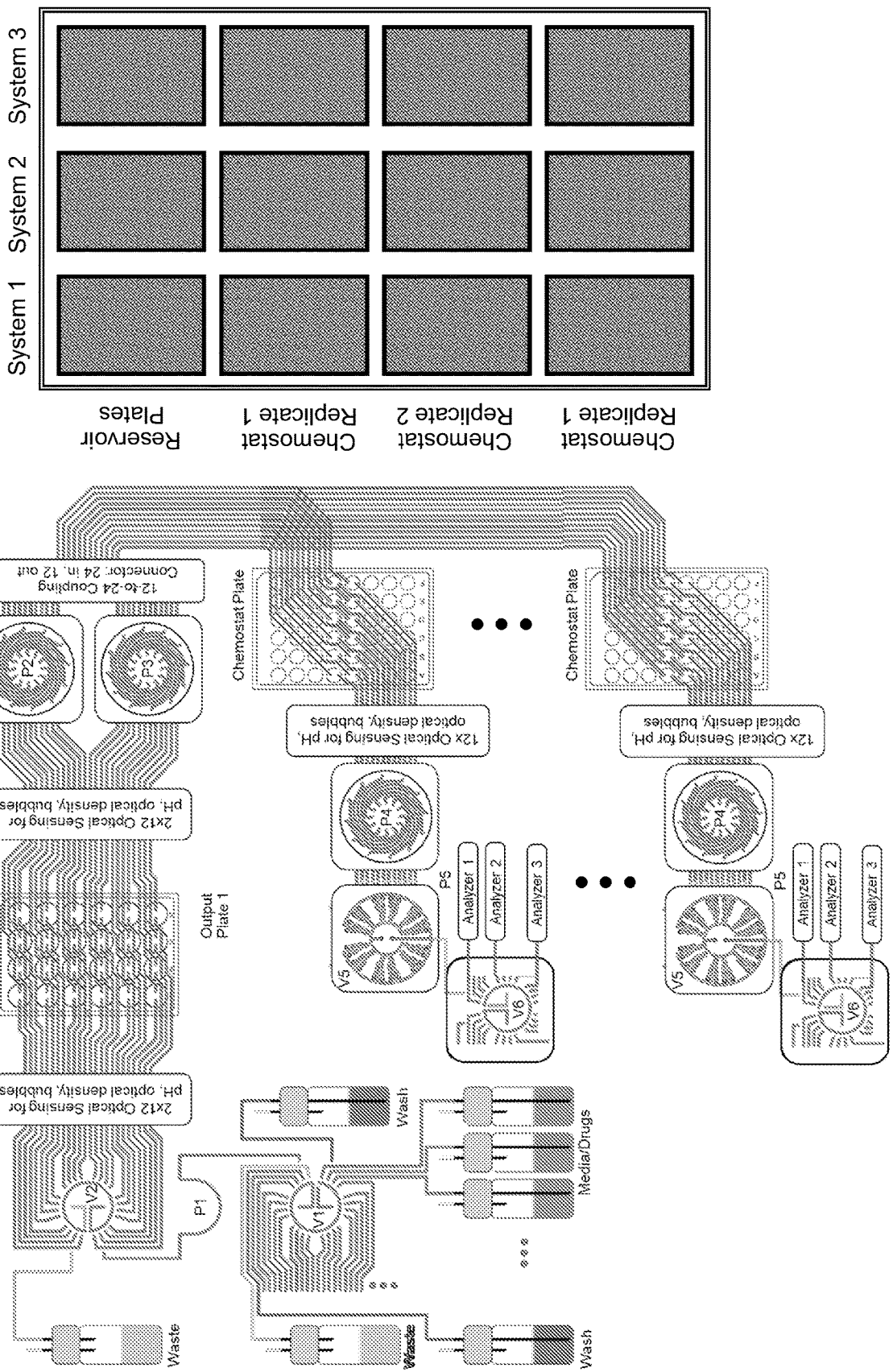

FIG. 9

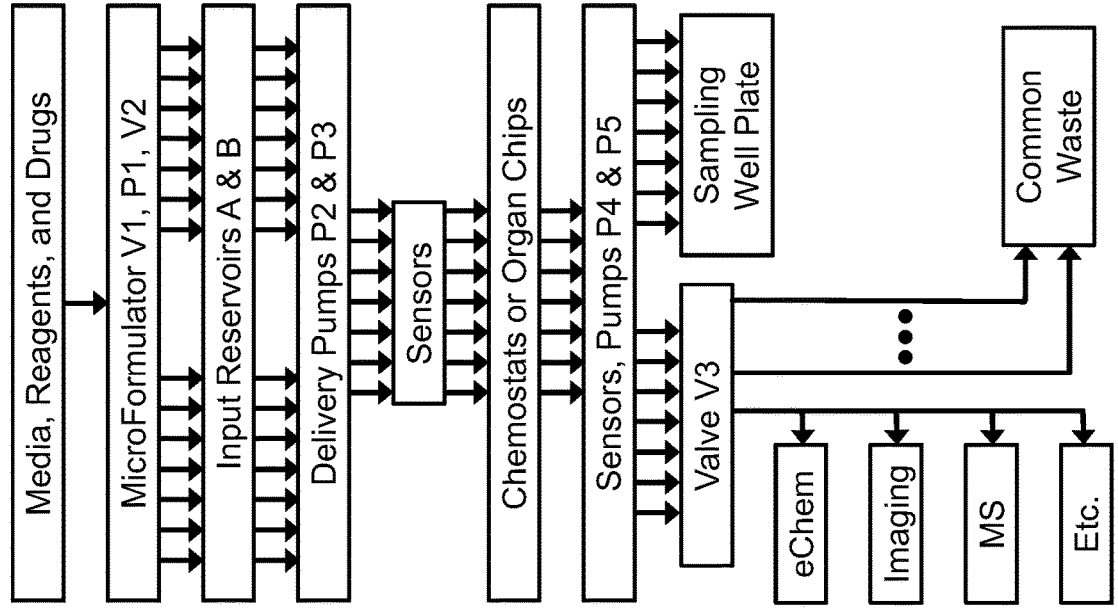

1) V1 selects media, reagents and drugs needed to formulate media for each chemostat, washing lines as required.
2) Using time-division multiplexing, V1-P1-V2 prepares the first media formulation for each chemostat.
3) V1-P1-V2 fills one input reservoir set from the microformulator.
4) V1-P1-V2 repeats steps 1-3 but for the second reservoir set.
5) P2 delivers first input reservoir set to each chemostat.
6) Sensors check for bubbles, measure baseline OD. Perfusion rate can be controlled if OD should be held constant.
7) Cycle steps 1-6 for continuous perfusion of all chemostats.
8) P4 continuously withdraws media during steps 5-7; V3 delivers the media from one chemostat at a time to one or more in-line sensors while sending the media from all other chemostats to a common waste. Sensors include electrochemical (eChem) metabolic sensors, cellular imaging, mass spectrometry (MS), etc.
9) P5 removes small samples for parallel sensing and returns them to the chemostats if desired.
10) P5 rapidly and in parallel removes a fraction of the media from each chemostat and delivers each aliquot to a sample-collection plate for off-line analysis of each chemostats cells and media.
11) Repeat cycles with parameters adjusted as necessary.

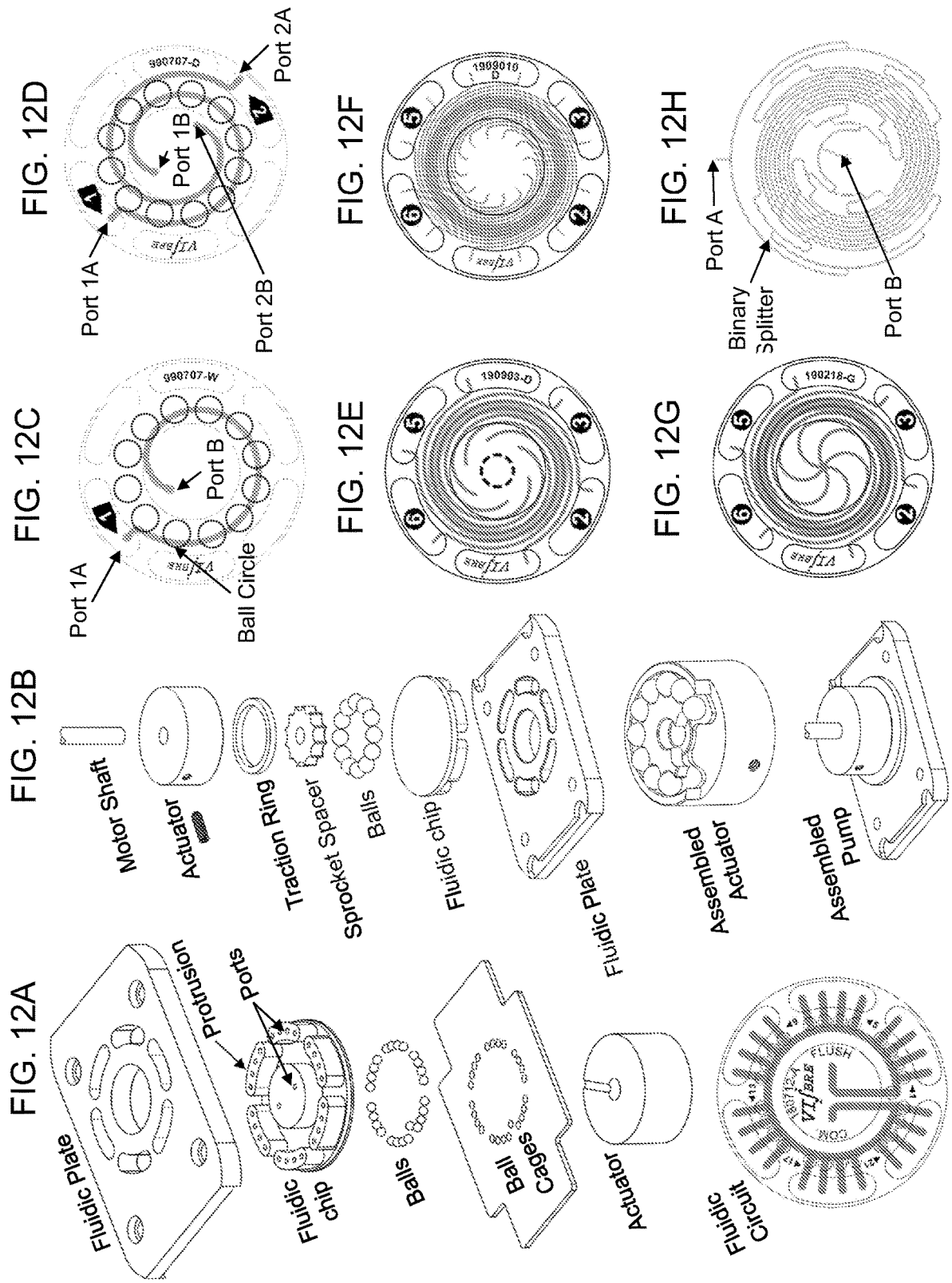

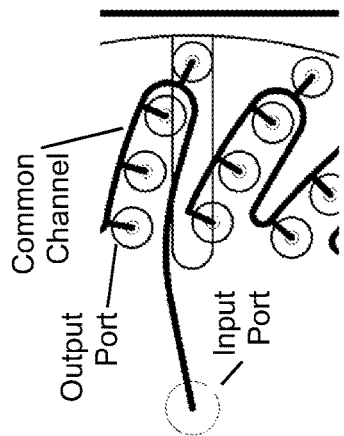
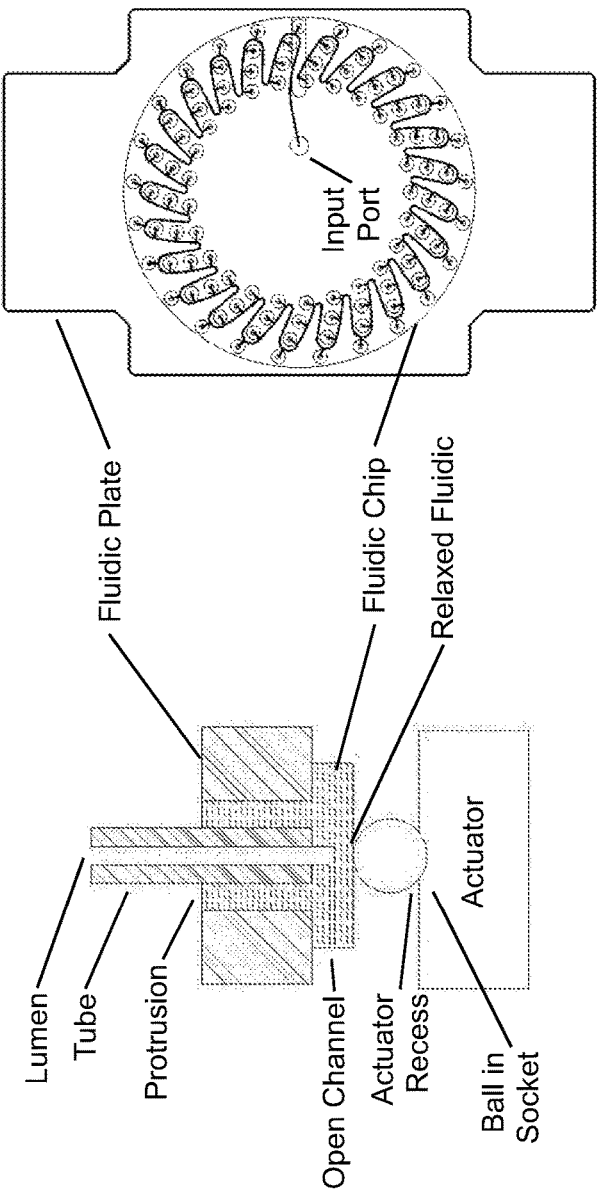
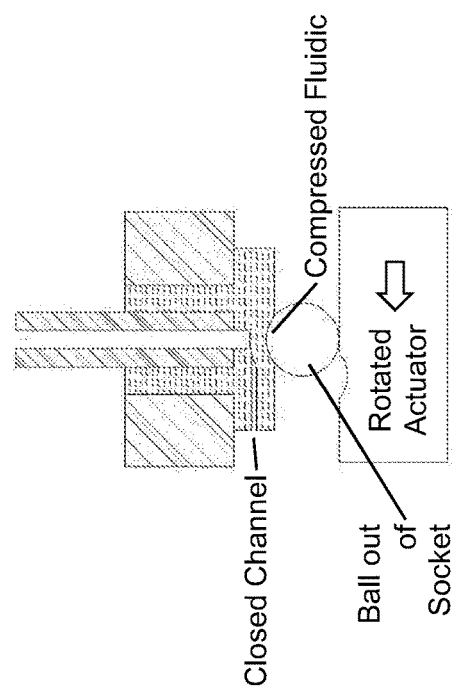

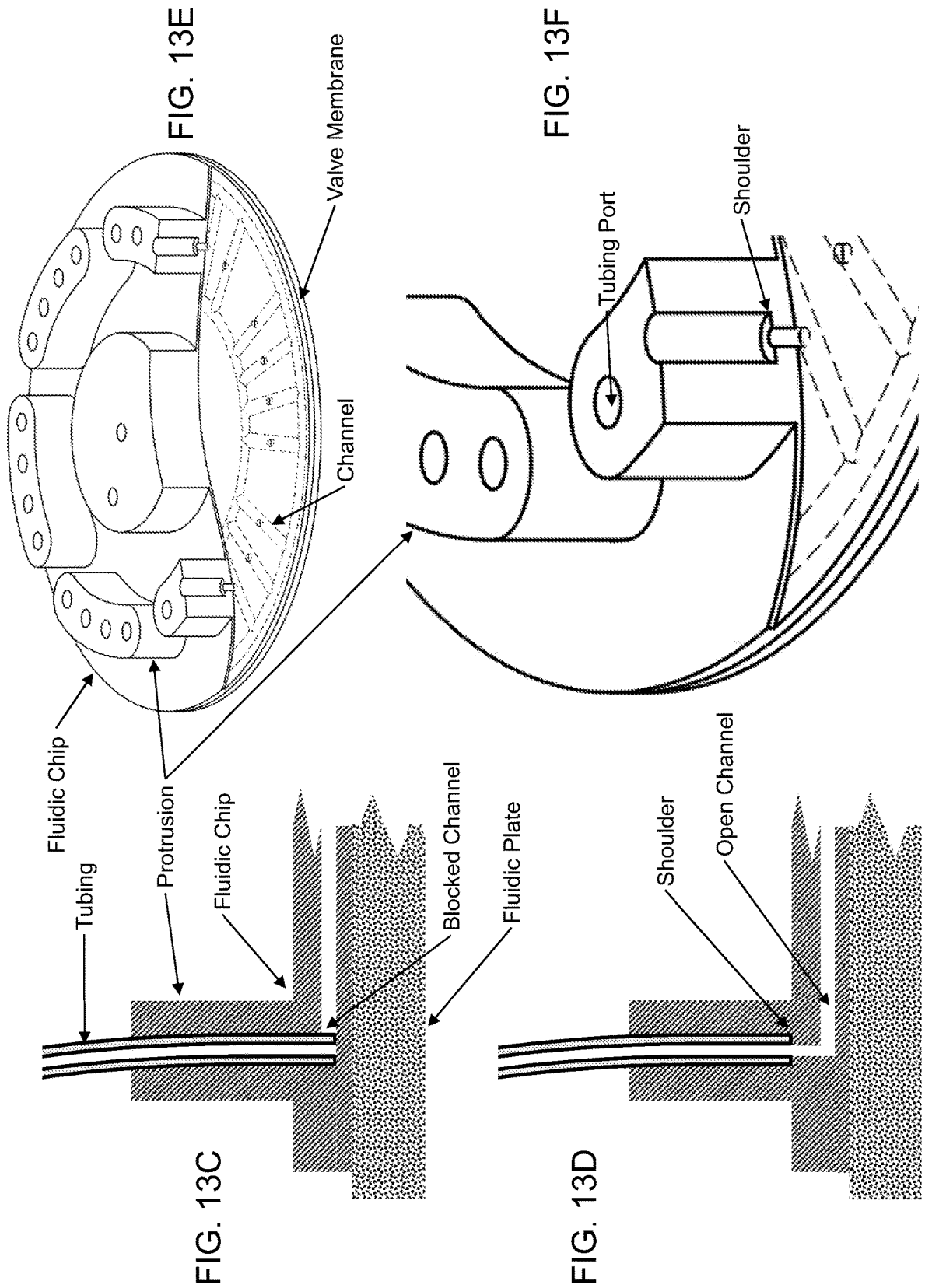

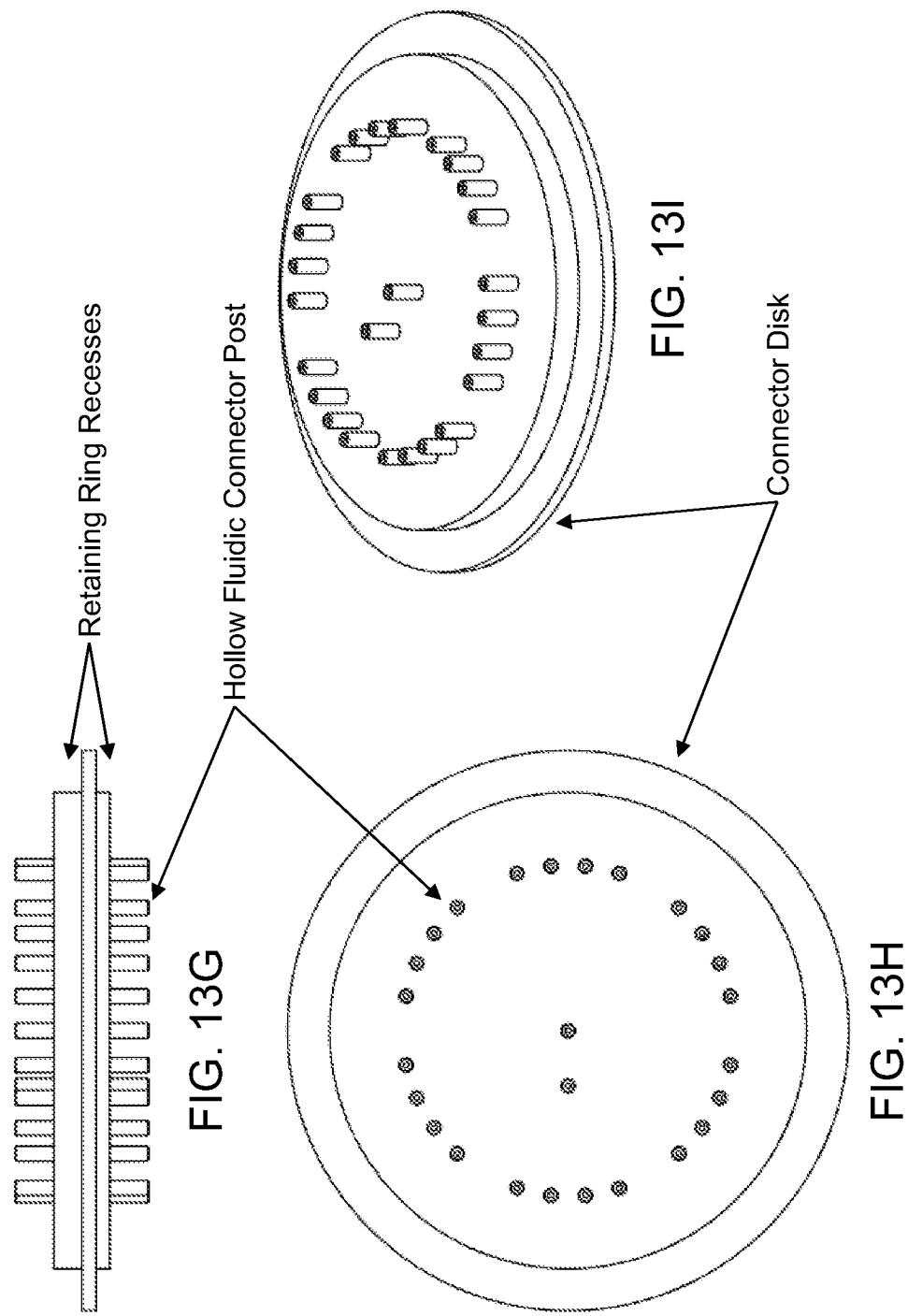

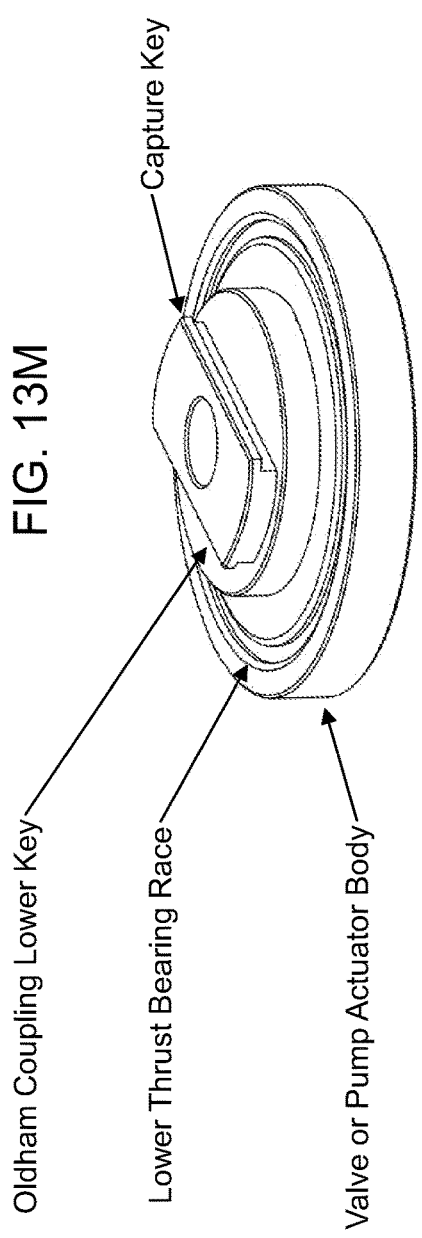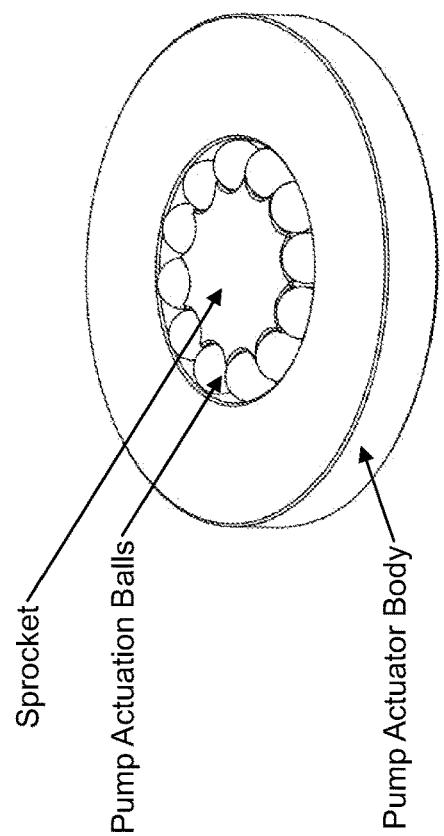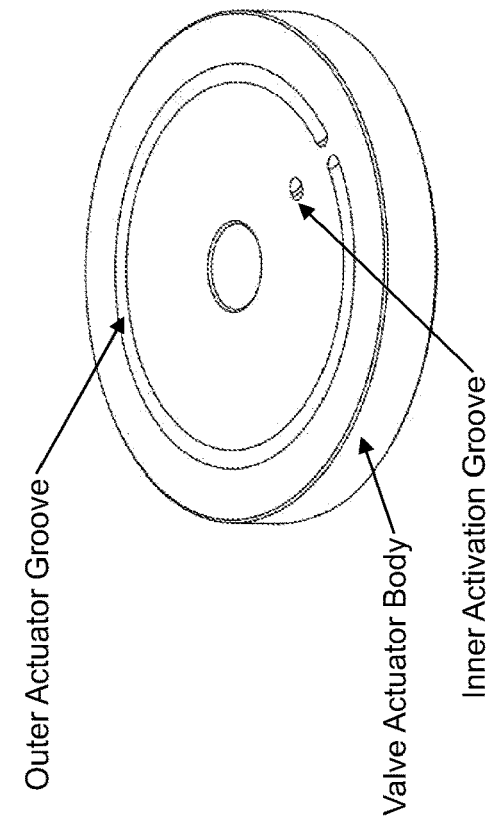

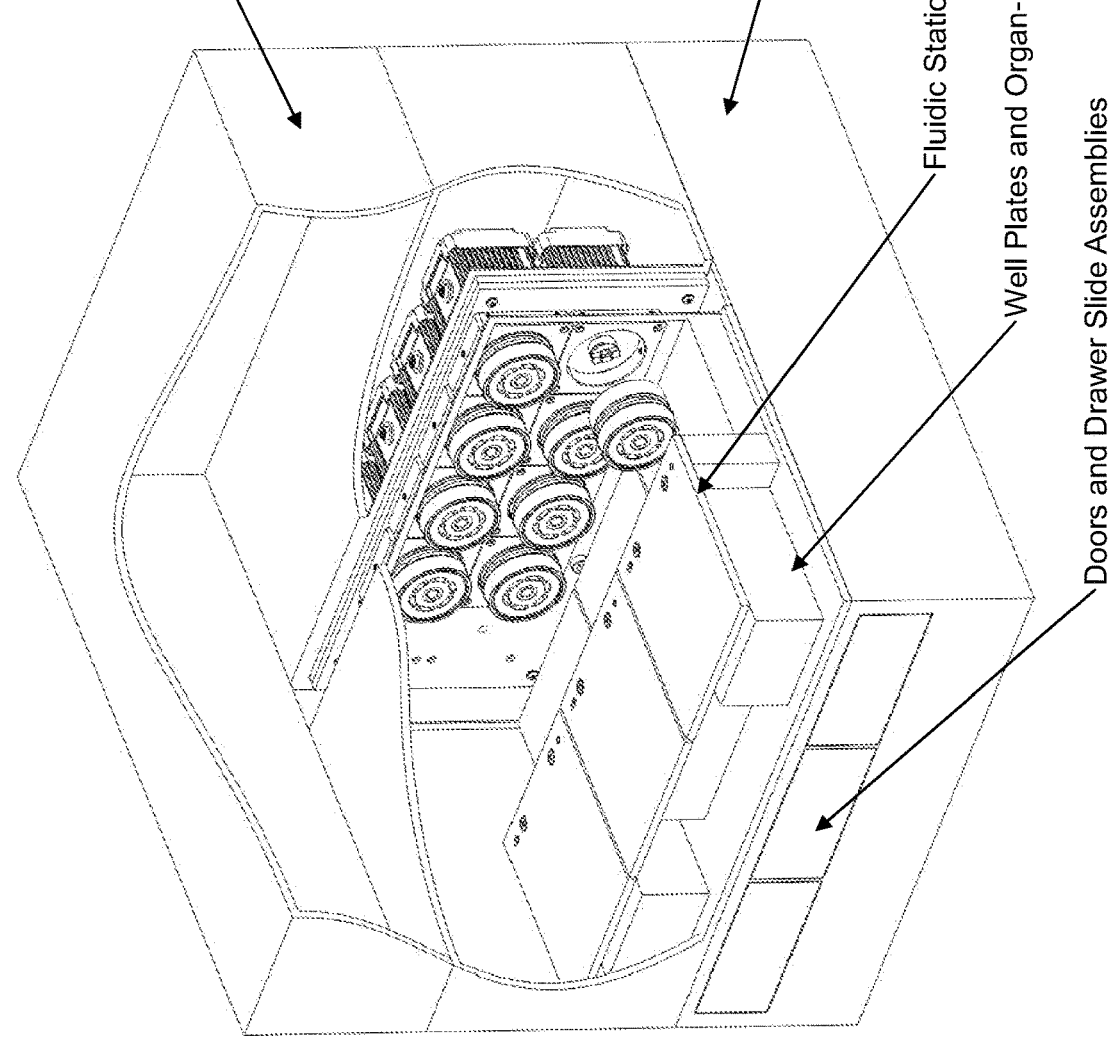

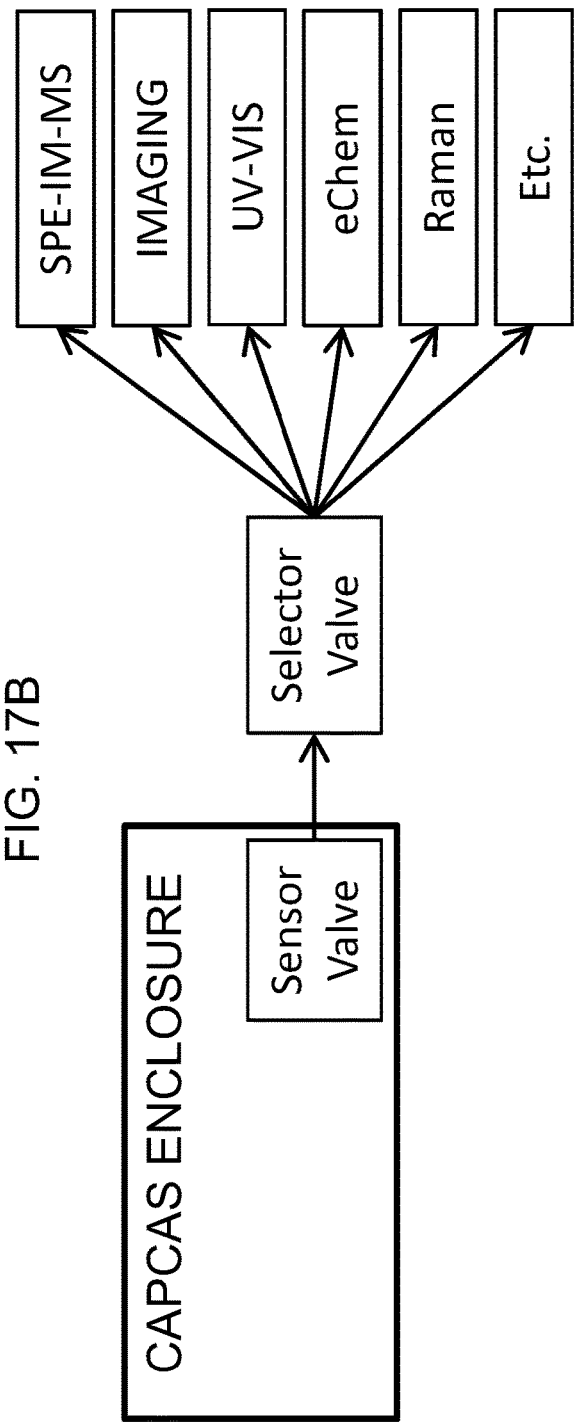

| Item \ Example | 1 | 2 | 3 | 4 | 5 | 6 | 7 | 8 | 9 | 10 | 11 | 12 | 13 | 14 | Units |
|---|---|---|---|---|---|---|---|---|---|---|---|---|---|---|---|
| Minimum time to analyze one sample with one mode of Rapid Fire SPE + MS | 15 | 15 | 15 | 15 | 10 | 10 | 10 | 10 | 10 | 10 | 10 | 10 | 10 | 10 | s/sample |
| Modes to run (e.g., positive + negative) | 6 | 6 | 6 | 6 | 6 | 6 | 6 | 6 | 6 | 6 | 6 | 2 | 1 | 1 | samples/well |
| Time per well | 90 | 90 | 90 | 90 | 60 | 60 | 60 | 60 | 60 | 60 | 60 | 20 | 10 | 10 | s/well |
| Wells per plate = X | 12 | 48 | 48 | 96 | 96 | 48 | 96 | 96 | 96 | 96 | 48 | 96 | 96 | 96 | wells/plate |
| Chemostat plates per deck | 1 | 1 | 3 | 4 | 9 | 4 | 12 | 12 | 9 | 9 | 6 | 5 | 10 | 10 | |
| Decks per CAPCAS | 1 | 1 | 1 | 1 | 1 | 7 | 9 | 9 | 1 | 1 | 4 | 8 | 10 | 10 | |
| Number of well plates = N | 1 | 1 | 3 | 4 | 9 | 28 | 108 | 108 | 9 | 9 | 24 | 40 | 100 | 100 | plates |
| Total number of wells | 12 | 48 | 144 | 384 | 864 | 1,344 | 10,368 | 10,368 | 864 | 864 | 1,152 | 3,840 | 9,600 | 9,600 | wells |
| Time per X-well plate | 1,080 | 4,320 | 4,320 | 8,640 | 5,760 | 2,880 | 5,760 | 960 | 5,760 | 5,760 | 2,880 | 1,920 | 960 | 960 | s |
| Time per X-well plate | 18 | 72 | 72 | 144 | 96 | 48 | 96 | 16 | 96 | 96 | 48 | 32 | 16 | 16 | min |
| Time for N well plates | 18 | 72 | 216 | 576 | 864 | 1,344 | 10,368 | 1,728 | 864 | 864 | 1,152 | 1,280 | 1,600 | 1,600 | min |
| Time for N well plates | 0.3 | 1.2 | 3.6 | 9.6 | 14.4 | 22.4 | 172.8 | 28.8 | 14.4 | 14.4 | 19.0 | 21.0 | 27.0 | 27.0 | hours |

FIG. 18H

| Count | Units |
|---|---|
| Normal-well-depth chemostats in a 48-well plate | |
| 48 | chemostats per chemostat plate |
| 3 | plates per module (input, chemostat, output) |
| 4 | modules per deck |
| 10 | decks per rack |
| 1,920 | continuously-perfused chemostats per rack |
| Normal-well-depth chemostats in a 96-well plate | |
| 96 | chemostats per chemostat plate |
| 3 | plates per module (input, chemostat, output) |
| 4 | modules per deck |
| 10 | decks per rack |
| 3,840 | continuously-perfused chemostats per rack |
| Normal-well-depth chemostats in a 96-well plate | |
| 96 | chemostats per chemostat plate |
| 3 | chemostat plates per module (input + 3) |
| 4 | modules per deck |
| 9 | decks per rack (plus innoculation deck) |
| 10,368 | continuously-perfused chemostats per rack |
| 1.0 mL stirred chemostats in a deep 48-well plate | |
| 48 | chemostats per chemostat plate |
| 3 | plates per module (input, chemostat, output) |
| 4 | modules per deck |
| 7 | decks per rack |
| 1,344 | continuously-perfused chemostats per rack |

| Count | Units |
|---|---|
| Continuous, gravity-perfused organ chips | |
| 2 | organ chips per plate box |
| 12 | plates per deck |
| 9 | decks per rack |
| 216 | organ chips per rack |
| Continuous, gravity-perfused organ chips | |
| 6 | organ chips per plate box |
| 12 | plates per deck |
| 9 | decks per rack |
| 648 | organ chips per rack |
| Continuous, gravity-perfused organ chips | |
| 6 | organ chips per plate box |
| 12 | plates per deck |
| 9 | decks per rack |
| 648 | organ chips per rack |
| Multiplex-perfused organoid wells | |
| 96 | organoid wells per plate |
| 12 | plates per deck |
| 9 | decks per rack |
| 10,368 | Multiplex-perfused organoid well per rack |

| Count | Units |
|---|---|
| 200 μL multiplex-perfused wells in a 96 well plate | |
| 96 | wells per plate |
| 1 | plate per module |
| 12 | modules per deck |
| 9 | decks per rack |
| 10,368 | multiplex-perfused wells per rack |
| Multiplex-perfused 24-well Transwells | |
| 24 | wells per plate |
| 1 | plate per module |
| 12 | modules per deck |
| 9 | decks per rack |
| 2,592 | multiplex-perfused Transwells per rack |
| 12-well TransWells with zebrafish embryos | |
| 5 | zebrafish embryos per well |
| 12 | wells per plate |
| 12 | plates per deck |
| 9 | decks per rack |
| 6,480 | zebrafish embryos per rack |

CAPCAS Overview

Reads from SQL Database during Experiment

Writes to SQL Database during Experiment

Experiment Structure

Systems Network

Device Pack – Initialization to Prime Tubing

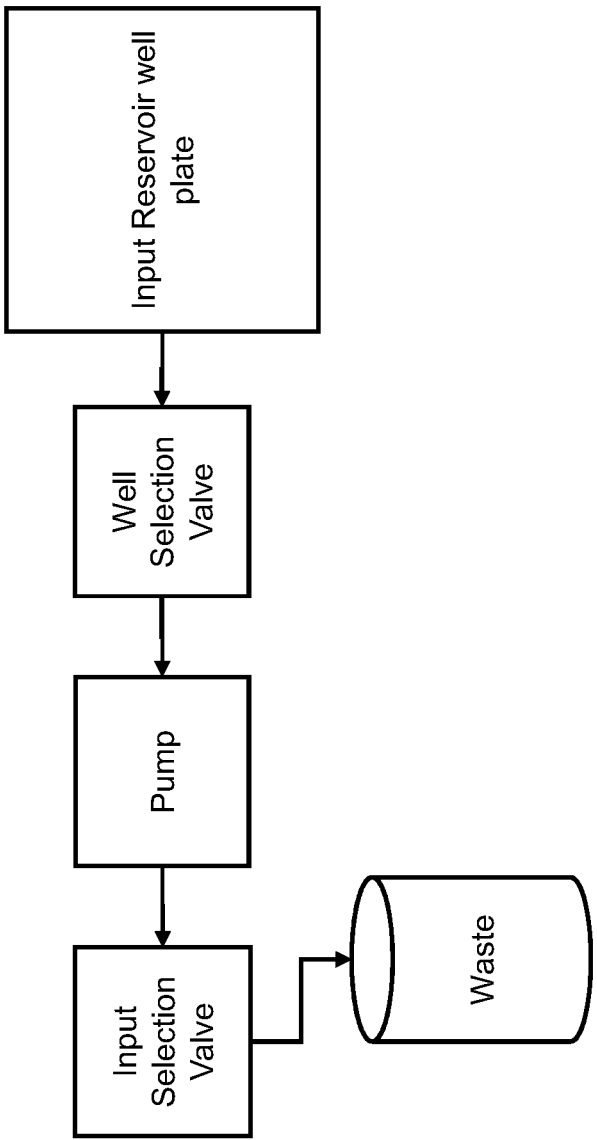
FIG. 19J Device Pack – Removal

Experiment Protocol: Initialization

Experiment Step Tracking and Execution

Device Pack and Dual Pumps Step Tracking

CONTINUOUS AUTOMATED PERFUSION CULTURE ANALYSIS SYSTEM (CAPCAS) AND APPLICATIONS OF SAME

CROSS-REFERENCE TO RELATED PATENT APPLICATIONS

This application is a continuation application of U.S. patent application Ser. No. 17/578,966, filed Jan. 19, 2022, now U.S. Pat. No. 11,447,734, which itself claims priority to and the benefit of U.S. Provisional Patent Application Ser. No. 63/139,138, filed Jan. 19, 2021, 63/163,160, filed Mar. 19, 2021, 63/257,149, filed Oct. 19, 2021, 63/277,329, filed Nov. 9, 2021, and 63/300,321, filed Jan. 18, 2022.

This application is also a continuation-in-part application of PCT Patent Application Serial No. PCT/US2021/042179, filed Jul. 19, 2021, which itself claims priority to and the benefit of U.S. Provisional Patent Application Ser. No. 63/053,388, filed Jul. 17, 2020; 63/139,138, filed Jan. 19, 2021; and 63/163,160, filed Mar. 19, 2021.

This application is also a continuation-in-part application of PCT Patent Application Serial No. PCT/US2020/040061, filed Jun. 29, 2020, which itself claims priority to and the benefit of U.S. Provisional Patent Application Ser. No. 62/868,303, filed Jun. 28, 2019.

Each of the above-identified applications is incorporated herein by reference in its entirety.

STATEMENT AS TO RIGHTS UNDER FEDERALLY-SPONSORED RESEARCH

This invention was made with government support under Grant No. UH3TR002097 awarded by the National Institutes of Health (NIH) National Center for Advancing Translational Sciences (NCATS), National Institute of Neurological Disorders and Stroke (NINDS), and Eunice Kennedy Shriver National Institute of Child Health and Human Development (NICHD); Grant No. U01TR002383 and (through Vanderbilt University Medical Center) UL1TR002243 awarded by NCATS; Grant No. U01CA202229 awarded by the National Cancer Institute (NCI), and Grant No. HHSN271201 700044C (through CFD Research Corporation) awarded by NCATS; by the National Science Foundation (NSF) under Grant No. CBET-1706155 and Grant No. 2117782; and by the National Aeronautics and Space Administration (NASA) under Grant No. 80NSSC20K0108. The government has certain rights in the invention.

FIELD OF THE INVENTION

The invention relates generally to fluidic systems, and more particularly to a continuous automated perfusion culture analysis system (CAPCAS)—a third-generation "robot scientist" that functions as a fully automated microfluidic system containing 1,000 or more biodevices such as chemostats, bioreactors, organ chips or other biodevices for parallel, independent, long-duration, machine-guided experiments to optimize biological function or infer the dynamics of signaling and metabolism of living systems, such as the single-cell eukaryotic yeast Saccharomyces cerevisiae, bacterial communities, Chinese hamster ovary (CHO) cells used in antibody production, single and coupled organs-on-chips, and other bio-objects that require regular media changes or even continuous perfusion. CAPCAS could also be used to conduct massively parallel biotic and abiotic chemical synthesis experiments.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

The complexity of biology is legendary: some human organs have billions of cells of many different types, a single cell may express between 10,000 and 15,000 distinct proteins at any one time, and protein-protein interactions are today innumerable, such that the human mind, or even tens of thousands of human minds, may never be able to fully unravel biological interconnections that are key to the health of humans, animals, and even the planet Earth. One of the most challenging tasks facing $21^{st}$ century science is the development of high-fidelity computational models of eukaryotic and prokaryotic cellular biology. Even simple unicellular organisms, such as S. cerevisiae and Escherichia coli, have thousands of different genes, proteins, and small molecules, all interacting in complex spatiotemporal ways. The development of computational models for cellular biology is central to the future of medicine and biotechnology.[1,2] One can argue that ultimately computational systems biology models might have Avogadro's number of coupled equations.[3]

Given this complexity, the existing dish, flask, well plate, Transwell, and bioreactor technologies for conventional cell culture shown in FIGS. 1A-1G, and even the well-plate-based high-throughput screening (HTS) systems illustrated in FIGS. 2A-2B, are proving inadequate. As we will discuss in more detail later, FIGS. 1A-1G show current cell culture devices such as (A) Petri dishes, (B) cell culture flasks, (C) well plates, (D) Transwell inserts in a well plate, (E) hollow fiber systems, (F) rolling bottle bioreactors, and (G) bead suspension bioreactors. FIGS. 2A-2B show a schematic representation of an automated robot well-plate handling system capable of automatic transfer, manipulation, and measurements of well plates between different stations: (A) a perspective view, and (B) a sectional view. Fluid delivery is accomplished by using automated micropipettes to transfer fluids between multiple well plates in a fluid-handling unit designed specifically for that purpose, as disclosed in U.S. Pat. No. 10,119,622 B2 to Block, III, et al., which is incorporated herein by reference in its entirety.

Furthermore, it is becoming recognized that the culture of a planar sheet of cells on a plastic dish or well plate, as shown in FIGS. 1A-1C, cannot recapitulate the dynamics of signaling that occurs in vivo between the cells and the extracellular matrix around them. This limitation is being addressed with the use of a two- or three-dimensional in vitro microphysiological systems (MPS), such as organoids and organs-on-chips (FIGS. 3A-3G, to be discussed in detail later), also known as tissue chips. Organ chips can be operated in isolation or fluidically coupled together, as shown in FIGS. 3A and 3B, and arrays of organ chips and compact control and analytical modules can be mounted on a common base or caddy (FIG. 3C) or operated as a linear "train" (FIG. 3D). In turn, collections of these assemblies can be operated in a temperature-, humidity-, and gas-controlled cabinet (FIG. 3E) or an automated linear incubator (FIGS. 3F and 3G). While the HTS system in FIGS. 2A-2B and the coupled organ-on-chip systems in FIGS. 3A-3G represent the state-of-the-art in biology, they do not support the level of closed-loop, feed-back sensing and control of these biological systems that will be required to probe the dynamic, non-linear, and redundant signaling and metabolic networks that are the basis for the extreme complexity of biology and are the focus of intense efforts in mathematical modeling. Hence there is a pressing need for an efficient means to design and conduct the massive number of open- and closed-loop experiments needed to parameterize, validate, and utilize these models to probe and even control biological systems.

Even in the near term, the exquisite complexity of cellular systems biology models means that developing and evaluating them will require the execution of many millions of hypothesis-led experiments. Only artificial intelligence (AI) systems, coupled with laboratory automation, have the ability to plan, execute, and record such a vast number of experiments.[4] A possible solution to the problem of unravelling the complexity of biology will be to create and utilize robot scientists, which are physically implemented laboratory automation systems that exploit techniques from the field of AI to automatically execute cycles of scientific experimentation: 1) form hypotheses, 2) design and select efficient experiments to discriminate between the hypotheses, 3) physically execute the experiments using laboratory automation equipment, 4) analyze and interpret the data, 5) test the hypotheses, 6) use the results to refine or replace the hypothesis, and 7) repeat the process ad infinitum.[4] Such a robot scientist would constitute a self-driving laboratory that would navigate a course through a scientific problem using more experimental observations and controlled parameters than could be tracked by the human mind, with higher efficiency, accuracy, and reproducibility and an infallible memory.

The Robot Scientist "Adam" was the first machine to autonomously discover scientific knowledge.[5] Adam had an automated −20° C. freezer, three liquid handlers, three automated +30° C. incubators, two automated plate readers, three robot arms, two automated plate slides, an automated plate centrifuge, an automated plate washer, two high-efficiency particulate air filters, and a rigid transparent plastic enclosure in a configuration that was similar to FIGS. 2A-2B. Autonomously, Adam specified and recorded 6,657,024 optical density measurements at 595 nm to form 26,495 growth curves, and formulated and tested 20 hypotheses concerning genes encoding 13 orphan enzymes.[4,6] Adam's successor, Eve, automated early-stage drug development[7] with a design that is now being widely copied in industry. Subsequently, Eve used a combination of multiple software tools with integrated laboratory robotics to execute three semiautomated cycles of improvement to models of the diauxic shift when yeast is forced to switch its metabolism from glucose to ethanol. All the experiments were formalized and communicated to Eve's cloud laboratory automation system for execution to expand the current model of the yeast diauxic shift. The final model adds a substantial amount of knowledge to the systems biology description of the diauxic shift in yeast: 92 genes (+45%) and 1,048 interactions (+147%).[8]

The first- and second-generation robot scientists Adam and Eve have already been shown by their creator, Dr. Ross King, to have superhuman scientific abilities: Adam and Eve have already demonstrated that a robot scientist can automatically originate hypotheses to explain observations, devise experiments to test these hypotheses, physically run the experiments using laboratory robotics, interpret the results to change the probability of hypotheses, and then repeat the cycle. Adam and Eve confirm that robot scientists are better than human scientists at recording scientific knowledge: as the experiments are conceived and executed automatically by computer, it is possible to completely capture and digitally curate all aspects of the scientific process—the hypotheses, the experimental goals, the results, etc. Robot scientists can work cheaper, faster, more accurately, and longer than human scientists; they can be easily multiplied; they can generate and compare astronomical numbers of hypotheses in parallel, while cognitive limitations mean that humans can only consider a few hypotheses at a time. Robot scientists can select near optimal (in time and money) experiments to test hypotheses; and they can fully record all aspects of the scientific process, increasing research reproducibility and knowledge transfer. Robot scientists will not replace human scientists; instead, they will empower systems biology and biotechnology researchers by providing unprecedented reasoning abilities and reliability of experimentation. Robot scientists will free human scientists from routine lab chores and enable them to concentrate on high-level intellectual tasks.

Robot scientists such as Adam and Eve could also be used for combinatoric chemistry in biotic and abiotic chemical synthesis processes wherein the fluid-handling systems could be used to deliver constituent chemical components to a large number of chemical synthesis reactions being conducted in parallel and remove and transfer solutions as required.

Despite their capabilities, one of the crucial limitations of the application of Adam and Eve to eukaryotic systems biology is that they both use batch culture to create growth curves. In common use, yeast does its work in batches, where it grows and multiplies until it runs out of food or creates an environment where it can no longer thrive. A small batch of yeast grown in a research laboratory might require a milliliter of growth media in one well of a multi-well plate, whereas a yeast bioreactor at a pharmaceutical company could hold a few thousand liters, and one in a brewery a million liters. As an example of a very small bioreactor, the upper portion of FIG. 4 shows the growth of *S. cerevisiae* in a 3.2 pL occlusion-limited trap that was one of many traps in a microfluidic device (lower left scale bar=40 μm). In the lower portion of FIG. 4, inverse optical density (IOD) of two traps is plotted as a function of time. The data were calculated from corresponding time lapse images acquired 1 min apart. IOD values for the trap encircled above are shown as diamonds and resulted in an approximately exponential growth curve (solid line) until the trap filled and the debris that blocked it was pushed away. Black points were taken from an already-full trap imaged simultaneously in the same field of view as the encircled trap. From Byrd, T. F., et al. (2014), "The microfluidic multitrap nanophysiometer for hematologic cancer cell characterization reveals temporal sensitivity of the calcein-AM efflux assay," Scientific Reports 4: Article 5117.[9] The rising portion of the growth curve shown in FIG. 4 represents a convolution of time-varying, biochemically fundamental rates, which complicates interpretation of the data and the generation of a biologically realistic model. Both Adam and Eve measured growth curves after computer-selected S. cerevisiae knock-out strains were batch seeded into different wells of a well plate with specific essential nutrients. It is widely recognized that substantial changes occur in gene expression, signaling, and metabolism as the cell population matures.[10]

FIGS. 5A-5D show a computer simulation of metabolic inhibition experiments using batch and continuous culture of adherent eukaryotic cells (left) and suspended microbial cells (right). FIGS. 5A and 5B simulate batch culture with media replacement every 24 hours, which maximizes the change at the end of each 24-hour period, but subjects the cells to continuously changing nutrient and metabolite concentrations. FIGS. 5C and 5D show continuous media replacement by delivery of fresh media at concentration $[S_o]$ (short dash) with a MicroFormulator or MicroFormulator-controlled chemostat so that the cells maintain a consistent level of nutrients and metabolites. Looking at the panels vertically, FIGS. 5A and 5C represent adherent cells in a well, while FIGS. 5B and 5D represent suspended, dividing yeast in a bioreactor. In all four cases, both the metabolite [Metab] (dash-dot) and the inhibitor [Inhib] (dash-dot-dot) reduce the metabolic activity of the cells, as evidenced by the reduction in the rate of consumption of the substrate [S] (solid). Comparison of FIGS. 5A and 5B with FIGS. 5C and 5D shows how continuous flow provides a much more stable, readily interpreted environment for the cells.

FIG. 5A simulates three sequential batch media replacements for a stable population of confluent cells, with the middle exchange including a metabolic inhibitor. The graphs show the time-dependence of the nutrient concentration [S] (solid) and [Metab] (dash-dot) for 80% media replacement at 0, 24, and 48 hours. A bolus of [Inhib] (dash-dot-dot) is delivered at 24 hours and removed at 48 hours. In batch culture, gene expression profiles change with continuously varying levels of nutrients, metabolites, and signaling molecules. An end point analysis may not be as affected by these changes as would be a growth rate determination.

FIG. 5B shows three serial-batch measurements of yeast growth with differing inhibitor concentrations. Steady increases in optical density (OD, long dash) begin immediately after a bioreactor is loaded with fresh media and yeast, which begin rapid division because of the high level of nutrients in the loaded media. There is no media addition until the reactor is emptied and reseeded at 24 and 48 hours. The concentration [S] of the rate-limiting nutrient S decreases with time from the initial loading of $[So]=10$. When [S] reaches zero, the yeast become quiescent and stop dividing, and OD is thereafter constant. Note that measurement of the effect of the inhibitor requires careful measurements of a rapidly changing OD at multiple time points to quantify the slower growth rates with increasing [Inhib] at 24 and 48 hours. Again, in batch culture, gene expression profiles change throughout the growth phase, with continuously changing levels of nutrients, metabolites, and signaling molecules. An end-point analysis may not be as affected by the gene expression changes as would be a growth rate determination.

FIG. 5C shows confluent cells undergoing continuous media replacement with a continuous-flow microformulator so that the adherent cells maintain a consistent level of nutrients and metabolites, such that [S] and [Metab] remain constant. 4% of the media is replaced each hour. The difference between the delivered [So] and the measured [S] represents the amount of [S] that is consumed in the steady state by the cells. Between 24 hours and 48 hours, the inhibitor is delivered with a realistic pharmacokinetic (PK) profile, with the long tail the result of the continuous partial media replacement after the drug injection ceases. Note that the cells are never subjected to extreme daily variations in [S] and [Metab]. The areas under the [Inhib] curve in (A) and (C) are the same. With continuous perfusion in a microformulator, gene expression profiles can be constant for long periods of time, which is ideal for quantitative multi-omic measurements of signaling and metabolism required for network reconstruction. Concentration changes can be either pharmacokinetic (shown) or step changes.

FIG. 5D represents a continuous-perfusion chemostat experiment that after seeding reaches a steady-state growth rate that represents a balance between inflow of media with the rate-limiting nutrient and efflux of cells and media. The graph shows the time-dependence of OD and [S] for a yeast chemostat, wherein media with nutrient concentration [So] is delivered continuously, and the outflow of the chemostat removes yeast at a rate equal to that of their steady-state growth. After the initial loading, [S] drops as the number of yeast in the chemostat grows until there is a steady-state balance between the delivery of the media and S and the efflux of yeast and conditioned media from the reactor, hence the name "chemostat." The difference between the delivered [So] and the measured [S] represent the consumption of S required to support that number of yeast in the bioreactor. [S] never goes to zero and the yeast cells continue to divide and are washed away at a constant rate. When the inhibitor is added at 24 hours and at a higher concentration at 48 hours, the yeast division rate is reduced, but since the media delivery and efflux rates are held constant, the number of yeast in the chemostat drops. Measurement of the OD versus [Inhib] can be used to quantify the effects of the inhibitor on the chosen rate-limiting nutrient, and the three long plateaus provide ample yeast and supernatant for untargeted transcriptomics, proteomics, and metabolomics. Note that the inhibitor concentration can be changed without reseeding the bioreactor. In chemostats, gene expression profiles are relatively constant for long periods of time, which is ideal for quantitative multi-omic measurements of signaling and metabolism required for network reconstruction.

The ultimate lesson from FIGS. 5A-5D is that batch feeding of adherent or suspension cells results in continuous changes in levels of nutrients and metabolites, and hence gene expression levels, while continuous perfusion of either adherent cells or ones suspended in a chemostat provides long periods of time with steady levels of cellular metabolic and signaling variables or ones that change in response to a physiologically realistic PK exposure profile. Computationally, it is challenging to infer the dynamics of the underlying changes in biochemistry that occur along the course of the growth curves in FIGS. 4, 5A, and 5B, and more straightforward with the situations that led to FIGS. 5C and 5D.

As an alternative to batches, a continuous-flow bioreactor, termed a chemostat, provides a steady supply of food and continuously removes excess yeast or even suspended mammalian cells and their metabolites to maintain steady-state growth. There is an increasing recognition that post-genomic biology and microbial systems biology can benefit from a return to continuous-flow culture systems,[10-16] such as the chemostat shown in FIG. 6A that was invented independently in 1950 by Monod[17] and Novick and Szilard.[18,19] FIG. 5C simulates three continuous-flow chemostat experiments using a device functionally equivalent to FIG. 6A.

We have already demonstrated a microfluidic MultiWell MicroFormulator[20-26] that can deliver a different time-dependent PK profile of drug concentration versus time to each well of a 24- or 96-well plate. FIG. 5C shows a simulation of how the microformulator in FIG. 6C could recapitulate in vitro a PK profile such as would be observed in an intact human or experimental animal. Comparison of FIG. 5C with FIG. 5A and FIG. 5D with FIG. 5B shows how continuous flow afforded by the MicroFormulator in FIG. 6C, used alone with adherent cells as in FIG. 5C or in conjunction with a chemostat as in FIG. 5D, provides a much more stable, readily interpreted environment for the cells that is well-suited for multi-omic analyses of gene transcription, protein expression, and metabolic activity.

The hardware shown in FIGS. 1A-1G, 2A-2B and 3A-3G is inadequate for a massively parallel application of "self-driving" and machine-learning (ML) technologies to advancing biological knowledge. Such an effort would benefit from a thousand or more chemostats or other bioreactors, organ chips or other biodevices operating in parallel under computer control. Neither commercial production nor research chemostats, bioreactors, well plates, organ-chip systems, or similar biodevices have the correct combination of size, cost, and automated instrumentation to serve as massively parallel robot scientists. There are no existing chemostat or bioreactor technologies that can be scaled to thousands of channels, and AI/ML tools for model development have yet to penetrate the marketplace. Commercially available bioreactors are deployed extensively by the biopharmaceutical and biomanufacturing industries, which operate them in either serial-batch, batch-fed, or chemostat modes to produce fermented beverages, industrial biomolecules, and pharmaceuticals including recombinant proteins, antibody fragments, and monoclonal antibodies. The industry-leading Sartorius product line offers bioreactor volumes ranging from 15 mL to 2000 L, each representing critical stages in scale-up to commercial biomolecule production. The Ambr15 and Ambr250 "high throughput systems" support 24 15 mL bioreactors[27-29] and 250 mL bioreactors, respectively.[30] These two systems have the advantage of producing results that are predictive of the growth rate and other properties achieved in the larger, industrial-production-scale bioreactors. It would be prohibitively expensive to scale either the Ambr15 or Ambr250 to thousands of bioreactors.

The biochemical activity of multiple bioreactors over the full range of volumes from 15 mL to thousands of liters can be accomplished using sensor systems such as the NovaBiomedical BioProfile Flex2 Automated Cell Culture Analyzer, which can withdraw samples from up to 10 bioreactors, count cells, and perform metabolic measurements every 10 minutes, with expendable supplies that need to be replaced based upon use or elapsed time. It could be economically prohibitive to use this system to monitor thousands of chemostats.

There are several useful examples of smaller volume systems, none of which scale to thousands of chemostats. The eVOLVER, an assembly of discrete components that operates 16 10 mL bioreactors, pumps, and control electronics, is an excellent example of an academic-derived open-source system that is producing useful results,[31-33] but its unpackaged electronics are not appropriate for long-term use of a thousand or more channels in a core facility, and the system does not support multiport valves or robotic plate handling. The Cytena c.Bird is a set of continuous-mixing modules that use pneumatic actuation to increase oxygen transfer rate in a 96- and 24-well plate. While it cannot operate as a chemostat, it is highly effective for the controlled clonal expansion of single mammalian cells. The Erbi Breez™ microbioreactor[34,35] has a 2 mL working volume with independent measurement of pH, dissolved oxygen (DO), optical density (OD), and temperature, can input up to four fluids, and controls three gases. While it has performance characteristics compatible with a self-driving laboratory, its physical size, configuration, cost, and the fact that a single system supports only four bioreactors would make this system impractical for scaling to a thousand channels. Another industry standard, the BioLector and RoboLector, are automated fed-batch, pipette-loaded fermentation systems that use either a single 48 flower-shaped shaken well plate or a microfluidic enabled one with four banks of eight bioreactors and two banks of eight reservoirs for pH and nutrient control. The system cannot operate as a chemostat, and the entire system can only operate a single well plate, making it impractical to study thousands of bioreactors or other biodevices in parallel.

There is also a need to create compact, low-cost, and readily reconfigurable hardware for biotic and abiotic chemical synthesis processes.

Therefore, a heretofore unaddressed need exists in the art to address the aforementioned deficiencies and inadequacies.

SUMMARY OF THE INVENTION

In view of the aforementioned deficiencies and inadequacies, one aspect of this invention provides a continuous automated perfusion culture analysis system (CAPCAS), comprising: one or more fluidic systems configured to operate large numbers of biodevices such as chemostats, bioreactors, organ-chips, well plates, and Transwell plates in parallel.

In one embodiment, each fluidic system comprises an array of biodevices configured such that each biodevice can have independent media delivery, fluid removal, stirring, and gas control.

In one embodiment, each fluidic system further comprises a media delivering means, and a media collecting means, wherein the array of biodevices is fluidically coupled between the media delivering means and the media collecting means.

In one embodiment, the media delivering means comprises a multichannel input selector valve fluidically coupled to input vials, an input pump fluidically coupled to the multichannel input selector valve, and a multichannel input director valve fluidically coupled to the input pump, configured such that the multichannel input selector valve operably selects media and/or drugs from the input vials, and the input director valve allows the input pump to deliver individually the selected media and/or drugs to each biodevice.

In one embodiment, the media collecting means comprises a multichannel output collector valve fluidically coupled to the array of biodevices, an output pump fluidically coupled to the multichannel output collector valve, and a multichannel output director valve fluidically coupled to the output pump, configured to remove media from each biodevice and deliver it to waste, a Turbidimeter, a microclinical analyzer, or a holding reservoir.

In one embodiment, each of the multichannel input director valve and the multichannel output collector valve has a connection to back-flush vials, and/or pressurized air or other gas to insert one or more bubbles between each sample.

In one embodiment, the CAPCAS further comprises a multichannel reservoir collection valve coupled to the holding reservoir of each fluidic system and configured to analyze media from any single biodevice in any of the one or more fluidic systems.

In one embodiment, the one or more fluidic systems comprises 100 fluidic systems, and the array of biodevices of each fluidic system comprises a 96-well plate, whereby the CAPCAS is a 9,600 biodevice system.

In one embodiment, the CAPCAS also comprises a low-pressure pump fluidically coupled to the multichannel reservoir collection valve for operably withdrawing the media from the holding reservoir that transiently retains the media and cells withdrawn from the desired biodevice or bioreactor well.

In one embodiment, the CAPCAS further comprises a bubble detector fluidically coupled to the low-pressure pump for operably identifying where one sample ends and another starts, when the low-pressure pump delivers the samples to a mass spectrometer.

In one embodiment, the CAPCAS also comprises a calibration valve fluidically coupled to the bubble detector for operably removing air through one port (A), sending leading portions of any sample to waste (W), and injecting either a reagent (R) or a calibration solution (C) into the mass spectrometer.

In one embodiment, each fluidic system comprises an input reservoir plate for receiving media; a biodevice plate comprising an array of biodevices fluidically coupled to the input reservoir plate, configured such that each biodevice has independent media delivery, fluid removal, stirring, and gas control, and each biodevice is capable of continuously receiving the media from the input reservoir plate; and an output plate fluidically coupled to the biodevice plate for real-time analysis and sampling.

In one embodiment, each fluidic system further comprises at least one microformulator fluidically coupled to the input reservoir plate for providing the media to the input reservoir plate. Each microformulator comprises: a plurality of feedstock solution reservoirs; at least one input selector valve (V1) fluidically coupled to the plurality of feedstock solution reservoirs to select at least one feedstock reservoir; at least one output director valve (V2) fluidically coupled to the input reservoir plate; and at least one pump (P1) fluidically coupled between the at least one input selector valve and the at least one output director valve for withdrawing fluid from the selected feedstock solution reservoir through the at least one input selector valve and delivering it to the input reservoir plate through the at least one output director valve.

In one embodiment, the at least one input selector valve is a multichannel input selector valve, the at least one pump is a single-channel pump, and the at least one output director valve is a multichannel output director valve.

In one embodiment, the at least one input selector valve is configured to select different feedstock solution reservoirs at different periods of time.

In one embodiment, the at least one pump is driven such that the fluid of the selected feedstock solution reservoir outputs from the at least one output director valve at a predetermined flow rate.

In one embodiment, the predetermined flow rate varies with time.

In one embodiment, through a sequence of selecting the plurality of reservoirs by the at least one input selector valve and pump speed and duration actuations of the at least one pump, the media is provided to have a different time-varying perfusion mixture for each biodevice.

In one embodiment, each microformulator further includes a single-channel optical sensing module coupled between the at least one pump and the at least one output director valve for tracking an intentionally injected bubble for measurement of flow rate, or identifying when a reservoir is emptied.

In one embodiment, the CAPCAS further comprises a biodevice media delivering means fluidically coupled between the input reservoir plate and the biodevice plate for continuous delivery of the media from the input reservoir plate to each biodevice.

In one embodiment, the input reservoir plate has two sets of media ports, and wherein the biodevice media delivering means comprises two multichannel pumps (P2, P3), each multichannel pump is fluidically coupled between a respective set of the media ports and the biodevice plate, such that one set is refillable while the other set is being delivered by a corresponding pump to each biodevice in the biodevice plate, thereby providing uninterrupted perfusion.

In one embodiment, the CAPCAS further comprises a biodevice media collecting means fluidically coupled between the biodevice plate, and the output plate and an analyzer for real-time analysis and sampling.

In one embodiment, the biodevice media collecting means comprises first and second multichannel pumps (P4, P5), and at least one output valve (V3), wherein the first multichannel pump (P4) is fluidically coupled between the biodevice plate and the at least one multimode output valve (V3), the second multichannel pump (P5) is fluidically coupled between the biodevice plate and the output plate, and the least one multimode output valve (V3) is fluidically coupled between the first multichannel pump (P4) and the analyzer.

In one embodiment, the second multichannel pump (P5) operates independent of the first multichannel pump (P4) to deliver the effluent from each biodevice to a separate well in the output plate for off-line transcriptomic or other off-line analysis.

In one embodiment, the at least one multimode output valve is configured to either divert effluent from each biodevice to the analyzer.

In one embodiment, the at least one multimode output valve is configured to divert, when one biodevice is being sampled, the media being pumped from the other biodevices to waste, with each biodevice being sampled serially.

In one embodiment, the at least one multimode output valve is configured to divert the effluent from all the biodevices to waste to ensure continuous perfusion when no sample is needed or the output plate is removed after bulk sample collection.

In one embodiment, the analyzer is equipped with a spiral microfluidic sorter, a filter, or tangential flow filtration for real-time separation of cells from media, and an in-line, microfluidic acoustic or electrical lyser.

In one embodiment, the CAPCAS further comprises a plurality of multichannel optical sensing modules.

In one embodiment, a first one of the multichannel optical sensing modules is coupled between the input plate and the biodevice plate, and a second one of the multichannel optical sensing modules is coupled between the biodevice plate and the outplate for measuring P02, $PCO_2$, pH, and/or optical density (OD) of the media entering and leaving each biodevice, respectively.

In one embodiment, a third one of the multichannel optical sensing modules is coupled between the at least one microformulator and the input plate for tracking an intentionally injected bubble for measurement of flow rate, or identifying when a reservoir is emptied.

In one embodiment, each biodevice comprises a lid structure for controlling operation of the biodevice, wherein the lid structure comprises a fluidic control layer that contains motors that drive the pumps and valves, and a lid beneath the fluidic control layer, wherein the lid supports vertical tubes that deliver and remove fluid from the well, with a long tube reaching nearly to the bottom of the well to allow the pump P5 to remove when desired some or nearly all of the media and cells in the well, a medium length tube being connected to the pump P4 to provide continuous removal of media from the biodevice and deliver it to the at least one multimode output valve V3, and a short tube being connected to the pumps P2 and P3 to deliver media to the biodevice with the end of the short tube being well above the liquid level to prevent back-contamination of the media delivery system.

In one embodiment, each biodevice further comprises a stirrer system.

In one embodiment, the stirrer system comprises an individual printed-circuit-board (PCB) motor, bearings, and a hollow rotating slotted-cylinder stirrer that operably serves as an impeller to provide unidirectional axial flow in one direction on the inside of the impeller tube and in the opposite direction outside while surrounding the short, medium length, and long tubes and two vertical tubes that connect a gas permeable tubing loop.

In one embodiment, the stirrer system comprises a rotatable slotted cylinder that has one or more spiral vanes on either the inside or outside or on both sides of the rotatable slotted cylinder stirrer to provide more vigorous vertical mixing of the cells, media, and dissolved gases contained within the biodevice.

In one embodiment, the stirrer system comprises a magnetic stir bar disposed on a bottom of the well, a rotating magnet positioned beneath each well for driving the magnetic stir bar to rotate, and a separate motor to drive each rotating magnet to allow each biodevice in the array to be stirred at a different speed.

In one embodiment, the biodevices are operably inoculated by using an external pipettor or robot to seed either the biodevice plate, which is removable, or a transfer plate that has one or more seeded wells and is then installed in place of the output plate with the at least one second pump run in reverse to deliver the selected cells into various biodevices to restart their culture.

In one embodiment, the fluidic system is placed in a single-deck benchtop enclosure comprising three drawers of which one for the input reservoir plate, another for the biodevice plate, and the third for the output plate, which are operably serviced by an external robot arm for plate-delidding and/or lifting.

In one embodiment, the single-deck benchtop enclosure further comprises compartments separated from the drawers for motors/electronics and fluidics.

In one embodiment, M N-channel fluidic systems are placed on a single deck in a single benchtop enclosure to provide M×N channels of biodevice in a single unit, with at least the M output plates being accessible to an external robot arm by means of a computer-controlled drawer mechanism with automatic de-lidding, where M, N are positive integers.

In one embodiment four N-channel fluidic systems are placed on a single deck in a single benchtop enclosure to provide 4×N channels of biodevice in a single unit, with at least the four output plates being accessible to an external robot arm by means of a computer-controlled drawer mechanism with automatic de-lidding. The system has a total of 12 plates in a single unit.

In one embodiment, a high-density CAPCAS that uses three independent sets of three 96-well biodevice plates each, eliminates all output plates, and rapidly perfuses three biological replicates at one time, would service a total of nine 96-channel biodevices containing a total of 864 biodevice wells.

In one embodiment, the use of a fast series or parallel microformulator that would 1) eliminate the need for the input reservoir plate, 2) use in-line and at-line analyses without the need to collect media in the output plate, and 3) use of a 96-well biodevice plate instead of a 48-well one would allow the support of twelve 96-channel modules on a single deck, i.e., 1,152 biodevices. With the faster serial or parallel microformulator, for example by increasing the speed of pump P1 and/or adding more parallel pumping channels and/or parallel outputs in V3, it would be possible to use rapid time-division multiplexing to formulate directly into each biodevice rather than into the reservoir plates. Given that the sensor valve (V5) can direct cells and media sequentially from each well to a selector valve V6 and then on to an on-line analytical instrument, the output plate would not be required. However, this embodiment does not support the collection of samples from all biodevices in the biodevice plate at the same time instant, as do other designs.

In one embodiment, the one or more fluidic systems are placed in an enclosure having a plurality of decks, each deck having a plurality of stations, each station being configured to accommodate a plate/module of a fluidic system.

In one embodiment, the enclosure is configured such that each station is accessible by a robot for plate/module installation and/or removal, and two or more robots are simultaneously operable on a deck without interference.

In one embodiment, the enclosure further comprises an elevator for moving a robot between decks.

In one embodiment, each deck is connected to a continuous circulation fluid bus and a power bus.

In one embodiment, the enclosure is configured to serve as an environmental chamber, with complete control over temperature, gas composition, and humidity, with HEPA filtering to maintain sterility.

In one embodiment, the one or more fluidic systems are configured to maintain automatically and without human intervention a uniformly high level of media in the delivery well of a gravity-perfused bioreactor while also removing fluid from the collection well to keep a low fluid level and hence a constant gravity perfusion rate.

In one embodiment, one or more fluidic systems are configured to perfuse a plurality of parallel, pump-perfused maternal-fetal interface chips and collect their effluent and deliver it to a number of series-connected, gravity-perfused bone-cartilage bioreactors.

In one embodiment, the microformulator is configured to operate in a bidirectional manner, wherein the pump P1 operates in both directions, such that intermediate reservoirs are usable to create mixtures of fluids from a variety of reservoirs, including ones that are downstream of the microformulator.

In one embodiment, operations of the CAPCAS are automated and computer-controlled wirelessly.

In one embodiment, the CAPCAS can be used for abiotic and biotic chemical synthesis processes.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 1A-1G show cell culture devices used in typical biological laboratories.

FIGS. 6A-6C present schematic representations of a single-well chemostat, a microclinical analyzer, and a multiwell microformulator, respectively, which provide foundational operations of the invention.

FIG. 8A-8J show embodiments of a multi-chemostat fluid control system that support 12, 48, 144 and more independent chemostats, according to the invention. FIG. 8A shows fluidic schematic for the 12-chemostat multiwell microchemostat module. A 48-channel system would have the same topology, except 48 chemostats and pumps, valves, and sensors with proportionally more channels. FIGS. 8B-8D show a robot-accessible single-deck benchtop enclosure for up to three 12- or 48-channel chemostats, each with three well plates. FIGS. 8E and 8F show an enclosure that contains three 48-well chemostat/bioreactor plates for a total of 144 independent chemostats/bioreactors. FIGS. 8G and 8H show a CAPCAS that contains four 48-channel units, for a total of 192 chemostats or bioreactors. FIGS. 8I and 8J show a high-density CAPCAS that uses 96-well chemostat/bioreactor plates, eliminates the output plate by relying on multiple copies of pumps P4 and valves V5 and V6 to direct the output of each chemostat to an on-line analyzer, and rapidly perfuses three biological replicates at one time for each of three independent systems, servicing a total of nine plates containing a total of 864 chemostat/bioreactor wells.

FIG. 9 outlines the procedural steps involved in the operation of a multi-well chemostat/bioreactor module, according to embodiments of the invention.

FIGS. 14A-14H present the subsystems of CAPCAS and how they can be implemented in hardware, according to embodiments of the invention.

FIGS. 17A-17C show how a variety of sensors could be included in a CAPCAS unit, according to embodiments of the invention.

FIGS. 18A-18H demonstrate various methods for perfusing organ chips in a CAPCAS unit, according to embodiments of the invention.

DETAILED DESCRIPTION OF THE INVENTION

Figure 2B:
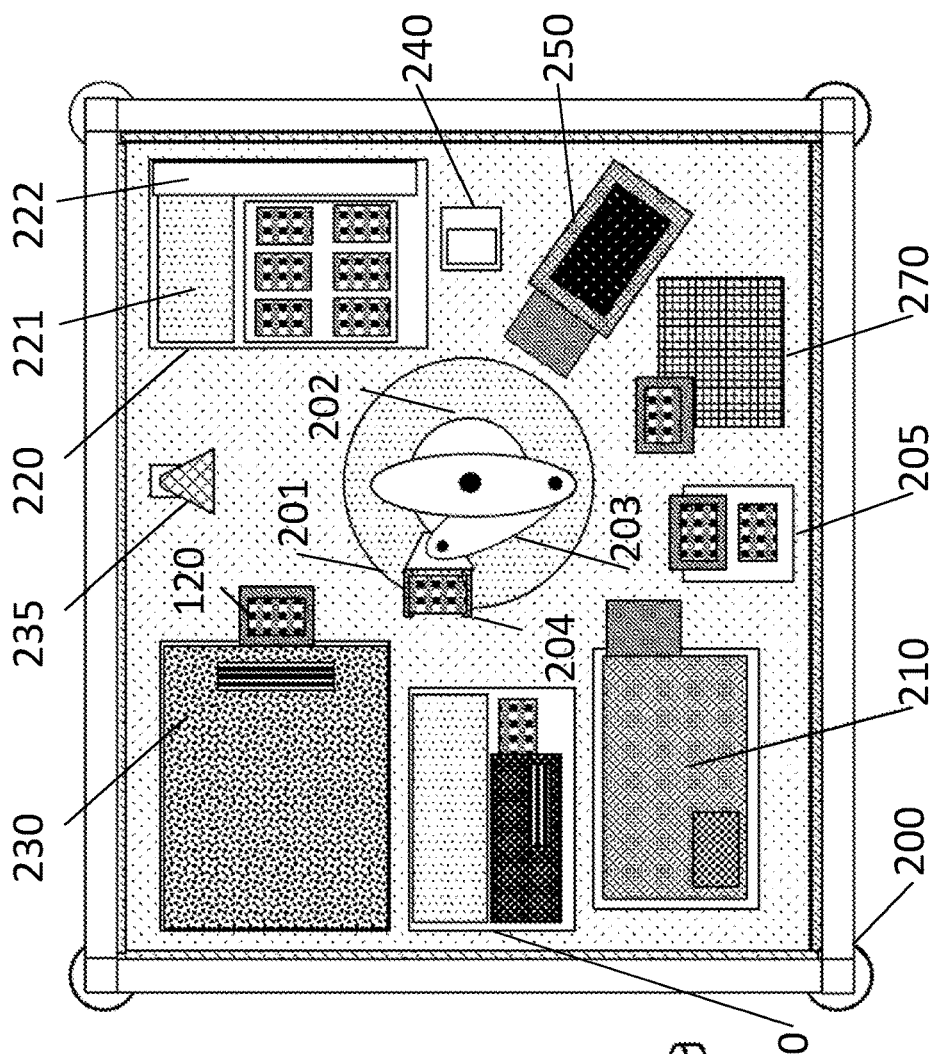
FIG. 2A-2B shows a schematic representation of an automated robot well-plate handling system.

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. As used herein, the term "and/or" includes any and all combinations of one or more of the associated listed items.

As used herein, the term "biodevice" refers to a well plate, a chemostat, an organ chip, a Transwell-plate, a bioreactor, an abiotic or biotic chemical synthesis reactor, or other fluidic reservoirs that are contained in a multi-element biodevice array.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In view of the aforementioned deficiencies and inadequacies in the background, one of the objectives of this invention is to address the need for better hardware with a distributed robotic system for fluid handling and transport of well plates, and arrays of microbioreactors and other biodevices that require continuous perfusion with media, or intermittent removal and replacement of media, or adjustment of the formulation of the media over time, with applications to chemostats and organ chips. In this context, the term "media" would include cell-culture media, nutrient solutions for model organisms such as zebrafish embryos, and even constituent chemical components and reactants in biotic and abiotic chemical synthesis processes. The hardware presented in this invention could enable the simultaneous and fully automated support, interrogation, and analysis of a thousand or more chemostats, bioreactors, well plates, organ chips or other biodevices or chemical reaction chambers, operating as self-driving systems biology laboratories. This system will enable new types of studies to understand, model, and control microbial populations, differentiating stem cells, antibody-producing cells, organoids, and tissue chips.

Self-Driving Laboratories and Robot Scientists

The self-driving biological laboratory has two major components: the hardware that is the subject of this invention and the artificial intelligence (AI) software that guides the machine-learning (ML) processes. Many of the AI applications to biology involve image and pattern recognition, for example using deep-learning neural networks, and are already routinely used to analyze data. For systems biology and pharmacology research, AI tools such as those that drive the Adam and Eve robot scientists use symbolic AI to form models, generate experiments, execute experiments, and refine models. This scientific cycle includes knowledge integration, experiment planning, experimental protocol generation, and interpretation of experimental results. However, even state-of-the-art AI systems alone are insufficient for closing this loop. The combination of third-generation robot scientists, like the current invention, operating as part of an integrated platform of data, hardware, and analytics offers a powerful solution for such a challenging task in scientific discovery. The development of an automated discovery platform is highly demanded not only in biology but also in any scientific and industrial field that needs 1) faster discovery, 2) cheaper experimentation, 3) cheaper labor, and 4) improved reproducibility, knowledge, and data sharing.

Other technological advances that enable the third-generation robot scientist that is the subject of this invention include improved computer hardware with faster processors designed to operate in parallel for computations and smaller and more powerful microprocessors for instrument control; rapidly growing databases describing biological molecules and their interactions; and, as covered by this invention and it antecedents, compact, multichannel, computerized pumps, valves, and sensors, and miniature robots and software capable of synchronizing the control of thousands of bioreactors in a single cabinet; and high-speed mass spectrometers that can analyze thousands of samples of bioreactor effluent each day to characterize a multitude of metabolic changes commanded by the robot scientist. While this third-generation, self-driving laboratory could be applied to any of a large number of biological systems used in basic research and industrial-scale biotechnology, the featured embodiments for this invention will focus on two applications: 1) massively parallel, independent, long-duration, machine-guided experiments on the single-cell microbe *Saccharomyces cerevisiae*, known as baker's or brewer's yeast, to decode the signaling and metabolic networks. This third-generation robot scientist will make it possible to maintain, interrogate, control, and modify thousands of yeast cultures at a much lower cost than is currently possible; and 2) the use of the continuous perfusion feature to maintain mammalian cells in culture, either in well plates, bioreactors, or organs-on-chips for studies in biology, toxicology, and pharmacology.

There are a multitude of other applications of a self-driving biological laboratory as described by the current invention. Microbes such as *S. cerevisiae* and the bacteria from the gut microbiome and extreme environments are expected to play an ever-increasing role in the production of vaccines, cancer therapies and other pharmaceuticals, enzymes, food protein, feedstock for the chemical industry, and microbes to better sequester carbon dioxide from the atmosphere, all areas of pressing societal need. Other applications that are not discussed in detail in this application include the optimization of commercial and scientific biotechnology processes that include but are not limited to the differentiation of induced pluripotent stem cells (iPSCs) into a desired progenitor or terminally differentiated cells for regenerative medicine or research and the production of pharmaceutical antibodies by Chinese hamster ovary (CHO) cells. Other applications not presented in detail include the imposition of hormonal, chemical, or optical circadian rhythms,[20] and the continuous or circadian feeding of zebrafish embryos in, for example, a 12-well Transwell plate, or the use of a fully automated cell culture system for the study of chemical and biological weapons and their therapeutics and prophylactics.

As a self-driving robot scientist, the invention will use machine learning and AI to accelerate the development of mathematical models that describe microbial and eukaryotic metabolism and growth. These will help us understand, and possibly optimize, for example, the interactions between the many different microbial species that comprise the human microbiome and play key roles in both health and disease. The ability of the invention to create computational models of cellular signaling and metabolism on its own should advance medicine, biotechnology, and fundamental biological knowledge, since such models are required to optimize experiments, interpret data to reveal the rules that govern biological processes, and guide scale-up to industrial-scale bioreactors.

The invention offers a breadth of very attractive technical challenges and scientific and social opportunities ideal for interdisciplinary research and training in AI, swarm robotics, machine learning, and the exploration of signaling and metabolic pathways in microbes and suspended mammalian cells. A first-principles appreciation of the complexity of biology could in fact be utilized to accelerate the solution of societal problems in nutrition, health, and medicine. The invention will allow scientists and engineers and their trainees to address a number of important scientific, commercial, and global problems by advancing our understanding of biology and disease and improving the efficiency of industrial production of biochemicals and pharmaceuticals. The invention also provides additional impact as a tool for classroom instruction, in that ultimately it will allow students to pose questions and use the invention to help design and conduct the experiments needed to answer them. The invention is being designed for mass production at low cost and in high volume, so that small laboratories could afford a small-scale system, and a pharmaceutical or biotechnology company could run tens of thousands of bioreactors in parallel under autonomous control to explore and optimize biomolecule production.

The invention addresses this need by using state-of-the-art, multi-channel microfluidic pumps and valves to control multiple multi-well chemostats, bioreactors, well plates, or organ chips over a wide range of conditions with different strains of yeast and other microbes. Swarm robots termed iPlateBots can transport 48 or more chemostats, bioreactors, or organ chips at a time in a single plate or plate box. Very high-throughput solid phase extraction (SPE) ion mobility (IM) quadrupole time of flight (QTOF) mass spectrometers (MS) that can make a broad, untargeted metabolic measurement every 10 or 15 seconds will generate terabytes of data that exceed the ability of humans to control, process, and interpret. AI can be used to identify high-order correlations buried deep in multi-omic data, or create computational models of cellular signaling and metabolism that could have thousands of equations and even larger numbers of parameters. The invention provides, for the first time, an efficient means to design and conduct the massive number of biological experiments needed to parameterize, validate, and utilize such models to probe and even control biological systems for specific applications. Its possible applications are without bound.

Experiments that would be readily possible with the robot scientist include basic research in cell signaling and metabolism in yeast, quantitative explorations of the metabolomic interactions of co-cultured bacterial species that together could produce protein for food and short-chain fatty acids for chemical feedstocks, experiments to track multiple, parallel evolutionary histories to determine which environmental and genetic factors are important for the evolution of microbial cooperation, and improved methods to use mammalian cells to produce therapeutic antibodies and other pharmaceuticals. Such systems will accelerate inquiries into the rules of life and the discovery of new solutions to some of society's pressing problems. At the heart of the subject robot scientist, standardized consumables will simplify system operation and increase efficiency.

The commercial prospects for the invention are excellent, with multiple proven markets that could benefit immediately from even a single 48-channel chemostat or bioreactor module. The iPlateBots represent a new class of holonomic plate-handling swarm robots that will allow the scale-up of the invention from 48 to 1,700 or more channels in a single, environmentally controlled instrument rack. The straightforward integration of an SPE-IM-QTOF-MS into the invention will enable the acquisition of five thousand high-resolution, untargeted metabolomic spectra each day, and self-driving laboratory software will guide not only the design of each experiment but the automated generation of computational systems biology models that will accelerate data interpretation and identification of biological mechanisms of action. The development of the invention is timed perfectly with the awakening of artificial intelligence applied to biology.

The Limitations of Current High-Throughput Biology

With this introduction and motivation, as we now return to FIGS. 1A-1G through 3A-3G to better appreciate the need for massively parallel microfluidic systems to control the continuous or intermittent delivery and removal of media, drugs, and toxins from chemostats, bioreactors, well plates and organs on chips, it is worthwhile to examine the prior art in cell culture and analysis techniques. As was discussed in U.S. Pat. No. 10,119,622 B2 to F.E.[36] Block, III, et al., which is incorporated herein by reference in its entirety, over the past 50 years engineers, scientists, and physicians working in biology, medicine, and physiology have constructed an entire, self-consistent intellectual framework using monolayer monocultures on plastic. Currently there are only a limited number of techniques for growth and maintenance of cell cultures. As shown in FIGS. 1A-1G, these include a Petri dish 100 that enables the culture of cells 103 in cell culture media 102; a culture flask 110 with removable cap 111; a well plate 120 with wells 121; and a well plate 120 that supports a Transwell device 130 that has as its bottom a porous filter 132 that supports cells 103 and enables communication through the cell layer of culture media 102 on the outside of the wall of the insert 131 with culture media on the inside. Cells are grown to high density in a perfused hollow fiber bioreactor 140 that has cells 103 growing on either the inside, outside, or both sides of hollow fibers 146. The end caps 142 and 143 couple the inlet and outlet flows 148 of culture media 102. Additional ports, not shown, can provide access to the fluid and cells outside of the fibers. Adherent or suspended cells can be grown in high volume in a rotating bioreactor 150, in which the bottle 151 with cap 111 is supported on rollers 153 that are rotated by a mechanism 155 to ensure continuous mixing of the solution inside the bottle, thereby nourishing the cells that are either adherent to the inner surfaces of the bottle or are suspended in the media 102. Cells can be grown at high density in a suspended bead bioreactor 160 that utilizes a magnetic stirrer 161 and magnet 168 or a direct mechanical connection 162 attached to the top 165 to rotate a paddle 167. As a result of the rotation of the paddle, cells 103 attached to neutral-buoyancy beads 169 are kept in close contact with the volume of media 102. These examples are representative of the many types of systems that have been devised to culture cells in vitro. The ultimate accomplishment of this fifty-year effort has been the introduction of the multi-well, micro-titer plate that can allow individual experiments to be conducted in as many as 1536 wells, each of which contains about 8 µL of cell culture media, serviced by an automated robot (FIGS. 2A-2B) that moves well plates between different preparation and measurement stations and incubators.

There are a number of major limitations of existing cell culture technology. The small-volume wells with a supposedly homogeneous cellular phenotype do not recapitulate the heterogeneous tissue microenvironment. Nutrient and metabolite transport is limited by diffusion. The local microenvironment, and hence the cellular phenotype and dynamic response, may differ between the corners and the center of each well. It is hard to create controlled concentration gradients. It is difficult to reverse the course of an experiment—it is easier to inject a drug, nutrient, or toxin than to wash it out. The plastic of Petri dishes, flasks, and well plates for growing adherent cells is quite foreign to a realistic biological environment: the Young's modulus for cell culture plastic is 10,000 to 100,000 times higher than that of living tissue. Only bone has a stiffness that approaches that of cell culture plastic. It is difficult to provide the shear forces that are required to maintain endothelial and epithelial polarization in Petri dishes or well plates. It is also difficult to provide appropriate mechanical forces to cells such as is experienced in the heart, skeletal and smooth muscle, lungs, and skin. The centralized robotic fluid handler and the isolated plate reader are not well suited for fast, real-time, closed-loop control of dynamic cellular processes. It is difficult to invoke complex exposure protocols or to create well-to-well connections that simulate organ-organ interactions. The most important convention in cell culture is the desire to change culture media only once every day or two. This infrequent media change results in the volume of culture media being approximately 1000 times that of the cells themselves. Hence paracrine and autocrine factors and metabolites secreted by cells are diluted a thousand-fold by the infrequent changing of the media above the cells. Paracrine factors that in biology would normally be washed away in vivo instead can linger and diffuse away slowly, and hence can inhibit in vitro cellular differentiation.[37]

Figure 2A:
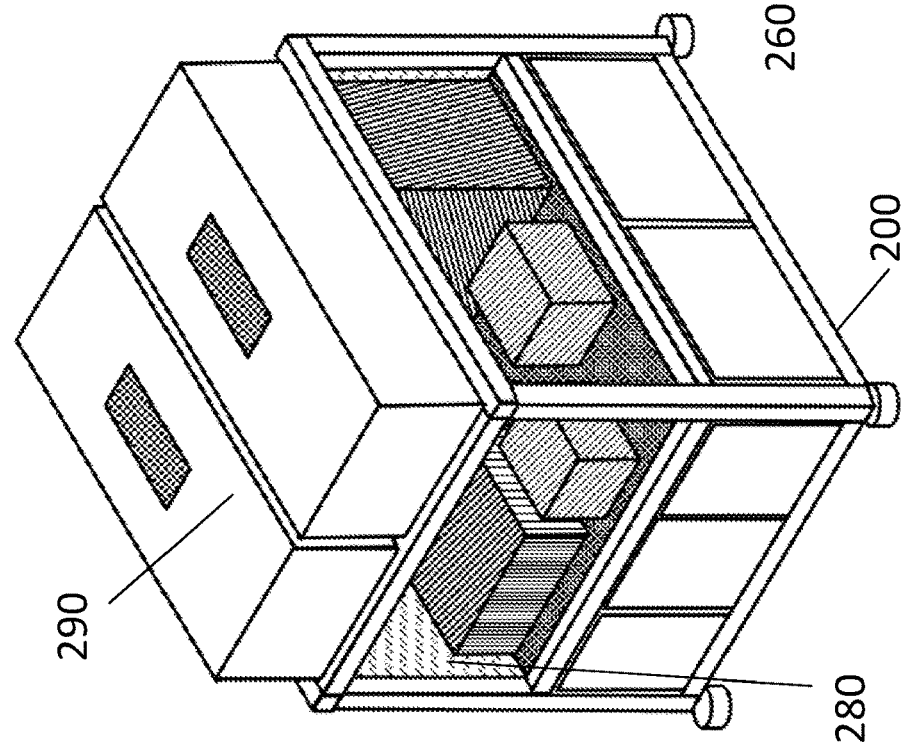

FIGS. 2A-2B show a robot well-plate handling system 200 including, for example, a robot well-plate manipulation system 201 with a rotating base 202 and an articulated arm 203 that has been optimized to allow a gripper jaw 204 to perform automated transfers of well plates 120 between various fixed stations, which include, but are not limited to, incubators 210, fluid handlers 220 with internal X-Y position control of pipettes 221 and 222, plate readers 230, bar-code readers 235, lid hotels 240, plate sealers 250, plate stackers 205, and other plate-oriented instruments 270 and 260, as shown in FIG. 2B. The entire system, if desired, can be enclosed in a sterile environment supported by windows 280 and HEPA filters 290, as shown in FIG. 2A. While it might be possible to create a jaw system 204 that can handle a pair of interconnected plates, as the number of interconnected plates grows it obviously becomes impractical to use this topology to manipulate the plates. Point-to-point transfer is not suitable for the manipulation of a plurality of interconnected modules.

Three commercial well-plate fluid-handling systems as indicated by 220 in FIGS. 2A-2B are in widespread use and are worthy of examining: the Agilent Bravo™ Liquid Handling System; the Agilent Encore Multispan™ Liquid Handling System, and the Hamilton MICROLAB® STAR Liquid Handling Workstation. The Bravo has a single 96-pipette movable head that can X-Y address (221, 222) a 3×3 array of well plates. It has an on-board gripper that can be used to move a well plate from one location to another. It provides no means for interconnecting multiple well plates or moving more than one well plate at a time. The newer Agilent Encore Multispan has an articulated robot arm, eight variable-span pipetters that provide independent X and Y axis motion. It can pipette to and from up to 24 well plates, and its gripper can reach up to 32 well plates stored on a common deck. It provides no means for interconnecting multiple well plates or moving more than one well plate at a time. The Hamilton MICROLAB® STAR system has both a 96 or 384 pipetting head and 8 or 16 multi-span individual pipettes and other features. It has both a plate gripper and a separate articulated arm gripper. In the context of this invention, it provides a variety of Eppendorf and well-plate carriers that can be manually delivered to an automatic feed system that uses a rack and pinion system to slide these carriers into predefined locations, with the gear-teeth of the rack being formed into the bottom of one side of the carrier. The system has 30 parallel tracks that can support tube or well-plate carriers. The carriers can be equipped with a variety of functions, including thermal regulation or on-board, addressable single-well imaging. Most important, the system does not provide the capability of the autonomous relocation of carrier from one predefined location to another, nor is there a provision to move these carriers from this instrument to an incubator or other instrument spatially separated from the fluid-handling unit. Normally, both of these operations must be performed manually. These systems are viewed as exemplary of an entire class of fluid-handling robots utilized for high-throughput well-plate screening. None of these support fluidic communication between different well plates.

Organs on Chips

The recognition of the limitations of conventional cell culture techniques is leading to an increased interest in the creation of heterogeneous cell cultures growing in three-dimensional (3D) extracellular matrices with organotypic perfusion and stiffness in addition to proper mechanical, chemical, and electrical cues. Furthermore, the advance of biology, medicine, and physiology will be facilitated by the introduction of tools and techniques that enable closed-loop control of biology, including the dynamic control of extracellular matrix chemistry and mechanical properties. The challenges of closed-loop control of biological systems are summarized in the review article: P. R. LeDuc, W. C. Messner, and J. P. Wikswo, "How do control-based approaches enter into biology?" Annu.Rev.Biomed.Engr. 13:369-396, 2011.[38] Tools and techniques enabling closed-loop control of biology would also support automated design of experiments, wherein cell type, matrix chemistry and architecture, and the addition or subtraction of metabolic and signaling molecules and other cues are adjusted automatically by machine-learning algorithms that are attempting to identify and test hypotheses related to biological function. As an example, there is a need to refine the selection and timing of the application of cytokines and other signaling molecules whose sequence and concentration are optimized to cause an induced pluripotent stem cell (iPSC) to differentiate into a desired, specific cell type.

Given the known limitations of the culture of confluent layers of cells on planar plastic or glass substrates,[14] there is a growing recognition that single or coupled organs-on-chips can provide a more physiological recapitulation of the cellular microenvironment and cell-cell and organ-organ interactions. An organ chip can be thought of as a two- or three-dimensional microbioreactor that benefits from quantitative, real-time measurements of a breadth of analytes that span different molecular classes, such as proteins, oligonucleotides, lipids, carbohydrates, peptides, and other small molecules. The difficulty is that most existing bioanalytical techniques are slow and require substantial sample volumes—both of which compromise the ability to control in real time a small 3D tissue bioreactor, and are often applied in a targeted manner that detects only preselected molecules of interest. Rapid, low-volume, untargeted assays are needed to track the complex biosignatures of cellular differentiation, development, and the response to growth factors, nutrients, toxins and other chemical, electrical, and mechanical stimuli.

Organs-on-chips (OoCs) and 3D tissue engineering present promising new technologies in the fields of automated biology and physiology, and the discovery, development, and toxicity/safety screening of new pharmaceuticals. Historically, many organs-on-chips are designed to study the physiology of a single organ and use either height differences in reservoir fluid levels, syringe pumps, on-chip or off-chip peristaltic pumps, or pressurized reservoirs to cause culture media to flow through single- or dual-chamber bioreactors. Many chips have been single-pass, perfused by the pressure from liquid in a pipette tip, or a syringe body connected to the chip directly or by a tube, or a pressurized reservoir. OoCs are unique in the sense that an OoC can provide significant data on drug/organ interactions and multi-organ physiology without the use of animal studies. To date, there has been little research into integrating these organ systems with intra-device fluid-handling. Two journal articles provide a critical review of coupled OoCs: "Engineering Challenges for Instrumenting and Controlling Integrated Organ-on-Chip Systems," Wikswo et al., IEEE Trans. Biomed. Eng., 60:682-690 (2013),[39] and "Scaling and Systems Biology for Integrating Multiple Organs-on-a-Chip," Wikswo et al., Lab Chip, 13:3496-3511 (2013),[40] which together provide one of the most thorough overviews of the major technical and biological challenges that need to be addressed in the development of coupled microphysiological systems. The challenges facing OoC design, development, and use are paralleled by comparable challenges in the engineering of tissue, for example, tissue-engineered cardiac valves, blood vessels, peripheral nerve, or skin grown from the iPSCs of a patient whose tissues are in need of repair or grafting due to illness or injury. A multi-disciplinary approach is required to integrate these "organs" with the required maintenance devices for their growth and support, and ultimately may enable use of machine-learning algorithms driving automated robotic scientists that can perform biological experiments without user intervention.

Figure 3A:
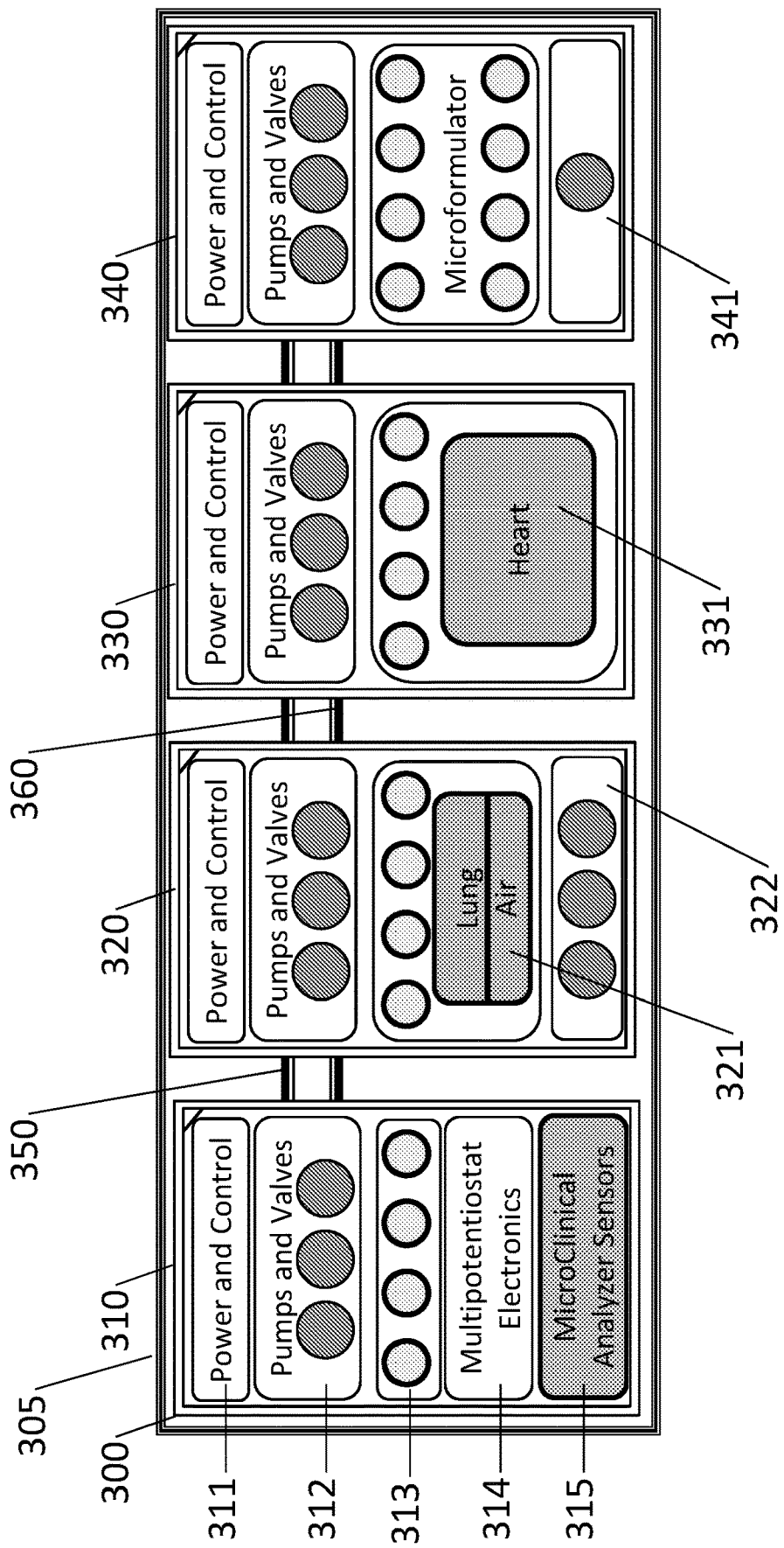
FIGS. 3A-3G shown various implementations of coupled organ-on-chip systems.

FIGS. 3A-3G provides an overview of several practical aspects of the application of organs-on-chips which can operate in isolation with the support of an instrumented organ-chip module (IOM). Coupled organ chips can operate as a set of coupled IOMs. FIG. 3A shows schematically a linear array of IOMs in which the four IOMs are integrated with interconnects according to one embodiment of the invention. Depending on the type of organ chip, a variety of supporting structures is required. In the embodiment shown in FIG. 3A, each organ module contains three motors and the required microfluidics 312, has a microcontroller and wireless connectivity 311, internal interconnects with septa for off-cartridge fluid transfer, autonomous control of fluid within organs, charging interconnects or wireless power transfer incorporated on the caddy 305 that supports one or more modules, on-board fluid storage 313, and a battery to power the module when it is detached from the platform for out-of-incubator operation. The electrical wiring connecting the motors to their microcontroller is not shown.

FIG. 3A presents an exemplary embodiment in which four generic modules 300 are interconnected to provide an integrated microclinical analyzer module 310, a lung module 320, a heart module 330, and a microformulator module 340 to support arterial 350 and venous 360 circulations. In this example, each module has a power and control subsection/unit 311, a set of pumps and valves 312, and reservoir bottles 313, all of which are interconnected by a microfluidic device (not shown). The microclinical analyzer 310 achieves its desired function by the inclusion in the generic module of multipotentiostat electronics 314, and microclinical analyzer sensors 315 using electrochemical or other types of sensor. The lung module 320 contains a lung chip 321, as well as additional pumps and valves 322 that allow the perfusion and control of the pulmonary epithelial cells growing on the air side of the alveolar membrane, and also control the respiration of the lung if desired. The heart module 330 contains the heart chip 331, which may contain either a working heart with one or more chambers with or without valves, or a nonworking cardiac construct utilized to ascertain the effects of drug on cardiac or valve tissue with perfusion provided by an external pump. The MicroFormulator module 340 contains an additional valve 341 and a plurality of vials 313 from which the solutions to be mixed are drawn.

Figure 3B:
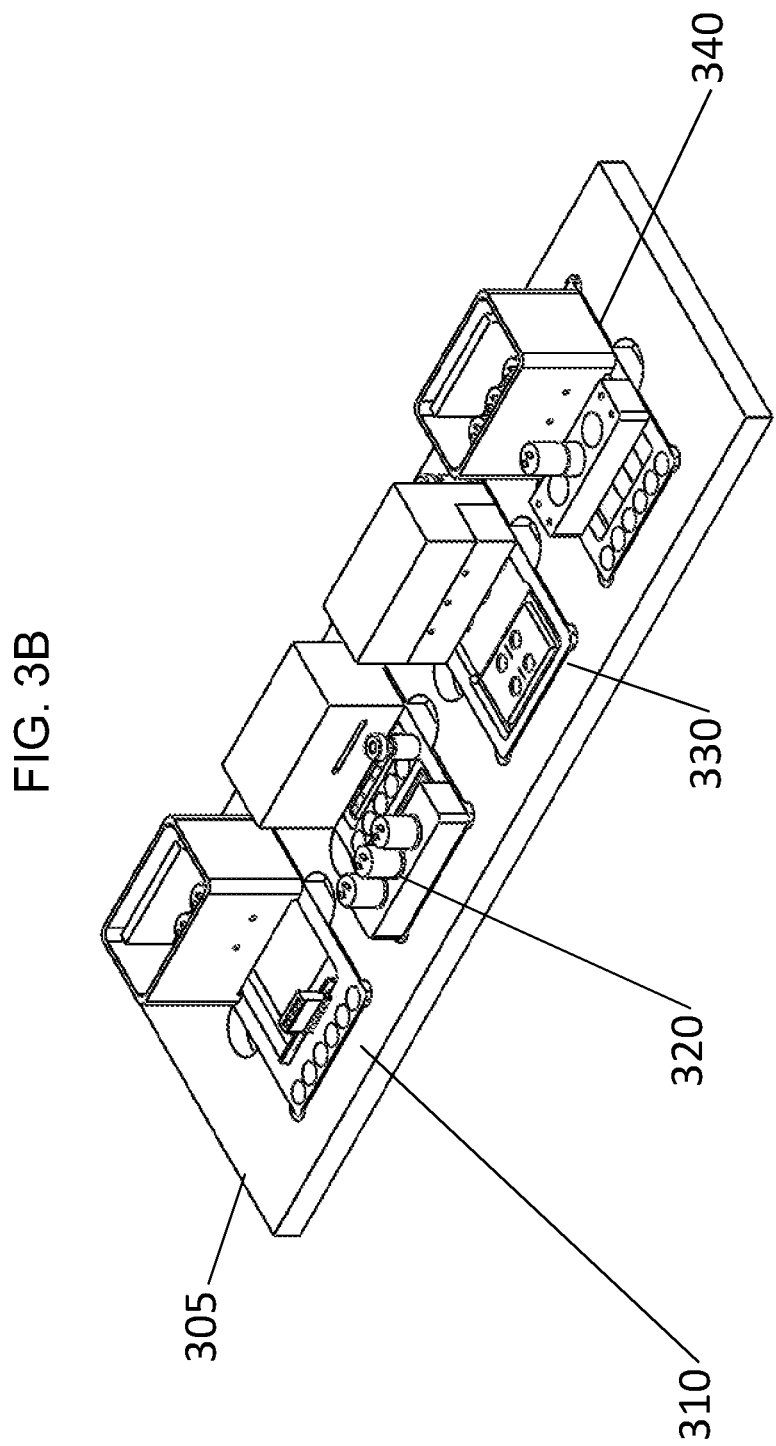

FIGS. 3A and 3B show two different views of the linear array of IOM, arranged on the caddy 305 containing a microclinical analyzer (μCA) 310, a two-sided lung Perfusion Controller (PC) 320, a heart Perfusion Controller 330, and a microformulator (μF) 340 that utilizes both rotary planar peristaltic micropumps (RPPM) and rotary planar valves (RPVs). This linear array can also be readily accessed by an external robot or other fluid-handling device that delivers or removes fluid from the modules or provides other services to the module array. Similarly, the module array can be moved past fixed devices such as fluid handlers, microscopes, or imaging units. The module array can be readily utilized in an incubator since with this design it is straightforward to utilize components that can operate without difficulty at 37° C. If required, the electronics and motor modules can be encapsulated for internal environmental control.

Figure 3C:
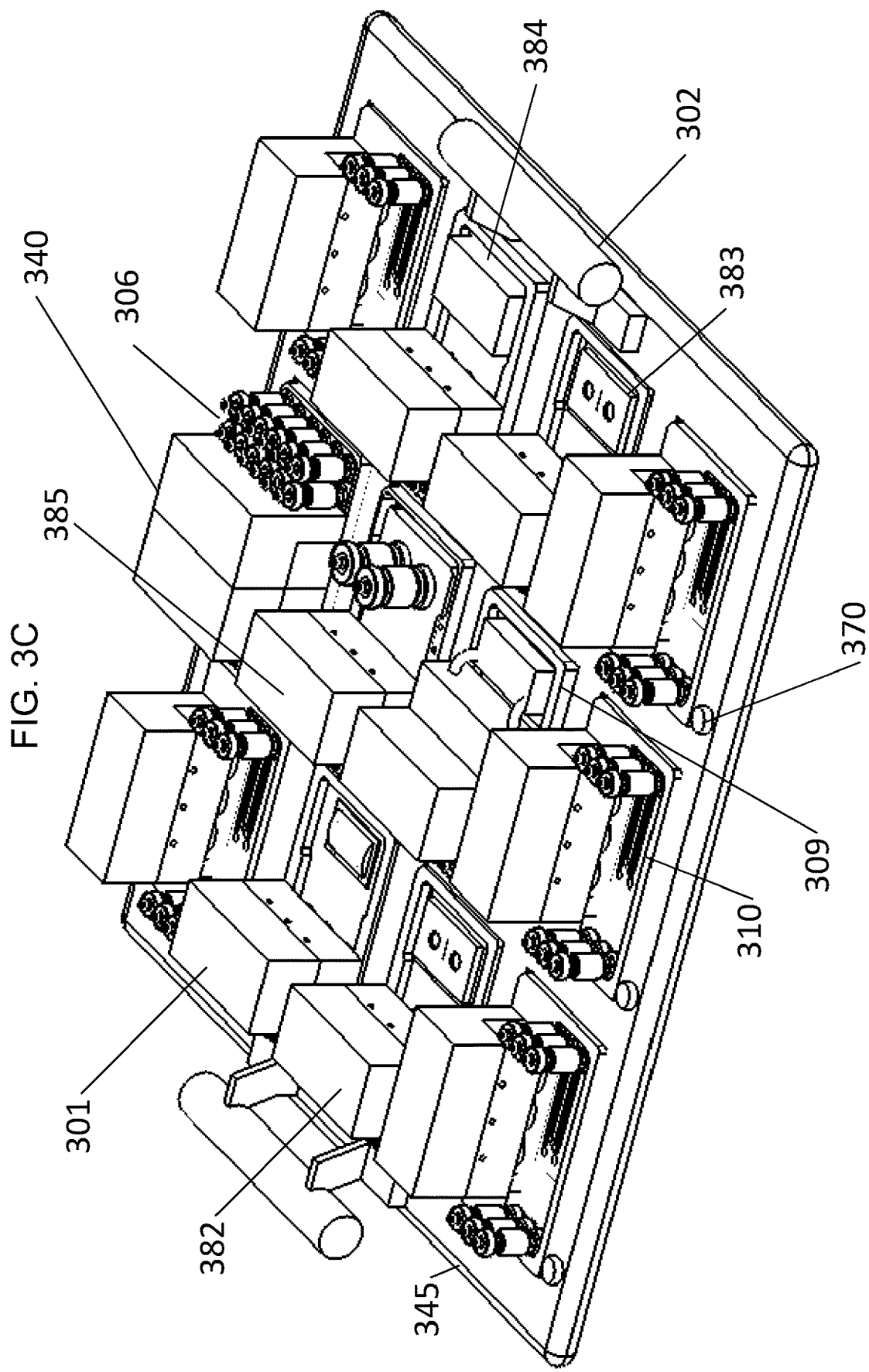

FIG. 3C shows an organ interconnect caddy (OIC) that is configured so that it fits into any commercially available 18" incubator. In contrast to the linear array in FIGS. 3A and 3B, FIG. 3C presents an alternative, rectangular arrangement of the 3×4 module caddy 345 that allows improved connectivity between a plurality of IOMs. The OIC contains the internal fluidic interconnections to route fluid between each respective organ. For instance, this embodiment provides a self-sealing atrial interconnect bus, a venous bus, and a storage system for fluid on the centralized microformulator 340. RPVs on each module determine whether the respective module is connected to a particular interconnect port. The eject buttons 370 adjacent to each IOM retract the internal fluidic connection between the interconnect system and the organ module. An individual IOM interfaces to the caddy through fluidic interconnection ports. The fluidic connection ports, not shown, can be self-sealing, septum-based interconnects to facilitate simple sterile interfaces to fluidic routing channels contained within the OIC without the loss of fluid or the addition of air. Appropriate fluidic switches can accomplish the same functions, particularly when the switch includes vent, drain, or flush positions to either empty or fill the volume of the interconnect without perturbing the fluids in the body of the module. When an integrated organ microfluidics module is removed from the organ interconnect platform, the septum seal or other interconnect sealing mechanism prevents fluid leakage. Hence, the central innovation of this design is not just simple tubing or channel connections between the modules, but a controlled interconnect system wherein the connections between modules and how these connections are routed within each module are dynamic and can be controlled by either the user or the automated control system.

As shown in FIG. 3C, each module resides in a rectangular arrangement of the caddy 345 that provides fluidic connection, power, and the ability to image. Handles 302 allow easy transport between the incubator and bench-top. Fluid interconnects between these modules are shared, and the fluidic routing is handled both internally and by the valves of each module. The valves are set to prevent leakage when the eject button 370 is pressed. The organs on this particular caddy include a liver 301, left heart 382, right heart 383, liver 309, and kidney 384. Each organ has its own respective microclinical analyzer 310. In one embodiment, a cardiopulmonary assist device 385 provides fluidic storage for the atrial and venous lines, as well as supporting perfusion pressures to the modules and gas exchange should the heart and lung not have the capacity to support the entire system alone. A centralized MicroFormulator 340 provides on-board reagent mixing and additional sample storage 306 for each organ.

Figure 3D:
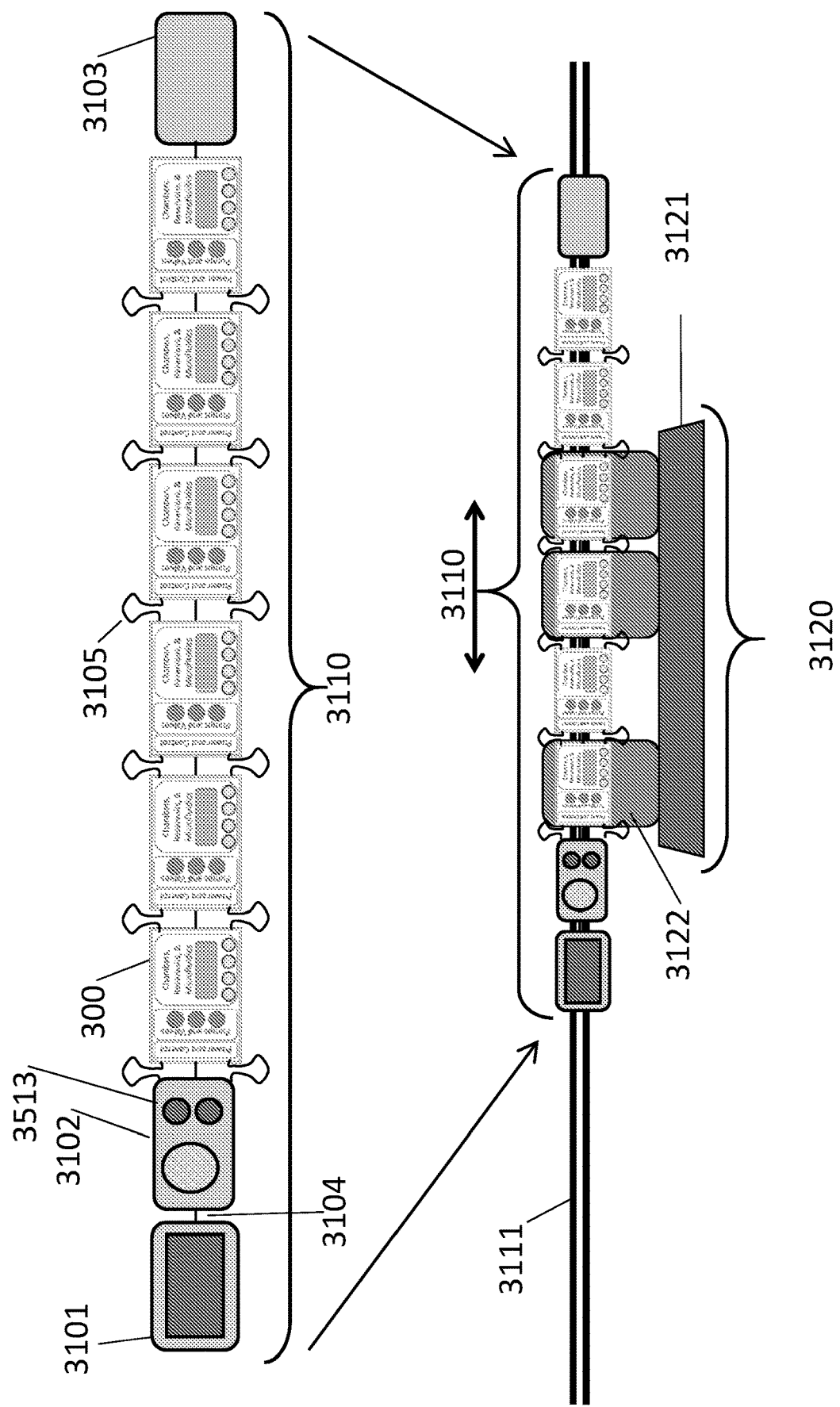

FIG. 3D shows a dynamic IOM topology/configuration wherein the ordering and connections between IOMs 300 can be made and broken, just as is done in assembling a freight train, or assembling sets of pathology samples along guideways in an automated clinical laboratory. In FIG. 3D, a linear array of modules 3110 includes several module types and is configured for running on a guideway 3111. A propulsion unit 3101 can apply a bidirectional traction force collinear with the linear array. A support module 3102 in one embodiment can contain a cardiopulmonary unit to ensure adequate perfusion and oxygenation of all organ/tissue modules, as well as large fluid reservoirs 3513 for fresh and spent perfusion media. A series of interconnected modules 300 can perform the various functions illustrated in FIGS. 3A through 3C. Additional analytic and control functions can be performed by specialized modules 3103 that might provide sample analysis by means of a miniature mass spectrometer. Because the modules are connected by a mechanical interconnect 3104, the linear array 3110 can be moved as a unit past a station 3120 that has multiple subsystems 3122 that are fixed in position by a base 3121 to perform a variety of analytical, mechanical, or other maintenance functions on the array, including, but not limited to, fluid handling, microscopy, and the removal of one module and its replacement with another. As such, when the train-based interconnect platform is moved at the predetermined positions, subsystems perform the above desired operations on the linear array of the integrated organ microfluidics. The motion of the array can utilize guideways, wheels, air bearings, roller bearings, low-friction pads, or other mechanisms on each module to ensure the required linear displacement without undue stresses on the mechanical 3104 or fluidic 3105 connections. As shown, a linear guideway 3111 is utilized for the movement, so that the linear array 3110 moves along a pair of parallel tracks, a central monorail, a lateral rail, a guiding channel, or an overhead conveyor system. If the fluidic and mechanical connections between the modules, 1105 and 1104 respectively, are made flexible, it is not necessary for the linear array to be held in a straight line, but the linear array can be curved as required to manipulate or move the array. There are multiple means by which the controlled movement of coupled modules along a chosen trajectory can be accomplished. In the context of CAPCAS, this system is an example where connected organ-chip modules move as a unit and can be delivered to analytical instruments.

Figure 3E:
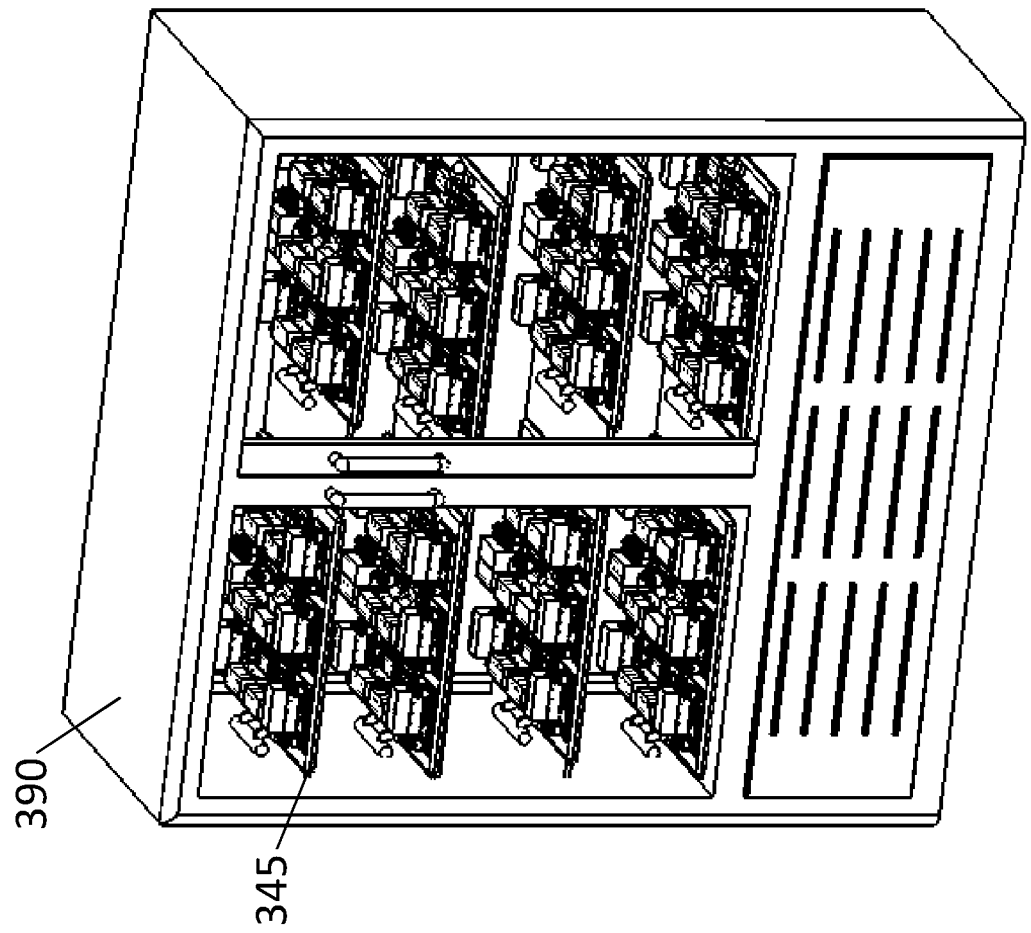

FIG. 3E shows schematically organ interconnect caddies 345 stored in an incubator 390. Note that when the organ interconnect platforms are located in an incubator environment, electrical connectors or wireless inductive power provide charging current for the on-board batteries, and an antenna located inside the incubator allows wireless communication to and from each instrumented Organ Module.

Figure 3G:
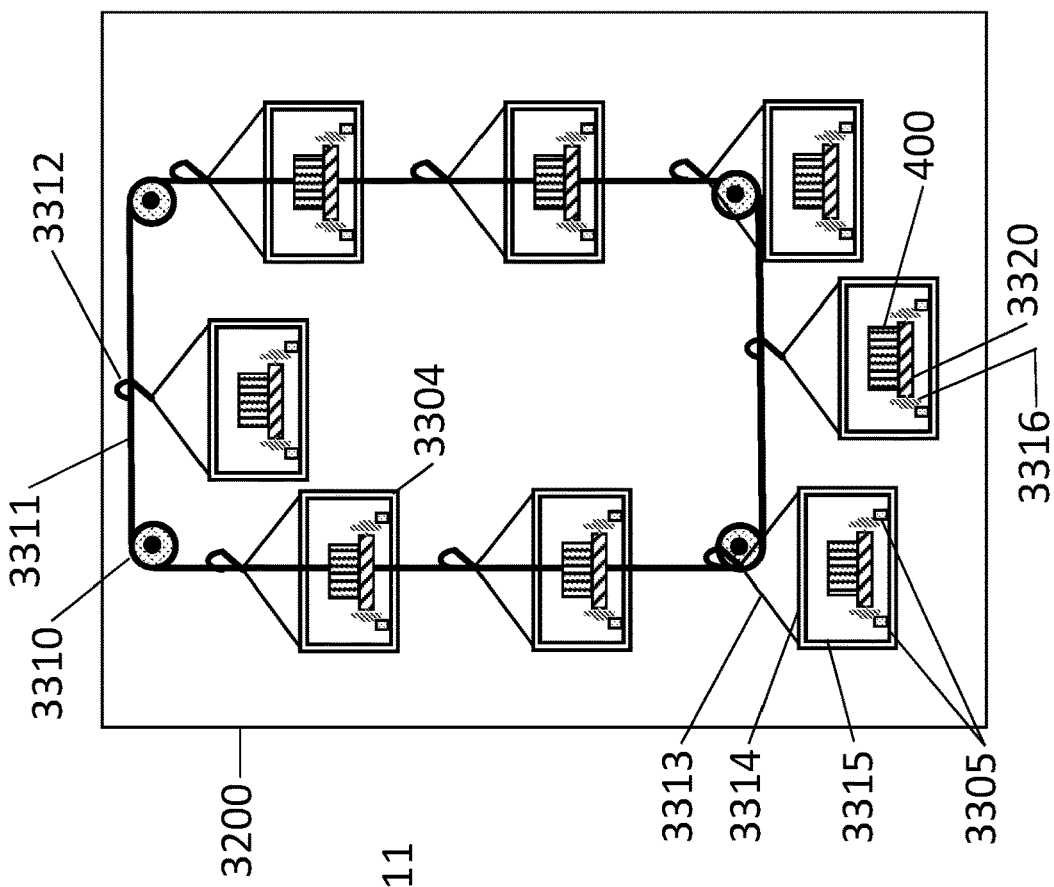
Figure 3F:
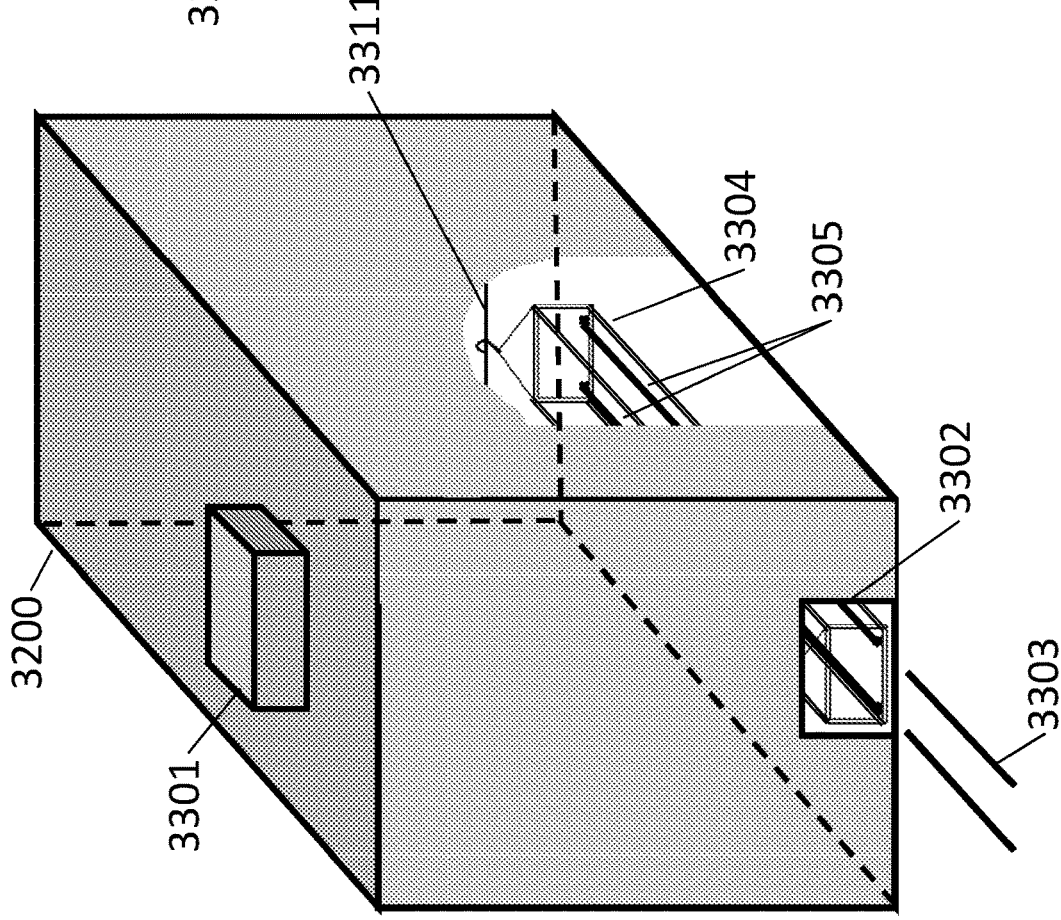

FIGS. 3F and 3G show a perspective and section views, respectively, of an IOM array vertical storage incubator, where an IOM array is placed into the incubator and moved to a storage location when not in use. The coupled organ arrays in FIGS. 3A and 3B can be stored in an "incubator tunnel" or vertical stacking incubator 3200 in FIG. 3F. In this embodiment, the incubator 3200 of FIG. 3F comprises a system shown in FIG. 3G wherein pulleys 3310, cables 3311, and attachment points 3312 enable the vertical storage of sections of guideway 3305 in guideway carriers 3304. The guideway carrier includes support devices 3313, 3314, and 3315 for the guideway 3305. Wheels 3316 on module carriers 3320 support IOMs 400. An opening in the incubator 3302 allows the array of modules to be driven into the module carrier, whose track 3305 is separated from the main track 3303 connecting the incubator to the larger system. The incubator has a temperature regulation means 3301.

It should be evident from FIGS. 3A-3G that new, advanced technologies must be introduced to enable massively parallel, closed-loop sensing and control of individual or coupled chemostats, bioreactors, or organ chips, as would be required for a self-driving laboratory or robot scientist that interrogated large numbers of organ chips, particularly ones that allow the asynchronous transport in three dimensions of well plates and organ-chip arrays.

Continuous Automated Perfusion Culture Analysis System (CAPCAS)

As stated above and illustrated in FIGS. 5A-5D, there are excellent reasons why continuous perfusion of chemostats, bioreactors, well plates, and organ chips is better suited for quantitative probing by a robot scientist than any batch-fed systems. FIG. 6A shows a conventional continuous-flow chemostat. The engineering challenge is to implement the chemostat shown in FIG. 6A not as a single, stand-alone unit or as part of a set of 4, 16 or 24 units in a single chassis, but in groups of hundreds, a thousand, or more in a format suitable for automated operation as part of a self-driving laboratory or robot scientist.

We have previously described a microclinical analyzer (FIG. 6B) that provides automated calibration of a multi-analyte electrochemical sensor and can serve as a single-channel microformulator,[41-45] also described in PCT Patent Application No. PCT/US2021/042179 by D. K. Schaffer, et al.,[46] which is incorporated herein by reference in its entirety. Building upon this concept, we have shown that rotary planar peristaltic micropumps (RPPMs)[36,47-51] and rotary planar valves (RPVs)[25, 26, 49, 50, 52-56] can be applied to create multiwell microformulators (FIG. 6C), which use time-division multiplexing to deliver a different, realistic pharmacokinetic (PK) profile of drug concentration versus time to each well of a 96-well plate (inset), and can separately store samples from each well of a 24-or 96-well plate.[20-26] The invention involves extending the microformulator concept to a multichannel system that provides continuous delivery of different media formulations to each well of a multi-well continuous automated perfusion culture analysis system (CAPCAS) that contains yeast, bacteria, or adherent or non-adherent mammalian cells and provides sensing that includes real-time measurements of optical density, pH and other process variables as well as using a direct-injection mass spectrometer for at-line solid-phase extraction (SPE) ion mobility-mass spectrometry (IM-MS) analyses with ten-second temporal resolution for untargeted metabolomics.

The invention builds upon prior inventions described above to create a new class of automated bioreactor systems. Specifically, the invention in one aspect, discloses a continuous automated perfusion culture analysis system (CAPCAS) comprising one or more fluidic systems configured to operate large numbers of biodevices such as chemostats, wells, bioreactors, abiotic or biotic chemical synthesis reactors, or other biodevice arrays in parallel.

In certain embodiments, each fluidic system comprises an array of chemostats or a well plate or a biodevice array configured such that each chemostat/well/biodevice has independent media delivery, fluid removal, stirring, and gas control.

In certain embodiments, each fluidic system further comprises a media delivering means, and a media collecting means, wherein the array of chemostats or the well plate is fluidically coupled between the media delivering means and the media collecting means.

In certain embodiments, the media delivering means comprises a multichannel input selector valve fluidically coupled to input vials, an input pump fluidically coupled to the multichannel input selector valve, and a multichannel input director valve fluidically coupled to the input pump, configured such that the multichannel input selector valve operably selects media and/or drugs from the input vials, and the input director valve allows the input pump to deliver individually the selected media and/or drugs to each chemostat.

In certain embodiments, the media collecting means comprises a multichannel output collector valve fluidically coupled to the array of chemostats, an output pump fluidically coupled to the multichannel output collector valve, and a multichannel output director valve fluidically coupled to the output pump, configured to remove media from each chemostat and deliver it to waste, a Turbidimeter, a microclinical analyzer, or a holding reservoir.

In certain embodiments, each of the multichannel input director valve and the multichannel output collector valve has a connection to back-flush vials, and/or pressurized air or other gas to insert one or more bubbles between each sample.

In certain embodiments, the CAPCAS further comprises a multichannel reservoir collection valve coupled to the holding reservoir of each fluidic system and configured to analyze media from any single chemostat or bioreactor or organ chip in any of the one or more fluidic systems.

In certain embodiments, the one or more fluidic systems comprises 100 fluidic systems, and the array of chemostats of each fluidic system comprises a 96-well plate, whereby the CAPCAS is a 9,600 chemostat system.

In certain embodiments, the CAPCAS also comprises a low-pressure pump fluidically coupled to the multichannel reservoir collection valve for operably withdrawing the media from the holding reservoir that transiently retains the media and cells withdrawn from the desired chemostat or bioreactor well.

In certain embodiments, the CAPCAS further comprises a bubble detector fluidically coupled to the low-pressure pump for operably identifying where one sample ends and another starts, when the low-pressure pump delivers the samples to a mass spectrometer.

In certain embodiments, the CAPCAS also comprises a calibration valve fluidically coupled to the bubble detector for operably removing air through one port (A), sending leading portions of any sample to waste (W), and injecting either a reagent (R) or a calibration solution (C) into the mass spectrometer.

Given the capabilities of our computer-controlled pumps, valves, and sensors, the entire CAPCAS could be operated by machine-learning AI software to create a self-driving robot scientist.

Figure 7A:
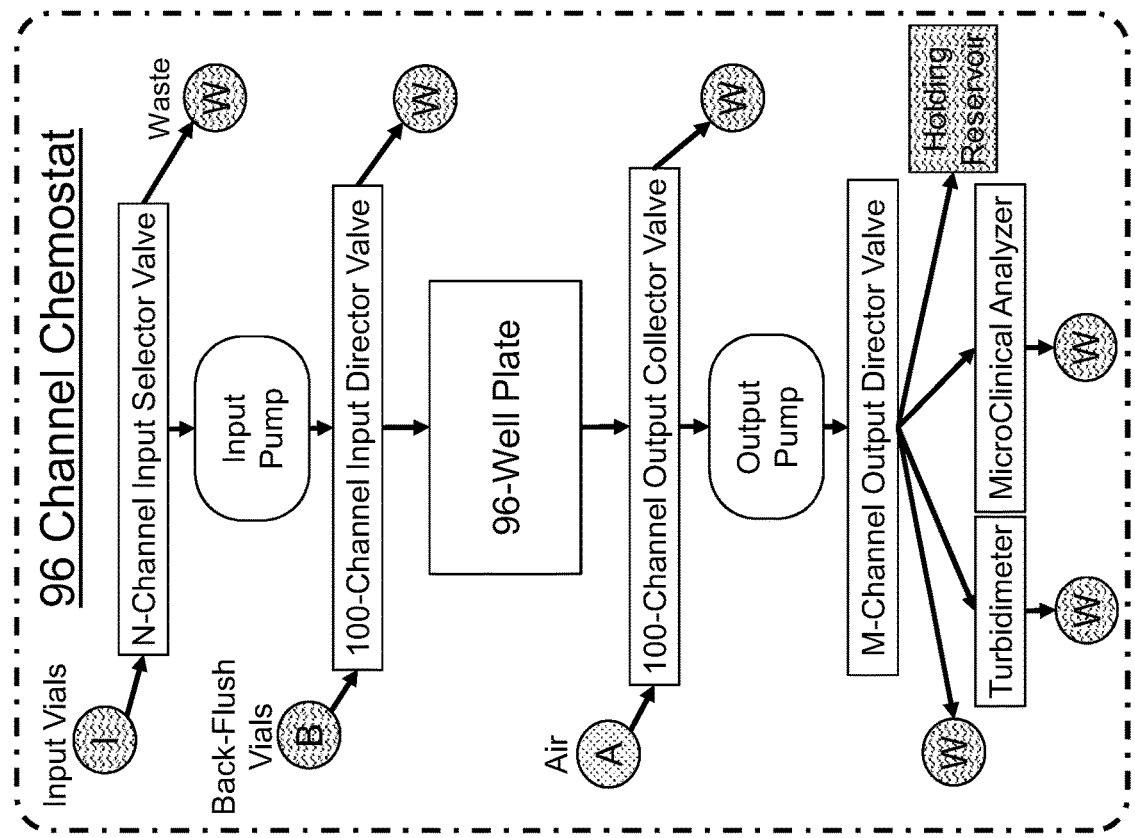
FIGS. 7A-7B present the conceptual design of a 96-channel chemostat/bioreactor, and shows how 100 of these units can be connected to create a 9,600 channel chemostat/bioreactor system, according to embodiments of the invention.

FIG. 7A shows how a 96-channel chemostat could be implemented using RPPMs and RPVs, wherein each well of the 96-well plate is in fact an independent chemostat that has media delivery, fluid removal, stirring, and gas control. An N-channel selector valve selects media and drugs from input vials and delivers them to a 100-channel input director valve (the 100-channel valve was previously disclosed in PCT Patent Application Serial No. PCT/US2021/042179 by D. K. Schaffer, et al.,[46] which is incorporated herein by reference in its entirety). Reversing the input pump allows fluid such as sterile saline to be used to wash either valve, and sends the wash water to waste reservoirs. The input director valve allows the input pump to deliver the individually formulated media to each well of the 96-well plate. The 100-channel output collector valve, the output pump, and the M-channel output director valve in concert remove media from each well in the 96-well plate and deliver it to waste, a Turbidimeter, a microclinical analyzer, or a holding reservoir, for example. Each of the valves has a connection to back-flush vials (B) and pressurized air or other gas (A) to insert one or more bubbles between each sample.

Figure 7B:
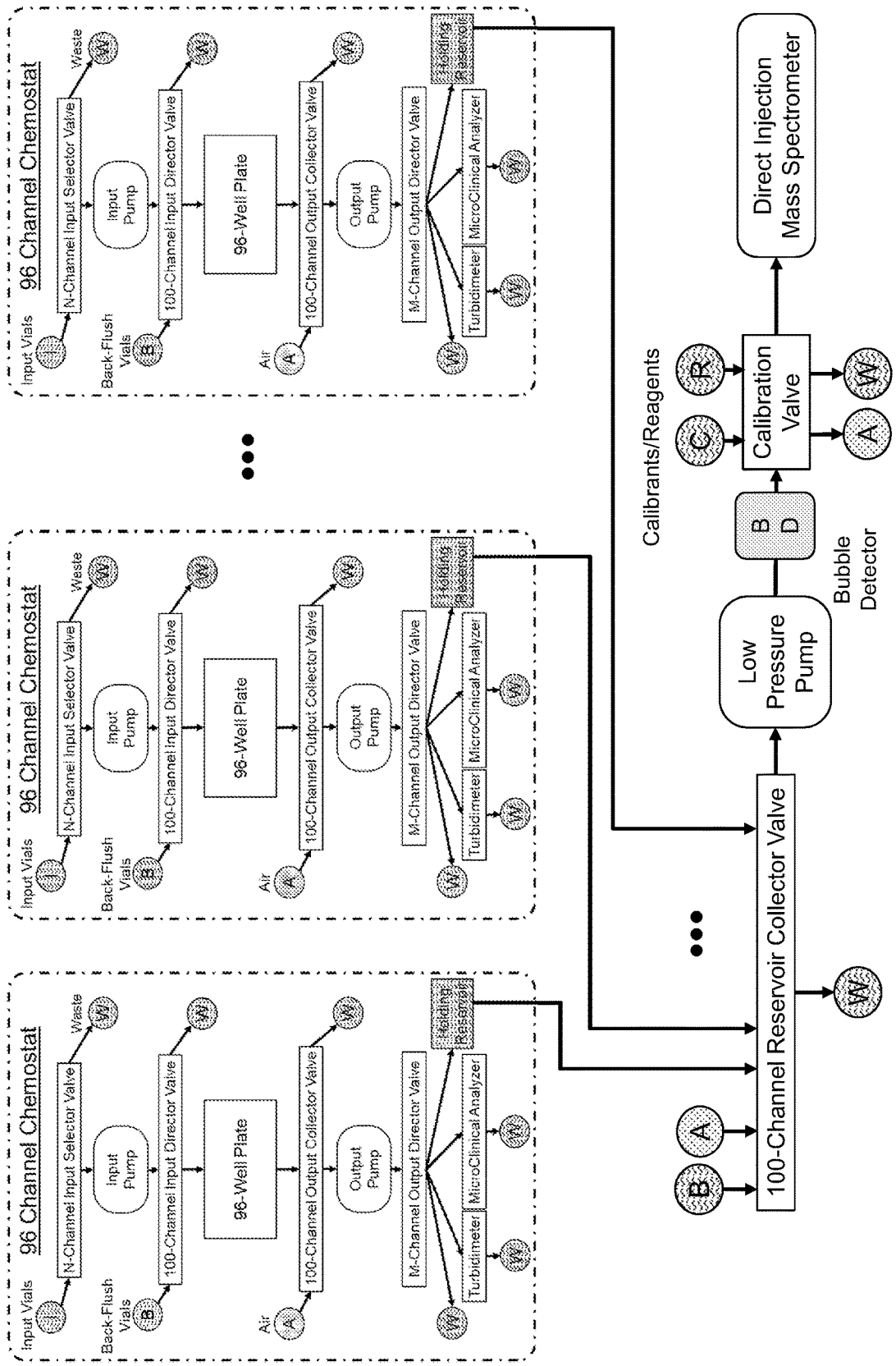

FIG. 7B illustrates how the addition of a second 100-channel valve, termed the reservoir collection valve, can be used to analyze media from any single chemostat in any of 100 96-well plate chemostat arrays, thereby creating a 9,600 chemostat system. By means of this valve, a low-pressure pump withdraws media from the holding reservoir that transiently retains the media and cells withdrawn from the desired chemostat or bioreactor well. A bubble detector identifies where one sample ends and another starts, as the low-pressure pump delivers the samples to the direct injection mass spectrometer. Note that depending upon the type of mass spectrometer, there may be a high-pressure pump for pressure-injection of the sample into either a liquid chromatography system upstream of the mass spectrometer or a sample ionization and injector at the mass spectrometer; these pumps would not use the technologies shown in FIG. 12. The calibration valve can remove air through one port (A), send the leading portions of any sample to waste (W), and inject either a reagent (R) or a calibration solution (C) into the mass spectrometer.

To demonstrate the feasibility of creating such a system with functional pumps and valves, we next present embodiments of the invention that will provide 12-, 48-, 144- and higher-channel versions of a CAPCAS comprising one or more fluidic systems configured to operate large numbers of chemostats or other biodevices in parallel.

In one embodiment, each fluidic system comprises an input reservoir plate for receiving media; a chemostat or bioreactor plate or a plurality of organ-chips comprising an array of chemostats or bioreactors or organ-chips fluidically coupled to the input reservoir plate, configured such that each chemostat has independent media delivery, fluid removal, stirring, and gas control, and each chemostat is capable of continuously receiving the media from the input reservoir plate; and an output plate fluidically coupled to the chemostat plate for real-time analysis and sampling.

In one embodiment, each fluidic system further comprises at least one microformulator fluidically coupled to the input reservoir plate for providing the media to the input reservoir plate. Each microformulator comprises: a plurality of feedstock solution reservoirs; at least one input selector valve (V1) fluidically coupled to the plurality of feedstock solution reservoirs to select at least one feedstock reservoir; at least one output director valve (V2) fluidically coupled to the input reservoir plate; and at least one pump (P1) fluidically coupled between the at least one input selector valve and the at least one output director valve for withdrawing fluid from the selected feedstock solution reservoir through the at least one input selector valve and delivering it to the input reservoir plate through the at least one output director valve.

In one embodiment, the at least one input selector valve is a multichannel input selector valve, the at least one pump is a single-channel pump, and the at least one output director valve is a multichannel output director valve.

In one embodiment, the at least one input selector valve is configured to select different feedstock solution reservoirs at different periods of time.

In one embodiment, the at least one pump is driven such that the fluid of the selected feedstock solution reservoir outputs from the at least one output director valve at a predetermined flow rate.

In one embodiment, the predetermined flow rate varies with time.

In one embodiment, through a sequence of selecting the plurality of reservoirs by the at least one input selector valve and pump speed and duration actuations of the at least one pump, the media is provided to have a different time-varying perfusion mixture for each chemostat.

In one embodiment, each microformulator further includes a single-channel optical sensing module coupled between the at least one pump and the at least one output director valve for tracking an intentionally injected bubble for measurement of flow rate, or identifying when a reservoir is emptied.

In one embodiment, the CAPCAS further comprises a biodevice media delivering means fluidically coupled between the input reservoir plate and the biodevice plate for continuous delivery of the media from the input reservoir plate to each biodevice.

In one embodiment, the input reservoir plate has two sets of media ports, and wherein the biodevice media delivering means comprises two multichannel pumps (P2, P3), each multichannel pump is fluidically coupled between a respective set of the media ports and the biodevice plate, such that one set is refillable while the other set is being delivered by a corresponding pump to each biodevice in the biodevice plate, thereby providing uninterrupted perfusion.

In one embodiment, the CAPCAS further comprises a biodevice media collecting means fluidically coupled between the biodevice plate, and the output plate and an analyzer for real-time analysis and sampling.

In one embodiment, the biodevice media collecting means comprises first and second multichannel pumps (P4, P5), and at least one output valve (V3), wherein the first multichannel pump (P4) is fluidically coupled between the biodevice plate and the at least one multimode output valve (V3), the second multichannel pump (P5) is fluidically coupled between the biodevice plate and the output plate, and the least one multimode output valve (V3) is fluidically coupled between the first multichannel pump (P4) and the analyzer.

In one embodiment, the second multichannel pump (P5) operates independent of the first multichannel pump (P4) to deliver the effluent from each biodevice to a separate well in the output plate for off-line transcriptomic or other off-line analysis.

In one embodiment, the at least one multimode output valve is configured to either divert effluent from each biodevice to the analyzer.

In one embodiment, the at least one multimode output valve is configured to divert, when one biodevice is being sampled, the media being pumped from the other biodevices to waste, with each biodevice being sampled serially.

In one embodiment, the at least one multimode output valve is configured to divert the effluent from all the biodevices to waste to ensure continuous perfusion when no sample is needed or the output plate is removed after bulk sample collection.

In one embodiment, the analyzer is equipped with a spiral microfluidic sorter, a filter, or tangential flow filtration for real-time separation of cells from media, and an in-line, microfluidic acoustic or electrical lyser.

In one embodiment, the CAPCAS further comprises a plurality of multichannel optical sensing modules.

In one embodiment, a first one of the multichannel optical sensing modules is coupled between the input plate and the biodevice plate, and a second one of the multichannel optical sensing modules is coupled between the biodevice plate and the output plate for measuring $PO_2$, $PCO_2$, pH, and/or optical density (OD) of the media entering and leaving each biodevice, respectively.

In one embodiment, a third one of the multichannel optical sensing modules is coupled between the at least one microformulator and the input plate for tracking an intentionally injected bubble for measurement of flow rate, or identifying when a reservoir is emptied.

The most recent implementation of the pumps and valves that can be utilized will be discussed below, but for now we will first demonstrate an exemplary embodiment of a fluidic system with FIG. 8A how a twelve-channel chemostat system can be created using a 25-port RPV (V1), a single-channel RPPM (P1), a twenty-five port RPV (V2), four 12-channel RPPMs (P2, P3, P4, and P5), a 12- or 24 port sensor or cut-in RPV (V3), an input reservoir well plate, and output plate, as well as multiple one- and twelve-channel optical sensors. As we will see, the 48- and 144-channel versions can have the same topology, except all wells in the chemostat plate would be populated to create 48 chemostats, and pumps, valves, and sensors would have proportionally more channels. The highest channel count systems would be similar in design, but would utilize a 96-well chemostat plate and minimize the use of input and output well plates to conserve space. Later we will discuss the details of the chemostats/bioreactors that provide thermal and gas control and stirring.

Figure 8A:
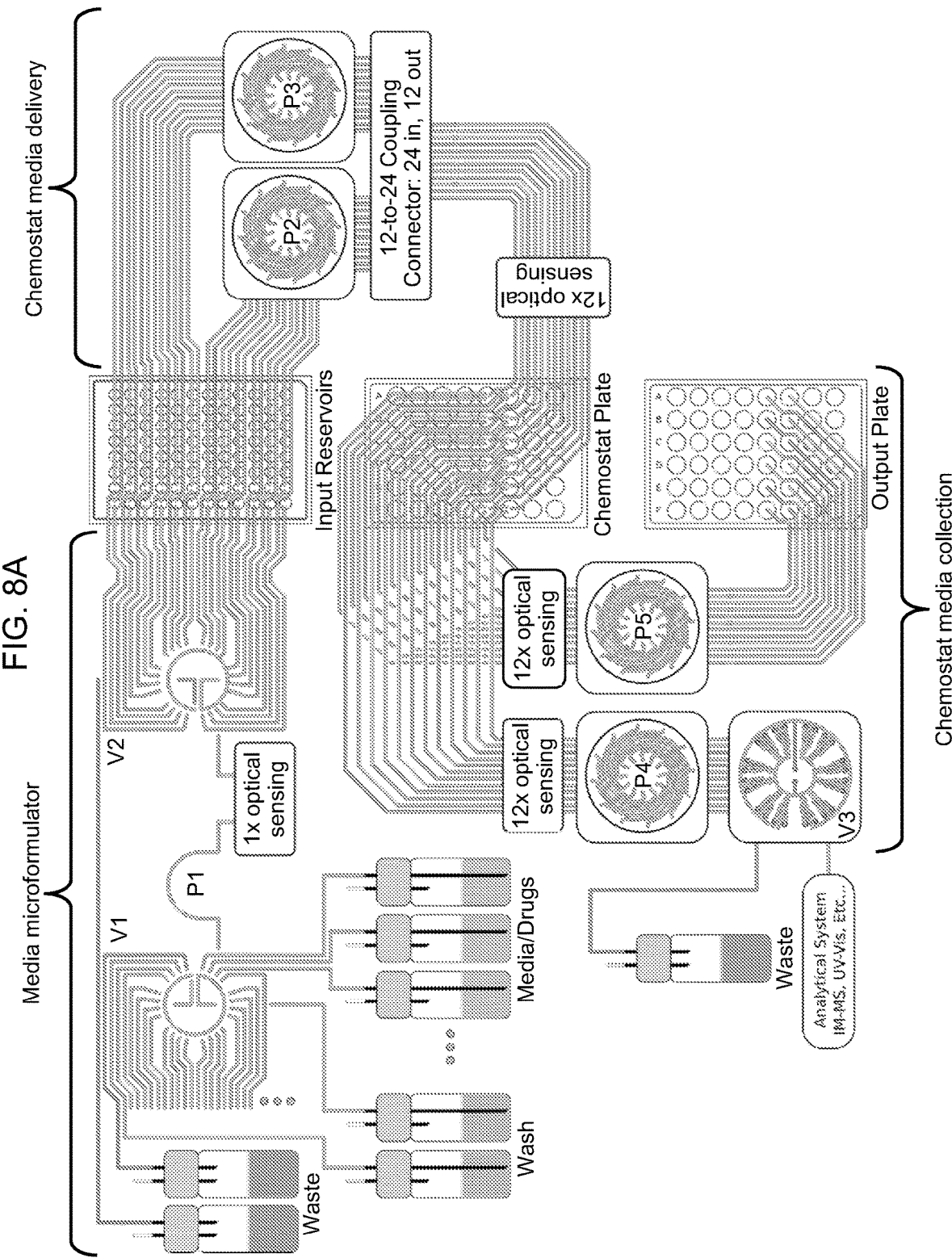

FIG. 8A shows how pumps, valves and sensors would be assembled to create a 12-channel chemostat that operated in 12 of the 48 wells of a round-bottom, deep-well plate. The first stage of the multiwell chemostat module is a media microformulator that has a 25-port input selector valve (V1), a single-channel pump (P1), and a 25-port output director valve[50] (V2) that together can create a different time-varying perfusion mixture for each chemostat. The microformulator output is delivered to two sets of 12 wells in the 96-well input reservoir plate, such that one set can be refilled while the second set is being delivered by twelve-channel spiral pumps' P2 or P3 to twelve populated wells in the 48-well chemostat plate, providing uninterrupted perfusion. Were the cells being cultured slowly growing, time-division multiplexing could be used by the microformulator (V1, P1, and V2) to deliver a different media formulation to each bioreactor or chemostat. However, the growth rate of some yeast is sufficiently high that the time interval for the microformulator to revisit each well would be too long and between visits there could be significant changes in nutrient and metabolite concentrations. The use of two sets of input reservoir wells in a single well plate (or possibly two well plates) and two associated and dedicated multichannel pumps, P2 and P3, ensures that one pump can deliver media from one set of reservoir wells simultaneously to each chemostat/bioreactor well, while the other set of reservoir wells is being refilled. This ensures that each chemostat/bioreactor can be perfused without any interruption or human intervention for very long periods of time. Elsewhere we discuss how a faster serial or parallel microformulator might obviate the need for the input reservoir plate, allowing direct delivery of formulated media to the chemostat/biodevice plate.

The effluent (cells plus media) from each chemostat well is collected by a 12-channel pump P4. If the pump speed of P4 is greater than that of P2 or P3, the level of the media in each bioreactor or chemostat will be determined by the height of the withdrawal tube in that well. By overpumping P4, there will be intermittent withdrawal of air and/or foam from each reactor, which can also be used to define a sample bolus for later analysis.

The output of P4 is delivered to the 12-port, multi-mode output/sampling valve V3. This valve will allow each effluent line, one at a time, to be diverted to an external analyzer, such as a VIIBRE/Waters rapid-cycling UPLC-IM-MS[57,58] or Agilent SPE-IM-MS,[59-61] a Raman[62-67] or UV-Vis spectrometer, optical[68] or electrochemical[36, 42-45, 69-77] metabolic sensors, or a planar microfluidic device that would allow visualization of individual yeast cells as they exit a chemostat.[9] When one chemostat is being sampled, valve V3 would direct the media being pumped from the other chemostats to waste, with each chemostat being sampled serially. As appropriate, the analyzer will be equipped with a spiral microfluidic sorter,[78-81] or a filter (alternating tangential flow (ATF) or tangential flow filtration (TFF)[82-85]) for real-time separation of cells from media, as well as an in-line, microfluidic acoustic[86,87] or electrical[88] lyser. In its third mode, V3 can divert the effluent from all chemostat wells to waste to ensure continuous perfusion when no sample is needed from any well.

The pump P5 operates independent of P4 to deliver the effluent from each chemostat well to a separate well in the refrigerating/freezing output plate for off-line transcriptomic or other off-line analysis. The output plate can be removed after bulk sample collection, while P4 continues to withdraw media from each chemostat/bioreactor.

Bidirectional washing of the microformulator, the input reservoirs, and even each well in the chemostat plate is possible. The chemostats can be inoculated by using an external pipettor or robot to seed either the chemostat plate before or after installation beneath the fluidic station. While the output plate would normally be empty at the beginning of an experiment, alternatively it could be used to inoculate an array of sterile chemostats at the beginning of an experiment. A transfer plate that has one or more seeded wells can be installed in place of the output plate with pump P5 run in reverse to deliver the selected cells into various chemostat wells to initiate their culture.

The single-channel optical sensing module after P1 will be used to track an intentionally injected bubble for measurement of flow rate, or to identify when a media or drug reservoir has been emptied. The three 12-channel optical sensing modules will measure, for example, P02, $PCO_2$, and pH and optical density (OD) of the media entering and leaving each chemostat.

While the spiral microfluidic sorter,[78-81] or alternating tangential flow or tangential flow filtration[82-85] could separate cells from extracellular media to allow separate analysis of the intracellular and extracellular proteomic and metabolomic profiles, the same technologies could also be used to return the cells to the bioreactor while allowing the conditioned media to exit the system, either for disposal or harvesting of secreted proteins and other cellular products. By including this separation, the chemostats would be converted to continuous perfusion bioreactors, wherein the cells were retained to increase in number and, if desired, continue to produce in quantity the targeted secreted proteins or other molecules. Hence with the addition of the appropriate spiral, ATF, or TFF separation, the robot-scientist, self-driving CAPCAS platform could then be applied to entirely different classes of industrial problems, including the production of antibodies, enzymes, food protein, or other biomolecules.

A 48-chemostat embodiment would have the same topology as that in FIG. 8A, except that the 12-channel pumps (P2-P5) and the 25-port valves V2 and V3 would be replaced with 50-channel tubing pumps and 100-port valves,[49] respectively. The sensor count would also be increased from 12 to 48. In this case, the fluidic circuit would service all 48 wells in the plate shown, but the topology would be identical. We do not draw the 48- or higher channel-counts circuit to simplify rendering and teaching these embodiments.

The use of the input reservoir plate and the pair of pumps P3 and P4 that ensure continuous perfusion of the chemostats/bioreactors requires, in this design, that the input reservoir plate have twice as many wells as the chemostat/bioreactor plate. Were a 96-well chemostat plate used, two 96-well input reservoir plates could be used, or the microformulator could either be parallelized or its speed increased to eliminate the need for the input reservoir plate or allow the input reservoir plate to be periodically refreshed rather than emptied.

Figure 8C:
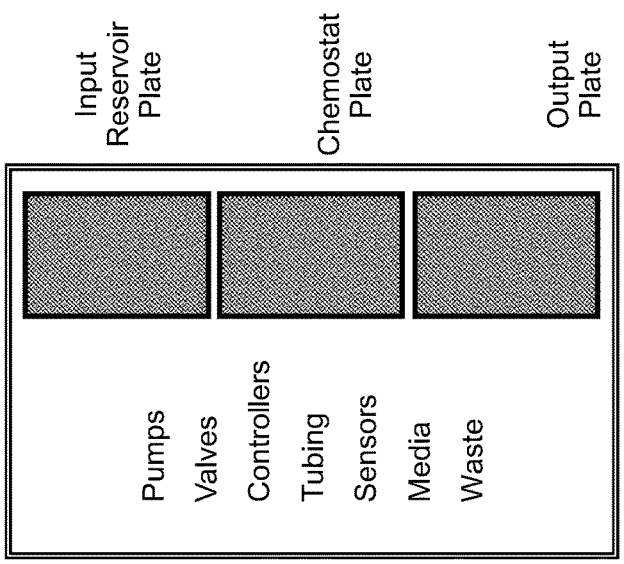
Figure 8B:
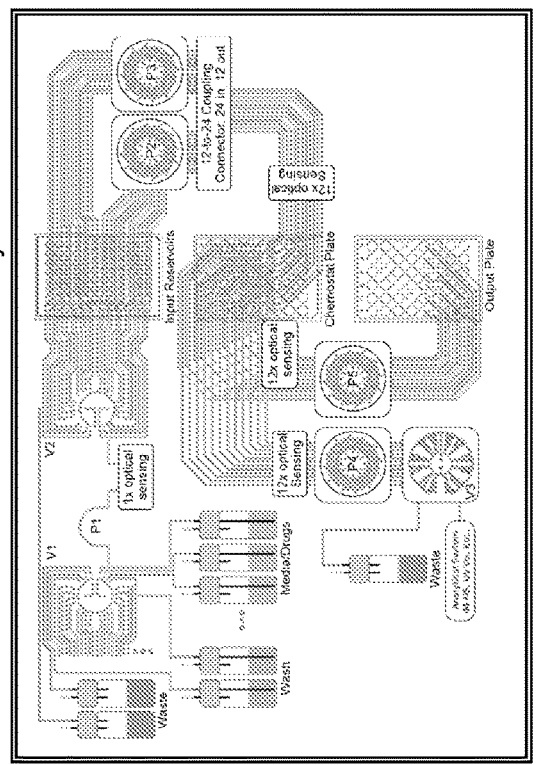
Figure 8D:
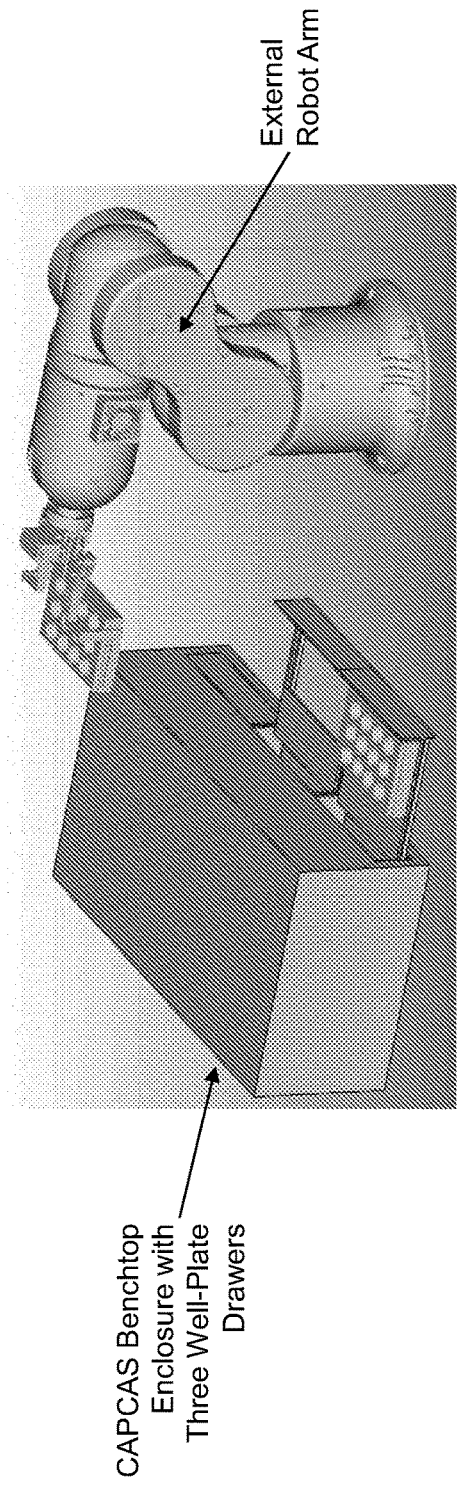

FIGS. 8B-8D show the fluidic circuit in FIG. 8A installed in an enclosure that could be serviced by an external robot arm, which would access the plates inside by means of three plate-de-lidding and lifting drawers. In this exemplary embodiment, the fluidic system is placed in the single-deck benchtop enclosure comprising three drawers of which one for the input reservoir plate, another for the chemostat plate, and the third for the output plate, which are operably serviced by an external robot arm for plate-de-lidding and/or lifting. The single-deck benchtop enclosure may further comprise compartments separated from the drawers for motors/electronics and fluidics.

Figure 8E:
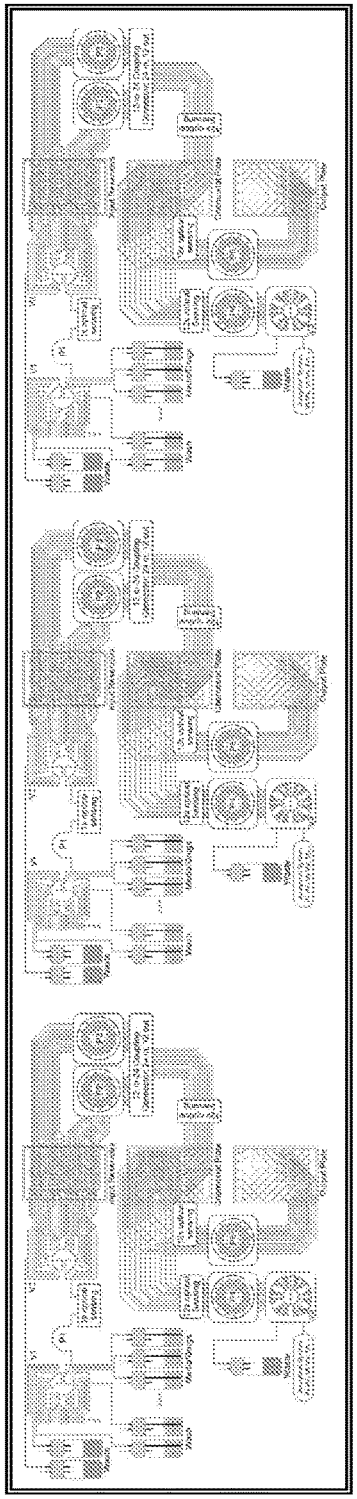
Figure 8F:
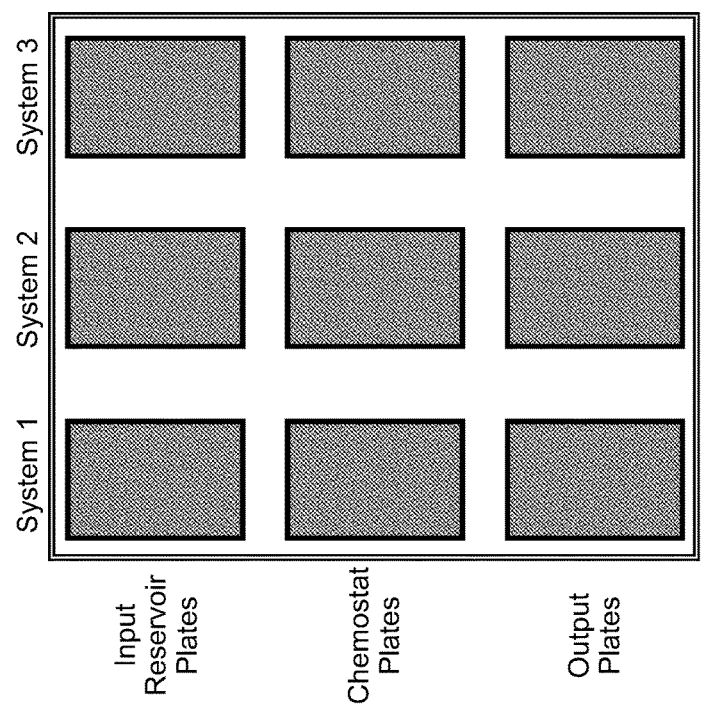

FIGS. 8E and 8F show how three 48-channel modules could be placed on a single deck in a single benchtop enclosure to provide 144 channels of chemostat in a single unit, with at least three output plates being accessible to an external robot arm by means of a computer-controlled drawer mechanism with automatic de-lidding.

Figure 8H:
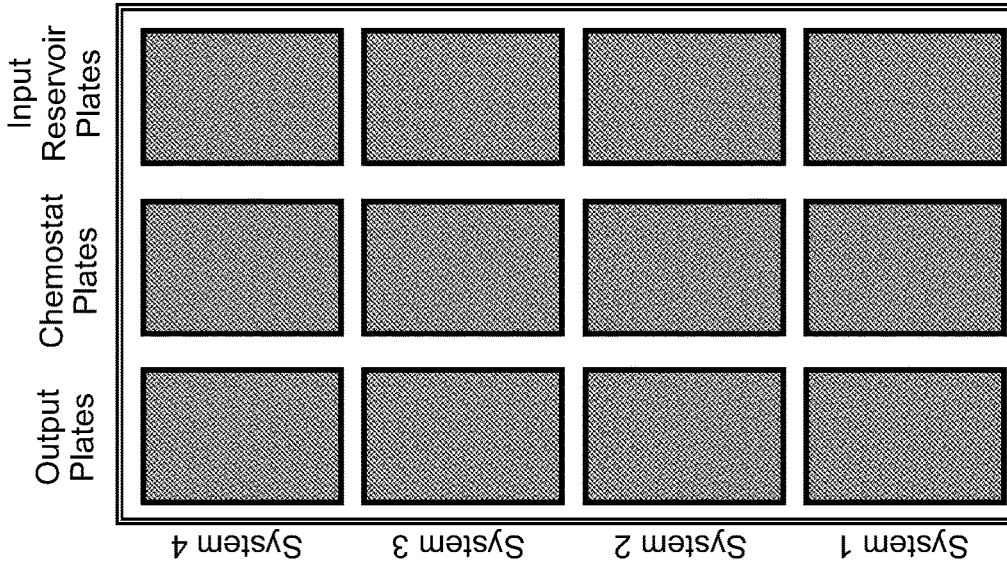
Figure 8G:
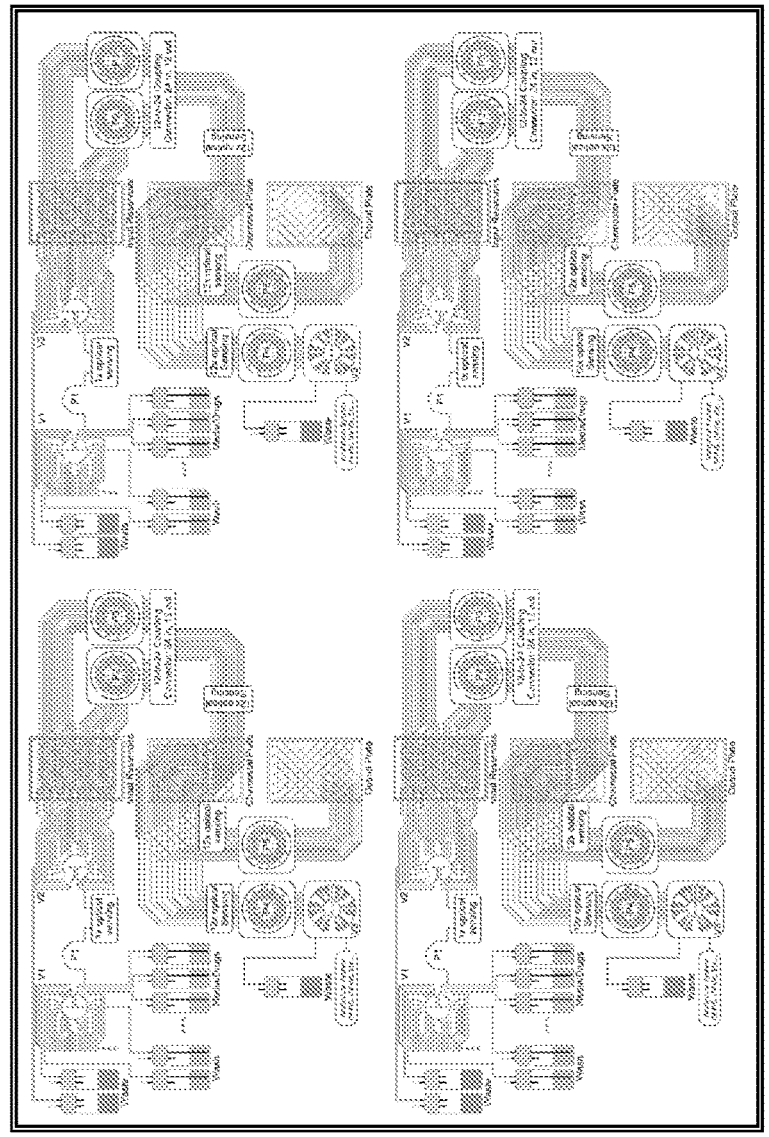

FIGS. 8G and 8H show a CAPCAS that contains four 48-channel units, for a total of 192 chemostats or bioreactors.

FIGS. 8I and 8J show a high-density CAPCAS that uses three sets of three 96-well chemostat/bioreactor plates each without any output plates, and rapidly perfuses the three biological replicates of each experiment at one time, servicing a total of 864 chemostat/bioreactor wells. It accomplishes this by using sharing a reservoir plate between a set of three parallel, replicate chemostat plates, and rather than having an output plate for off-line analysis, relies on multiple copies of pumps P4 and valves V5 and V6 to deliver sequentially a sample from each of the chemostat wells to one or more different analytical instruments. As we will see later, an enclosure that would support nine independent 864-channel decks would perfuse a total of 7,776 chemostats in a single CAPCAS enclosure.

Not shown is the embodiment wherein 1) the use of a fast series or parallel microformulator would eliminate the need for the input reservoir plate, 2) the use of in-line and at-line analyses without the need to collect media in the output plate, and 3) the use of a 96-well chemostat plate instead of a 48-well one would allow the support of twelve 96-channel modules on a single deck, i.e., 1,152 chemostats. The faster serial or parallel microformulator could be achieved, for example, by increasing the speed of pump P1 and/or adding more parallel pumping channels and/or parallel outputs in V3, such that it would be possible to use rapid time-division multiplexing to formulate directly into each chemostat rather than into the reservoir plates. Given that the sensor valve (V5) can direct cells and media sequentially from each well to a selector valve V6 and then on to an on-line analytical instrument, the output plate would not be required. However, this embodiment does not support the collection of samples from all chemostats in the chemostat plate at the same time instant, as do other designs.

Timing of Operations in a CAPCAS Multi-Well Chemostat

FIG. 9 outlines the procedural steps involved in the operation of a multi-well chemostat/bioreactor module. These steps include:

Step 1, V1 selects media, reagents and drugs needed to formulate media for each chemostat, washing lines as required;

Step 2, Using time-division multiplexing, V1-P1-V2 prepares the first media formulation for each chemostat;

Step 3, V1-P1-V2 fills one input reservoir set from the microformulator;

Step 4, V1-P1-V2 repeats Steps 1-3 but for the second reservoir set;

Step 5, P2 delivers first input reservoir set to each chemostat;

Step 6, Sensors check for bubbles, measure baseline OD. Perfusion rate can be controlled if OD should be held constant, thereby converting the system to a turbidistat rather than a chemostat;

Step 7, Cycle steps 1-6 for continuous perfusion of all chemostats;

Step 8, P4 continuously withdraws media during Steps 5-7; V3 delivers the media from one chemostat at a time to one or more in-line sensors while sending the media from all other chemostats to a common waste.

Sensors include electrochemical (eChem) metabolic sensors, cellular imaging, mass spectrometry (MS), etc.;

Step 9, P5 removes small samples for parallel sensing and returns them to the chemostats if desired;

Step 10, P5 rapidly and in parallel removes a fraction of the media from each chemostat and delivers each aliquot to a sample-collection plate for off-line analysis of each chemostats cells and media; and Step 11, Repeat cycles with parameters adjusted as necessary.

These steps would be repeated as required, and all could be controlled by the AI/ML robot scientist software that would select the strain of yeast that would be loaded into the chemostats prior to the initiation of the experiment, the concentration of nutrients, drugs, and other factors that comprise the input media and determine its pH, the rate of media replacement, the stirring velocity, gas concentrations, temperature, and other chemostat parameters. Samples would be withdrawn serially from each chemostat for real-time analysis as well as in parallel as required from all chemostats in a module.

Figure 10A:
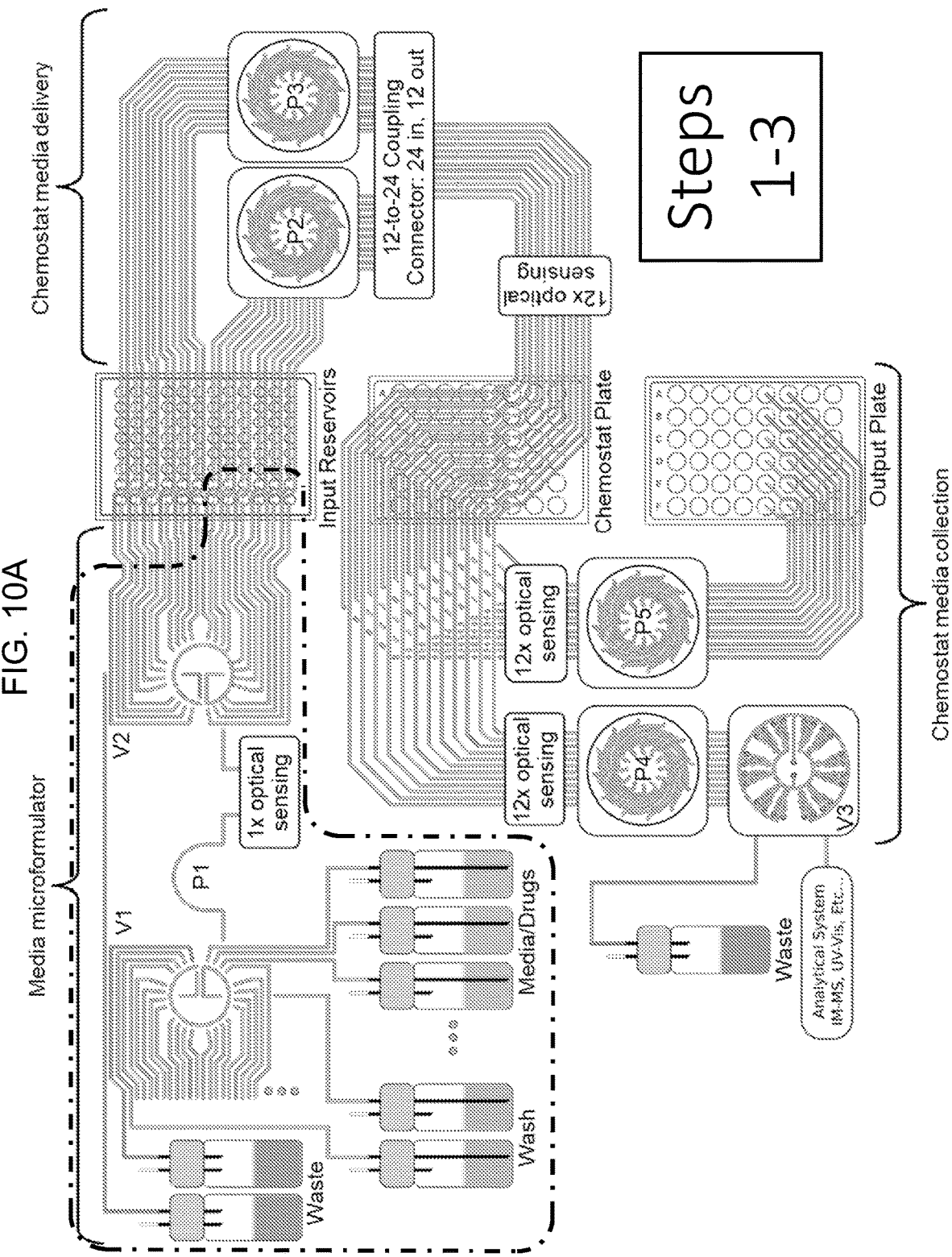
FIGS. 10A-10F show a fluidic circuit of a continuous automated perfusion culture analysis system (CAPCAS) with a visual grouping of CAPCAS pumps and valves during the operational steps, according to embodiments of the invention.
Figure 10B:
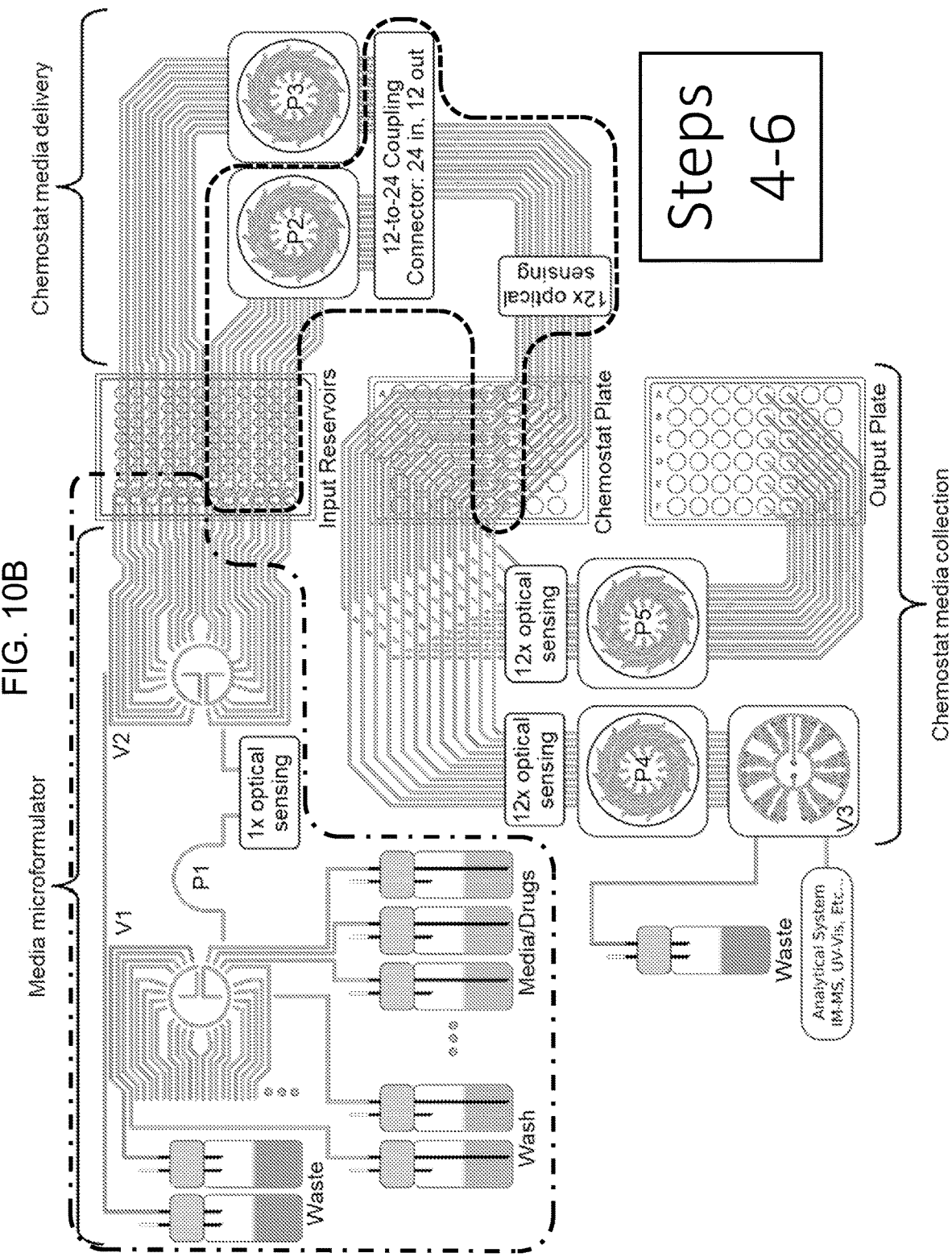
Figure 10C:
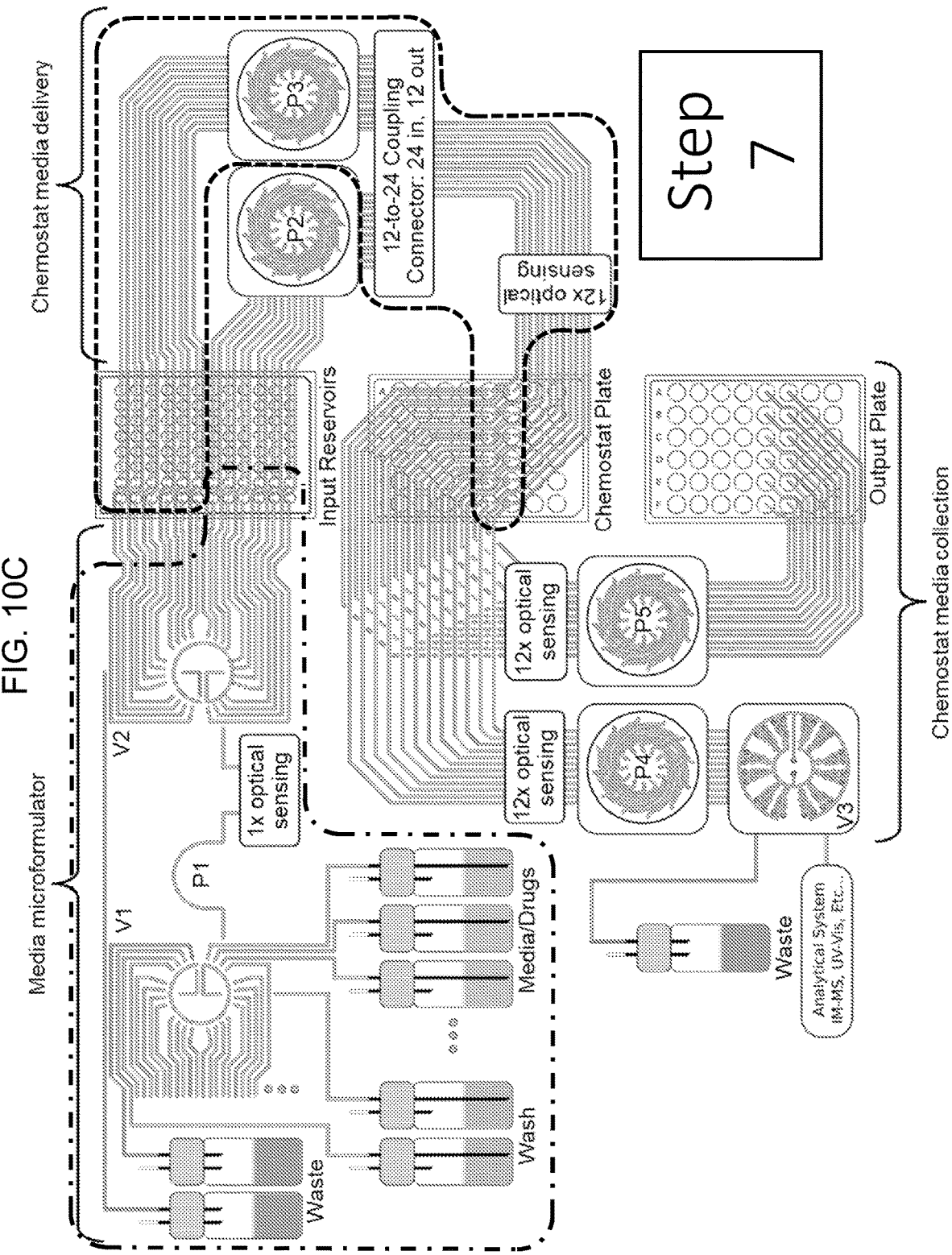
Figure 10D:
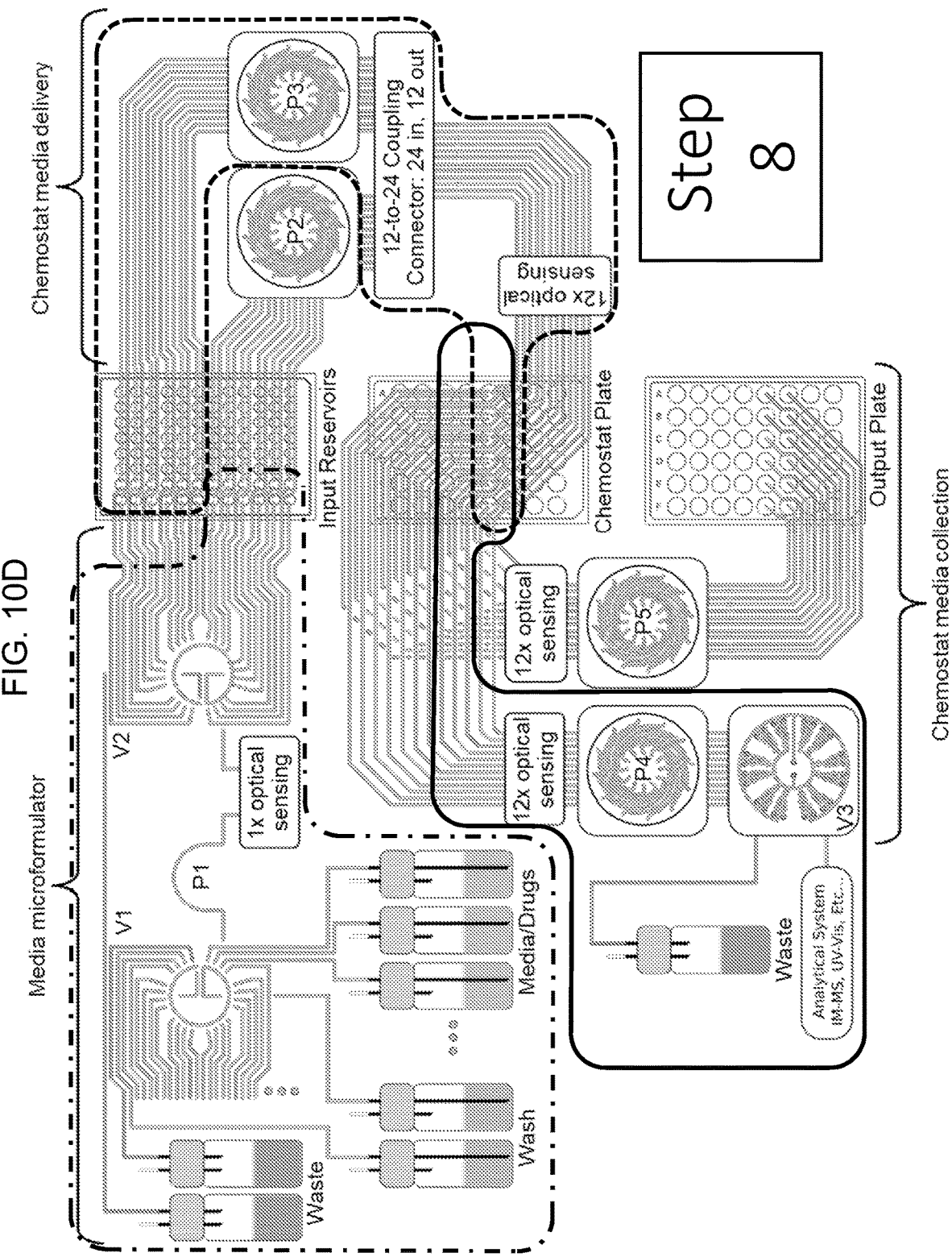
Figure 10E:
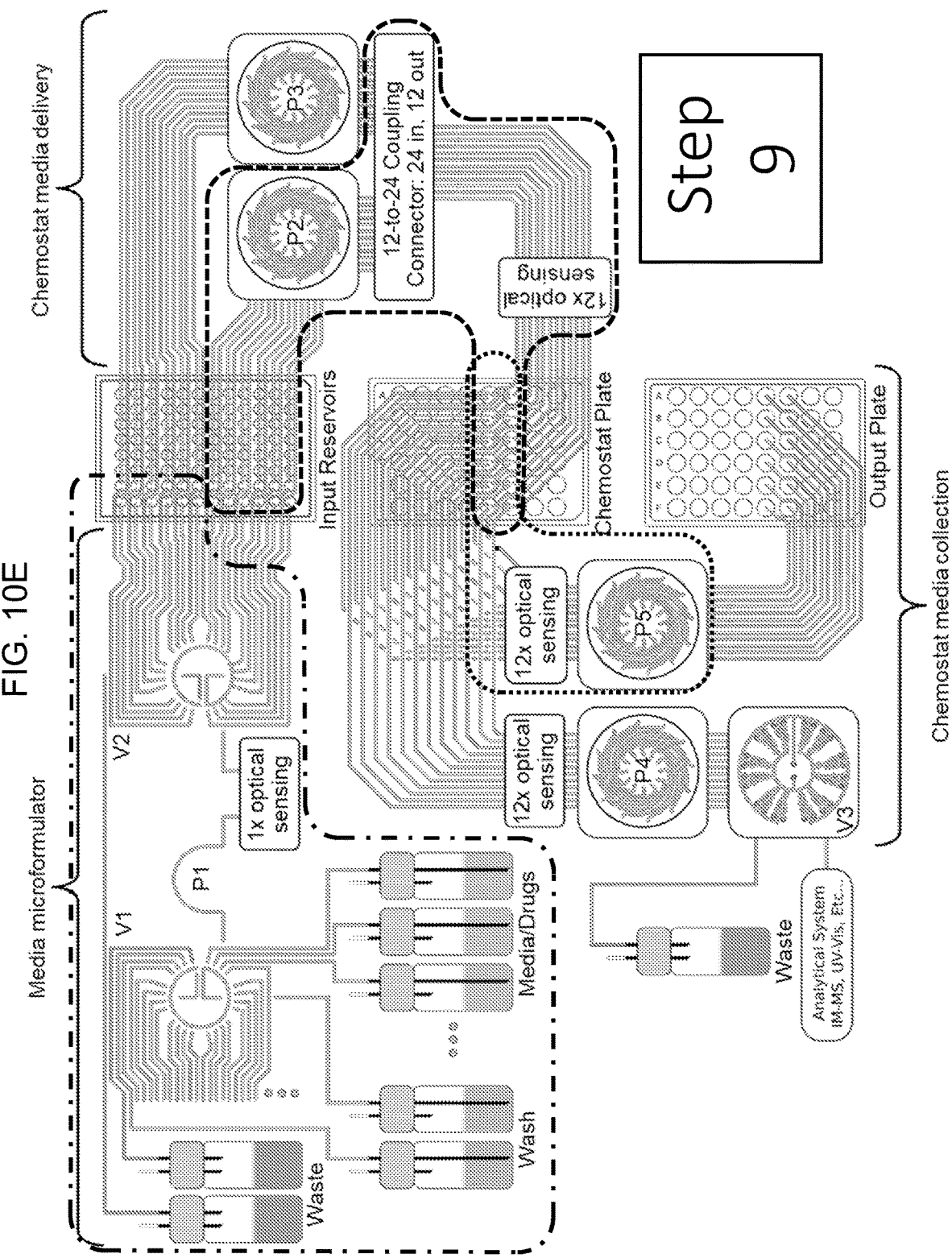
Figure 10F:
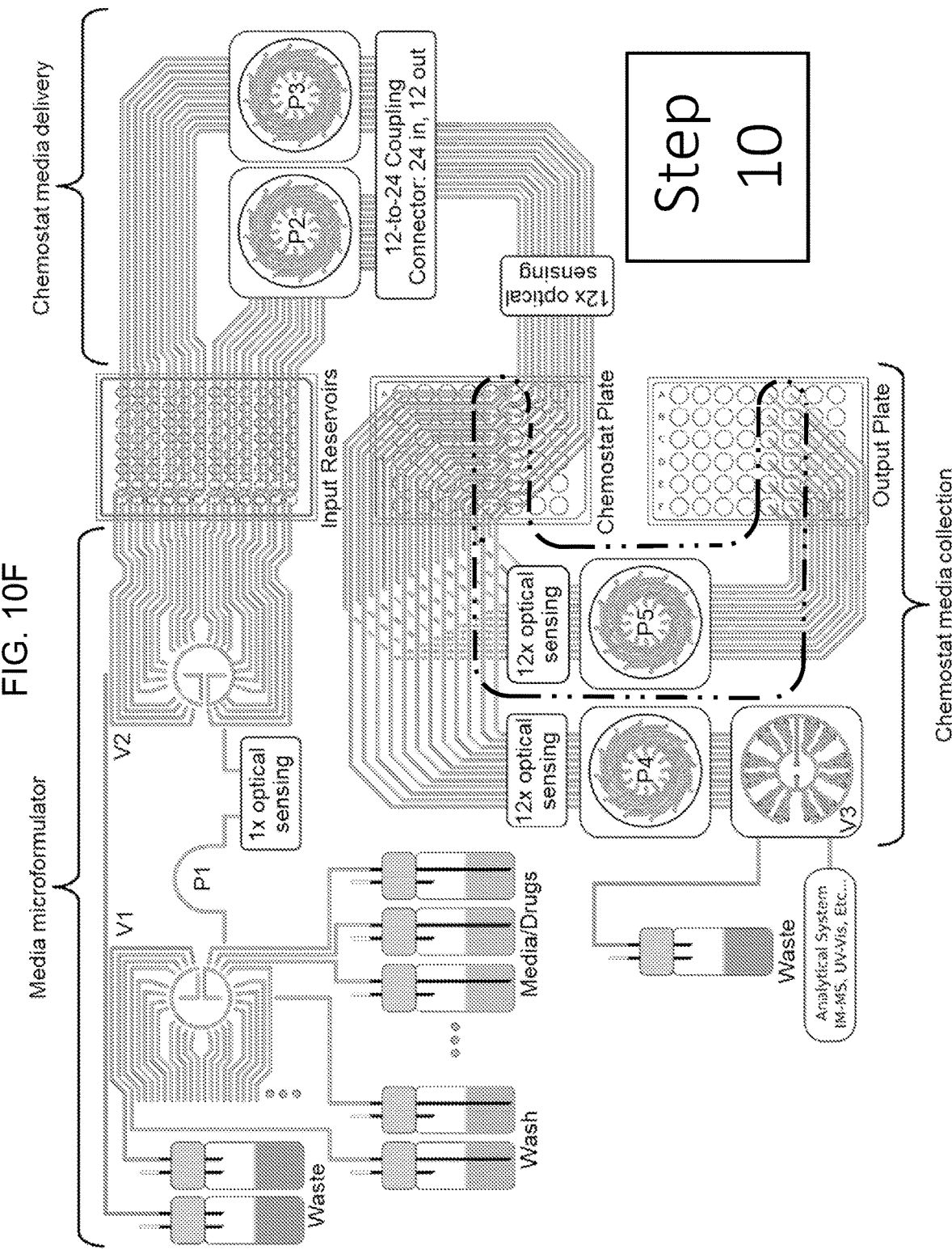

FIGS. 10A-10F provide a visual grouping of CAPCAS pumps and valves during the operational steps. FIG. 10A summarizes Steps 1-3, wherein the lower bank of input reservoirs is formulated. FIG. 10B shows Steps 4-6 with the formulation of the upper bank of input reservoirs while the lower bank of input reservoirs is pumped in parallel into each of the chemostats in the chemostat plate. FIG. 10C shows Step 7 with the return to the formulation of the lower bank of input reservoirs while the upper bank of input reservoirs is being pumped into the chemostat array. FIG. 10D shows Step 8 with the continuous removal of media from chemostats that is sent to analysis and waste, while formulation of the lower bank of input reservoirs and the pumping of the upper bank of input reservoirs into the chemostats continues. FIG. 10E illustrates how in Step 9 a small volume of media from chemostats could be transiently withdrawn by P5 to an optical pH sensor and returned back to the chemostat to measure pH without reducing the amount of media and cells in the chemostat, all during, in this case, formulation of the upper bank of input reservoirs and pumping of the lower bank of input reservoirs into the chemostats. Finally, in this series of examples, FIG. 10F shows Step 10, the end-of-experiment situation where the microformulator and reservoir pumping are stopped and media is rapidly transferred from all of the chemostats to the output plate for freezing and transcriptomics, etc. If desired, half of the media in each well can be transferred, followed by rapid removal of both the chemostat and output plates so that the two plates can undergo orthogonal analyses, e.g., transcriptomics and intracellular MS proteomics and metabolomics.

Embodiments of a CAPCAS Chemostat

FIGS. 8A-8J through 10A-10F have outlined embodiments of the sensing and fluidic control system to operate large numbers of chemostats in parallel. The next challenge is to create chemostat units that are sufficiently compact that 48 or 96 of them could be arranged to fit on the space offered by the lid of a 48- or 96-well plate.

According to the invention, each chemostat/bioreactor in one embodiment comprises a lid structure for controlling operation of the chemostat, wherein the lid structure comprises a fluidic control layer that contains motors that drive the pumps and valves, and a lid beneath the fluidic control layer, wherein the lid supports vertical tubes that deliver and remove fluid from the well, with a long tube reaching nearly to the bottom of the well to allow the pump P5 to remove when desired some or nearly all of the media and cells in the well, a medium length tube being connected to the pump P4 to provide continuous removal of media from the chemostat and deliver it to the at least one multimode output valve V3, and a short tube being connected to the pumps P2 and P3 to deliver media to the chemostat with the end of the short tube being well above the liquid level to prevent back-contamination of the media delivery system.

In one embodiment, each chemostat further comprises a stirrer system.

In one embodiment, the stirrer system comprises an individual printed-circuit-board (PCB) motor, bearings, and a hollow rotating slotted-cylinder stirrer that operably serves as an impeller to provide unidirectional axial flow in one direction on the inside of the impeller tube and in the opposite direction outside while surrounding the short, medium length, and long tubes and two vertical tubes that connect a gas permeable tubing loop.

In one embodiment, the stirrer system comprises a rotatable slotted cylinder that has one or more spiral vanes on either the inside or outside or on both sides of the rotatable slotted cylinder stirrer to provide more vigorous vertical mixing of the cells, media, and dissolved gases contained within the chemostat.

In one embodiment, the stirrer system comprises a magnetic stir bar disposed on a bottom of the well, a rotating magnet positioned beneath each well for driving the magnetic stir bar to rotate, and a separate motor to drive each rotating magnet to allow each chemostat in the array to be stirred at a different speed.

In one embodiment, the chemostats are operably inoculated by using an external pipettor or robot to seed either the chemostat plate, which is removable, or a transfer plate that has one or more seeded wells and is then installed in place of the output plate with the at least one second pump run in reverse to deliver the selected cells into various chemostats to restart their culture.

Figure 11A:
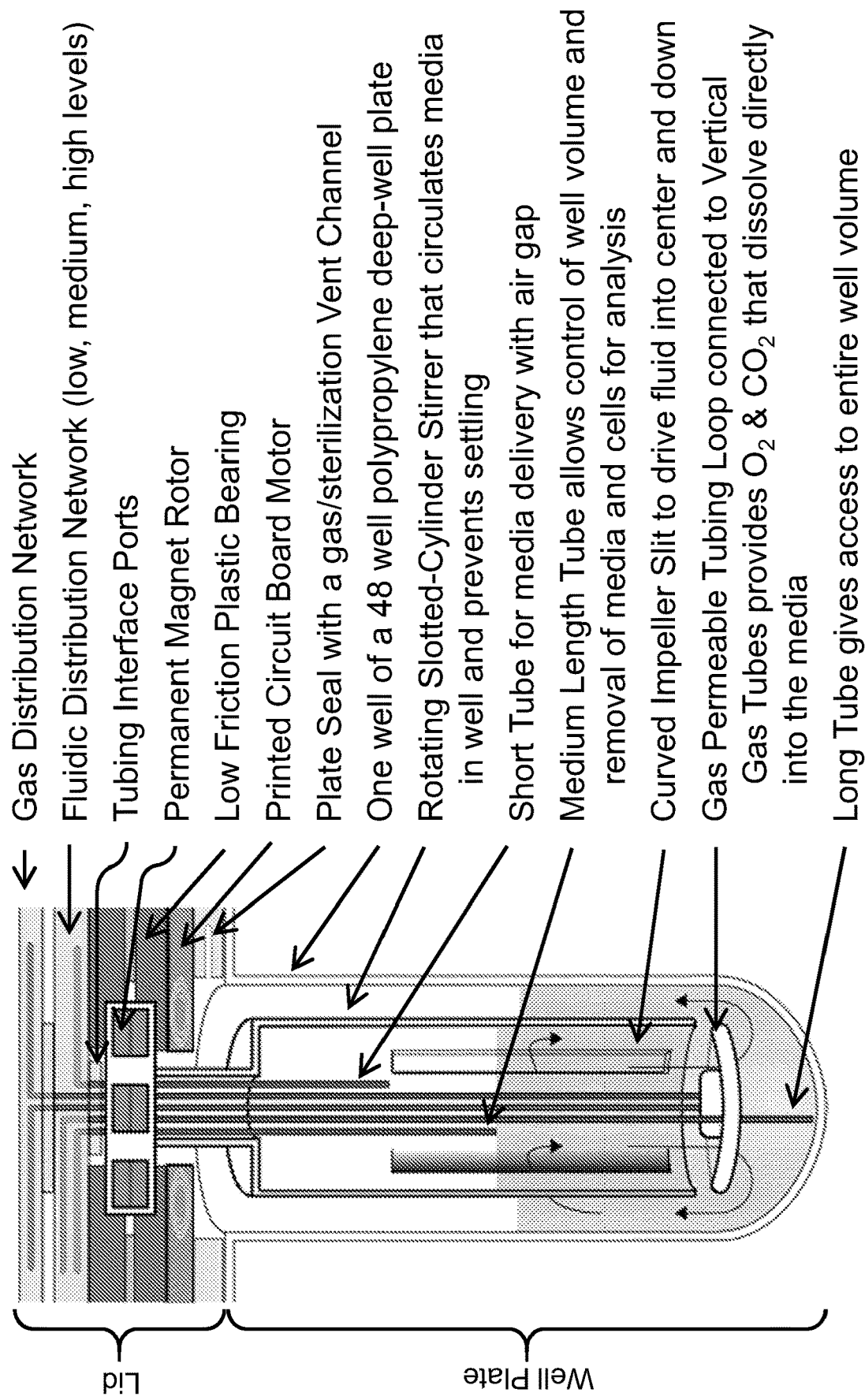
FIGS. 11A-11C show embodiments of a CAPCAS chemostat well and its associated hardware, according to embodiments of the invention.

FIG. 11A shows one embodiment with the requisite features. The operation of the chemostat in this embodiment is controlled by structures entirely attached to the lid. As shown schematically in the figure, several different layers will comprise the lid to each chemostat plate. Not shown, but above or adjacent to the lid, is the fluidic control layer that contains the seven motors that drive the pumps and valves shown in FIGS. 10A-10F. Beneath that layer is a cast or otherwise fabricated lid that supports the vertical tubes fabricated from PEEK or another biocompatible material that deliver and remove fluid from the well, with the long tube reaching nearly to the bottom of the well to allow P5 to remove when desired some or nearly all of the media and cells in the well. The medium length tube is connected to P4 to provide continuous removal of media from the chemostat and deliver it to the sensor valve V3. The short tube is connected to P2 and P3 to deliver media to the chemostat, with the end of the tube being well above the liquid level to prevent back-contamination of the media delivery system. Having the removal pump P4 operate at a higher pumping rate than either delivery pump P2 or P3 ensures that the medium length tube sets the maximum height of the media and cells in the chemostat, as shown in FIG. 6A. Note that this approach of overpumping will result in minor, repeating fluctuations in fluid level as the media rises to make contact with the medium length tube, at which time the pump begins to remove media and the fluid level drops until the meniscus between the bottom of the tube and the media breaks, after which time P4 will withdraw air or foam from above the media, whose level once again begins to rise. One advantage of this approach is that it may minimize or eliminate defoaming agents that could interfere with cellular biological processes.

In the embodiment shown, the stirrer system for each well has an individual printed-circuit-board (PCB) motor,[89] bearings, and a hollow rotating slotted-cylinder stirrer that serves as an impeller to provide unidirectional axial flow in one direction on the inside of the impeller tube and in the opposite direction outside while surrounding the short, medium length, and long tubes as well as the two vertical tubes that connect the gas permeable tubing loop. The design and operational parameters for this stirrer can be adjusted as necessary to produce a chemostat whose results scale to much larger volume chemostats and bioreactors.

The gas delivery layer in the lid has a planar gas manifold to support the delivery and removal of gas from the vertical gas tubes. Immediately below the gas and fluid distribution layers are the individual custom planar PCB brushless DC motors, or (not shown) miniature commercial motors that drive a hollow-bore vertical impeller in each chemostat well that serve as mechanical stirrers. A loop of oxygen-permeable Teflon AF tube[90] will deliver to each chemostat well $O_2$ or a mixture containing additional gases such as $N_2$ and $CO_2$, The combination of the tubing loop and the stirrer would ensure five-second mixing[10] and uniform, controlled oxygenation.[91]

Figure 11C:
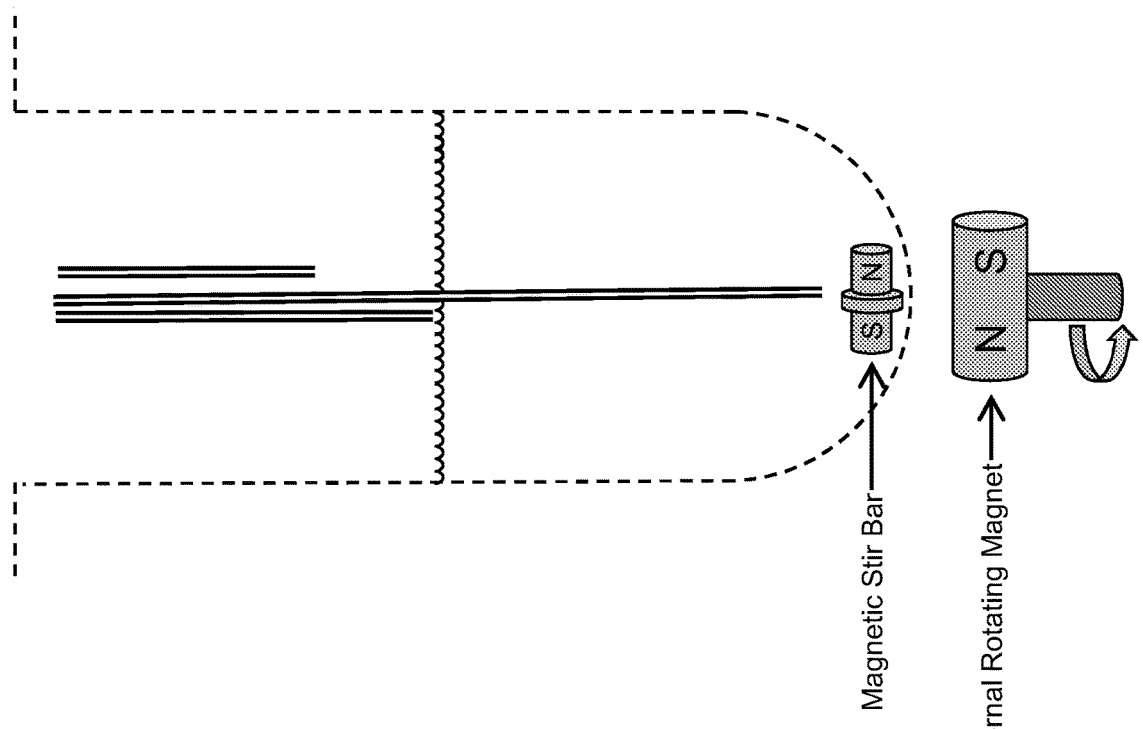
Figure 11B:
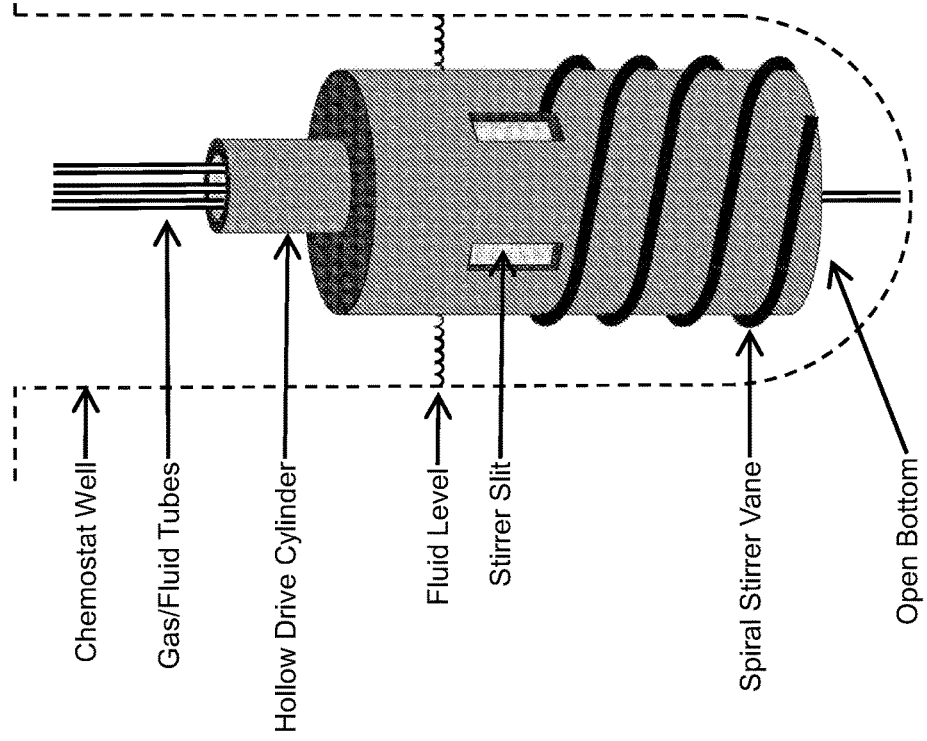

The primary advantage of the hollow cylindrical stirrer is that the space inside the cylinder can contain the long, medium, and short fluid delivery or removal tubes and the two tubes required for gas delivery and removal. An alternative stirrer embodiment could use the rotating slotted cylinder shown in FIG. 11B that has one or more spiral vanes on either the inside or outside or on both sides of the rotating slotted cylinder stirrer to provide more vigorous vertical mixing of the cells, media, and dissolved gases contained within the chemostat. Alternatively, a shaft could extend downward from the lid into the well to drive one or more stirring blades, but this approach would interfere severely with various tubes in the small diameter of a well. Yet another embodiment, shown in FIG. 11C, could utilize a long tube that does not reach to the bottom of the well to leave room for a magnetic stir bar driven by a rotating magnet positioned beneath each well; having a separate motor to drive each rotating magnet would allow each chemostat in the array to be stirred at a different speed. The advantage of this approach is ease of construction and installation; the disadvantage of this approach as compared to stirring from the top plate is that the space beneath the wells must be permanently occupied, defeating the random XY access afforded to the iPlateBot robots that allows them to reach any and all plates on a fluidic station above deck without disturbing any already-suspended plates.

FIG. 11A also shows a number of features worthy of being included in the chemostats, including a gasket or seal to ensure that there is no cross-talk of gases or microbes between adjacent chemostats, a vent output required for system sterilization, tubing interface ports, and gas and fluid distribution networks. The various gas and fluid distribution channels could be fabricated directly into the fluidic station that is affixed above the well plate. Not shown are overfill detection electrodes or optical fibers, or in-well dissolved oxygen, pH, or other sensors.

Continuous Perfusion Systems Components

The sequence of events outlined in FIGS. 7A-7B through 10A-10F requires an exquisite level of control of multi-channel fluidic pumping and valving functions that can operate at flow rates that typically are between 1 μL and 1 mL per minute, well beyond the flow capability of the classic pneumatic microfluidic which require a dedicated and expensive high-speed solenoid as well as a separate compressed gas line for each solenoid. Other valves, such as microfluidic rocker valves or rotating disk valves, are typically too large and too expensive, or are unable to perform complex valving operations required for the functions shown, for example, in FIGS. 10A-10F. We now describe rotary planar peristaltic micropumps (RPPMs) and rotary planar valves (RPVs) specifically configured to perform the requisite operations shown in FIGS. 7A-7B through 10A-10F.

FIG. 12A provides details for the sensor valve (V3) in FIG. 8A. The fluidic circuit is fabricated from polydimethylsiloxane. A collection of balls trapped in ball cages is either pressed up into the fluidic chip to close a channel, or allowed to drop to open the channel. The fluidic chip is pressed into the fluidic plate and held in place laterally by protrusions that also serve as tubing ports.

FIG. 12B shows a rotating planar peristaltic micropump whose actuator contains a groove around which balls roll, with an elastomeric traction ring ensuring that the balls roll rather than slide. A free-floating sprocket spacer maintains a uniform separation of the balls.

FIG. 12C shows a single channel spiral pump, with the shape of the spiral optimized to minimize peristaltic oscillations and backflow.

FIGS. 12D, 12E, and 12F show two-, six-, and twelve-channel spiral pumps.

FIG. 12G shows a six-channel pump with a common central port and six independent outer ports, as would be used for either combining or separating multiple flows.

FIG. 12G shows an eight-channel binary-splitter pump that has a single input and a single output, but multiple internal channels to provide a high pumping rate. The width of the channels need not be uniform but can be scaled in proportion to the flow through each section. Such a pump could be fabricated with any number of channels that is a power of two.

FIGS. 12I and 12J show the ports of a 100-channel valve, where the location of a groove in the actuator determines whether or not a ball is pressed into the elastomer to compress the elastomer of the fluidic and close the channel.

FIGS. 12K and 12I show the layout of the 100-channel valve, including the single input port, the common channel, and the 100 output ports.

Figure 12Q:
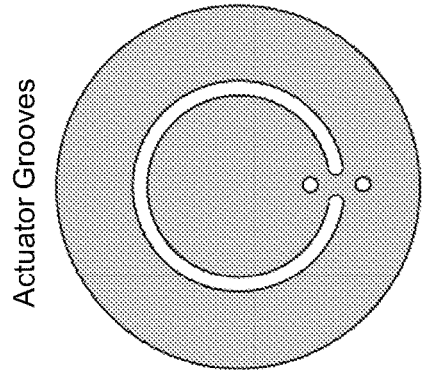
FIGS. 12A-12R show construction details of the pumps and valves that can be used to implement a CAPCAS, according to embodiments of the invention.
Figure 12R:
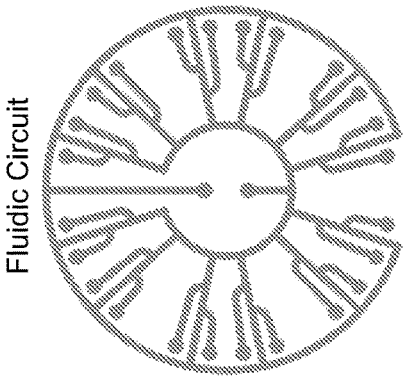
Figure 12P:
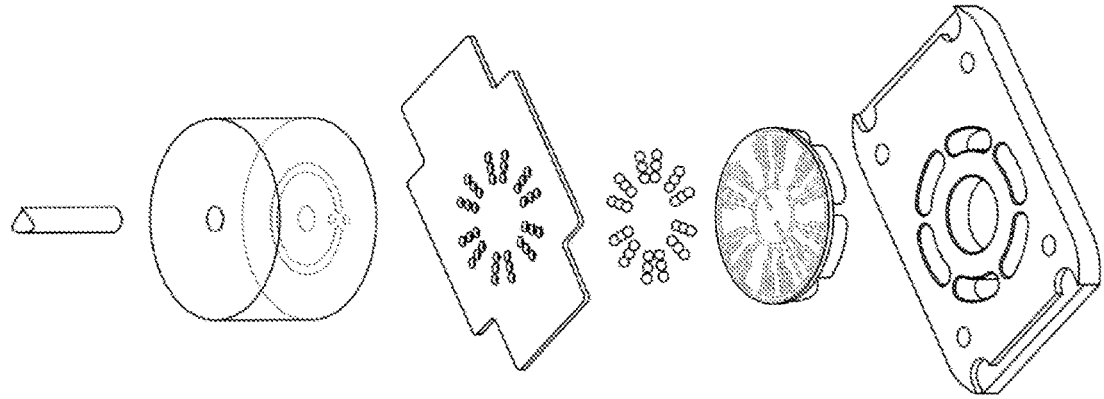
Figure 12N:
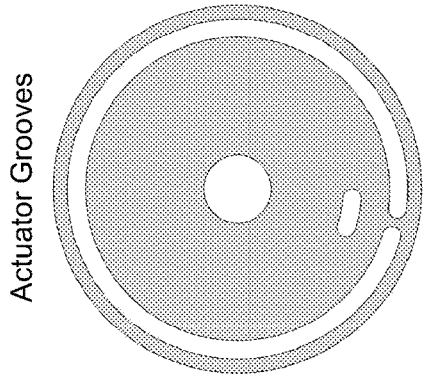
Figure 12O:
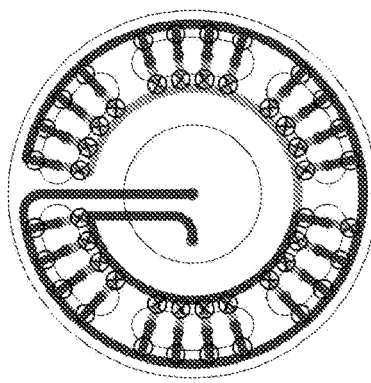
Figure 12M:
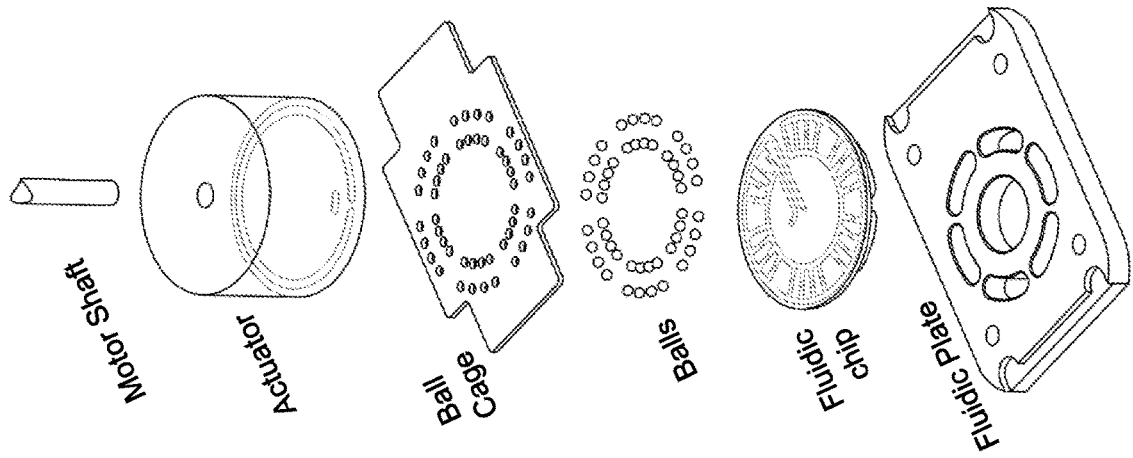

FIGS. 12M, 12N, and 12O provide construction details of the sensor valve, which is designed to allow any one of 24 lines to be directed to a sensor while the remaining 23 channels are directed to a common waste. FIGS. 12P, 12Q, and 12R provide construction details for the cut-in valve, which allows 11 of 12 channels to flow independently, and the chosen $12^{th}$ channel to be diverted to another fluidic circuit, which would allow destructive analysis of the cells and media in that channel and the injection of make-up media downstream of the valve. Either valve could be used for V3 in FIG. 8A; most of our discussion has assumed that V3 will be a sensor valve. The use of a cut-in valve might allow the elimination of P5 and the connection of P4 and V3 to the output plate.

We have previously described motor cartridges that were cuboidal, totally enclosed, and wipe-sterilizable in U.S. Pat. No. 11,135,582 B2 by D. K. Schaffer, et al.,[50] which is incorporated herein by reference in its entirety. We have invented a number of enhancements to our motor cartridges to improve the alignment of the fluidic channels, the fluidic-chip protrusions, the actuator, and the motor, simplify fabrication and assembly, and streamline the process of compressing the fluidic, thereby producing a more compact cylindrical pump and valve cartridge that can be produced in quantity more economically, is more robust and reproducible, and more readily serviced. Because the motor can be quickly separated from the fluidics, the latter can be thermally or radiation sterilized without damaging either the motor or its microcontroller. For some embodiments, these cylindrical pump and valve cartridges can be readily fabricated by starting with commercially available, anodized aluminum, threaded lens tubes and retaining rings in widespread use for optical systems.

Figure 13A:
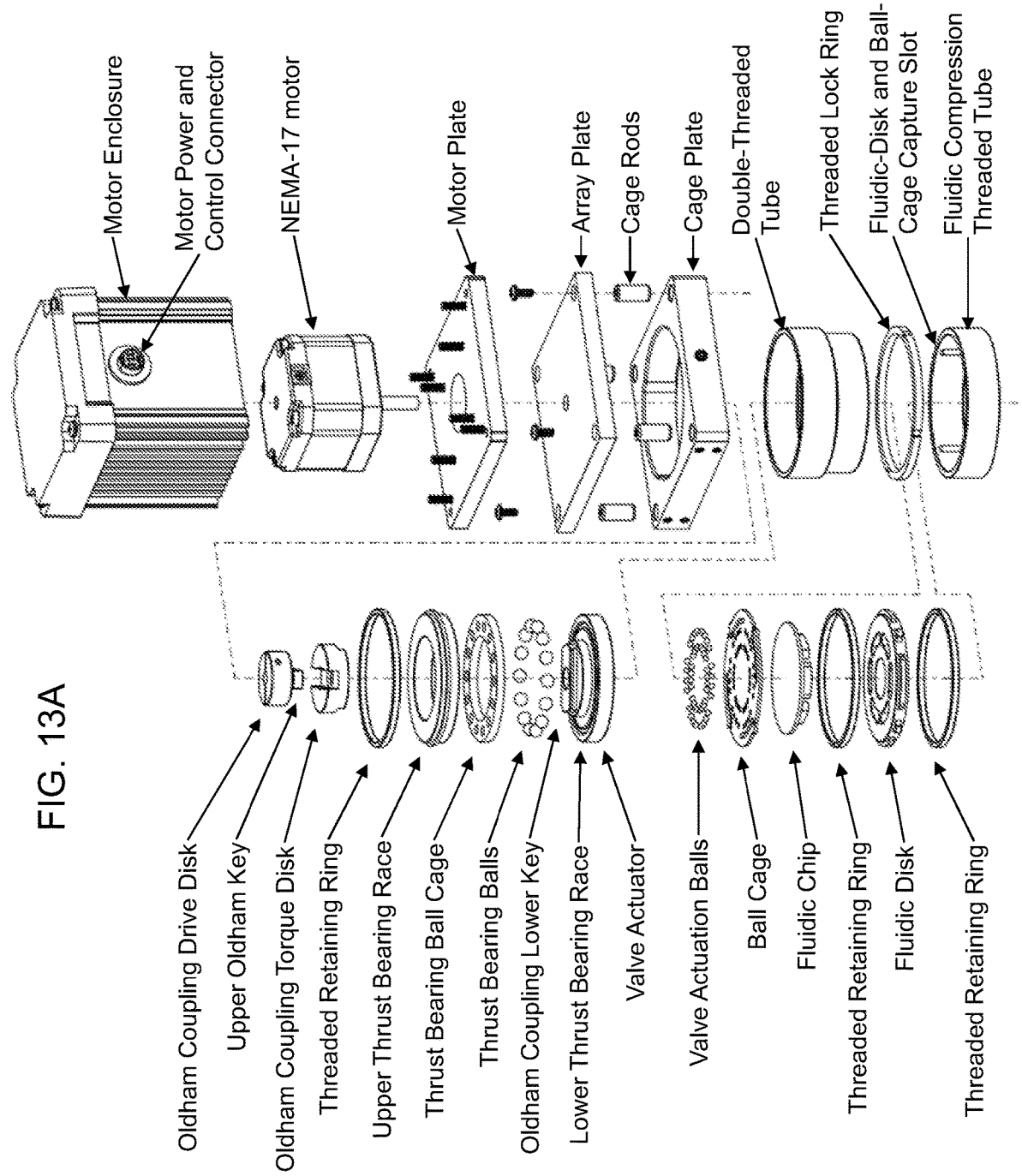
FIGS. 13A-13O show exploded, perspective, and sectional views of cylindrical motor cartridges that contain the pumps and valves required for CAPCAS units, according to embodiments of the invention.
Figure 13B:
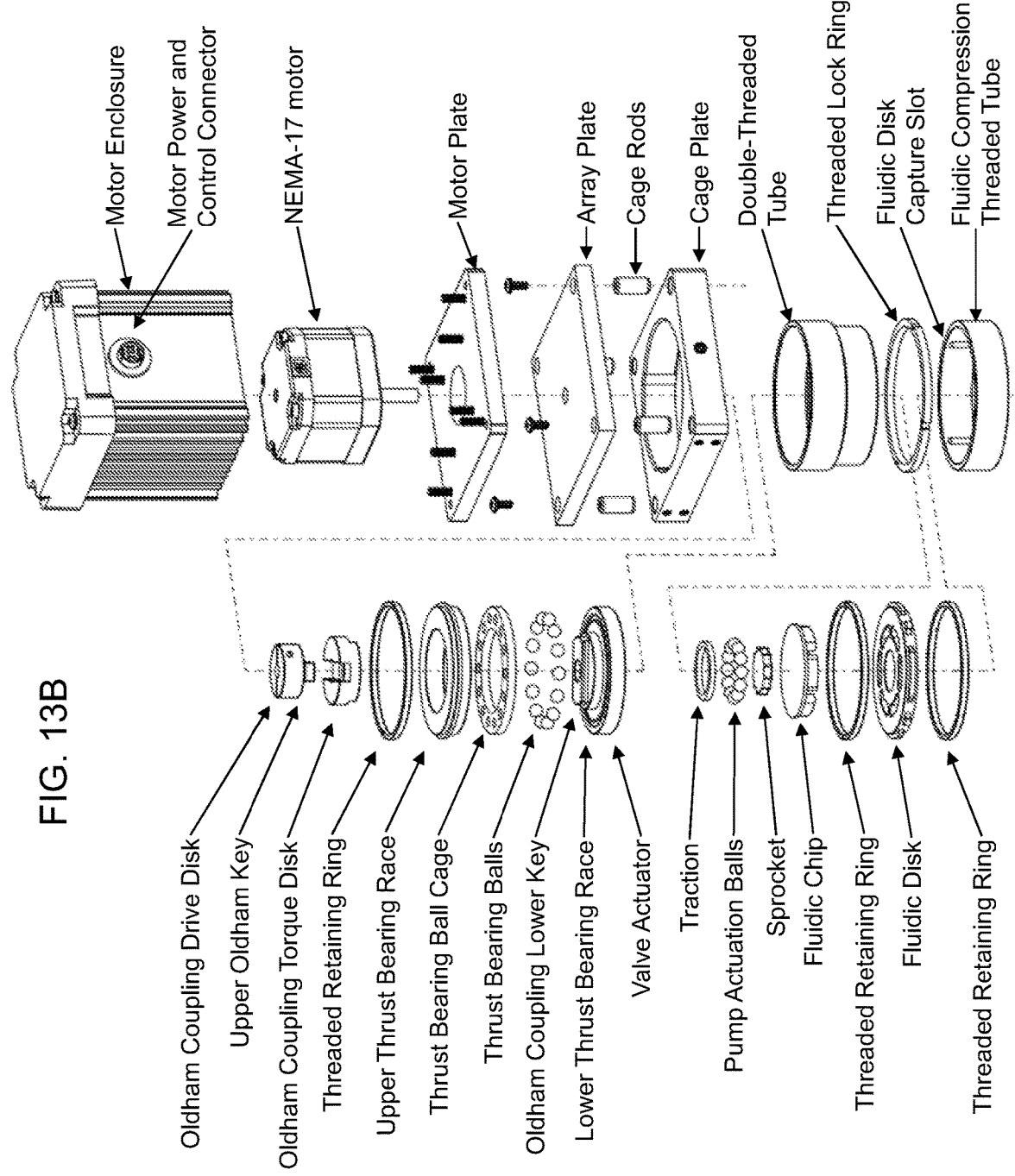

FIGS. 13A and 13B are exploded views of a 24-channel sensor valve cartridge and a 12-channel spiral pump with all components labeled. The Oldham coupling not only accommodates any misalignment of the motor axis with that of the fluidic and its actuator, but it also provides a simple means to separate and reconnect a motor from the cylindrical fluidic cartridge. The motor microcontroller (not shown) can be located inside the motor enclosure.

Classically, the ports in PDMS microfluidic chips are punched after the chip is produced by replica casting. One of the failure modes of this type of chip is that the Tygon tube that is inserted into this punched port can be pressed so deep as to occlude the channel, as shown in FIG. 13C. In theory, this can be avoided by cutting the end of the tube at an angle, but that requires care to insert the tube into the port with the correct orientation so that the tip of the tube doesn't block the channel. Furthermore, the punched holes are typically sharp-edged and tapered, and the punching process can introduce tears in the PDMS, which can lead to PDMS fragments being pushed into the channel by the end of the tube, spontaneous expulsion of a tube from a port, or leaks. These problems are all avoided by designing molds that allow the production of cast-in-place ports with shoulders that limit the insertion of the tube to a point well above the transverse microfluidic channel, as shown in FIGS. 13D, 13E, and 13F.

A major advantage of the cast-in-place ports is that the location of all ports in a valve or pump are precisely determined. This then makes it possible to connect to the fluidic chip with a rigid fluidic connector. FIGS. 13G, 13H, and 13I show a male-male connector that can be readily produced by either machining or injection molding of a rigid plastic.

Figure 13J:
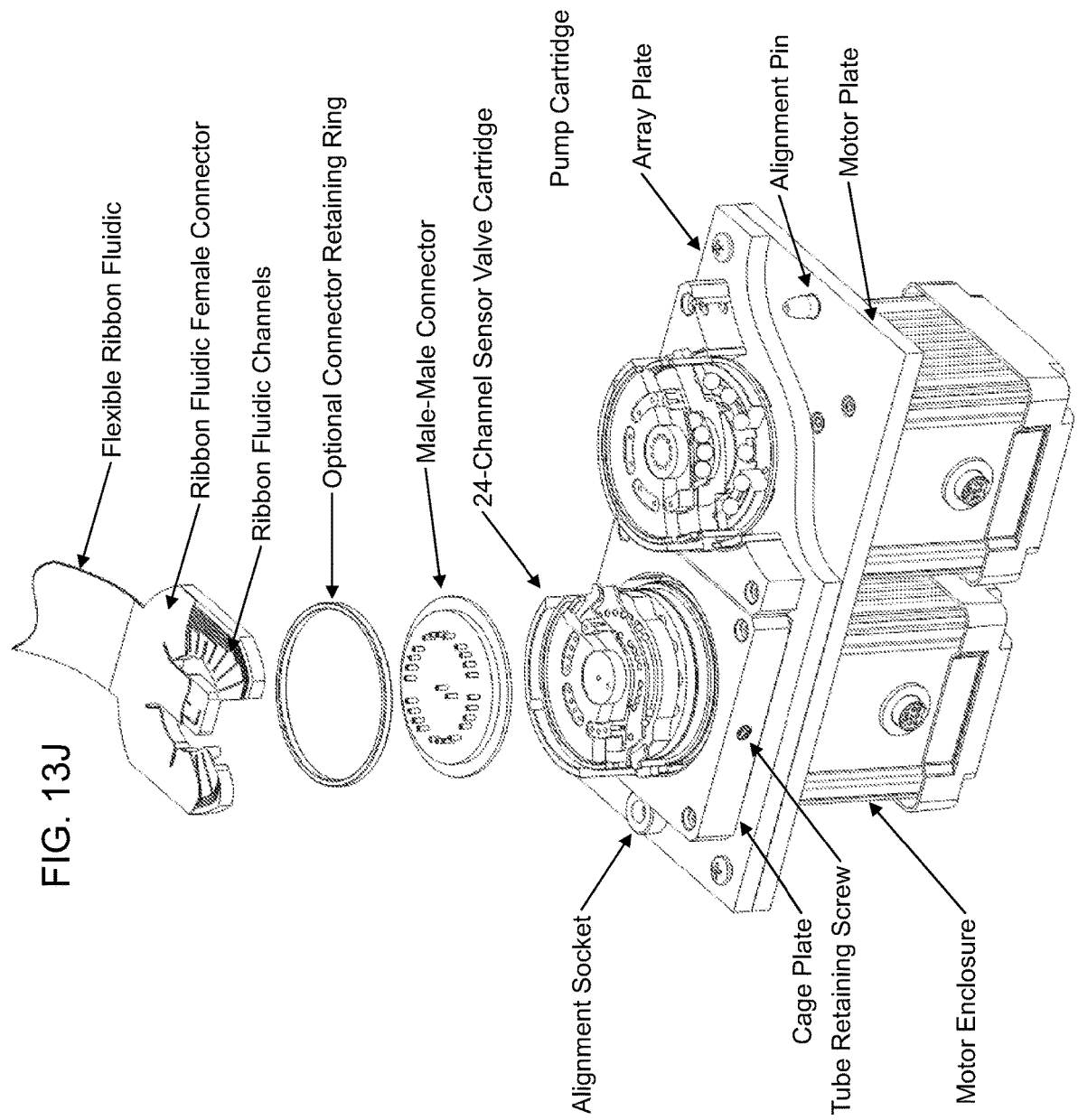

FIG. 13J shows two motors, one driving a 24-channel sensor valve and the other a 12-channel spiral pump, with the two motors being supported by a common motor plate and the cylindrical fluidic cartridges being held to an array plate by commercially available cage plates. FIG. 13J also shows how a flexible ribbon fluidic can be connected to a valve by a male-male connector. The use of alignment pins and sockets simplifies separation and reconnection of the motors on the motor plate from the fluidic cartridges on the array plate.

Figure 13K:
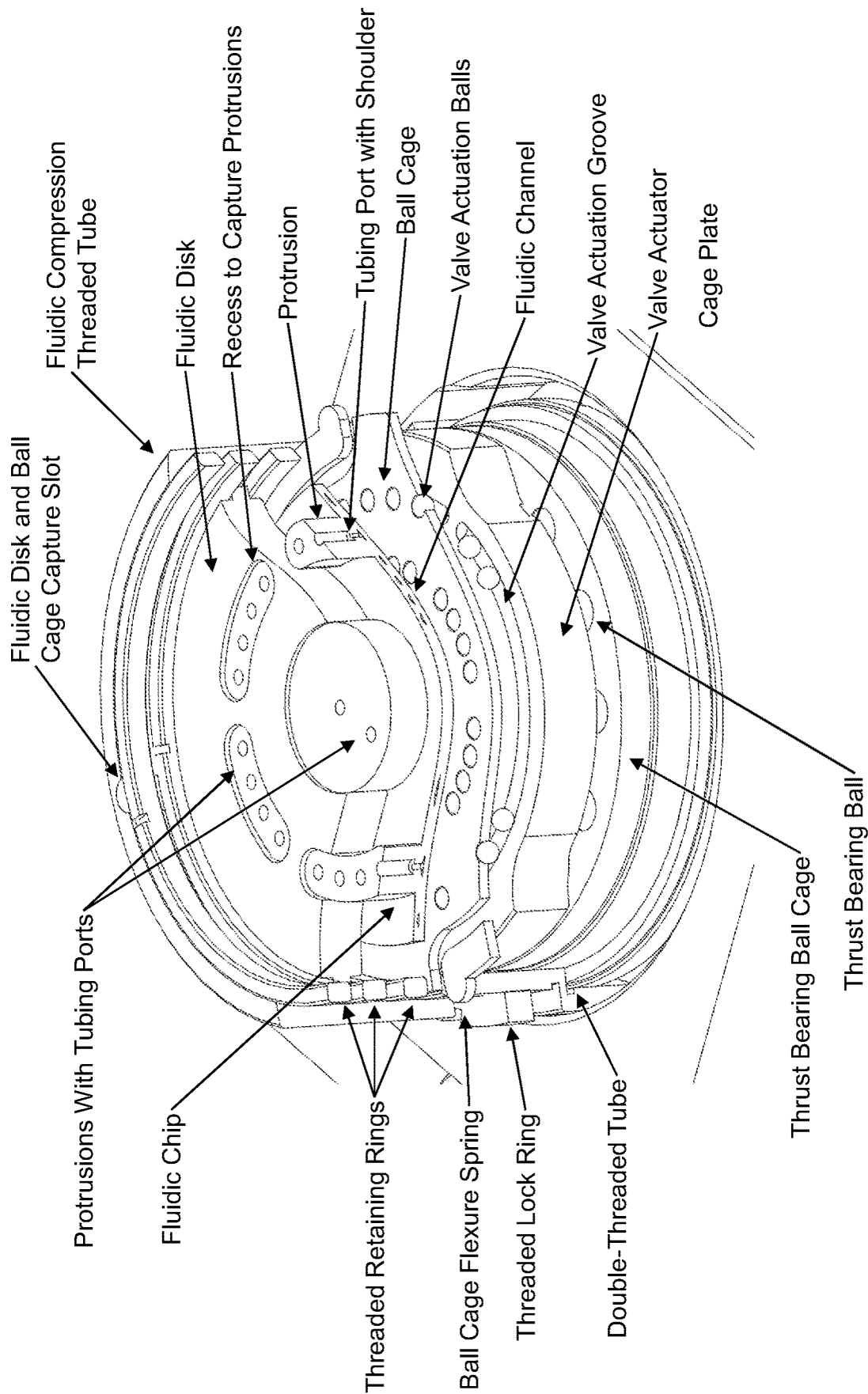
Figure 13L:
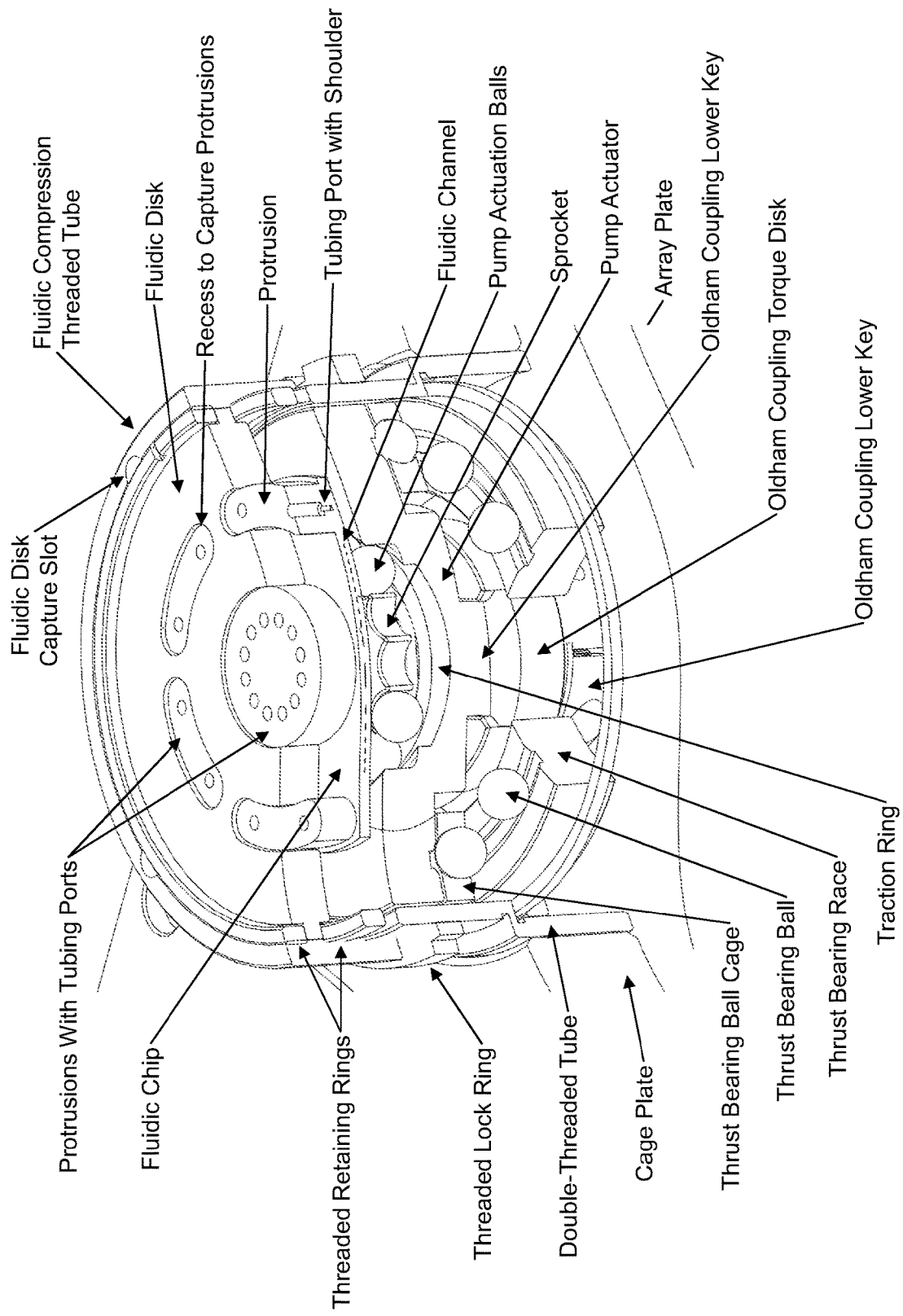

FIGS. 13K and 13L show cut-away views of the valve and pump cylindrical cartridges. The use of a double-threaded tube makes it possible to adjust the compression of a pump or valve simply by rotating the fluidic compression threaded tube and locking it in place with the threaded lock ring. The fluidic cartridge, once compressed, can be inserted into the array plate and held in place with a single tube retaining screw (FIG. 13J).

FIGS. 13M, 13N, and 13O provide details of the valve and pump actuators. FIG. 13M shows the motor-side of the actuator body, with the Oldham coupling key having a capture key so that it will hold in place the Oldham coupling traction disk (FIGS. 13A and 13B) when the motor plate is separated from the array plate. The configuration of the fluidic-side of the Actuator depends upon whether it is for a valve (FIG. 13N) or a pump (FIG. 13O). Other types of valves and pumps could have different details on the fluidic side of the Actuator.

The modularity of the components in these pump and valve cartridges is central to the economics of this design, which allows the production of CAPCAS with hundreds of pumps and valves.

Continuous Automated Perfusion Culture Analysis System Embodiment

Figure 14A:
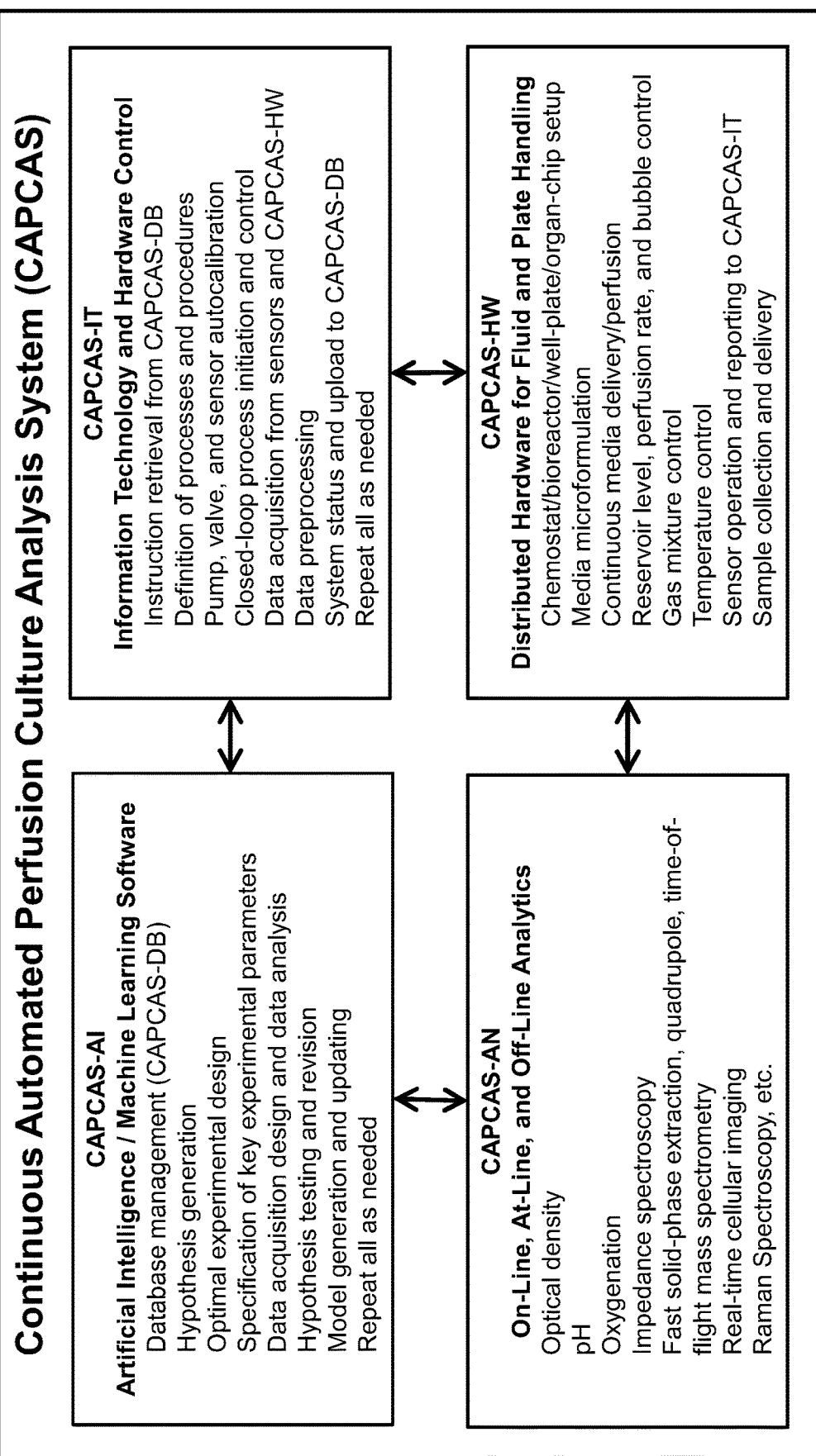
Figure 14E:
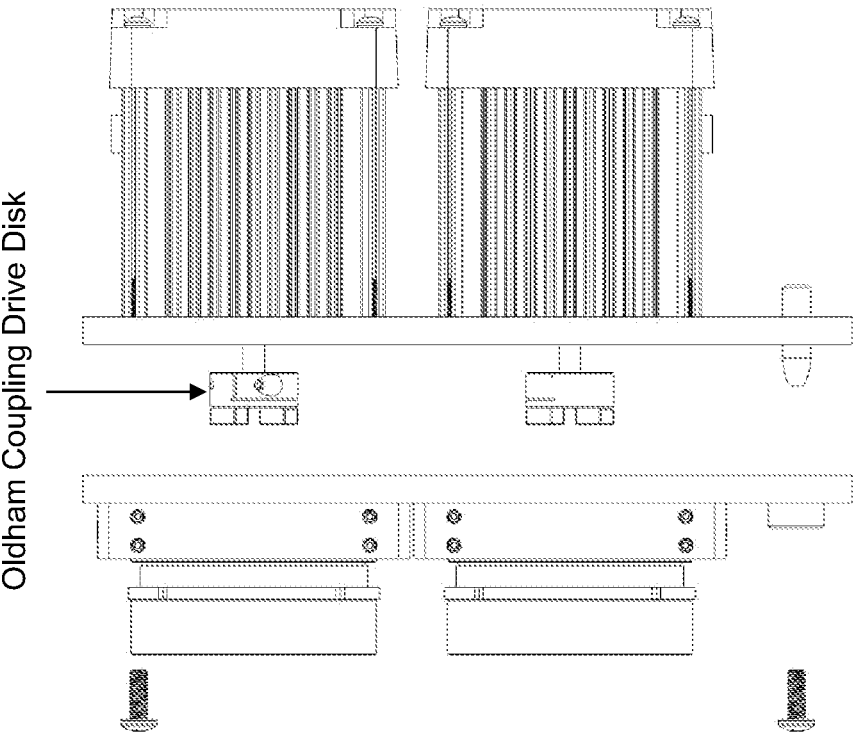
Figure 14D:
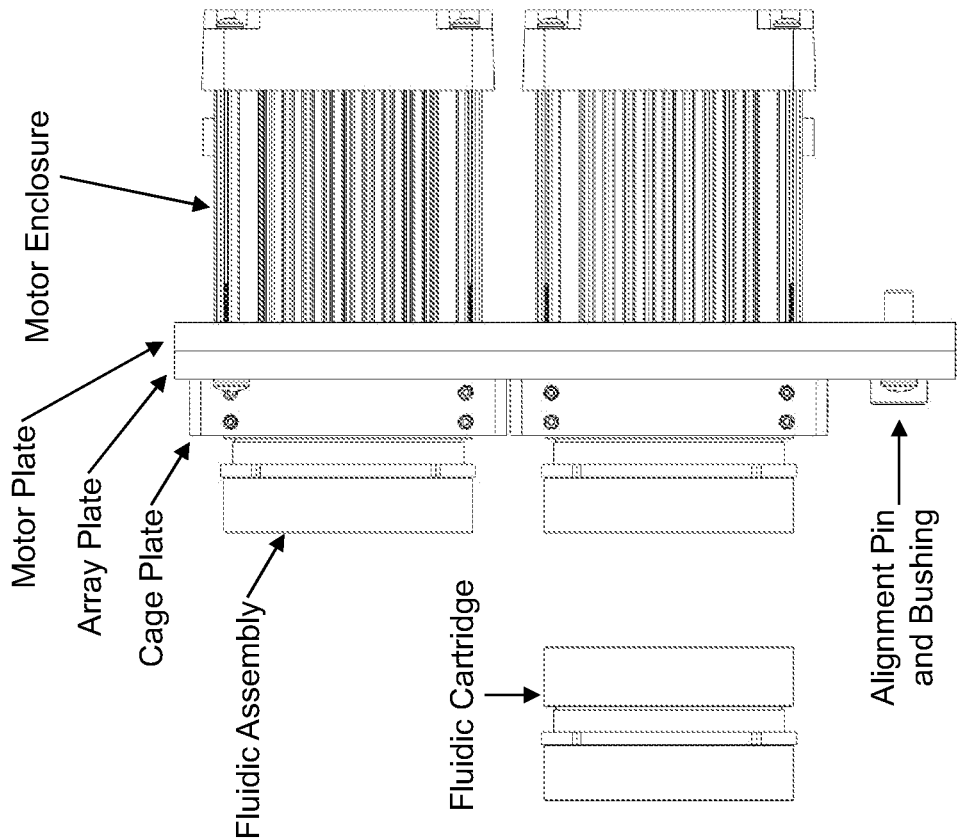
Figure 14H:
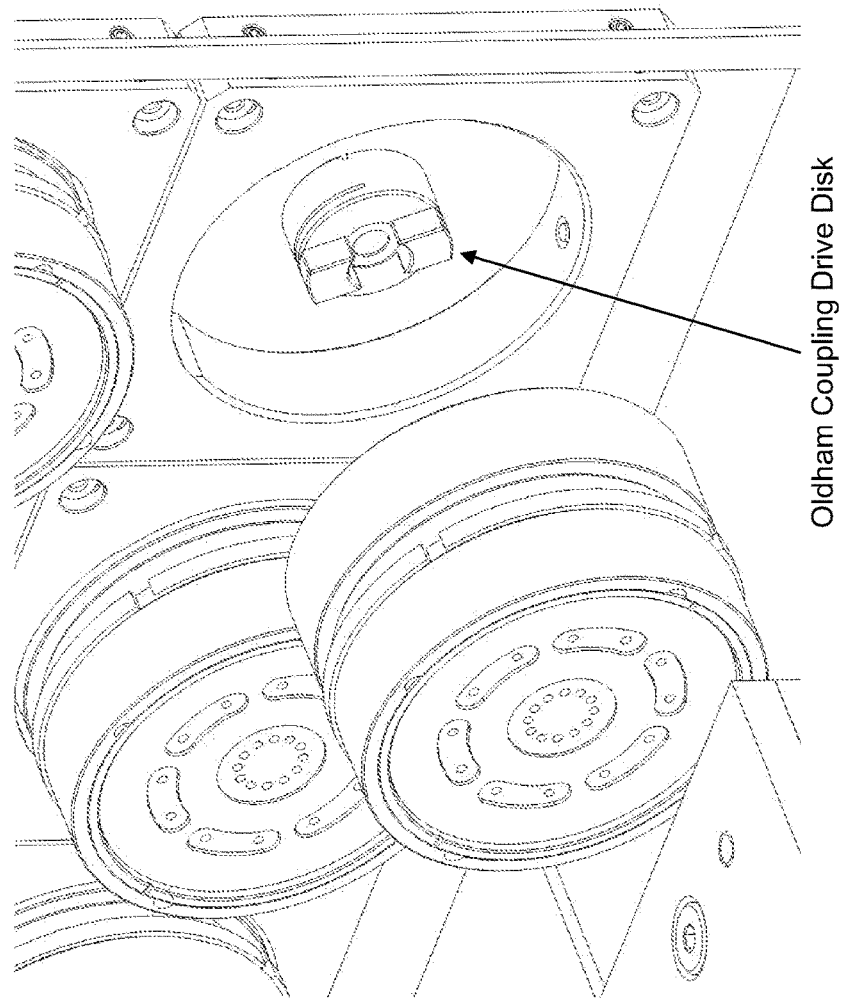
Figure 14F:
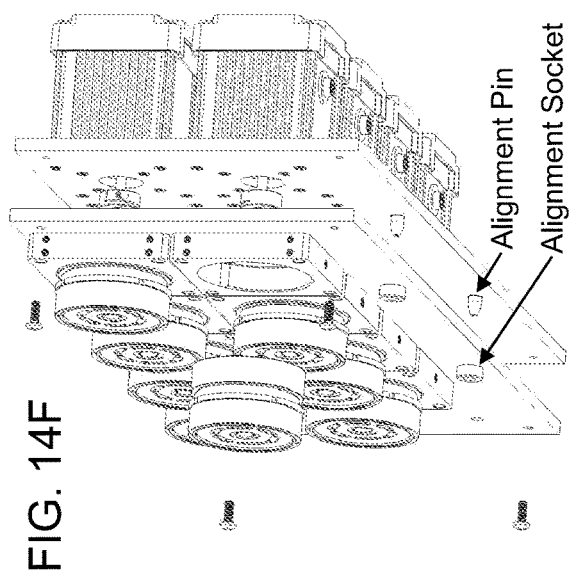
Figure 14G:
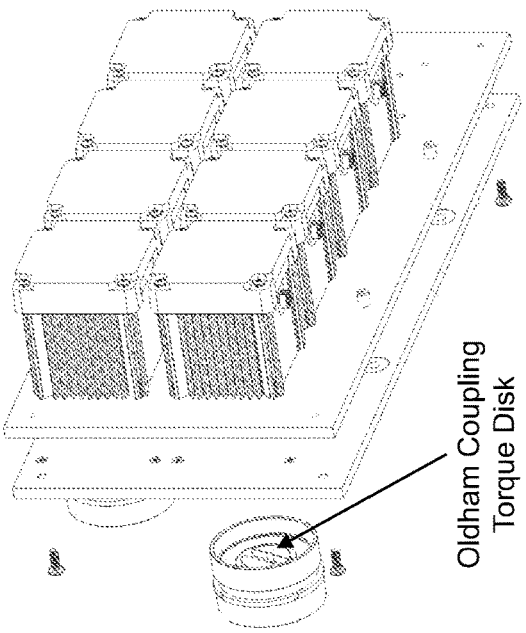

Coordination of both hardware and software is required to implement a robust robot scientist. FIG. 14A shows the four subsystems required to create a continuous automated perfusion culture analysis system (CAPCAS): artificial intelligence/machine-learning software (CAPCAS-AI), information technology and hardware control (CAPCAS-IT), distributed hardware for fluid and plate handling (CAPCAS-HW), and on-line, at-line, and off-line analytics (CAPCAS-AN). FIG. 14A summarizes the operations associated with each subsystem.

FIGS. 14B and 14C show one embodiment of the chassis that could contain one of the 12- or 48-channel fluidic module shown in FIGS. 8A-8J. The chassis is self-contained and provides sterility, thermal, and gas control. There are three drawers, one for the single 96-well input reservoir plate, another for the 48-well deep-well chemostat plate, and the third for one 96-well sample-transfer well plate. The drawer slide mechanisms can provide for full extension of the plate outside of the enclosure to allow access of the plate by an external robotic arm (FIGS. 16D and 16E), automatic de-lidding upon insertion, and automatic elevation of the de-lidded plate to engage with the fluidic station that is suspended above the drawer. Drawers could be configured to handle more than one plate at a time.

To provide thermal control and ensure easy sterilization of the components in contact with biological samples, there are separate compartments for motors/electronics and fluidics. With this approach, the fluidic circuits in FIG. 8A are divided into sub-modules that can be installed and/or replaced individually and treated as assemblies that would be disposed of or reconditioned after a series of experiments: the input module that contains the media microformulator and the input reservoir plate, the chemostat modules that include the chemostat media delivery pumps, and the output module for chemostat media collection. FIGS. 14D-14G provide details that demonstrate how the motor and fluidic assemblies can be readily connected or separated, as required for exchange of fluidic cartridges to revise an experimental design, to replace worn fluidics, or for sterilization. This approach would obviate the need for a user to interact with the electronic assemblies within the motor compartment. Matching bulkhead connector mounts on the motor plate and the array plate would support connection of the sensors shown in FIG. 8A with control electronics in the motor compartment.

An embodiment based upon FIGS. 14A-14H can easily support 48 chemostats using the fluidic layout in FIG. 8A, or up to 144 chemostats if drawer access was needed only for the output plates and the chassis were to hold three 48-well chemostats.

Automating and Parallelizing Continuous Perfusion

A key limitation of conventional well-plate robotics as shown in FIGS. 2A-2B is that a limited number of plate-moving stations or tools become the workflow choke points between single-operation work stations, such as incubators, fluid handlers, and plate readers. This can be acceptable in simple, synchronous, linear "load-expose-read" high-throughput screening for drug discovery workflows, which seldom have any in-process adjustments. However, this is not an optimum topology for a massively parallel, robot-scientist workflow: Within a single CAPCAS unit, each of 48 wells in a multi-well chemostat plate could be running a different experiment, each of dozens of chemostat plates implementing a totally different protocol independent of the timing stage of other plates, and all protocols being evolved in real time in response to on-board sensors and machine learning.

Accordingly, the CAPCAS units are placed in an enclosure having a plurality of decks, each deck having a plurality of stations, each station being configured to accommodate a plate/module of a fluidic system.

In one embodiment, the enclosure is configured such that each station is accessible by a robot for plate/module installation and/or removal, and two or more robots are simultaneously operable on a deck without interference.

In one embodiment, the enclosure further comprises an elevator for moving a robot between decks.

In one embodiment, each deck is connected to a continuous circulation fluid bus and a power bus.

In one embodiment, the enclosure is configured to serve as an environmental chamber, with complete control over temperature, gas composition, and humidity, with HEPA filtering to maintain sterility.

To support such a multi-threading robot-scientist environment, we will develop a compact, autonomous, holonomic iPlateBot, a four-wheeled plate-transporting robot (FIGS. 15A-15D), which will be able to move in arbitrary x-y directions on a CAPCAS deck (FIGS. 16A-16E), and lift a plate into position beneath any of multiple stations at which the automated perfusion systems are suspended. Computer-controlled latches at the station (FIGS. 15C and 15D) will hold the plate once delivered, freeing the iPlateBot for another task. For the embodiment in FIGS. 8A-8J, a single module has three plate stations, while a single deck shown in FIGS. 8E and 8F will hold three modules and hence have 9 plate stations—three input reservoir plates, three chemostat plates, and three output plates. The WiFi-controlled microprocessors on the iPlateBot will control the motor on each holonomic wheel so that the iPlateBot can, for example, enter from the front of a plate and depart from the side, allowing for a streamlined, self-organizing, and coordinated flow of multiple iPlateBots on a single deck. The embodiment in FIGS. 8G and 8H would have four three-plate modules per deck, all serviceable by multiple iPlateBots. FIGS. 8I and 8J would further increase the number of chemostats on a deck by eliminating the Output Plate by utilizing only on-line analyzers, such as direct-inject SPE-IM-MS systems and using a single set of reservoir plates to service three chemostat plates, which would serve as biological replicates.

Different iPlateBots can be configured for specific functions. Since the CAPCAS iPlateBots will operate without the physical constraints of tracks or fixed arm geometry, optical sensors and kinematic alignment fixtures will ensure that the iPlateBot arrives at each location with the specified accuracy. One or more decks could have a charging station to which an iPlateBot can return when necessary. We estimate that two iPlateBots can service a deck without interference, but we could add more if needed. The iPlateBots will in effect provide swarm servicing of the CAPCAS multi-well chemostats and bioreactors. Consumers now enjoy autonomous household vacuum robots, and CAPCAS will have the equivalent for plate handling, thereby breaking the bottleneck posed by conventional laboratory automation.

Other stations external to the CAPCAS unit could serve as pickup and drop stations for well plates, wherein the iPlateBot would deposit or pick up a well plate at a particular location that would be available for pickup or deposit by an external robot arm, respectively. As an alternative to having an iPlateBot deliver a well plate to a HTS system, as shown in FIGS. 2A-2B, the CAPCAS unit could be placed next to a HTS work center, as shown in FIG. 16E.

Figure 15A:
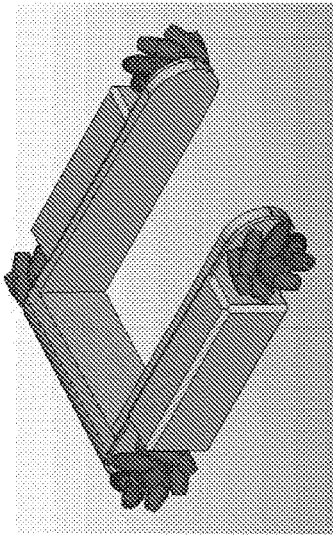
FIGS. 15A-15D show the iPlateBot holonomic plate-handling robot, according to embodiments of the invention.
Figure 15B:
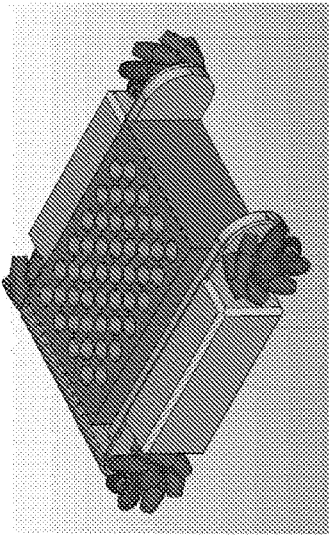
Figure 15C:
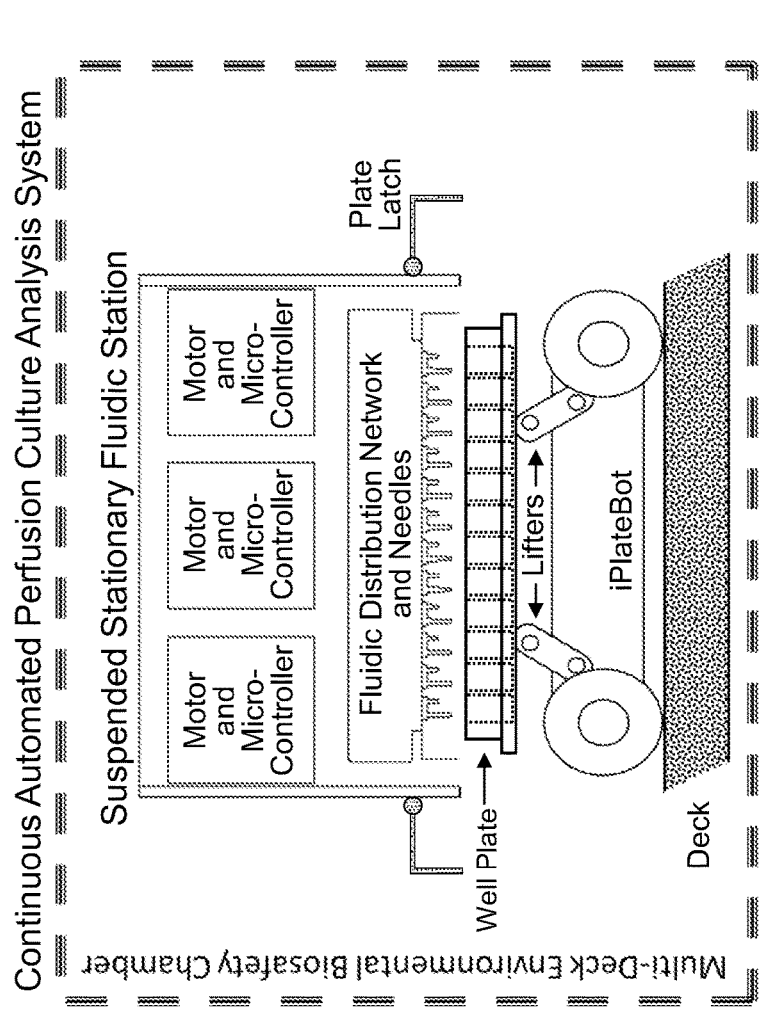
Figure 15D:
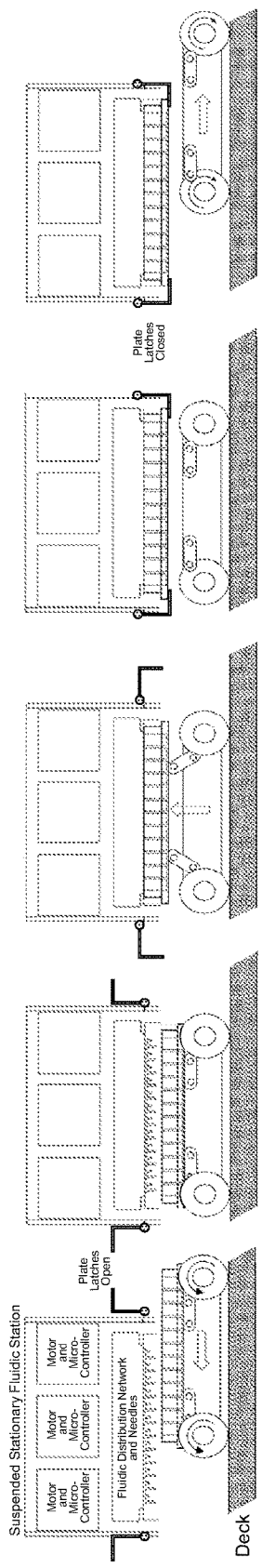

FIGS. 15A-15B show details of the iPlateBot holonomic robot that can be used within CAPCAS. Because the center of the iPlateBot is open, as shown in FIG. 15A, has by design a low height, can engulf a well plate as shown in FIG. 15B, and has a means to lift the plate vertically into an overhead fluid-handling station, as shown in FIGS. 15A-15B, the iPlateBot can drive up to the lid storage station, lift the lidded plate into a lid-retention mechanism such that the lid is latched in place, lower the de-lidded plate, move to an adjacent fluid-handling station, lift the plate into the plate-retention mechanism such that the plate is latched in place, lower its lifting mechanism, and depart that station for another assignment. The sequence can be summarized as drive in, store the lid, lower the plate, move the plate to a fluid-handling station, lift the plate, latch the plate, and leave. When the fluid-handing operations, such as a long chemostat or bioreactor run, are complete, an empty iPlateBot can return to the fluid-handling station, lower the plate, relid it, and take it to its next destination.

Specialized iPlateBots can provide other services within the multideck enclosure, including local UV sterilization, replacement of fluid-handling modules, delivery of a compact plate reader to any plate, delivery of a multi-motor well-stirring system, and delivery of reagent supply plates or reservoirs. The iPlateBot can deliver bulk media to fluid-handling stations, for example media that is stored in a small box that contains degassed media frozen in gas-impermeable bags, allowing fully automated media transport and delivery. We have shown that it is possible to create a box/bag system that has auto-sealing Luer locks such that a robot such as the iPlateBot or a robot arm could use a push-to-fit bag connector to deliver multiple bags with premixed contents to a fluidic control station. Small collection bags can hold 12 mL, and larger ones can hold 60 mL. This bag system could also provide sterilization solutions, such as strong acids or bases, or serve as wash or waste containers on each end of a valve system (e.g., the first and last port).

Because they are compact, low inertia, low traction, and low speed, the iPlateBots do not present an impact risk to humans, as do robot arms, so the iPlateBots can operate inside of a cell culture hood that is being used simultaneously by a human without endangering the human. Entrance and exit to the iPlateBot can either be through a bench-top-level portal in the back or side of the hood, or a simple elevator installed in the bench top connecting to a tunnel to another hood or multi-chemostat enclosure. Because of the low height of the iPlateBot, it can even enter or leave a hood by moving under the sash without having to raise the sash above the normal height that allows a human to insert a gloved forearm into the hood.

Figure 16B:
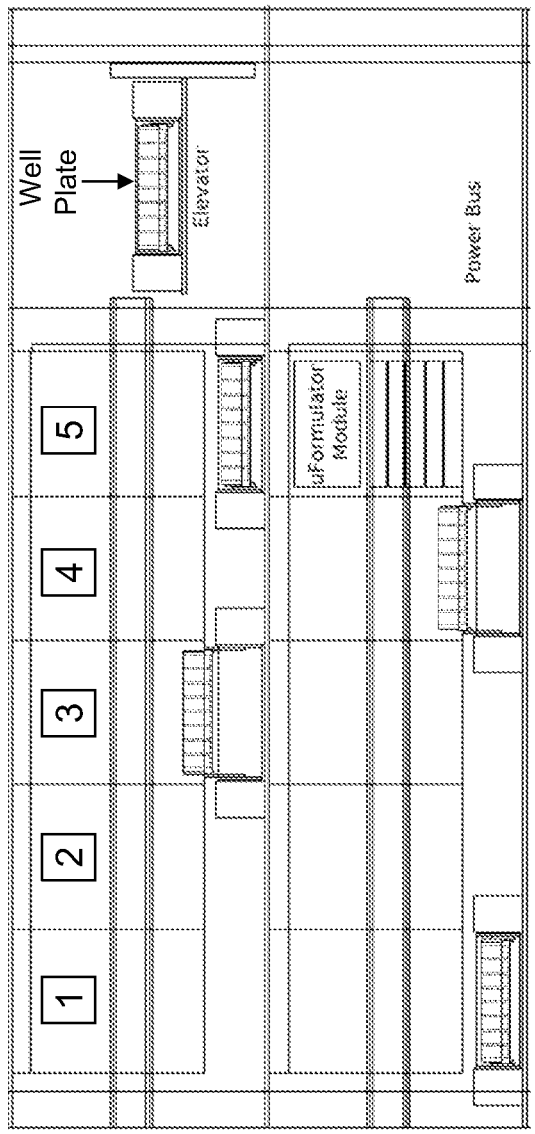
FIGS. 16A-16E show how iPlateBots would operate in a CAPCAS enclosure, according to embodiments of the invention.
Figure 16A:
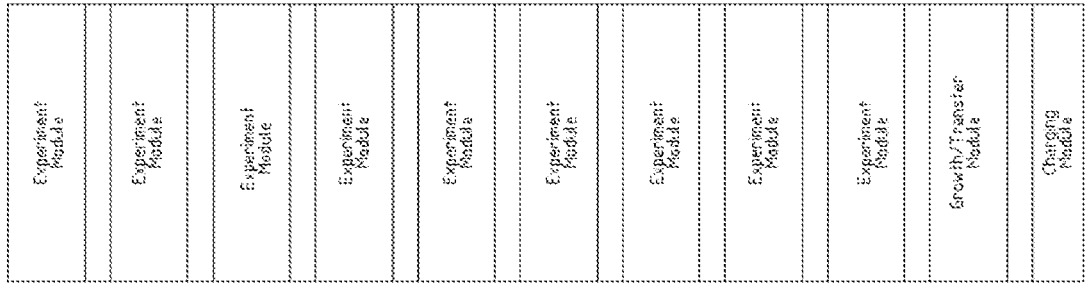
Figure 16C:
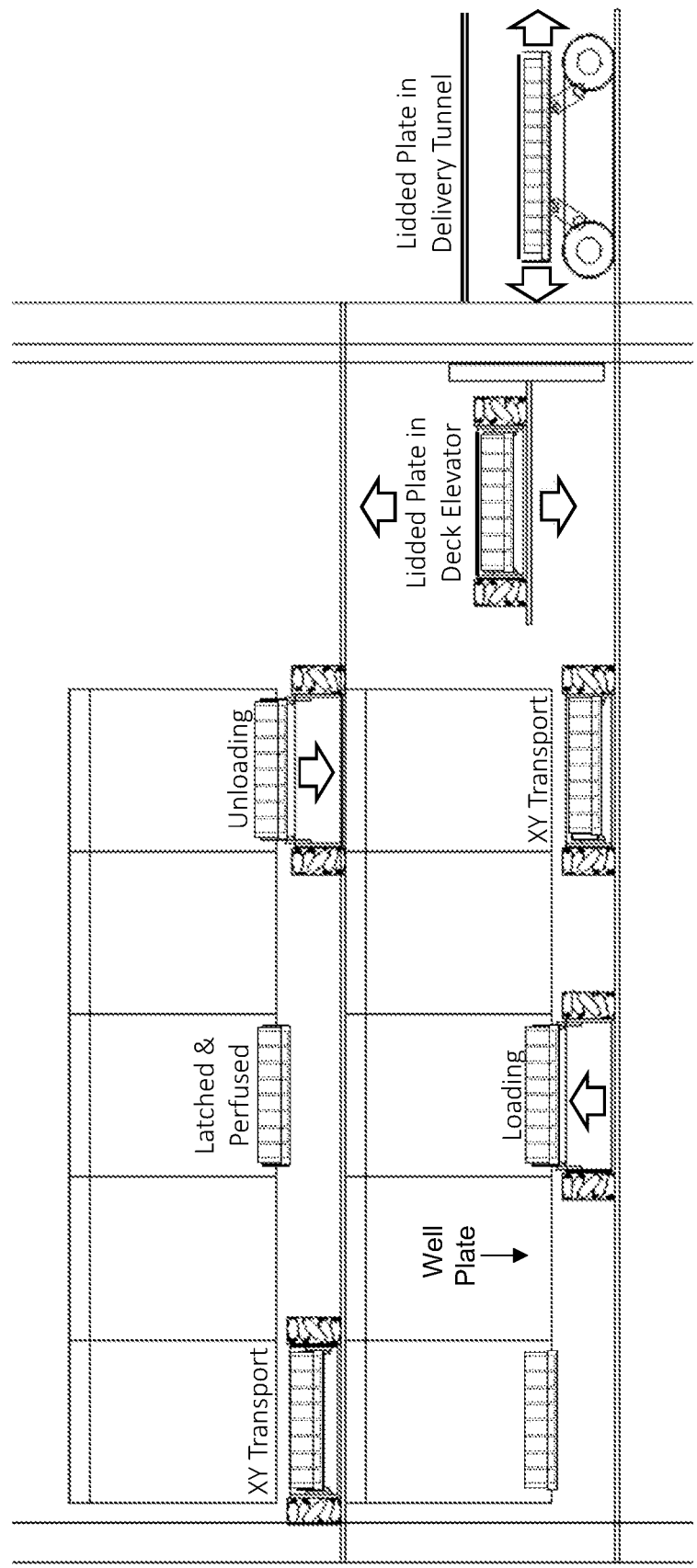
Figure 16D:
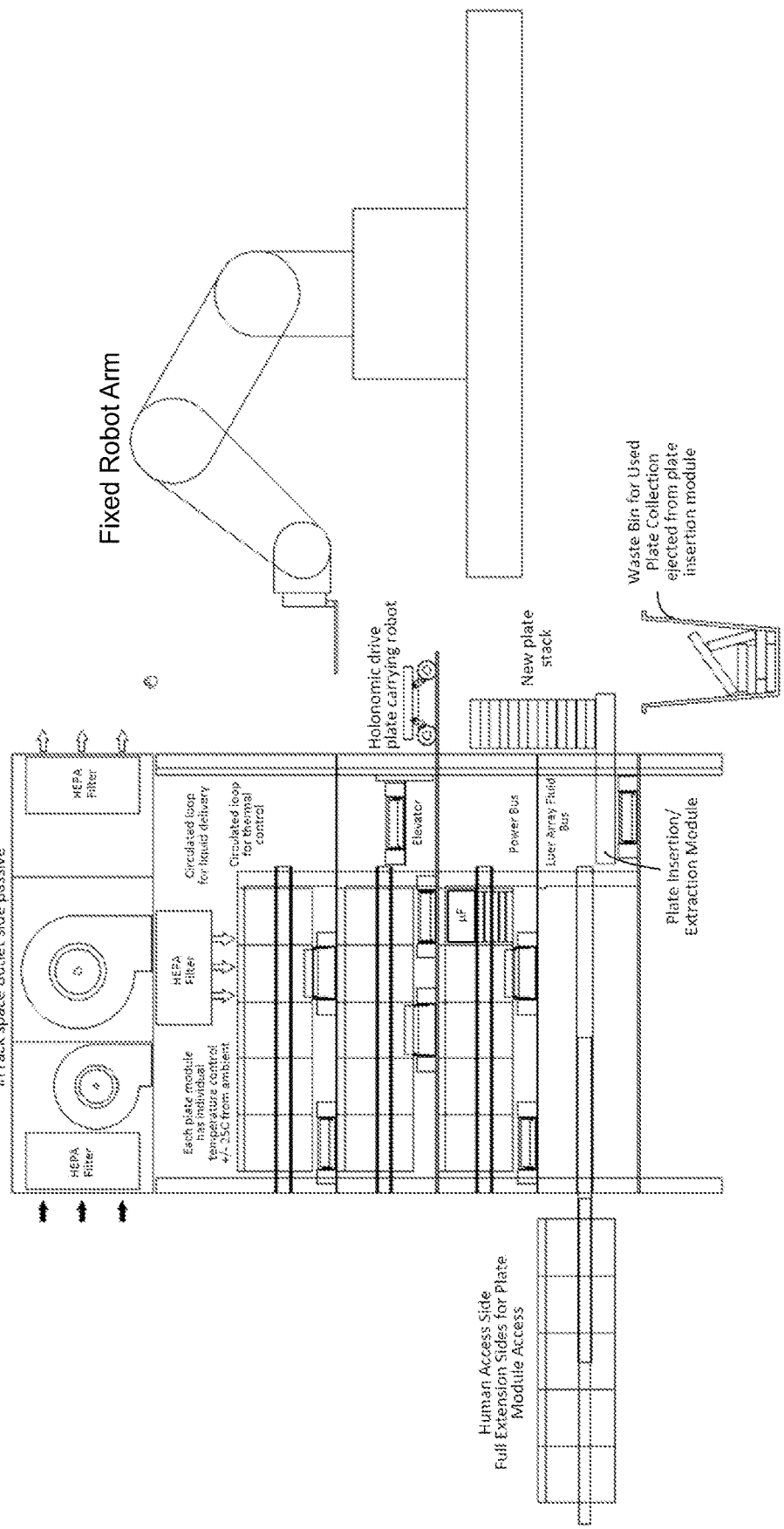
Figure 16E:
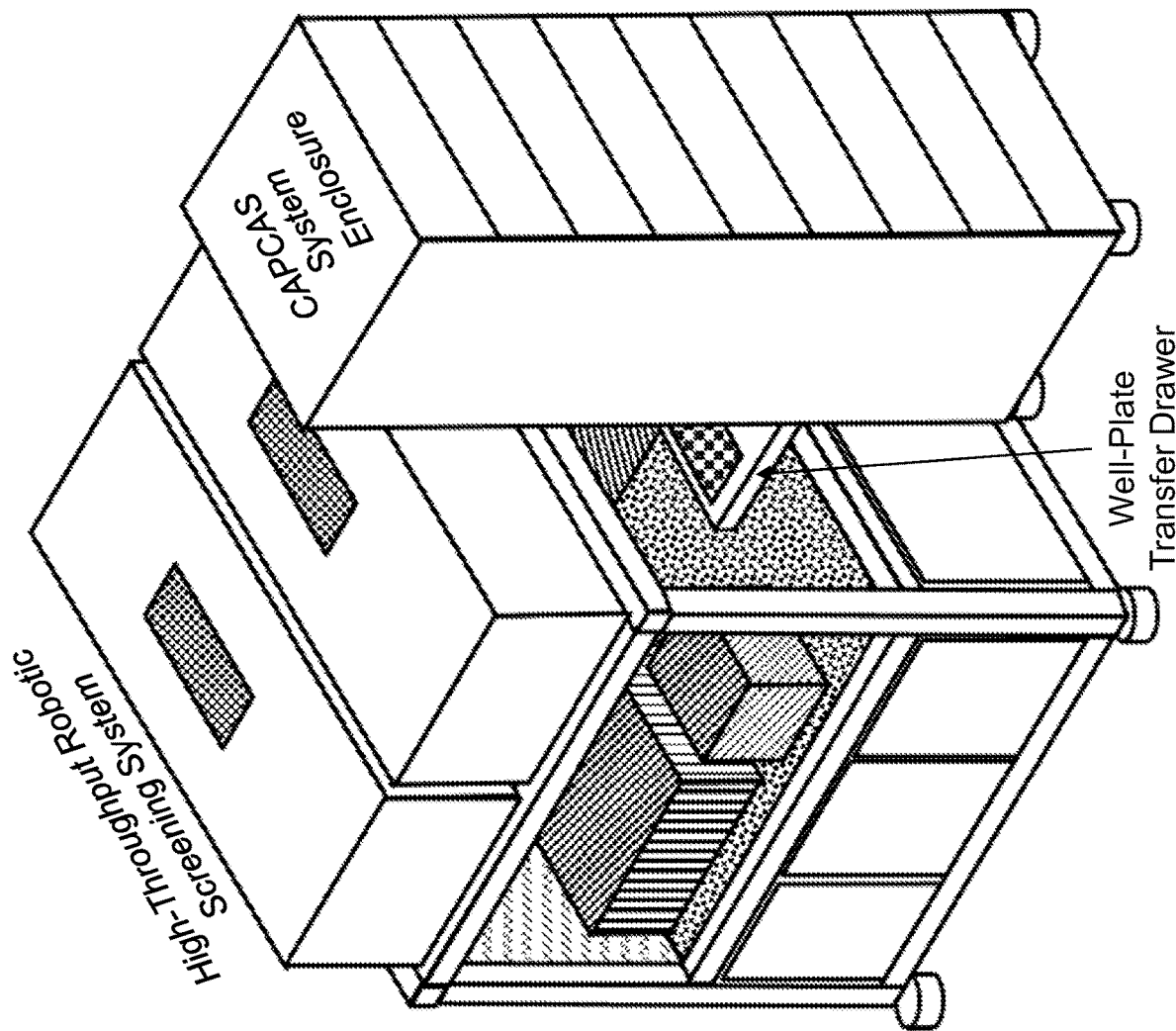

FIGS. 16A-16E shows one embodiment of how modules can be positioned and serviced in the system rack. In FIG. 16A, the system is installed in a 42U telecom/server rack, where one "U" or rack unit is a measurement of the height of a piece of computer or network gear that is designed to fit into a standard 19" or 23" electronics rack. In the rack, this embodiment has nine experiment modules that are 4U tall and have 12 plates each. One module in the rack will be dedicated to cell growth and plate inoculation, and another will be dedicated to charging the iPlateBot robots. In an alternative embodiment, a charge-in-place scheme will be implemented on the plate receiver modules. The rack is insulated and appropriately sealed so that it also acts as a sterile cell culture incubator.

FIG. 16B shows one possible configuration for two of the 4U segments of a telecom/server rack incubator: Stations 1-4 are plate receiver modules for plate perfusion, while Station 5 has a fluidic MicroFormulator to provide mixed media to all modules on the level plus storage space for lids. Each level can be connected to a continuous circulation fluid bus and a power bus.

FIG. 16C shows iPlateBots in an automated incubator. The iPlateBot delivers a plate to an assigned fluidic station in the incubator. The plates are raised and latched into the fluidic handling station. The iPlateBot departs for another assignment with the elevator, and if the plate it is carrying is needed outside the incubator, the iPlateBot can depart through a delivery tunnel. The fact that a large number of independent iPlateBots can operate within a single enclosure and move both vertically and horizontally in an asynchronous, swarm-based manner enables a level of parallel plate-processing that cannot be achieved in a HTS robotic system which might have at most several different robot arms, each of which can serve only a fraction of the footprint of the HTS system. Plates that are in use either for compound or cell delivery, as active chemostats, or plates that collect cells and media for analysis are suspended from above, leaving the space beneath each plate open for an iPlateBot to move in the X or Y directions on that deck. If a 12-position deck has, for example, nine fluid-handling stations, a plate-filling station, and two lid storage areas, multiple iPlateBots can move between any of these stations and also pick up and deliver plates at stations on other decks in the enclosure or even to other enclosures or workstations connected by tunnels or transiently opened drawers.

FIG. 16D shows the invention operating in a rack that is fully equipped to serve as an environmental chamber, with complete control over temperature, gas composition, and humidity, with HEPA filtering to maintain sterility. The human access side can be opposite to that serviced by the robot arm to protect the human operators.

FIG. 16E shows an embodiment in which the rack that serves as the multiwell chemostat system enclosure can be placed immediately adjacent to the HTS robotics system in FIGS. 2A-2B such that a computer-controlled drawer in the chemostat system's enclosure can open and receive well plates from the HTS system, or the chemostat system can deliver a well plate to the HTS system for processing or analysis.

In comparison to the robot-arm-based HTS systems such as FIGS. 2A-2B, the iPlateBot operating both vertically and horizontally within the chemostat system enclosure provides a compact means to have a large number of independent iPlateBots moving in the X, Y, and Z directions. With appropriate configuration of each fluid-handling hardware and needle array above each station, it will be possible for an enclosure to contain a variety of different fluid-handling stations, including ones for 6, 12, 24, 48, 96 and higher-density well plates. Fluid-handling stations could likewise be configured to exchange fluids or even continuously perfuse one or both sides of 6, 12, and 24 Transwell plates. As we will show later, the fluid-handling stations can readily service gravity-fed organ chips, providing, for the first time, a means to massively parallelize organ-chip assays. Similarly, the fluid-handling systems could be configured to provide long-term fluid maintenance for organoid and biopsy chips.

System Sensors

Central to using self-driving laboratories to advance systems biology research is the ability to acquire massive amounts of data from a variety of sources. We next outline what types of data have already been shown suitable for massively parallel acquisition and would be readily incorporated into CAPCAS.

We have previously described the use of multi-potentiostats to quantify the metabolic activity of cultured cells.[71,73,75,76,94] Sensors for electrochemically quantifiable analytes such as glucose, lactate, oxygen, pH, glutamate, alcohol, and neurotransmitters could be implemented either at the level of each channel, or at the directed output of a sensor valve. FIG. 6B shows our previously reported micro-clinical analyzer,[41-43] which provides automated calibration of electrochemical sensors, which are prone to drift,[71,73,75,76,94] and was the basis for the microformulator in FIG. 6C.

Figure 17A:
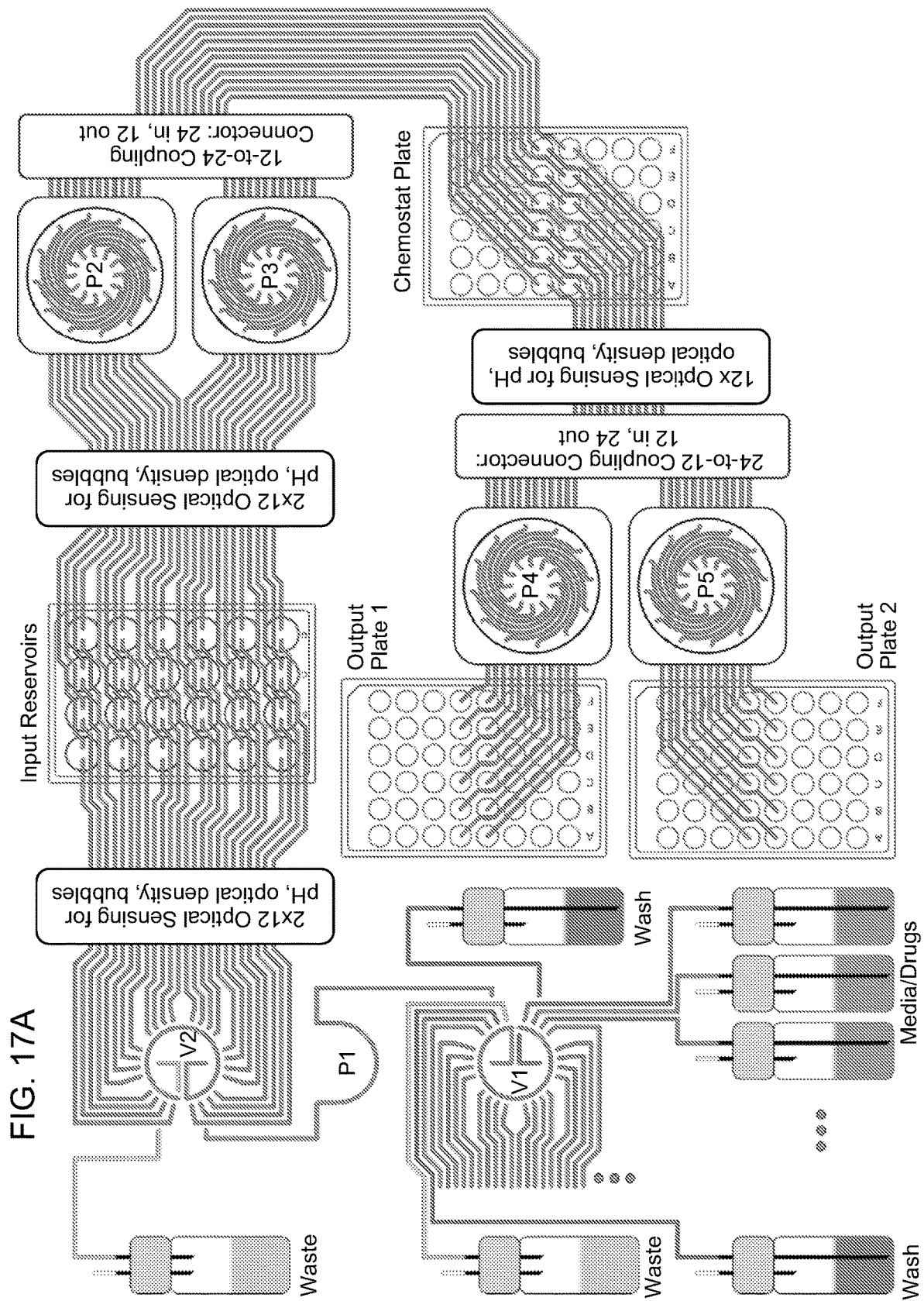

The sensing and regulation of pH, possibly every minute, is critical to the operation of microbial chemostats, particularly when cells are in the log-growth phase. Individual electrochemical pH (or other analyte) sensors could be installed either in the fluidic lines on both the input and output of the chemostat or bioreactor plate, e.g., as shown in FIGS. 8A and 17A. The sensors could be electrochemical sensors driven by potentiostats, or optically reporting sensor disks. Alternatively, the culture medium could include one or more colorimetric pH reporters for optical measurement of pH. If there were concerns about the biological effects of the colorimetric pH reagents, they could be added not at the input of the bioreactors/chemostats, but at the outputs, where even higher concentrations would be acceptable since the cells could be disposed of after measurement.

There are several ways in which pH can be controlled in the massively parallel CAPCAS. The easiest would be to formulate parallel sets of input reagents that feed V1 in FIG. 8A, one with low pH and another with high pH. The formulation process specified by the CAPCAS control software could then adjust the ratio of all solution pairs used to formulate the media that will be delivered to each well. The time response of this system will be determined by the cycle time between the two input reservoir sets in FIG. 8A, which in turn would be set by the volume delivered to each set of input reservoir wells. To achieve the fastest possible pH control, another set of pumps and valves, and possibly needles, could be inserted into each chemostat/bioreactor to allow direct injection of a strong acid or a strong base, as needed to adjust the pH of that well to the desired value. Similarly, the correcting acid or base could be delivered by two dedicated ports in V1. In any case, the CAPCAS control software would be responsible for the concentration and pH calculations needed to control any or all of the microformulator deliveries.

Critical to chemostat and suspension bioreactors is the measurement of cell density and characteristics. A key challenge in the use of small-volume suspended-cell bioreactors is to measure the number of cells in the bioreactor or the bioreactor effluent. A standard means to do this is to measure optical density (OD), which may require sequential dilutions to allow measurements over a wide range. This is difficult to do with adequate dynamic range using small fluid volumes. As shown in FIG. 17A, it will be possible to include in each chemostat/bioreactor effluent channel an optical sensor with a defined optical path along which the optical density can be measured by using a light source such as a light-emitting diode (LED) and a photodetector such as a phototransistor. Appropriate control of the LED intensity and detector gain can extend the range of OD measurements with a single instrument. Similarly, the optical path length can be chosen to match the experimentally encountered range of ODs to the dynamic range of the OD sensor. Alternatively, sensors with different path lengths could be operated in parallel. Finally, a valve could be added to dilute effluents with very high ODs, again with the diluted fluids being sent to waste rather than being reinjected into the process stream. Finally, an OD sensor could be configured to support measurements or even imaging of the transverse scattering of light along the optical path length, which contains information about the cell size distribution.

The OD measurement system or an equivalent LED/photodetector pair can be used to detect bubbles in any of the lines shown in FIG. 8A or 17A. Given that the pumps and valves can be controlled by the CAPCAS-IT software, the presence, absence, or speed of a bubble can serve as an excellent indicator of whether a reservoir is empty, or the end of a time- and space-limited sample has passed the detector. By proper timing of both pumps and valves, small bubbles could be intentionally injected into any tube, a pair of bubble detectors could be used to measure the time-of-flight of the bubble, and hence the pump flow rate. The bubble could then be ejected from the same port from which it was drawn. We have shown that this approach can be used cyclically with a single bubble to measure flow rates at different pump speeds.

An alternative is to measure the electrical impedance of the cell suspension. One embodiment of this is as follows. Each line that removes fluid from a chemostat or suspension bioreactor or other biodevice would contain at least four in-line electrodes, possibly in the form of hollow silver cylinders whose interior surfaces were chlorided. The proximal and distal electrodes would be utilized to deliver a known current that flowed through the interior of the tube between the proximal and distal electrodes. The two middle electrodes would then be used to measure the AC voltage generated by the electrical impedance of the cells and the media within the tube. An impedance bridge circuit would be used to interpret the relationship between the amplitudes and phases of the drive current and the measured voltage in terms of a complex electrical impedance. By sweeping the frequency over a predetermined range of frequencies, it would be possible to identify the contributions to this complex impedance from the electrical conductivity of the fluid, the dielectric properties of the cell membranes, and the electrical conductivity of the cytosol within the cells. The four-electrode system would have reduced sensitivity to biofouling than a two-electrode impedance-measuring system. Electrical impedance would provide substantially more information than a measurement of optical density, and should reflect cell size and shape. Electrical multiplexing may be easier and less expensive than optical multiplexing. With appropriate electronic or mechanical switching, a single impedance bridge system could interrogate multiple fluidic lines. The required electronics and microprocessors are sufficiently compact and inexpensive that a large number of systems could be employed. Electrical connections between the tubing and the impedance bridge would be simpler to make and break than optical connections and would be consistent with the use of a totally disposable fluidic system.

Measurement of environmental variables within the CAPCAS enclosure would ensure that the chemostats/bioreactors were operating at the needed temperature, humidity, and gas concentrations (if the gas control is through the well-plate headspace rather than in a sealed volume above each well). Airflow and pressures could be measured to ensure that the CAPCAS enclosure pressures were appropriate for the required biocontainment, for example at negative pressure for use in BSL-3 and BSL-4 facilities.

Mass spectrometry can be incorporated into CAPCAS, a feature that will make CAPCAS ideal as a robot scientist in that the samples from each chemostat or bioreactor will be directly injected, after on-line processing, into an on-line mass spectrometer for untargeted metabolomics. We have already shown that it is possible to couple, in real time, the effluent of microfluidic traps containing Jurkat cells to a custom, automated ultraperformance liquid chromatography (UPLC) desalting system and an ion mobility-mass spectrometer (IM-MS). This allowed us to study with three-minute temporal resolution how the cellular metabolome is affected by drugs.[57,95] While not yet done on-line as will be possible with CAPCAS, we have used UPLC-IM-MS and MS-MS to study the metabolomic and transport responses of cells in an organ-on-chip model of the blood-brain barrier.[96-98] All of these measurements could be readily performed with CAPCAS.

Figure 18B:
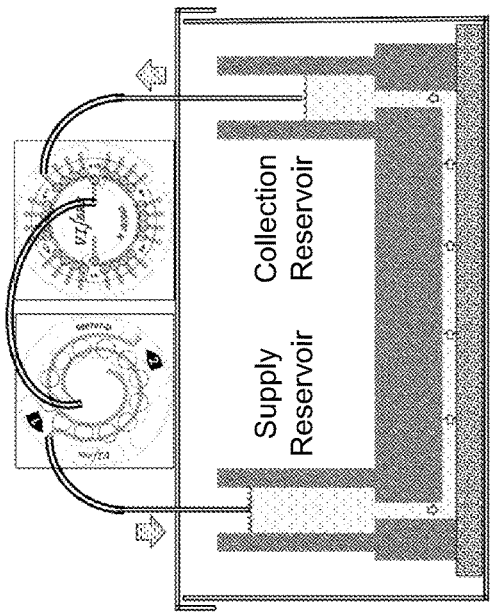
Figure 18D:
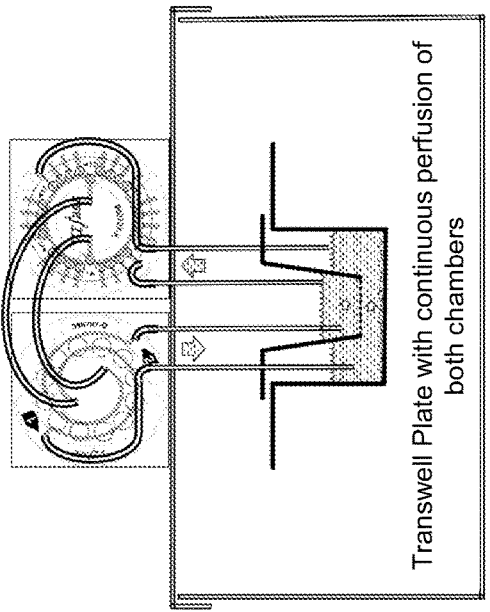
Figure 18A:
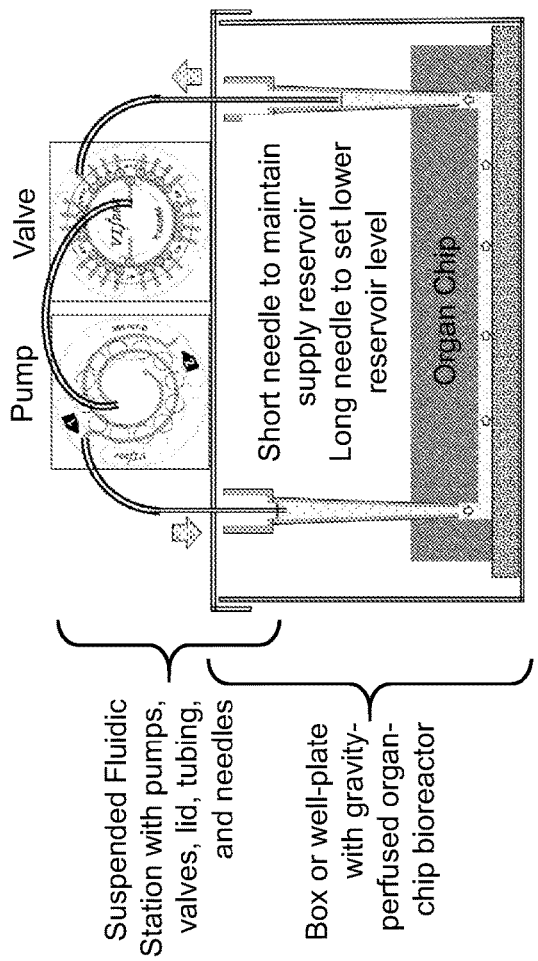
Figure 18C:
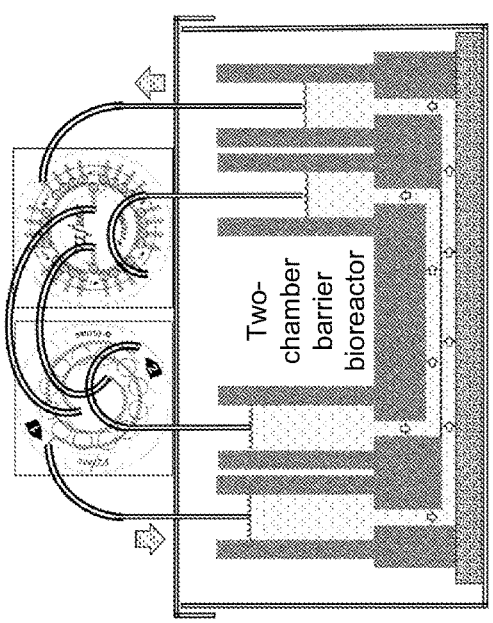
Figure 18F:
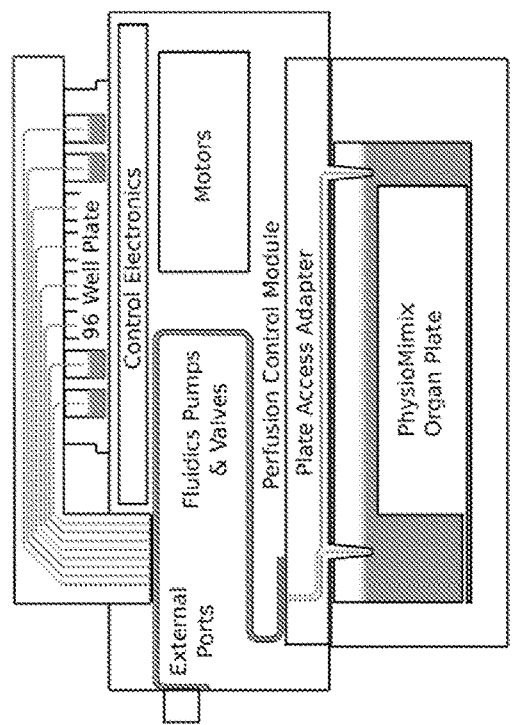

The heart of the CAPCAS embodiments shown in FIGS. 7B, 8A and 17B would be an instrument capable of untargeted metabolomics or proteomics measurements, such as would be conducted by direct injection of chemostat effluent into an ion mobility-mass spectrometer (IM-MS)[57,95,99,100] that is preceded by an Agilent RapidFire Solid Phase Extraction (SPE) desalting system[59] that in turn delivers the desalted sample to an Agilent 6560 ion mobility quadrupole time-of-flight (IM-qTOF) mass spectrometer. RapidFire uses 4 ml SPE cartridges with 10 sample volumes. The aspirate, load/wash, elute, and re-equilibrate phases require only 10 seconds, and the automatic and rapid SPE cartridge changer allows sequential analysis using different cartridges (e.g., C18, HILIC, and graphitic carbon) for the broadest untargeted metabolite coverage. At 10 seconds per sample, the SPE-IM-MS system will be able to perform three SPE separations in both positive and negative mode for each of the 1144 chemostats in Example 6 in FIG. 17C every 22.4 hours. Alternatively, a single chemostat could be sampled continuously with a time resolution of 10 s, or other arbitrary combinations can be used. FIG. 17C presents SPE-IM-MS processing times that could be achieved in various CAPCAS embodiments. FIG. 18F lists the numbers of bioreactors, chemostats, well plates and organ chips that could be achieved in different CAPCAS embodiments.

Transcriptomics data for the cells within each chemostat or bioreactor would be facilitated by the use of the output plate in FIG. 8A, in that at the end of an experiment, half of the cells would be removed and delivered, well-by-well, to the output plate, while the other half would remain in the chemostat plate. Both plates can be quickly removed from CAPCAS, one processed for both extracellular and intracellular proteomics and metabolomics,[101] and the other for untargeted transcriptomics using RNAseq or another platform. The advantage offered by CAPCAS is that hundreds or even thousands of different experiments could be conducted in parallel, providing correlated multiomics data sets that would be ideally suited for analysis by deep-learning neural networks and other AI techniques to establish heretofore unrecognized correlations between genes, proteins, and metabolites. Such experiments could be performed in either classical, open-loop mode with the human operator specifying the experimental parameters and cell strains studied, or in a robot-scientist, closed-loop mode where the AI/ML software guided these selections. It is worthy of note that any delays associated with cell processing, measurement, and the AI/ML analysis of the large multiomics data sets could be accounted for by interleaving multiple experimental series into a master set of experiments, such that the time interval between any particular experiment type would be set by the total analysis delays for that group. The longer the delays, the larger the number of different experiments that would be interleaved in the master set of experiments.

There is an extensive literature on the use of Raman spectroscopy to monitor metabolism during yeast fermentation, the culture of other microbes, and the culture of mammalian cells.[62-67, 102-104] FIG. 17B shows how easy it would be to connect the CAPCAS Sensor Valve (V3) in FIG. 8A or the Sensor Selector Valves (V6) in FIG. 8I to one or more analytical instruments.

Figure 4:
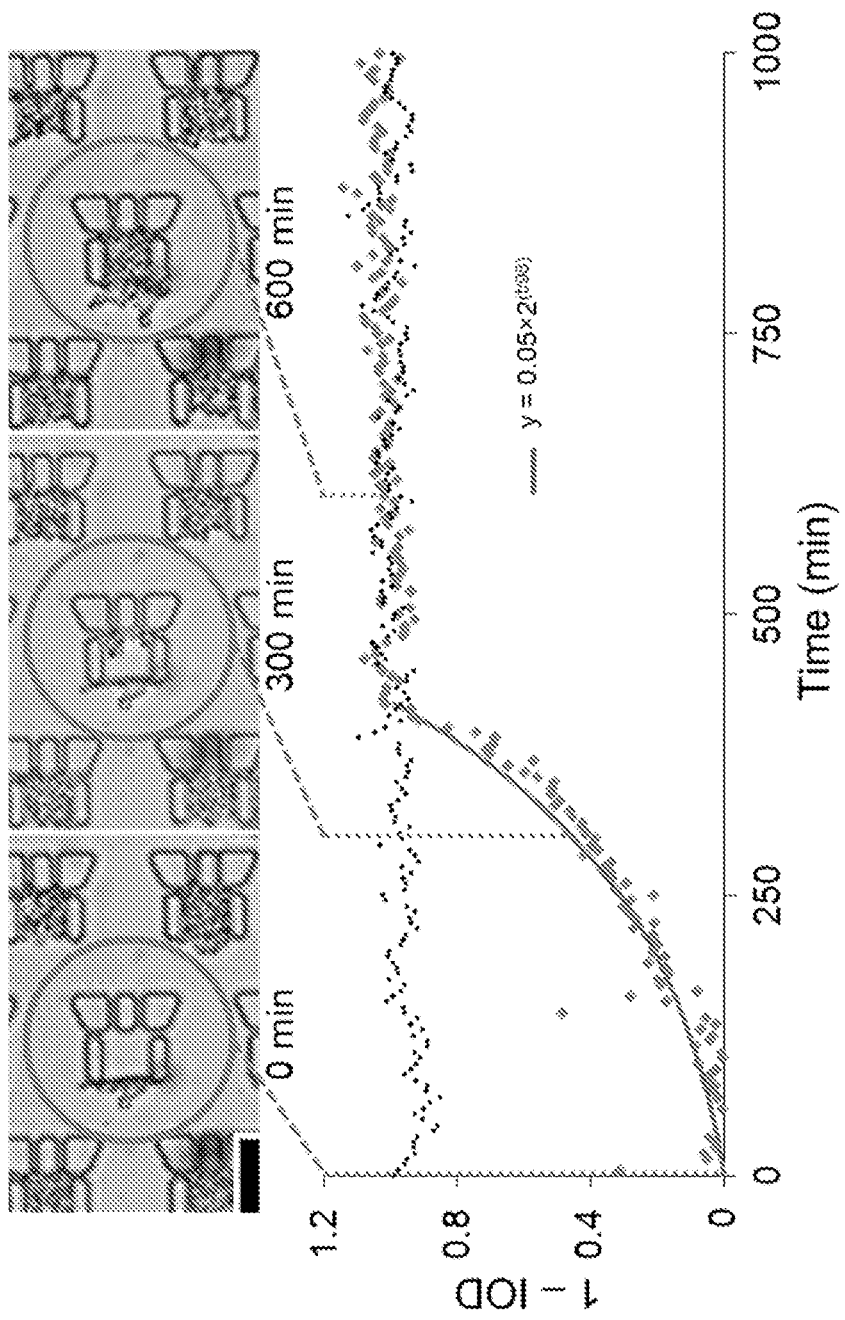
FIG. 4 shows the exponential growth of S. cerevisiae in a 3.2 pL occlusion-limited trap[9].
Figure 5B:
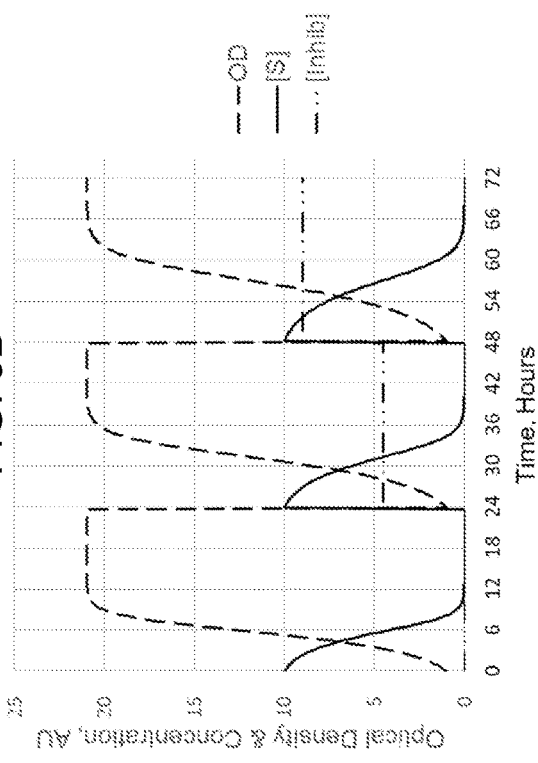
FIGS. 5A-5D show computer simulations of metabolic inhibition experiments using batch and continuous culture of adherent eukaryotic cells and suspended microbial cells.
Figure 5A:
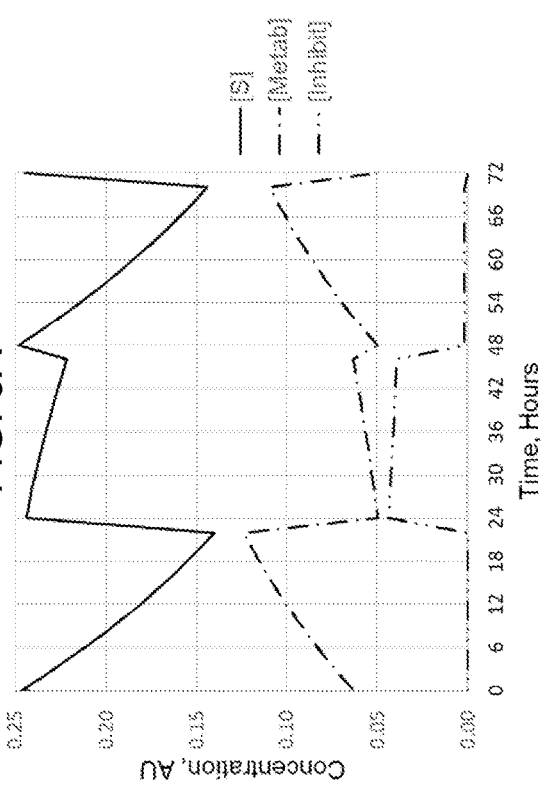
Figure 5D:
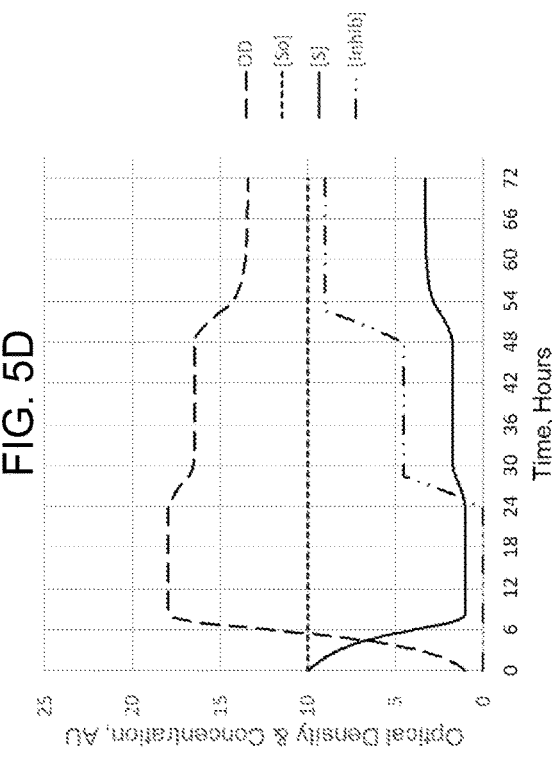
Figure 5C:
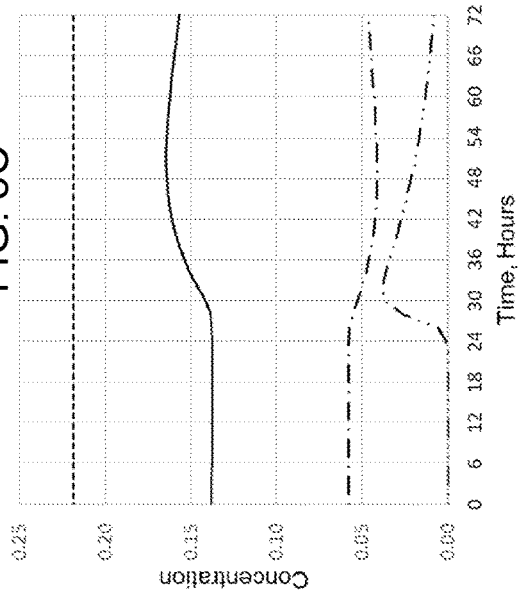

UV-Vis spectroscopy or imaging could be readily accomplished by using the same valves in FIG. 8A or 8I, and would enable the quantification of genetically encoded reporter genes that reflect a particular signaling or metabolic pathway. Cell morphology could be assessed on the cells exiting the chemostat or bioreactor by having some fraction pass through a microfluidic imaging system, as that which produced the yeast image in FIG. 4, either as continuous flow with a fast camera or stop-flow with a slower one. Similarly, the chemostat effluent could be connected to a microfluidic or larger Coulter Counter, a microfluidic cell sorter,[105] fluorescence-activated cell sorter (FACS), or a CyTOF instrument. While FACS and CyTOF and other analytical instruments are expensive, having them directly connected to a large version of CAPCAS would be cost effective because hundreds or thousands of different experiments might be operating at the same time, keeping the instrument fully occupied and not requiring manual sample handling.

For many of these approaches, sample preprocessing might be required, which could be accomplished using on-line microfluidics, for example parallel spiral cell sorters' that could allow the use of two output plates, one with media only and the other with highly enriched cells or cell lysers.[106, 107] It may be necessary to mix the chemostat effluent stream with agents to halt metabolism or lyse cells prior to freezing.

CAPCAS Interfaces

With the growing recognition that continuous culture provides major scientific benefits over batch culture in well plates and bioreactors, there is a pressing need for parallel, small volume, automated perfusion bioreactor systems. CAPCAS will provide researchers with a large array of instrumented and precisely controlled microliter-per-minute or faster perfusion systems that enable massively parallel microbial- and mammalian-cell experiments that can be connected directly to an SPE-IM-MS system for metabolomics and operated as self-driving laboratories that benefit from the power of machine learning. Basic microbial science, pharmacology, and commercial biomanufacturing will all benefit from massively parallel experiments that can refine models of cellular signaling and metabolism, allowing researchers to explore connections that were previously beyond their grasp. CAPCAS provides a platform that can be produced in quantity and will be replicated at a cost well within the reach of both academic and industrial research groups.

A key difference between cells cultured in static media on flat plastic or Transwells and cells grown in organ chips is that the latter, because of their small fluid volumes, are most often perfused dynamically using syringe pumps, peristaltic pumps, gravity acting on input reservoirs that are higher than the outlet reservoirs, and pressurized reservoirs. The improved physiological recapitulation afforded by organ chips and the desire to avoid anoxic cores in thick tissue bioreactors and large organoids are contributing to a rapid growth in the perfusion of a variety of cell culture preparations. Some organ chips are operated on a rocker, with fluidic channels typically configured to provide bidirectional flow as an array of chips are rocked back and forth. It is possible to create fluid channels that support unidirectional flow, but these are not yet widely utilized. Gravity perfusion, syringe pumps and pressurized reservoirs all suffer from the limited volumes of reservoirs and the difficulty in having the effluent from one organ perfuse a second, downstream organ. The flow rate in stationary gravity-perfused systems drops steadily as media flows from the input or supply reservoir, whose level drops, into the outlet or collection reservoir, whose level rises. The steadily decreasing difference in reservoir height translates into a steadily decreasing flow rate. Typically, on a daily basis or even more frequently, media is manually withdrawn from the collection reservoir and either new or conditioned media is added to the input reservoir. The required rate of media replacement to maintain cell viability is determined primarily by the number of cells being cultured, with the rule-of-thumb that a cell with a picoliter volume requires a nanoliter of fresh media each day. While rocker and pumped systems allow reuse of media, the problem of media replacement remains.

Syringe pumps and pneumatic and roller-based peristaltic pumps can be used to perfuse and even interconnect organ chips, but it is important to avoid the introduction of bubbles into vascular channels, since a passing bubble can severely disrupt the endothelial cells that line the channel. Hence these perfusion systems often include a bubble trap to capture any pump-introduced bubbles or bubbles that appear within a length of tubing or a microfluidic channel due to temperature changes affecting gas solubility. In contrast to pumped systems, gravity-perfused ones seldom encounter bubble problems because the reservoirs are open and any bubbles rise to the surface, burst, and disappear.

Regardless of the perfusion method, organ chips typically require a high level of human attention to refill syringes and pressurized reservoirs, provide fresh media to peristaltic-pumped and gravity-perfused systems, and remove waste media. This in turn severely restricts the level of parallelization and automation that has been achieved with organs on chips.

Many of these problems can be overcome by using a CAPCAS unit in a way that merges pumped and gravity-perfused systems and enjoys the benefits of both. The fluidic control system of this invention can be used to maintain automatically and without human intervention a uniformly high level of media in the delivery well of a gravity-perfused bioreactor while also removing fluid from the collection well to keep a low fluid level and hence a constant gravity perfusion rate, in contrast to the ever-decreasing rate in unattended gravity perfusion systems. Gravity perfusion on organ chips frequently uses water column heights of 20 mm or less, as can be readily achieved with a pipette tip inserted into a microfluidic chip. This corresponds to a pressure of approximately 200 Pa. FIG. 18A shows how a short supply needle and a long collection needle can be inserted in the upper and lower gravity perfusion reservoirs, respectively. These needles can be connected to CAPCAS pump and valves just as were the chemostats and bioreactors, such that the delivery, removal, and analysis of fluids does not require human intervention. If one or more organ chips are placed in a well-plate-sized box, the iPlateBot can move these chips between different stations in an enclosure. Interconnections between organ chips can be designed into the pump, valve, tubing, and needle networks but connecting, for example, the collection needle from the outlet reservoir of one organ chip to the inlet reservoir of another organ chip. While FIG. 18A shows this for a pipette-tip gravity-perfused system, FIG. 18B extends this concept to an organ chip with integral fluid reservoirs. The decision of what fraction of the media is to be returned to a supply reservoir need not be made at the time of the fabrication of the chips, but instead by controlling the settings of pumps and valves already in the CAPCAS unit. FIG. 18C shows that the addition of more needles and more pump and valve channels allows this approach to be applied to a two-chamber barrier reactor, such as a neurovascular unit and the blood-brain barrier that it contains. Finally, closely placed needles would allow both the insert and the outer well of a Transwell chip to be perfused separately, as shown in FIG. 18D. While these drawings show only a simple pump and valve on a single organ chip or Transwell, the CAPCAS fluidic circuits already described could support multiple organ chips as easily as they support arrays of chemostats or bioreactors.

The pump and valve above each of these boxes is meant to serve as a schematic representation of a multi-channel fluid-delivery and removal/perfusion/recirculation system. An array of such systems could be suspended above CAPCAS decks, and the iPlateBot could transport these boxes between various stations. The purpose of the boxes is to ensure sterility and humidification of the open reservoirs used to perfuse each biodevice. When the box is being transported, it is covered with a lid, just as is a well plate being transferred. When the box is delivered to the CAPCAS fluidic interface station as shown in FIGS. 18A-18D, the box can be de-lidded and lifted into position beneath a suspended fluidic interface station using the same sequence of events as shown for a well plate in FIGS. 15A-15D, with the possibility that more vertical distance will be required between the deck and the de-lidding or fluid interface stations to accommodate the height of the box being greater than a well plate. When the box is in place in the fluidic interface station, the lid built into that station will ensure sterility of the contents of the box, including the sterile reservoirs therein.

The full automation of organ-chip perfusion would be particularly useful now that organ-chip viability is extending to many months, i.e., for long intervals of time that would otherwise require dedicated and attentive human technicians to both maintain chips and conduct pharmacology and toxicology experiments on them.

Figure 18E:
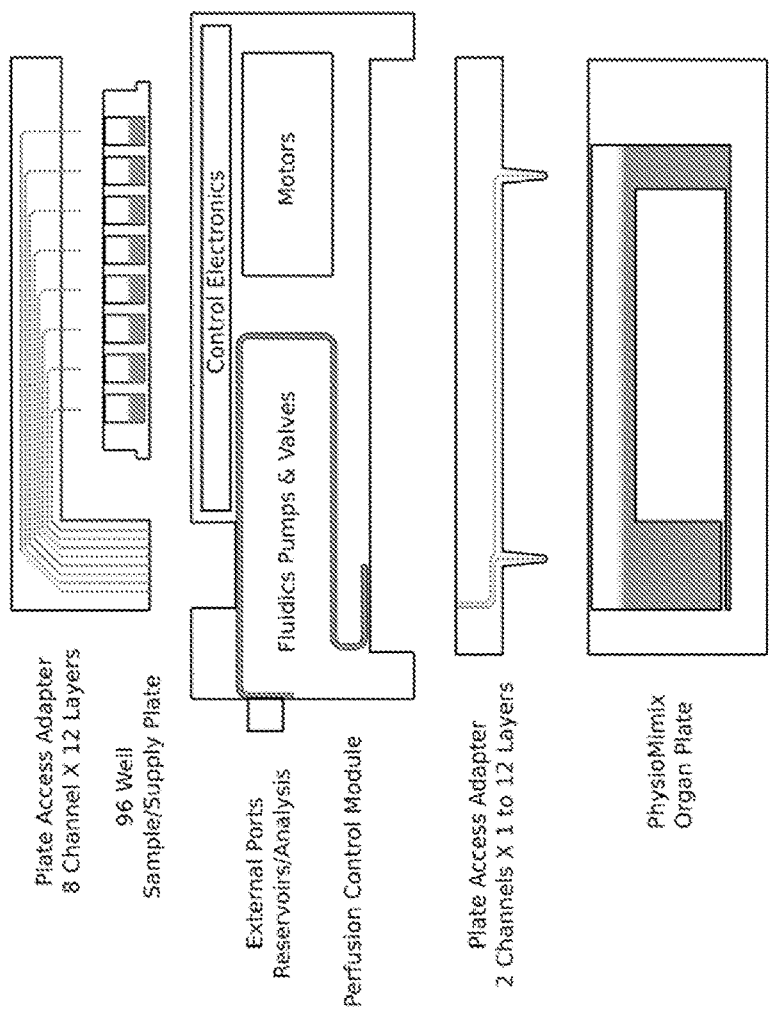

FIGS. 18E and 18F show another example of how CAPCAS hardware could be integrated with existing organ-chip technologies. The PhysioMimix organ plate is a system of individual or coupled bioreactors with a well-plate footprint. Pneumatic lines to the intra-incubator plate holder drive on-chip peristaltic pumps that recirculate fluid within the PhysioMimix organ plate, which has both open and Transwell-like reservoirs. FIG. 18E shows how a set of needle adapter plates, pump and valve fluidics, and motors in a fluidic perfusion station can be used to add or remove drugs and media from any organ on the plate or move media from one organ to another. FIG. 18F shows how the use of flexible ribbon fluidics would allow the various components to be assembled into a compact perfusion station such as those in FIGS. 15C and 16A-16C. Similarly, ribbon-fluidic designs can interconnect different types of well plates and microfluidic devices, bioreactors, and organ chips.

Figure 18G:
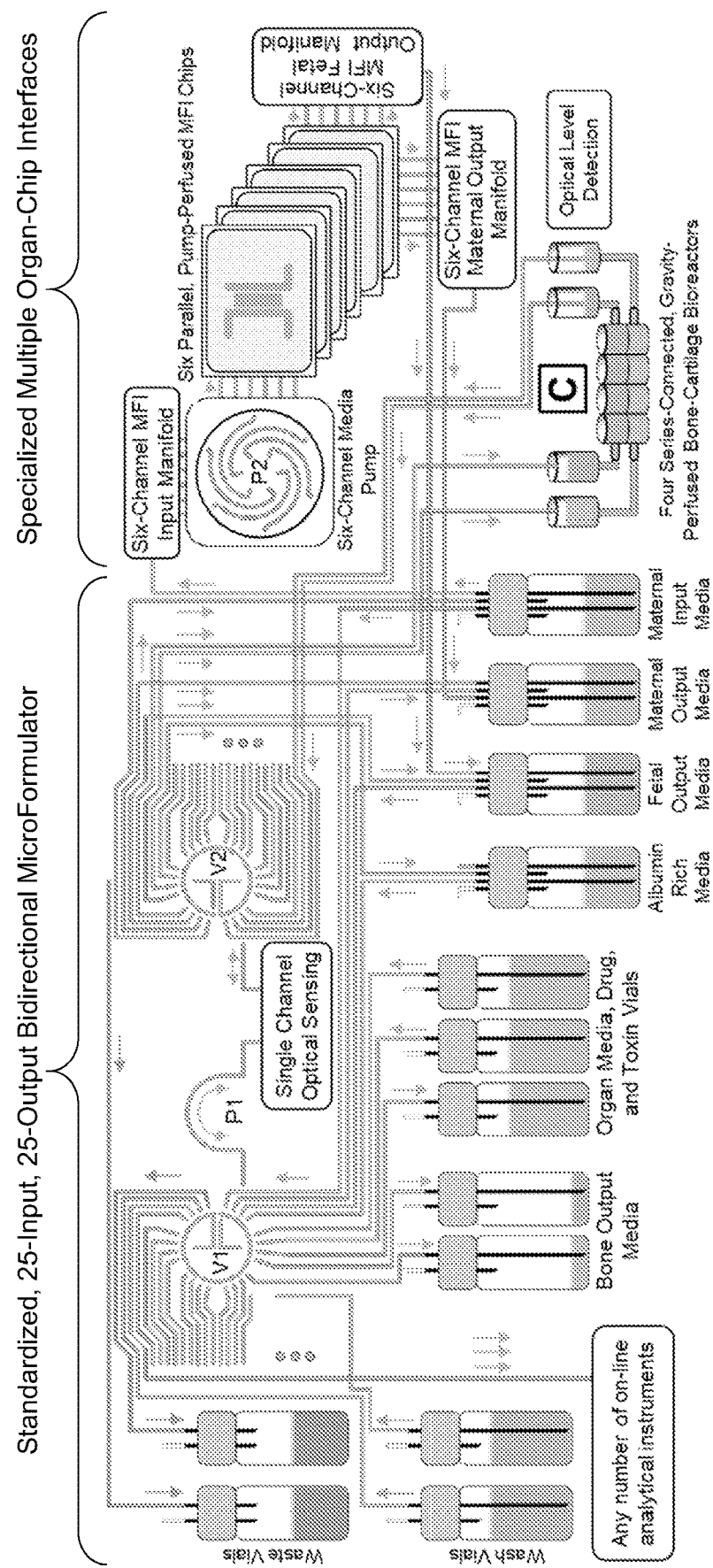

FIG. 18G shows a fluidic circuit based upon that in FIG. 8A that is configured to perfuse six parallel, pump-perfused maternal-fetal interface chips and collect their effluent and deliver it to four series-connected, gravity-perfused bone-cartilage bioreactors, all compatible with the CAPCAS architecture. A major advance in this design is to use the microformulator in a bidirectional manner, such that intermediate reservoirs can be used to create mixtures of fluids from a variety of reservoirs, including ones that are downstream of the microformulator. This requires that pump P1 operate in both directions, and that the lengths of the reservoir tubes are appropriate as required for fluid delivery and removal.

Pressurized Reservoir Organ Chips. Because the pumps shown in FIGS. 12A-12Q are pressure-tight against back pressure, as are the valves when in the closed state, when higher perfusion pressures are required without using taller reservoirs and longer needles it would be instead possible to add pressure-tight seals to both the reservoir lid and the lid to the organ-chip plate to allow the fluidic control system to service pressurized-reservoir organ chips such as those manufactured and used by Cell ASIC, Nortis, and Emulate. Similarly, it would be possible to insert pressurized input reservoirs in the fluidic circuit in FIGS. 8A-8J, since the pumps and valves that service that portion of the circuit would act as check valves to maintain the pressure in the reservoir, with the pressure being developed by the pump P1. If desired, this would allow pumps P2 and P3 to be replaced with a valve that would switch the downstream organs from one set of pressurized reservoirs to another.

As another example, zebrafish embryos are used extensively in physiological studies because of their small size and transparency and the ease with which they can be altered genetically. The care and feeding of massive farms of these embryos can be time consuming, as are pharmacological experiments on them. Because CAPCAS can perfuse Transwells such as those used to grow zebrafish embryos, it would be a straightforward extension of CAPCAS to the study by a robot scientist of zebrafish physiology.

FIG. 18H provides a tabulation of the number of chemostats, bioreactors, organ chips, perfused wells, and zebrafish that could be studied in a self-driving CAPCAS laboratory. We know of no other technologies capable of this massive parallelization of these biological models.

System Control Hardware

Given the large number of chemostats, bioreactors, well plates, or organ chips that will be serviced by this system, it will be necessary to implement a number of different automated control systems. Our novel microfluidic rotary planar peristaltic micropump (RPPM)[36, 47, 48] and rotary planar valve (RPV),[52] both powered by NEMA-17 stepper motors with a custom microcontroller and computer software to drive the system, enable the combination of a pump and valve in the microclinical analyzer in FIG. 6B, and the microformulator in FIG. 6C. In present embodiments, the motors in the pumps and valves are DC stepping motors, often with angle encoders. Other motor types could be used, including brushed and brushless DC motors. In any case, to achieve the level of control of angle, velocity, and torque required for proper operation of the systems, each motor requires an independent controller, for example in the form of a dedicated microprocessor that controls the motor driver chip based upon factors such as the motor drive current and angular displacement of the motor. These controllers can be housed either within the motor enclosure or outside it, depending upon the design parameters and requirements for the system.

We have previously described our Automated MultiPump Experiment Running Environment (AMPERE) software to control the pumps, valves, and ancillary equipment used in our microfluidic systems. AMPERE is digitally interfaced to CCD cameras for flow tracking, electronic scales for gravimetric autocalibration of RPPM/RPV systems, WiFi routers and a Network Time Protocol (NTP) server, and a variety of commercial flowmeters, valves, and other hardware. AMPERE could control the hundreds of motors that will be operating within an embodiment of CAPCAS, but as we will discuss below, its architecture does not support parallel, asynchronous operations that have feedback to control conditional operations. In this section, we discuss the physical controls that are needed to operate CAPCAS such as the embodiment in FIGS. 8A-8J.

A number of chemostat parameters would need to be controlled, including temperature, pH, media feed rate, nutrient and inhibitor levels, dissolved oxygen, and possibly carbon dioxide. There should be corresponding sensors to validate that these parameters are in fact accurately controlled. It is necessary to determine the physical extent of the control. While it will be possible to control nutrient levels at each well, it will be possible but more complicated to provide different gas concentrations to adjacent wells. Thermal conductivity issues would suggest that a single plate should be at a uniform temperature; some embodiments of CAPCAS require that in a multi-plate system, each chemostat/bioreactor plate would be isothermal. One of the advantages of having AI/ML software design the individual experiments would be that experiments with similar parameter values, such as oxygen concentration, could all be performed on the same plate at the same time. It would then be possible to change these parameters during the next fermentation experiment.

In addition to motor control, Plate Control is needed to move plates in and out of the operational envelope while maintaining the sterility and cleanliness of each plate. The sequence of events would be as follows: The user inserts the well plate into the tray in the open drawer shown in FIG. 8D. The tray moves into the operational envelope; if lidded, the lid will be removed and stored in such a way that it will be put back on the plate when the plate is extracted. The plate tray is lifted up to mesh the plate with the fluidic interface element. A secondary (plate) cart within the drawer mechanism will provide the full horizontal extension of the plate so that it can be reached by an external robot arm, as indicated in FIG. 16D. At the end of the travel the secondary cart will engage with a stationary rack that will drive an idler which will in turn drive the plate tray at twice the distance of the primary cart. This will be the extension past the outer edge of the operational envelope for user access. During this operation, the air flow must be increased to maintain sterility of the operational envelope while the access door is open.

CAPCAS must provide gas control to supply mixed gases to the operational envelope while maintaining the sterility and cleanliness of the gas and prevent cross contamination of adjacent control elements. Proportional valves can be used to provide a mixture of two or more gases, which are supplied by compressed gas bottles regulated externally, for example, to 15 PSI. A typical configuration could consist of Gas 1 being supplied by a medical grade $N_2$ compressed cylinder and Gas 2 being supplied by a medical mixed gas cylinder of 20% $O_2$ and 80% $N_2$. This allows an $O_2$ range of 0-20% into the operational envelope. Eliminating pure $O_2$ increases safety and allows for the use of more standard air controls without having to comply with pure $O_2$ requirements for valves and regulators. One embodiment of CAPCAS consists of two proportional valves feeding into the distribution manifold which is connected to each of the plate elements. The gas will provide positive pressure to the plate element plenums, which will prevent the entry of air from the rest of the operational envelope. One CAPCAS embodiment utilizes two Enfield Technologies Miniature Proportional Valves connected to the plate plenums through individual manifolds to the gas mixing/thermal control blocks.

Air Flow Control is required for CAPCAS to ensure the sterility and cleanliness of the air entering and leaving the operational envelope and to provide air circulation for heating and cooling. In some embodiments, this system consists of several HEPA-filtered fans to supply clean air to all subsystems that require standard air flow (heat sinks).

Thermal Control is required to maintain the desired temperature within the operational envelope and provide thermal isolation between plate plenums. Where gas enters the plate plenums, a thermoelectric (TE) block will ensure that the gas temperature matches the temperature setpoint of that plenum. The structure of the TE block also provides thorough mixing of the source gases.

Solution Control & Storage would provide storage and distribution means for solutions to be supplied to the microformulator inputs and outputs. This may consist of a small refrigerator with an access port cut in one side. It may be better to go with a PVC foam board set up as a collapsible cabinet with a TE heating/cooling unit.

Model-Based Control would be a straightforward extension of the AI/ML algorithms that could drive CAPCAS. The CAPCAS control software uses the Robot-Scientist-derived systems model to predict the value of key system parameters at some future time, and when that time is reached, uses the observed differences from the predictions to adjust control variables. This may be particularly important in the regulation of pH, where the acid-base dissociation curve can be highly non-linear.

System Control Software

The CAPCAS hardware embodiments described in FIGS. 7A-7B through 18A-18H present the means by which multiple chemostats, bioreactors, well plates, and organ chips can be continuously perfused and analyzed. In order to create a robot scientist that can function as a self-driving biological laboratory, each of the pumps and valves must operate under carefully timed computer control that is informed by a variety of sensors that are distributed throughout the system. In contrast to open-loop systems without feedback control of pH or other biological variable that might operate with a simple set of serial instructions, many of the CAPCAS operations must be carefully coordinated; for example, only when a bioreactor becomes acidic should a pair of valves be switched, or when the optical density becomes too high, a pump speed should be increased, a pump should be turned off when a bubble is detected but the valve should not be switched to another pump if either pump is still running. Furthermore, the control must interface bidirectionally with the artificial intelligence/machine-learning (AI/ML) software that designs the experiments and analyzes the resulting data, termed CAPCAS-AI. However, such conditional logic and bidirectional communication are not supported in the Automated MultiPump Experiment Running Environment (AMPERE) that has previously been used to control our microfluidic pumps and valves, for example in our Multiwell MicroFormulator.

Figure 19A:
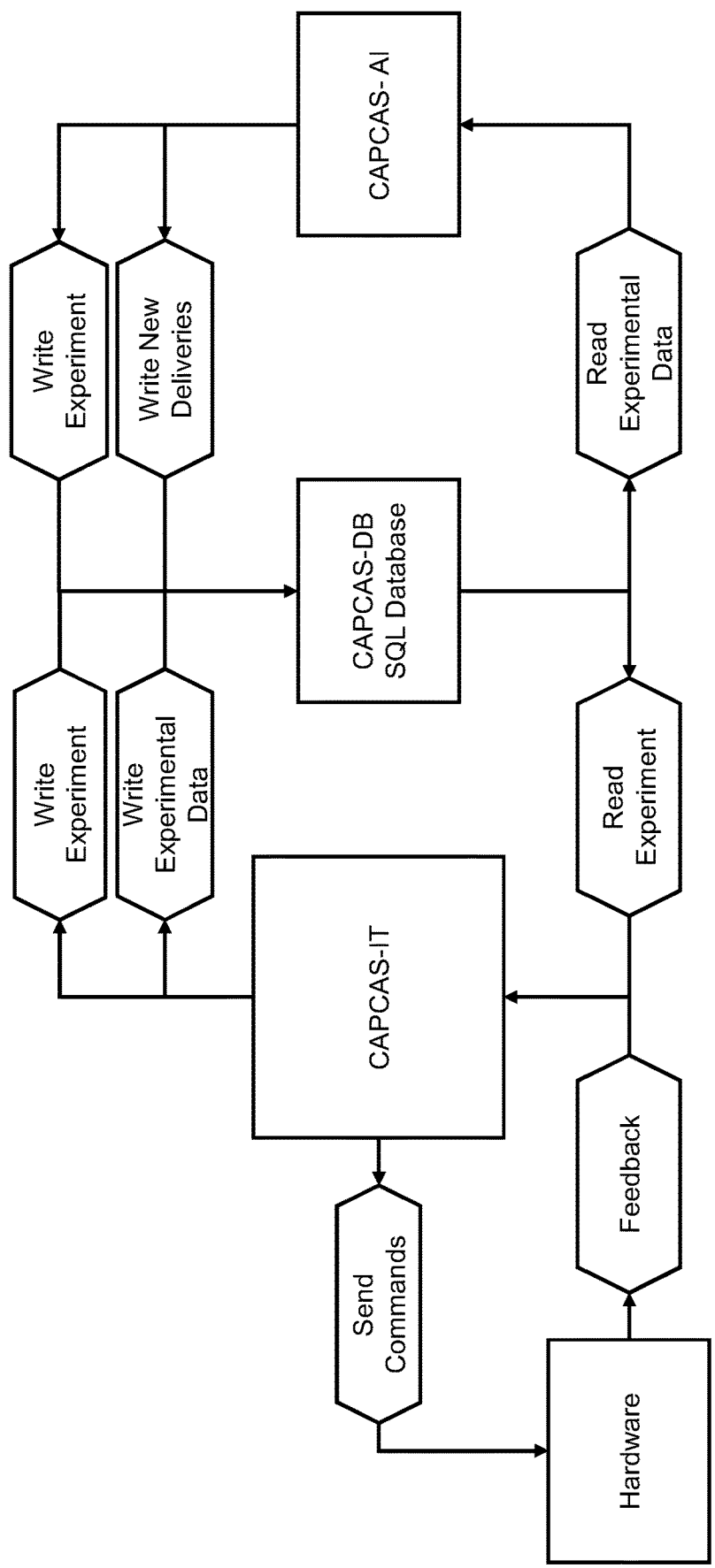
FIGS. 19A-19P show overviews and flowcharts of how the various hardware and software entities that comprise the CAPCAS function and interact, according to embodiments of the invention.

Addressing the need for conditional logic for distributed control of CAPCAS and the bidirectional interface to CAPCAS-AI requires a dedicated software system, termed CAPCAS-IT, which is a software application that enables control over hardware through its own protocol-building capabilities or remotely through a structured query language (SQL) database, termed CAPCAS-DB. CAPCAS-IT communicates with connected hardware to perform operations to run an experiment and receive feedback on hardware functions and measurements. CAPCAS-IT can also read and write settings and experimental data to CAPCAS-DB. This can occur periodically during the running of an experiment. This allows CAPCAS-IT to keep up to date when changes are made to CAPCAS-DB. FIG. 19A provides an overview of how these various entities and functions are interconnected in the particular embodiment that supports the hardware configuration in FIG. 8A.

Figure 19B:
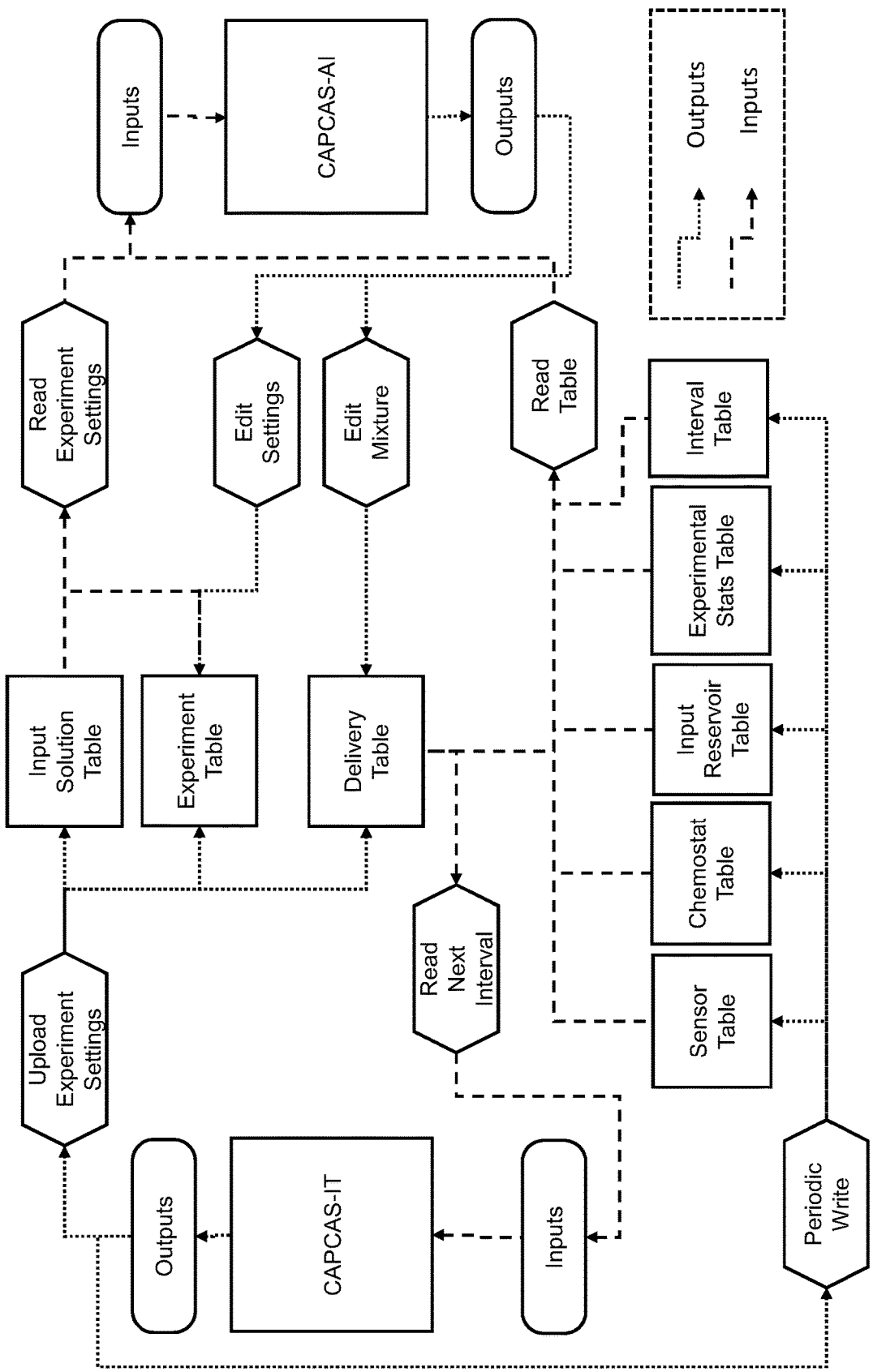
Figure 19C:
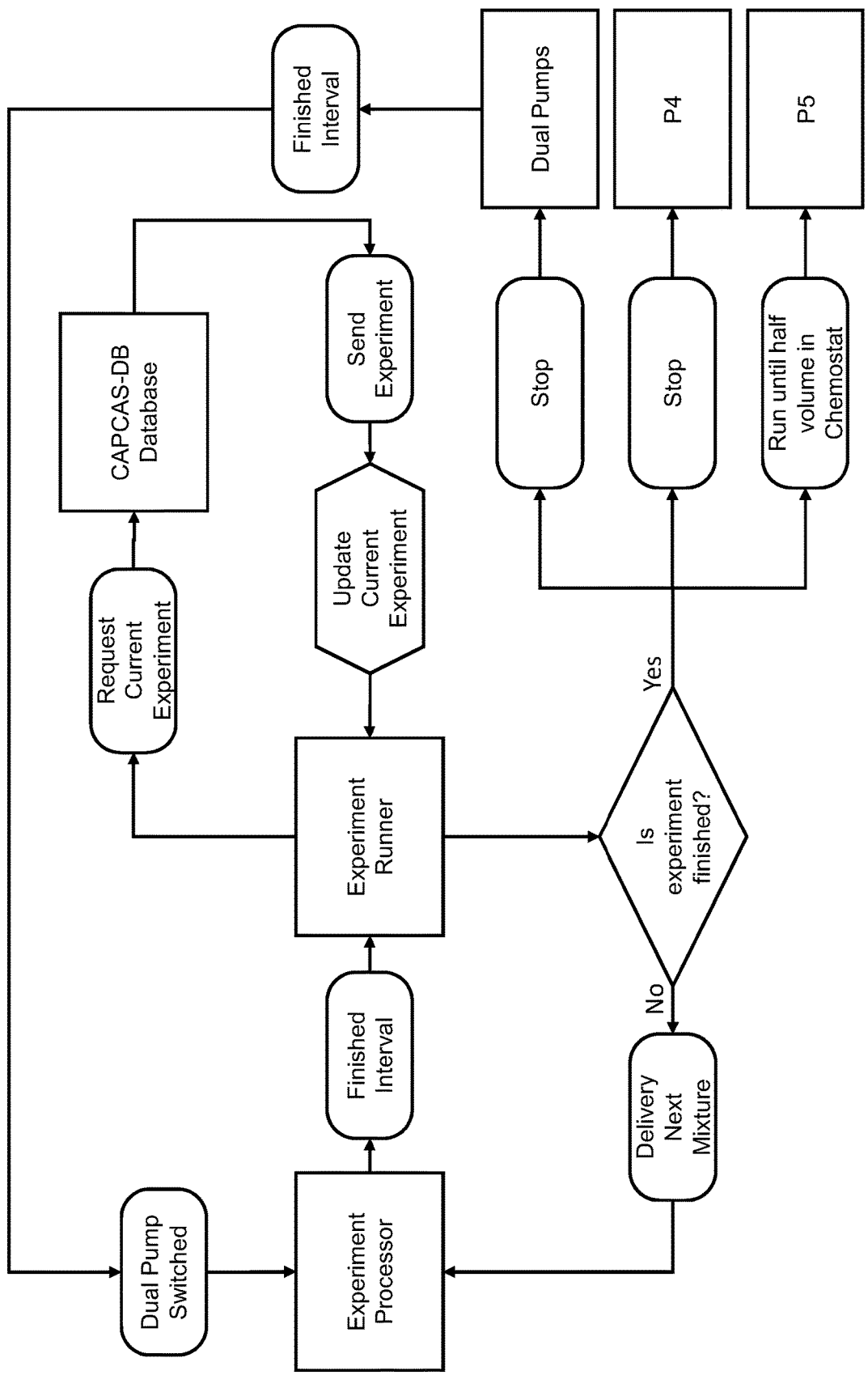
Figure 19D:
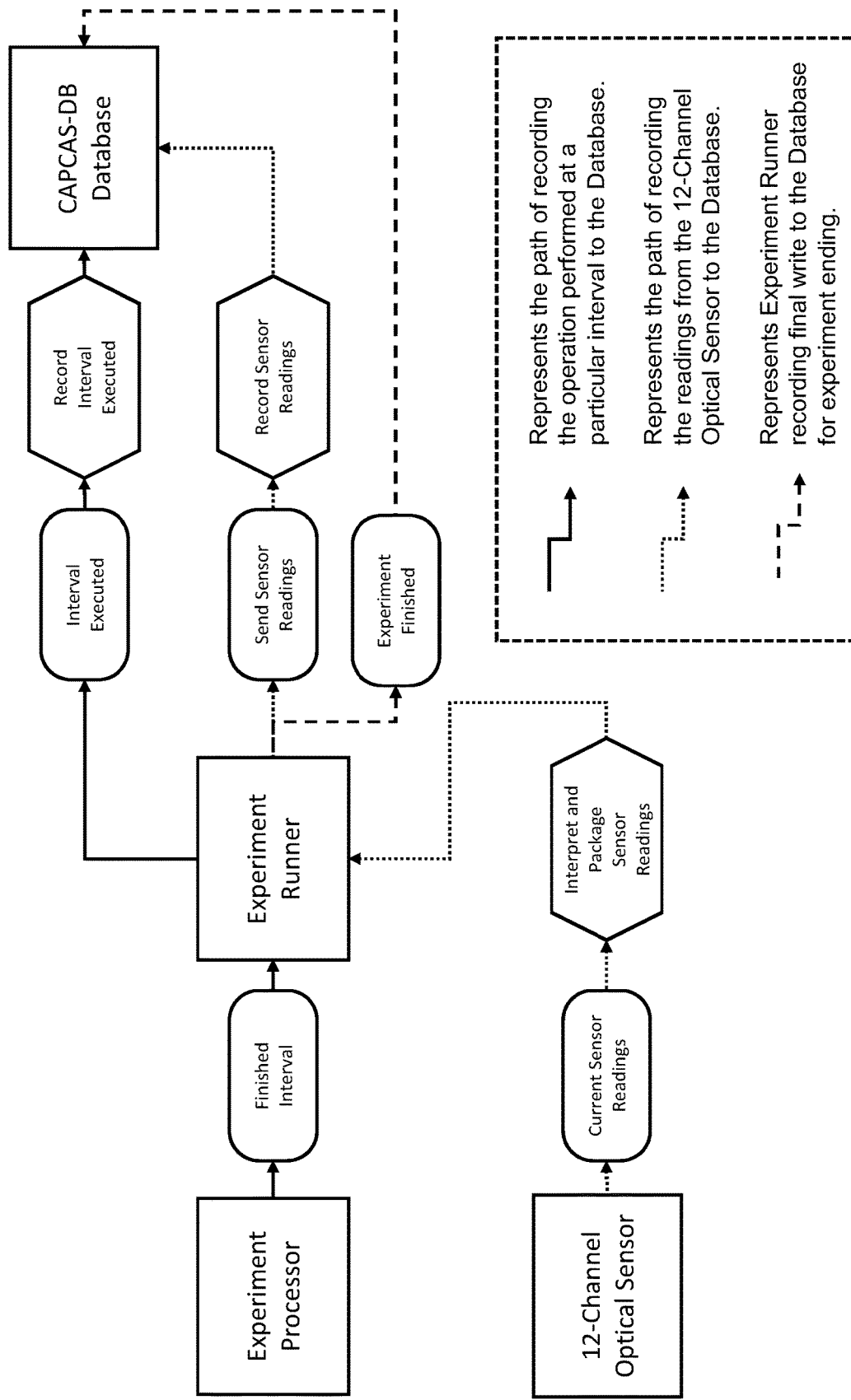

The CAPCAS-IT software has the ability to interact with a modifiable database, as illustrated in the embodiment in FIG. 19B. This creates an intermediary for interactions between the CAPCAS-IT software and the CAPCAS-AI software, for example that developed by Ross King for the Adam and Eve Robot Scientists. The CAPCAS-AI software will take readings published to the common database by the CAPCAS-IT software and modify the deliveries in the experiment that is currently running. The CAPCAS-IT software will read in these requested deliveries from the online database to perform the next step in the experiment. This will require the software to both read and write to the CAPCAS-DB database. Multiple tables comprise CAPCAS-DB:
- Input Solution Table
- Experiment Table
- Delivery Table
- Sensor Table
- Chemostat Table
- Input Reservoir Table
- Experiment Stats Table
- Interval Table FIG. 19C shows how CAPCAS-IT reads from the CAPCAS-DB SQL database during an experiment and is able to make changes to an experiment during a run. These changes will be made in the database. Therefore, it is important that the software read the Database for changes to modify its current experiment while the experiment is being conducted. The following steps are followed:

On Start:
Experiment Runner requests "Experiment" from Database.
Experiment is read and parsed by Experiment Runner.
Experiment Runner resets current interval to zero.
Experiment Runner tells Device Pack to deliver mixture.
Allow signals between Dual Pumps and Experiment Processor.
On each finished interval (signaled by Experiment Processor):
Experiment Runner requests Experiment from Database.
Experiment Runner is read and updates currently stored experiment.
Experiment Runner increments interval.
Experiment Runner makes decision based on interval:
If last interval:
Instructs Dual Pumps and P4 to stop running.
Disables signals between Dual Pumps and Experiment Processor.
P5 is instructed to run until Chemostat Plate is at half volume.
Else:
Sends next Mixture to Experiment Processor based on current interval The writing to the SQL database during an experiment is outlined in FIG. 19D. CAPCAS-AI will adjust an experiment during a run based on information on the Database. Therefore, the software needs to periodically upload its data to the Database during a run:

On Interval Finished:
Experiment Processor sends finish signal to Experiment Runner.
Experiment Runner sends finished executed step to Database.
On Experiment Finished:
Experiment Runner sends finished experiment to Database.
On 12-Channel Optical Sensor Reading:
12-Channel Optical Sensor sends its data to Experiment Runner.
Experiment Runner interprets and converts data.
Data is sent to Database.

Figure 19E:
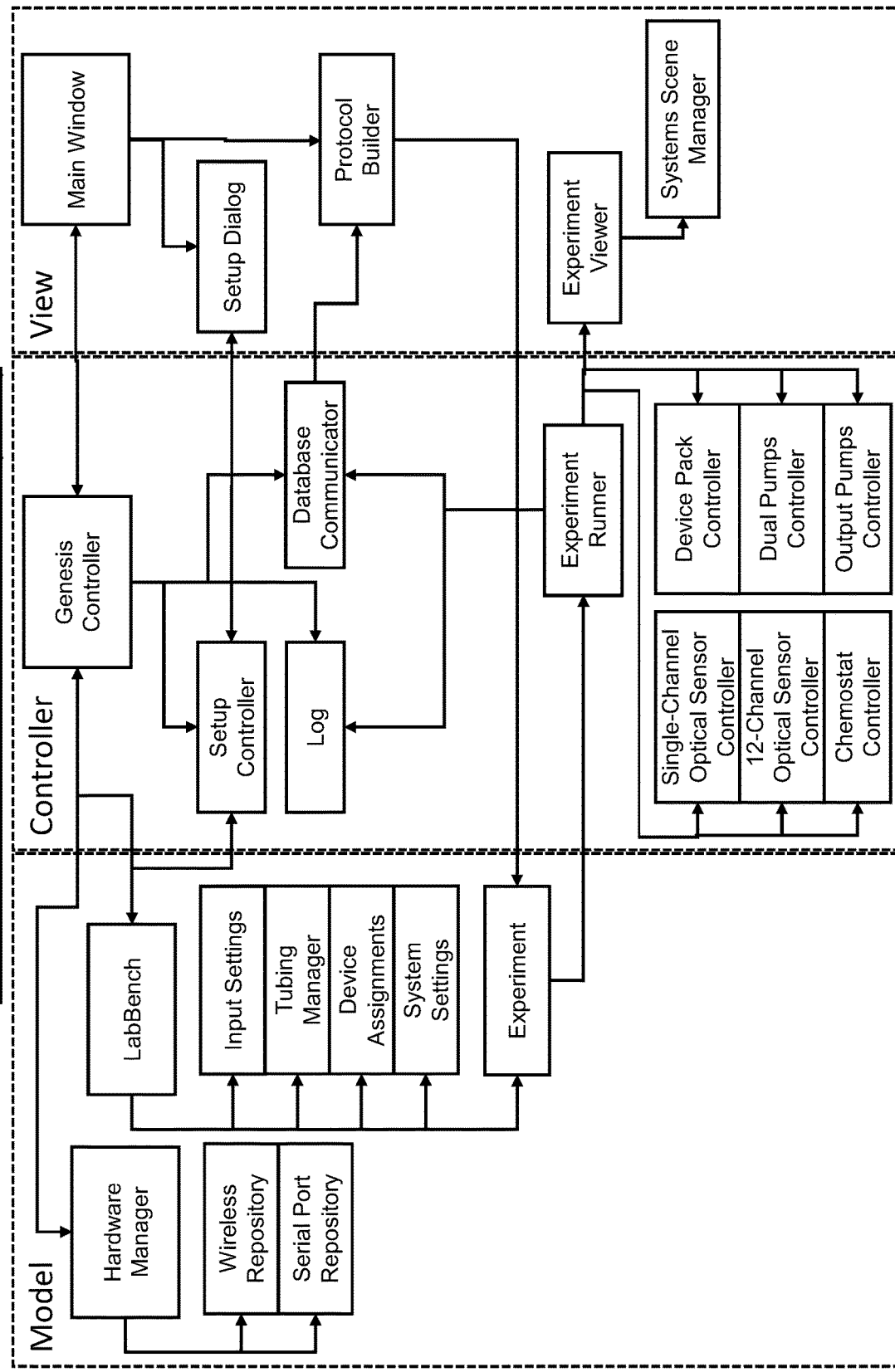

The architecture of the Model View Controller (MVC) is presented in FIG. 19E. Qt is the framework that is used in this embodiment of the software. Qt can create desktop applications that are designed around the model view controller approach. This architecture creates a separation of data from the view. This allows data and view to be more modular and adheres to the Single Responsibility Principle, wherein "every module, class or function in a computer program should have responsibility over a single part of that program's functionality, and it should encapsulate that part. All of that module, class or function's services should be narrowly aligned with that responsibility."[108, 109] The details of the MVC are as follows:

The CAPCAS Controller acts as the main controller class.
Main Window acts as the main view class. It displays all the GUI elements. It also calls all the menus from under it.
Hardware Manager holds all the connections to the hardware, including the wireless and serial devices.
Database holds the connection to the SQL database to make read and write calls.
LabBench holds all the settings and experiment.
Experiment Runner takes in an Experiment and runs it based on the settings. It sends commands to the various controllers which subsequently communicate with their connected hardware.

Figure 19F:
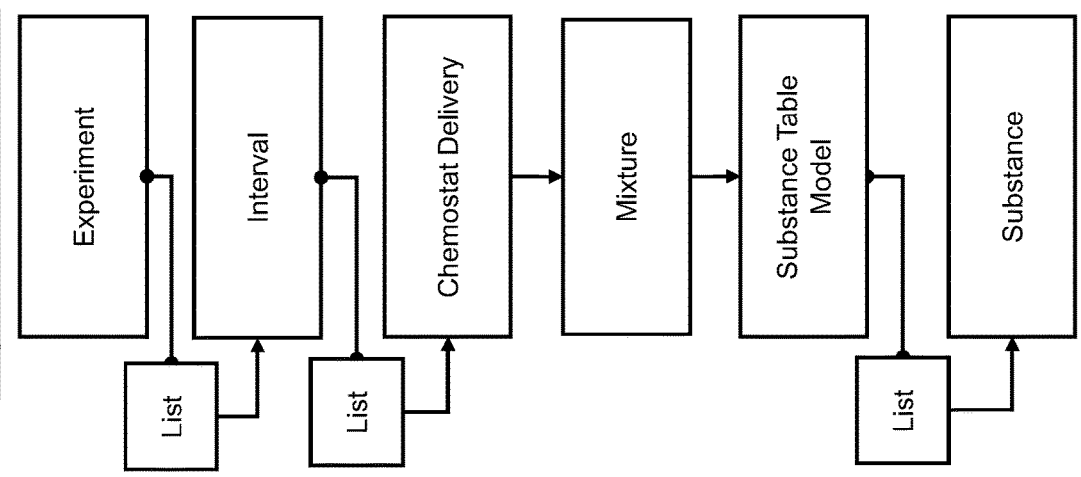
Figure 19G:
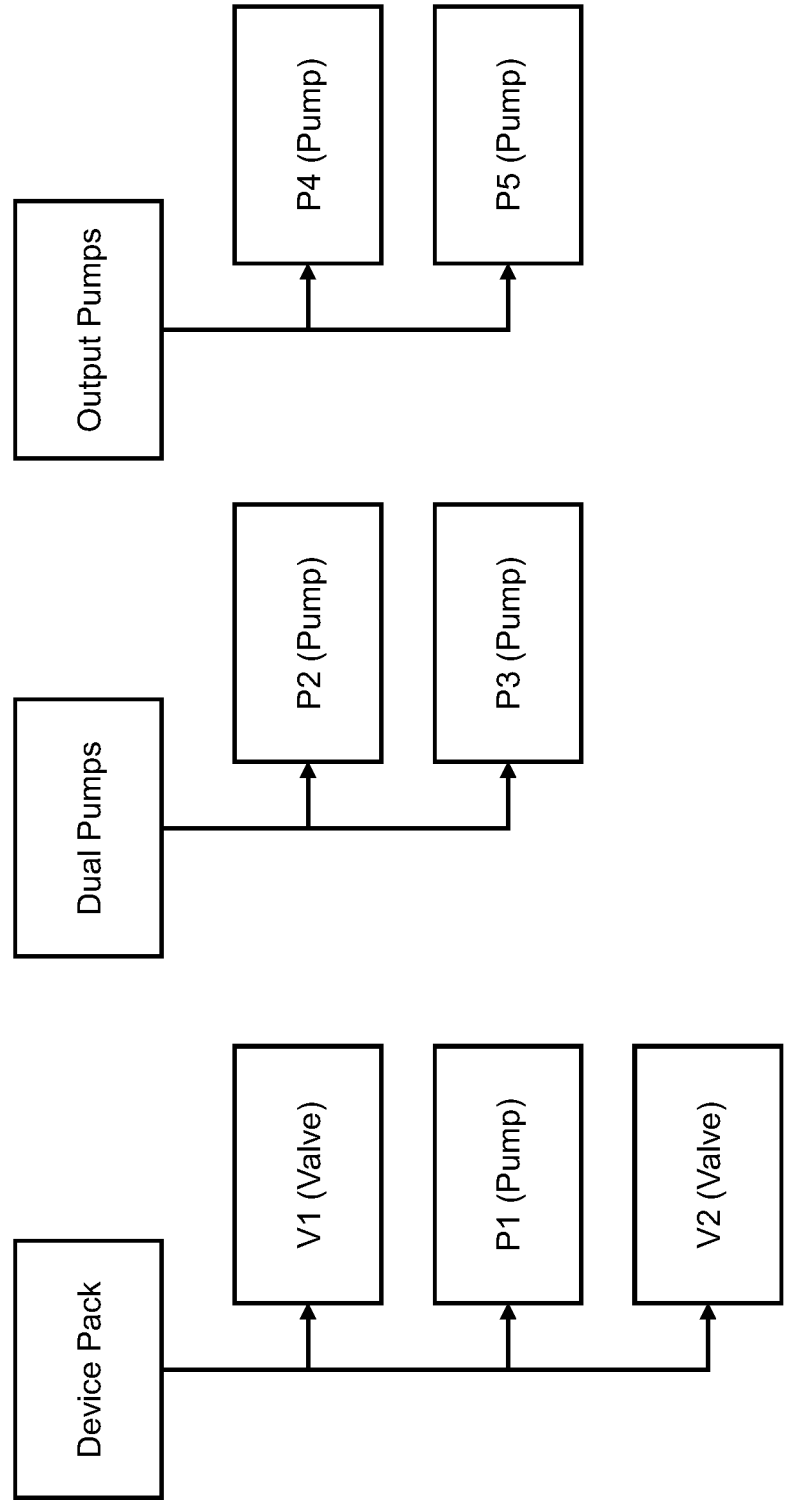
Figure 19H:
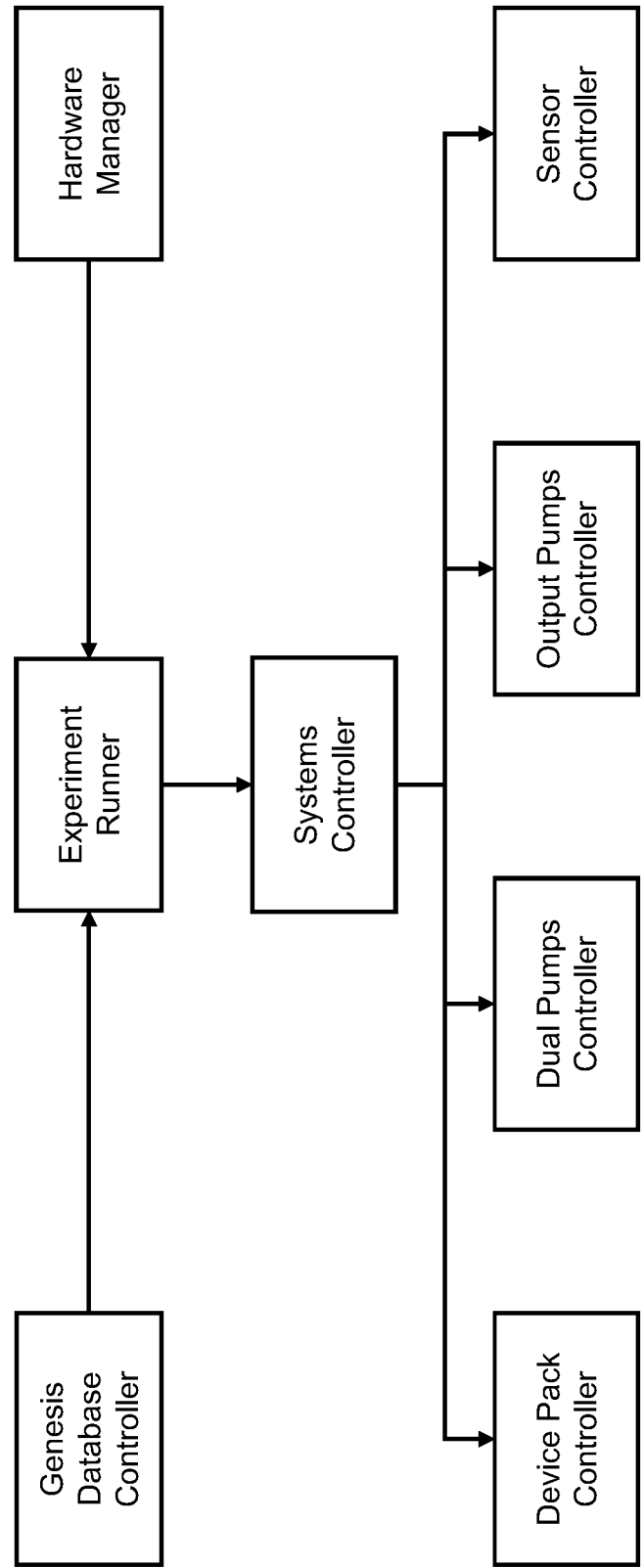

CAPCAS-IT has an experiment structure that is defined by the Experiment Class shown in FIG. 19F. The Experiment class is responsible for protocol settings that will be run by the algorithm and consists of the following hierarchy of classes and properties:

Experiment
  Name
  Target pH
  List of Intervals
Interval
  List of ChemostatDelivery
  In future, may hold info about when to start, duration, and when to switch P2 and P3
ChemostatDelivery
  Chemostat ID
  Mixture
Mixture
  List of Substance
  Will also contain code to figure how media inputs are based upon a list of Substances Substance
  Solution ID
  Target Concentration
For the embodiment presented in FIG. 8A, the grouping in CAPCAS-IT of the particular systems is shown in FIG. 19G. Devices can be grouped into a "System" for simplification of the algorithm:
  Device Pack
  Device Pack is responsible for the delivery of an input to a well on the Input Reservoir well plate.
  Device Pack is responsible for the removal of liquid from a well on the Input Reservoir well plate to waste.
  Dual Pumps
  Dual Pumps is responsible for the delivery of mixtures in the Input Reservoir well plate to the Chemostat well plate.
  Dual Pumps is responsible for emptying its tubing contents into the Input Reservoir well plate.
  Output Pumps
  Output Pumps is responsible for the overflow control of the Chemostat well plate.
  Output Pumps is responsible for delivering fluid from Chemostat well plate to Output well plate.
FIG. 19H shows the CAPCAS Network, with the following connection:
  Experiment Runner holds references to CAPCAS Database Controller and Hardware Manager.
  Experiment Runner holds instance of Systems Controller.
  Systems Controller holds instances of Device Pack Controller, Dual Pumps Controller, Output Pumps Controller, and Sensor Controller.
  Experiment Runner issues commands via Systems Controller based on current step.

Figure 19I:
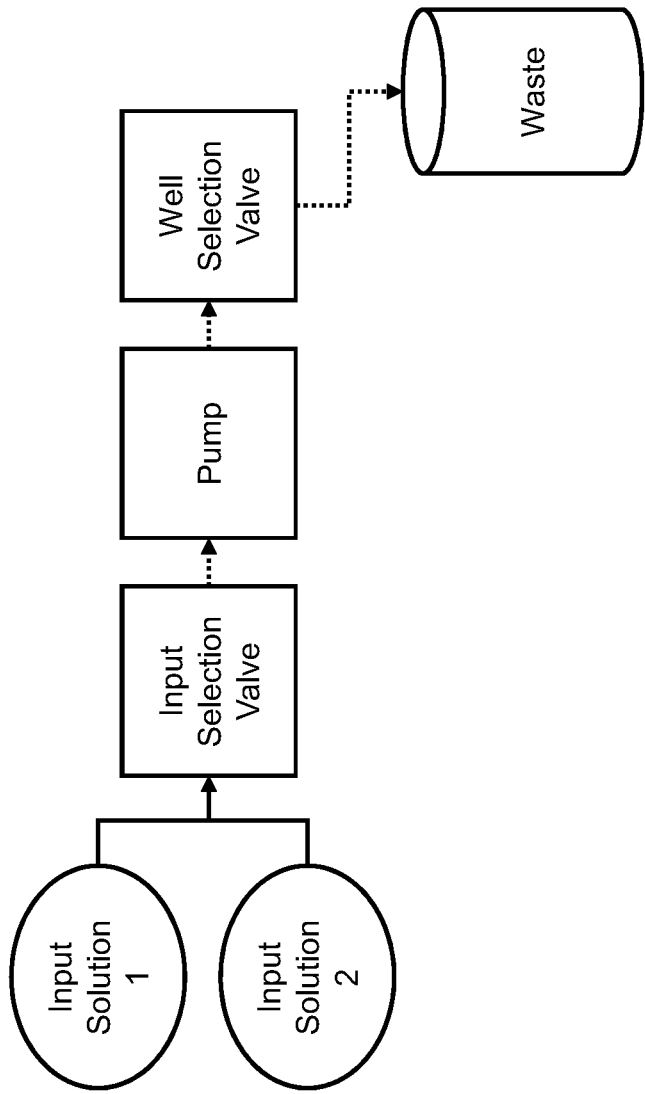

The MicroFormulator in FIG. 8A is in CAPCAS-IT termed a "device pack," and is shown schematically in FIG. 19I. An initialization protocol is required to prime the tubing at the beginning of an experiment. The following system parameters or controlled variables must be specified:
  Priming Rate
  Default wash port
  Tubing volume/distance from Input Solution to Input Valve
  Tubing volume/distance from Input Valve to Waste
  Active solution ports
  Float Constant for threshold fill (i.e., 0.1f)
  Wash Cycles
The following steps are then followed:
Initial Step
1. Move Input Valve to default wash Input Solution
2. Move Well Valve to waste port
3. Run Pump at priming rate for [Tubing distance before Input Selection Valve]*1.10 (to ensure it passes)
For all Other Inputs
1. Move Input Valve to next Input Solution
2. Run Pump at priming rate for [Tubing distance before Input Selection Valve]*1.10
3. Move Input Valve to default wash Input Solution
4. Run Pump for [Tubing distance after Input Selection Valve]*1.10*Wash Cycles
5. Repeat for each active solution In this second sequence, steps 2 through 5 implement a "wash" function. Note that priming of both device packs can be done in parallel.

Figure 19K:
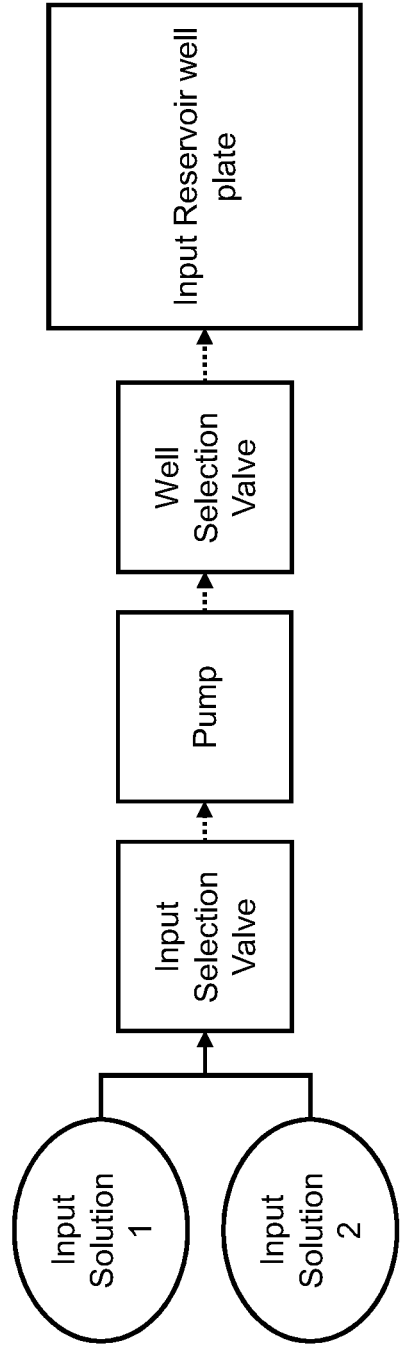

Should CAPCAS-AI need to request a change in media composition before the current set of Reservoir Plate wells is emptied, or to ensure that all wells are empty at the end of delivery of media from that set of wells, it is necessary to remove whatever media remains in the Reservoir Wells. This is done through "Device Pack—Removal" as shown in FIG. 19J, with the following variables specified:
  Empty Rate
  Tubing distance/volume from Reservoir Plate to Waste of Input Valve
and a sequence of steps:
1. Move Input Valve to waste port
2. Move Well Valve on next well
3. Run Pump at empty rate for tubing distance*1.10 (to ensure it passes)
4. Repeat at Step 2 for each well The delivery by the Device Pack of formulated media to the Input Reservoirs, shown in FIG. 19K, requires specification of several parameters and variables:
  Prime Rate
  Fill Rate
  Mixture for each Well
  Default wash port
  Increment Volume
  Target Well Volume
and the following steps:
1. Prime mixture
   1. Move Well Valve to waste port
   2. Move Input Valve to next solution in mixture
   3. Run Pump at priming rate for increment volume multiplied by percentage of solution
   4. Repeat for each solution in mixture
2. Deliver from Well Valve to Reservoir Plate Well
   1. Move Well Valve to next well
   2. Add Mixture until at target well volume
      1. Move Input Valve to next solution in mixture
      2. Run Pump at fill rate for increment volume multiplied by percentage of solution
      3. Repeat for each solution in mixture
   3. Repeat for all wells
3. Run wash (i.e., fill with media through waste)

Figure 19L:
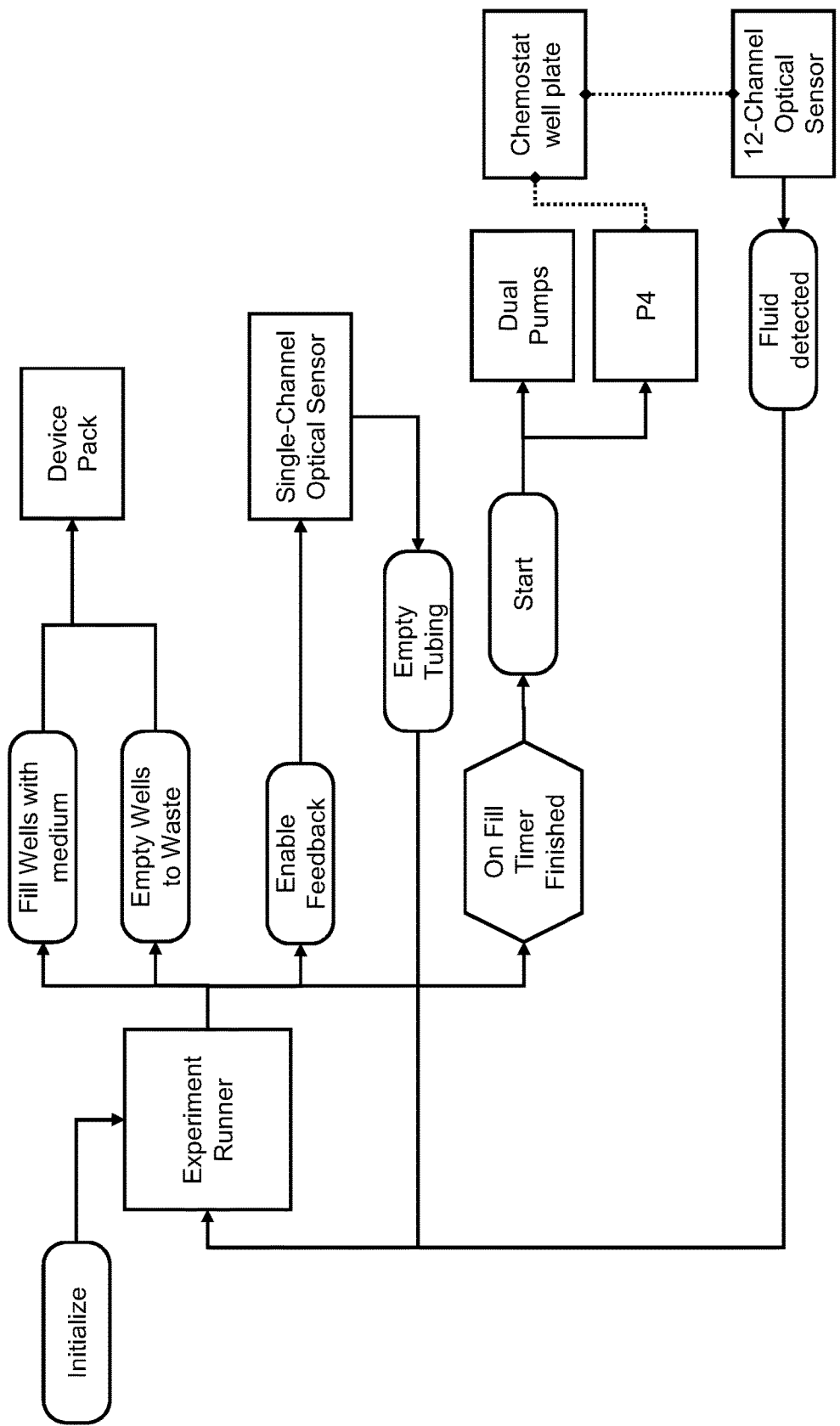

The initialization of the Experiment Protocol is outlined in FIG. 19L. The Initialization protocol will ensure that the tubing of each input before the Input Selection Valve is filled. The steps are as follows:
On Start:
  Instruct Device Pack A and B to fill each well with medium at a fast flow rate. (Reservoir Feeder will automate refilling until told to stop)
On filling complete:
Initialize Dual Pumps to P2.
Start Dual Pumps (Dual Pumps will automate switching until told to stop)
Start P4
Start Device Pack A and B into auto-filling protocol (medium only)
On 12-Channel Optical Sensor reports non-empty tubing:
Stop Dual Pumps.
Stop P4.
Instruct Device Pack A and B to stop pumps.
Instruct Device Pack A and B to empty Input Reservoir wells completely to Waste.
On Single-Channel Optical Sensor reports empty tubing:
Instruct Device Pack A and B to stop pumps.

Note that solutions, medium, acid, and base may not necessarily be filled at start. That may need to be tracked by the tool. Otherwise, initialization could handle this.

Figure 19M:
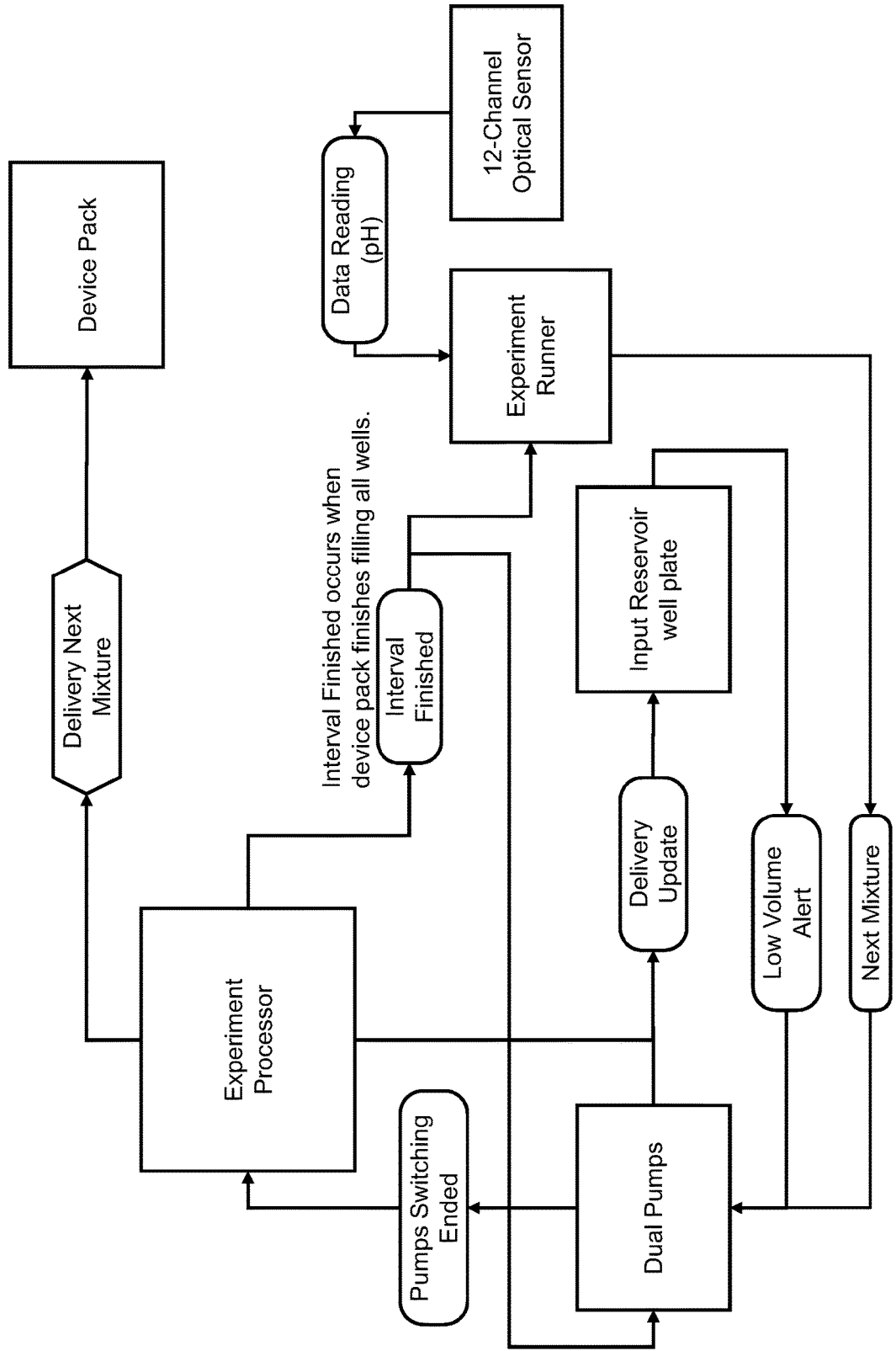
Figure 19N:
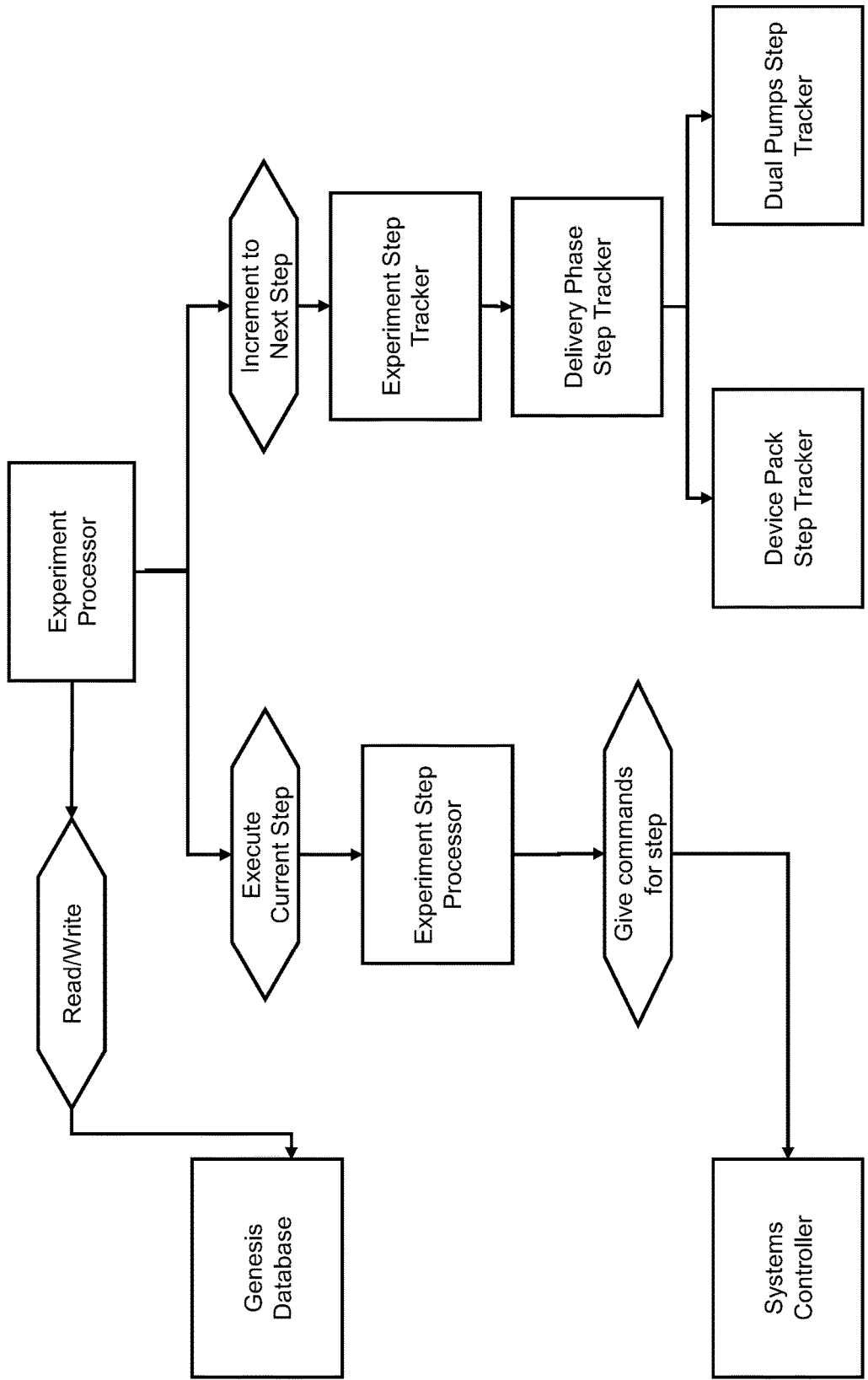
Figure 19O:
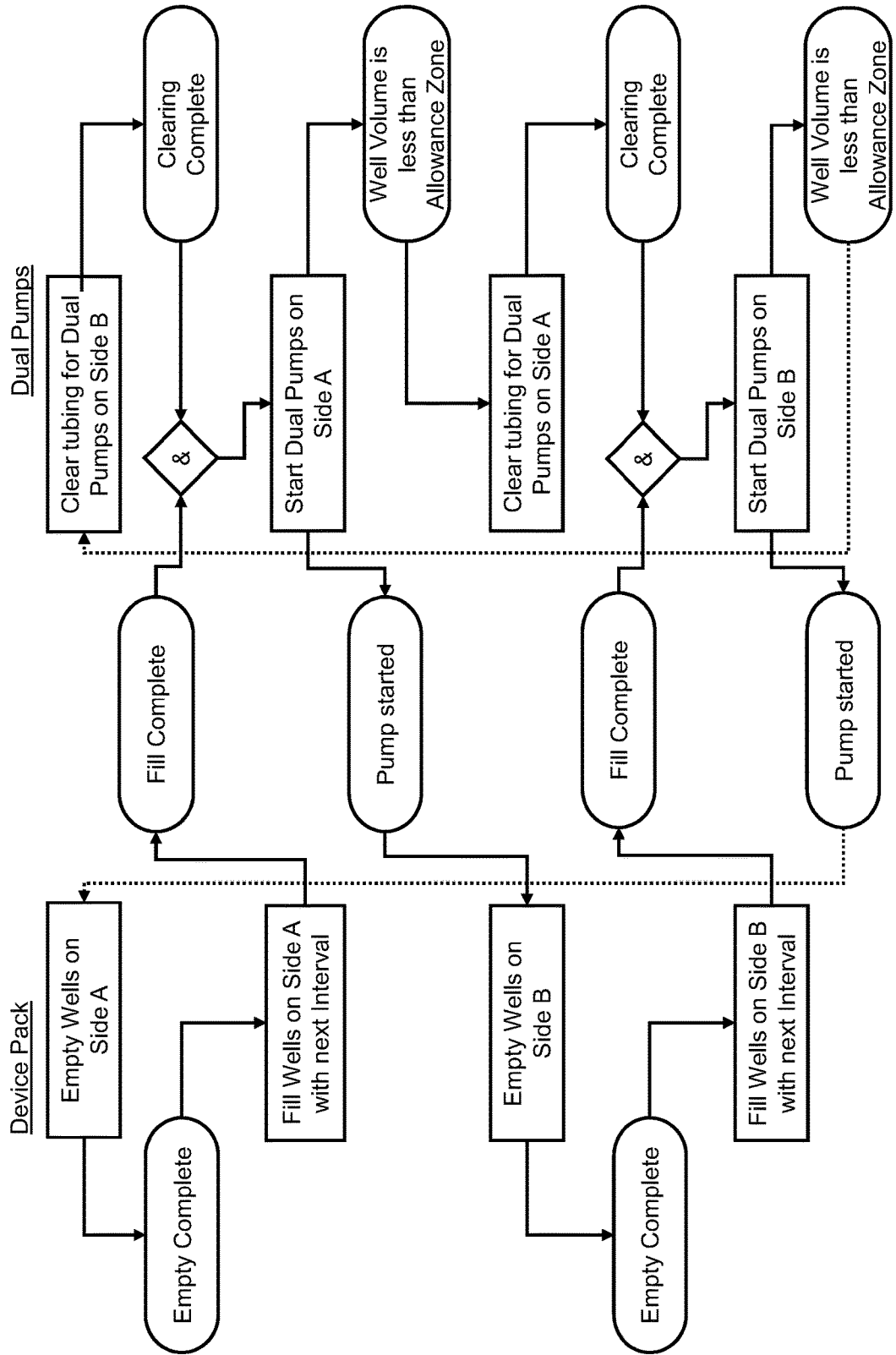

The Device Pack and Dual Pumps Delivery Protocol is shown in FIG. 19M. Mixtures of fluid will be delivered to the chemostats from the Input Reservoir well plate. The Input Reservoir well plate needs to be filled with the correct substances in each well for a particular interval of the experiment prior to its delivery to the chemostat. The steps to be followed are:
Initial
On Start:
  Start Input Reservoir Delivery protocol for Device Pack on Side A.
  Device Pack on Side B should be stopped.
On completion of initial fill:
  Start Dual Pumps.
  Start P4.
  Experiment Runner should confirm next step. On confirmation, send next cocktail to Reservoir Feeder.
  Reservoir Feeder should instruct Device Pack B to start filling Side B with next cocktail.
Main Loop
On Device Pack fill completion:
  Stop filling on non-active side. (Active is defined as the side being emptied by the Dual Pumps.)
  Alert Dual Pumps that Side is ready. (This will be used by Dual Pumps to confirm that it may switch pumps.)
On 12-Channel Optical Sensor reports pH:
  Send pH reading to Experiment Runner
  Update target pH in stored Experiment
Finish
  Stop Dual Pumps FIG. 19N presents the steps for experiment step tracking and execution. The Experiment algorithms step through three main phases:
Initialization Phase
  Read CAPCAS Database for current experiment
  Clear tubing for Dual Pumps
  Prime tubing for solutions used
  Empty Input Reservoir well plate
Delivery Phase
  Read CAPCAS Database for current experiment
  Run P4
  Deliver mixture for each chemostat
  Record delivery time in Interval table
  Move to next interval and repeat this phase until all intervals are complete
Output Phase
  Stop P4
  Run P5 until half of fluid from Chemostat well plate is delivered The Device Pack and Dual Pumps relationship is specified in FIG. 19D.

The Device Pack and Dual Pumps have a set of operations that they run independent of other systems. The Device Pack has two operations:
  Empty all wells.
  Fill wells with next delivery.
The Dual Pumps perform two operations:
  Clear tubing.
  Deliver fluid from Input Reservoir well plate to Chemostat well plate.

The start times of these operations are dependent on each other. It is important that wells are filled by the Device Pack prior to the Dual Pumps attempting to deliver those same wells to the Chemostat well plate. It is also important that the Device Pack does not fill wells that are currently being delivered by Dual Pumps. Therefore, we outlined a protocol to ensure that operations act independently but can be triggered by events related to other simultaneous operations.

Figure 19P:
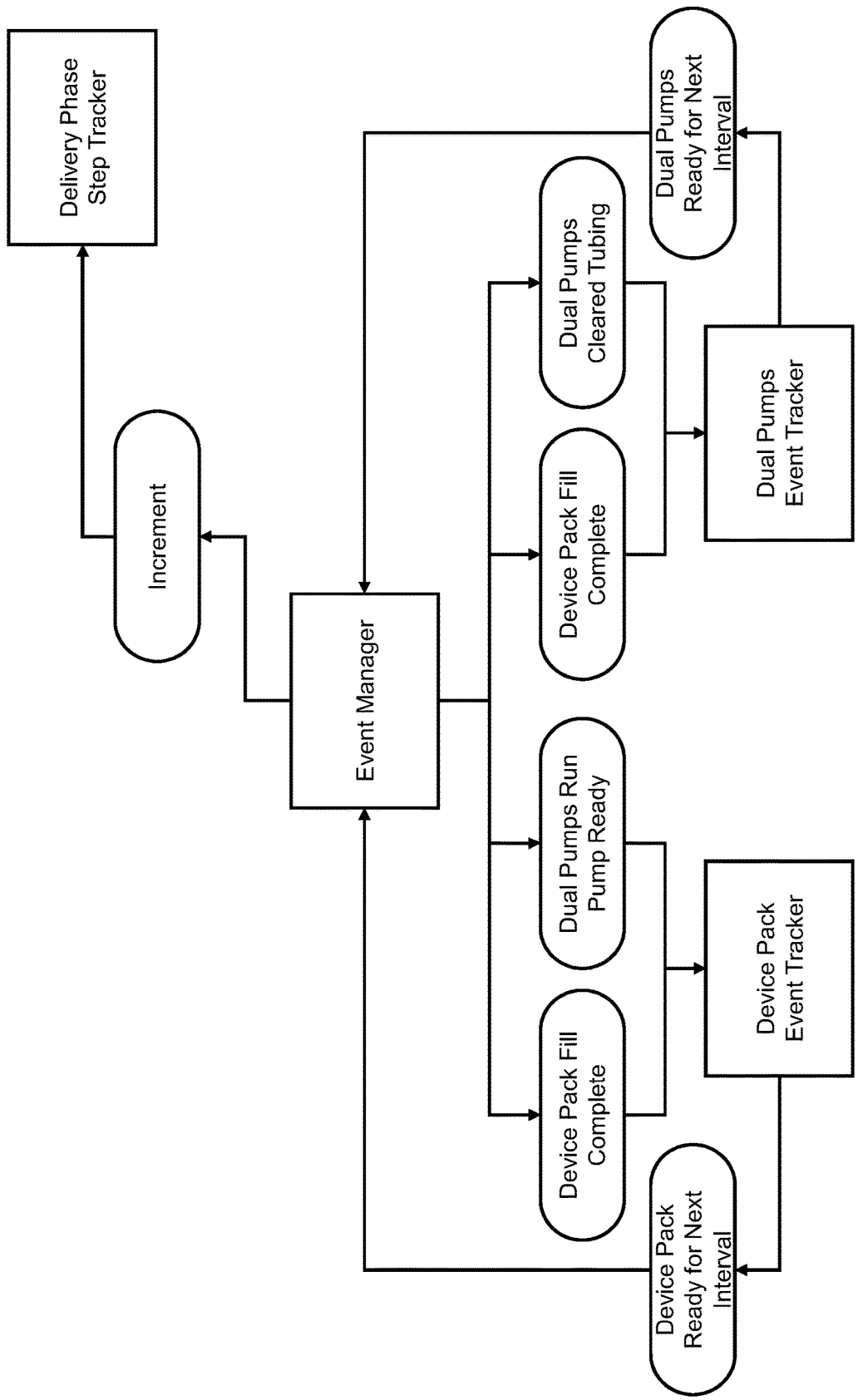

It is necessary to track the steps taken by the Device Pack and Dual Pumps, as shown in FIG. 19P. To accomplish this, the Delivery Phase Step Tracker maintains an Event Manager.

The Event Manager monitors for events from Device Pack and Dual Pumps Controller to determine if current step has been finished.

When all required events have been received, then an increment signal is emitted by Event Manager.

Given this software structure for commands and reports, it is possible for CAPCAS-AI to write experimental designs to CAPCAS-DB, which are read by CAPCAS-IT, and executed by CAPCAS-HW. We have presented just one embodiment of how the hardware in the invention might be controlled; there are innumerable means by which the same tasks could be accomplished. Alternative hardware embodiments could require different control protocols, but central to the invention is the close interaction between artificial intelligence/machine-learning software, sophisticated hardware, and a breadth of different biological systems, with the connections being designed to have the system function autonomously as a self-driving biological laboratory or robot scientist that could greatly accelerate the rate at which biological systems could be optimized for particular outputs or functions, and computational models of these systems developed and applied.

Alternative Embodiments

While the scale of the systems presented herein focuses on well plates, the topology and operation of such a CAPCAS unit can be scaled to large or smaller fluidic volumes. The addition of fluidic buses could be used to reduce the size of each unit, or increase the speed with which media was formulated. The sizes of the enclosures described are set by laboratory convention, and respect the height and width of doorways, but larger or smaller enclosures would be possible. Coupled organs could be implemented by the use of a bidirectional microformulator, or by means of connections hard-plumbed into the lid or a fluidic bus. An important feature of the CAPCAS approach is that a large number of chemostat or bioreactor plates can be operated over long periods of time without being disturbed by creating a fluid-handling system that can perfuse the chemostats or bioreactors without interruption, something that is not possible in conventional HTS systems where a fluid handler outside the incubator is needed to refresh the media of wells that would otherwise be held in an incubator. Other robot designs could deliver well plates to fluidic stations, or compact fluidic stations could be delivered to fixed plates.

In summary, the CAPCAS platform that is the subject of this invention offers an alternative to large, room-sized high-throughput screening systems that rely on daily media changes and transport of plates or organ chips between incubator, fluid handler, and plate reader. However, CAPCAS would be compatible with and interfaceable to existing well-plate robotics. It would be ideal for any experiment that requires continuous or controlled perfusion, particularly over the long term. It would be useful for any bioreactor or culture system that could fit in a well-plate footprint, and would be particularly well suited for long-growth-time models that would require frequent feeding or media adjustments. The fluidic control and delivery systems are supported in a station above the working deck and can replace rocker systems for gravity perfusion. The CAPCAS chassis would not require an incubator and could be small enough that a single-chemostat-plate unit could sit on a laboratory bench or within a cell culture hood, or it could be a large free-standing unit that operated a thousand or more independent chemostats. The use of multiple iPlateBots would enable parallel, asynchronous delivery and removal of well plates from multiple CAPCAS fluidic control stations. The Robot Scientist software that drives CAPCAS can design and execute complex experiments and generate and test hypotheses in a manner that is vastly more efficient than what humans alone can achieve.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

Literature Cited

1. Alberghina, L, and Westerhoff, H V. Systems biology: definitions and perspectives, Topics in current genetics, Springer, New York, NY 2005. https://doi.org/10.007/b95175
2. Omenn, G S. Grand challenges and great opportunities in science, technology, and public policy. Science, 314: 1696-1704. 2006.
3. Huang, S, and Wikswo, J. Dimensions of systems biology. In: Reviews of Physiology, Biochemistry and Pharmacology. S. G. Amara, E. Bamberg, T. Gudermann, S. C. Hebert, R. Jahn, W. J. Lederer, et al., eds. pp 81-104. 2007.
4. King, R D, Whelan, K E, Jones, F M, Reiser, P G K, Bryant, C H, Muggleton, S H, Kell, D B, and Oliver, S G. Functional genomic hypothesis generation and experimentation by a robot scientist. Nature, 427:247-252. 2004.
5. King, R D, Rowland, J, Oliver, S G, Young, M, Aubrey, W, Byrne, E, Liakata, M, Markham, M, Pir, P, Soldatova, L N, Sparkes, A, Whelan, K E, and Clare, A. The automation of science. Science, 324:85-89. 2009.
6. King, R D, Rowland, J, Aubrey, W, Liakata, M, Markham, M, Soldatova, L N, Whelan, K E, Clare, A, Young, M, Sparkes, A, Oliver, S G, and Pir, P. The Robot Scientist Adam. Comp, 42:46-54. 2009.
7. Williams, K, Bilsland, E, Sparkes, A, Aubrey, W, Young, M, Soldatova, L N, De Grave, K, Ramon, J, de Clare, M, Sirawaraporn, W, Oliver, S G, and King, R D. Cheaper faster drug development validated by the repositioning of drugs against neglected tropical diseases. J. R. Soc. Interface, 12: 20141289. 2015.
8. Coutant, A, Roper, K, Trejo-Banos, D, Bouthinon, D, Carpenter, M, Grzebyta, J, Santini, G, Soldano, H, Elati, M, Ramon, J, Rouveirol, C, Soldatova, L N, and King, R D. Closed-loop cycles of experiment design, execution, and learning accelerate systems biology model development in yeast. Proc. Natl. Acad. Sci. U.S.A., 116:18142-18147. 2019.
9. Byrd, T F, Hoang, L T, Kim, E G, Pfister, M E, Werner, E M, Arndt, S E, Chamberlain, J W, Hughey, J J, Nguyen, B A, Schneibel, E J, Wertz, L L, Whitfield, J S, Wikswo, J P, and Seale, K T. The microfluidic multitrap nanophysiometer for hematologic cancer cell characterization reveals temporal sensitivity of the calcein-AM efflux assay. Sci. Rep., 4: 5117. 2014. PMCID: PMC4038811.
10. Hoskisson, P A, and Hobbs, G. Continuous culture—making a comeback? Microbiol.-SGM, 151:3153-3159. 2005.
11. Kadouri, A, and Spier, R E. Some myths and messages concerning the batch and continuous culture of animal cells. Cytotechnology, 24:89-98. 1997.
12. Ziv, N, Brandt, N J, and Gresham, D. The Use of Chemostats in Microbial Systems Biology. J. Vis. Exp., 80: e50168. 2013.
13. Croughan, M S, Konstantinov, K B, and Cooney, C. The Future of Industrial Bioprocessing: Batch or Continuous? Biotechnol. Bioeng., 112:648-651. 2015.
14. Watson, D E, Hunziker, R, and Wikswo, J P. Fitting tissue chips and microphysiological systems into the grand scheme of medicine, biology, pharmacology, and toxicology. Exp. Biol. Med., 242:1559-1572. 2017. PMCID: PMC5661772.
15. Bielser, J M, Wolf, M, Souquet, J, Broly, H, and Morbidelli, M. Perfusion mammalian cell culture for recombinant protein manufacturing—A critical review. Biotechnol. Adv., 36:1328-1340. 2018.
16. Karst, D J, Steinebach, F, and Morbidelli, M. Continuous integrated manufacturing of therapeutic proteins. Curr. Opin. Biotechnol., 53:76-84. 2018.
17. Monod, J. La technique de culture continue théorie et applications. Ann. Inst. Pasteur (Paris), 79:390-410. 1950.
18. Novick, A, and Szilard, L. Description of the Chemostat. Science, 112:715-716. 1950.
19. Novick, A, and Szilard, L. Experiments with the Chemostat on Spontaneous Mutations of Bacteria. Proc. Natl. Acad. Sci., 36:708-719. 1950.
20. Cyr, K J, Avaldi, O M, and Wikswo, J P. Circadian hormone control in a human-on-a-chip: In vitro biology's ignored component? Exp. Biol. Med., 242:1714-1731. 2017. PMCID: PMC5832251.
21. "Interconnections of multiple perfused engineered tissue constructs and microbioreactors, multi-microformulators and applications of the same," Wikswo, J P, Block III, F E, and Samson, P C, U.S. Pat. No. 10,577,574 B2 (Mar. 3, 2020)
22. "System and method for microdialysis imaging and regional fluidic delivery and control and applications of same," Wikswo, J P, Reiserer, R S, and Hawkins, K, U.S. Pat. No. 10,538,726 B2 (Jan. 21, 2020)
23. "Interconnections of multiple perfused engineered tissue constructs and microbioreactors, multi-microformulators and applications of the same," Wikswo, J P, Markov, D A, Samson, P C, Block III, F E, Schaffer, D K, and Reiserer, R S, U.S. Pat. No. 10,023,832 B2 Published as China Patent ZL201710014601.1 (Jul. 17, 2018)

24. "System and method for microdialysis imaging and regional fluidic delivery and control and applications of same," Wikswo, J P, Hawkins, K G, and Reiserer, R S, National Phase Patent application Ser. No. 16/397,019 (Apr. 29, 2019)
25. "Interconnections of multiple perfused engineered tissue constructs and microbioreactors, multi-microformulators and applications of the same," Wikswo, J P, Markov, D A, Samson, P C, Block III, F E, Schaffer, D K, and Reiserer, R S, European Patent Application published as EP3415611 (Dec. 19, 2018)
26. "Interconnections of multiple perfused engineered tissue constructs and microbioreactors, multi-microformulators and applications of the same," Wikswo, J P, Markov, D A, Samson, P C, Block III, F E, Schaffer, D K, and Reiserer, R S, European Patent Application published as EP3190172 A3 (Aug. 30, 2017)
27. Ratcliffe, E, Glen, K E, Workman, V L, Stacey, A J, and Thomas, R J. A novel automated bioreactor for scalable process optimisation of haematopoietic stem cell culture. J. Biotechnol., 161:387-390. 2012.
28. Davis, D, Lyons, D, and Ross, S, Modeling perfusion at small scale using ambr15™, In: Integrated Continuous Biomanufacturing II, ECI Symposium Series. C. Goudar, S. Farid, C. Hwang and K. Lacki, eds. 2015. https://dc.engconfintl.org/biomanufact_ii/128.
29. Zoro, B, and Tait, A, Development of a novel automated perfusion mini bioreactor "Ambr® 250 perfusion", In: Integrated Continuous Biomanufacturing III, ECI Symposium Series. S. Farid, C. Goudar, P. Alves and V. Warikoo, eds. 2017. https://dc.engconfintl.org/biomanufact_ii/128.
30. Bareither, R, Bargh, N, Oakeshott, R, Watts, K, and Pollard, D. Automated Disposable Small Scale Reactor for High Throughput Bioprocess Development: A Proof of Concept Study. Biotechnol. Bioeng., 110:3126-3138. 2013.
31. Zhong, Z W, Wong, B G, Ravikumar, A, Arzumanyan, G A, Khalil, A S, and Liu, C C. Automated Continuous Evolution of Proteins in Vivo. ACS Synth. Biol., 9:1270-1276. 2020.
32. Heins, Z J, Mancuso, C P, Kiriakov, S, Wong, B G, Bashor, C J, and Khalil, A S. Designing Automated, High-throughput, Continuous Cell Growth Experiments Using eVOLVER. J. Vis. Exp.: e59652. 2019.
33. Wong, B G, Mancuso, C P, Kiriakov, S, Bashor, C J, and Khalil, A S. Precise, automated control of conditions for high-throughput growth of yeast and bacteria with eVOLVER. Nat. Biotechnol., 36:614-623. 2018.
34. Lee, K S, Boccazzi, P, Sinskey, A J, and Ram, R J. Microfluidic chemostat and turbidostat with flow rate, oxygen, and temperature control for dynamic continuous culture. Lab Chip, 11:1730-1739. 2011.
35. Bower, D M, Lee, K S, Ram, R J, and Prather, K L J. Fed-batch microbioreactor platform for scale down and analysis of a plasmid DNA production process. Biotechnol. Bioeng., 109:1976-1986. 2012.
36. "Organ on chip integration and applications of the same," Block III, F E, Samson, P C, Werner, E M, Markov, D A, Reiserer, R S, McKenzie, J R, Cliffel, D E, Matloff, W J, Block Jr, F E, Scherrer, J R, Tidwell, W H, and Wikswo, J P, U.S. Pat. No. 9,874,285 B2 (Jan. 23, 2018)
37. Shin, W, Hinojosa, C D, Ingber, D E, and Kim, H J. Human Intestinal Morphogenesis Controlled by Transepithelial Morphogen Gradient and Flow-Dependent Physical Cues in a Microengineered Gut-on-a-Chip. Iscience, 15:391-406. 2019.
38. LeDuc, P R, Messner, W C, and Wikswo, J P. How do control-based approaches enter into biology? Annu. Rev. Biomed. Eng., 13:369-396. 2011.
39. Wikswo, J P, Block III, F E, Cliffel, D E, Goodwin, C R, Marasco, C C, Markov, D A, McLean, D L, McLean, J A, McKenzie, J R, Reiserer, R S, Samson, P C, Schaffer, D K, Seale, K T, and Sherrod, S D. Engineering Challenges for Instrumenting and Controlling Integrated Organ-on-Chip Systems. IEEE Trans. Biomed. Eng., 60:682-690. 2013. PMCID: PMC3696887.
40. Wikswo, J, Curtis, E L, Eagleton, Z E, Evans, B C, Kole, A, Hofmeister, L H, and Matloff, W J. Scaling and systems biology for integrating multiple organs-on-a-chip. Lab Chip, 13:3496-3511. 2013.
41. Miller, D R, Schaffer, D K, Neely, M D, McClain, E S, Travis, A R, Block III, F E, McKenzie, J R, Werner, E M, Armstrong, L, Markov, D A, Bowman, A B, Ess, K C, Cliffel, D E, and Wikswo, J P. A bistable, multiport valve enables microformulators creating microclinical analyzers that reveal aberrant glutamate metabolism in astrocytes derived from a tuberous sclerosis patient. Sens. Actuators B Chem., 341: 129972. 2021.
42. "Integrated Organ-on-Chip Systems and Applications of the Same," Wikswo, J P, Cliffel, D E, Markov, D A, McLean, J A, McCawley, L J, Samson, P C, Reiserer, R S, Block, F E, and McKenzie, J R, U.S. Pat. No. 10,444,223 B2 (Oct. 15, 2019)
43. "Integrated human organ-on-chip microphysiological systems," Wikswo, J P, Samson, P C, Block III, F E, Reiserer, R S, Parker, K K, McLean, J A, McCawley, L J, Markov, D, Levner, D, Ingber, D E, Hamilton, G A, Goss, J A, Cunningham, R, Cliffel, D E, McKenzie, J R, Bahinski, A, and Hinojosa, C D, 9,725,687 B2 (Aug. 8, 2017)
44. "Device and Methods for Detecting the Response of a Plurality of Cells to at Least one Analyte of Interest," Cliffel, D, Baudenbacher, F J, Wikswo, J P, Eklund, S, Balcarcel, R R, and Gilligan, J M, U.S. Pat. No. 7,713,733 B2 (May 11, 2010)
45. "Apparatus and methods for monitoring the status of a metabolically active cell," Baudenbacher, F J, Wikswo, J P, Balcarcel, R R, Cliffel, D, Eklund, S, Gilligan, J M, McGuinness, O, Monroe, T, Prokop, A, Stremler, M A, and Werdich, A A, U.S. Pat. No. 7,704,745 B2 (Apr. 27, 2010)
46. "Microfluidic systems for multiple bioreactors and applications of same," Schaffer, D K, Reiserer, R S, Geuy, M D, and Wikswo, J P, Application PCT/US21/42141 (Jul. 19, 2021)
47. "Peristaltic micropump and related systems and methods," Gould, P A, Hoang, L T, Schaffer, D K, Reiserer, R S, Samson, P C, and Wikswo, J P, U.S. Pat. No. 10,781,809 B2 (Sep. 22, 2020)
48. "Peristaltic micropump and related systems and methods," Gould, P A, Hoang, L T, Scherrer, J R, Matloff, W J, Seale, K T, Curtis, E L, Schaffer, D K, Hall, D J, Kole, A, Reiserer, R S, Tidwell, H, Samson, P C, and Wikswo, J P, 10,487,819 B2 (Nov. 26, 2019)
49. "Microfluidic systems, pumps, valves, fluidic chips thereof, and applications of same," Reiserer, R S, Schaffer, D K, Samson, P C, Markov, D A, Geuy, M D, McCawley, L J, and Wikswo, J P, PCT Patent Application PCT/US20/40061 (Jun. 29, 2020)

50. "Cartridge systems, capacitive pumps and multi-throw valves and pump-valve systems and applications of same," Schaffer, D K, Markov, D A, Reiserer, R S, McCawley, L J, Geuy, M, Britt, C M, and Wikswo, J P, U.S. Pat. No. 11,135,582 B2 (Oct. 5, 2021)
51. "Multichannel Pumps and Applications of Same," Wikswo, J P, Reiserer, R S, Schaffer, D K, Markov, D A, and Britt, C M, PCT Patent Application PCT/US19/47190 Published as WO2020/041260 A1 (Feb. 27, 2020)
52. "Normally closed microvalve and applications of the same," Block III, F E, Samson, P C, and Wikswo, J P, 9,618,129 B2 (Apr. 11, 2017)
53. "Microbioreactor with vertical-via rotary metering valves and applications of same," Schaffer, D K, Wikswo, J P, Reiserer, R S, Geuy, M D, Spivey, E C, Britt, C M, Brown, J A, Markov, D A, Faley, S, McCawley, L J, and Samson, P C, US Provisional Patent Application 63/017744 (Apr. 30, 2020)
54. "Microfluidic systems for multiple bioreactors and applications of same," Wikswo, J P, Reiserer, R S, and Schaffer, D K, PCT Patent Application 63/053,388 (Jul. 17, 2020)
55. "Pressure regulation system, pressure release valves thereof, passive pressurized fluid reservoirs, and applications of same," Samson, P C, Schaffer, D K, Reiserer, R S, Schatzki, L, Markov, D A, Britt, C M, and Wikswo, J P, PCT Patent Application PCT/US19/47324 Published as WO2020/041357 A2 (Feb. 27, 2020)
56. "Multicompartment microfluidic bioreactors, cylindrical rotary valves and applications of same," Wikswo, J P, Spivey, E C, Schaffer, D K, Reiserer, R S, Seale, K T, and Block, F E, PCT Patent Application PCT/US2019/034285 Published as WO2019/231977 A1 (Dec. 5, 2019)
57. Enders, J R, Marasco, C C, Wikswo, J P, and McLean, J A. A Dual-Column Solid Phase Extraction Strategy for Online Collection and Preparation of Continuously Flowing Effluent Streams for Mass Spectrometry. Anal. Chem., 84:8467-8474. 2012. PMCID: PMC3518407.
58. Marasco, C C, Goodwin, C R, Winder, D G, Schramm-Sapyta, N L, McLean, J A, and Wikswo, J P. Systems-level view of cocaine addiction: The interconnection of the immune and nervous systems. Exp. Biol. Med., 239: 1433-1442. 2014. PMCID: PMC4216763.
59. Zhang, X, Romm, M, Zheng, X Y, Zink, E M, Kim, Y M, Burnum-Johnson, K E, Orton, D J, Apffel, A, Ibrahim, Y M, Monroe, M E, Moore, R J, Smith, J N, Ma, J, Renslow, R S, Thomas, D G, Blackwell, A E, Swinford, G, Sausen, J, Kurulugama, R T, Eno, N, Darland, E, Stafford, G, Fjeldsted, J, Metz, T O, Teeguarden, J G, Smith, R D, and Baker, E S. SPE-IMS-MS: An automated platform for sub-sixty second surveillance of endogenous metabolites and xenobiotics in biofluids. Clin. Mass Spectrom., 2:1-10. 2016.
60. May, J C, Dodds, J N, Kurulugama, R T, Stafford, G C, Fjeldsted, J C, and McLean, J A. Broadscale resolving power performance of a high precision uniform field ion mobility-mass spectrometer. Analyst, 140:6824-6833. 2015. PMCID: PMC4586486.
61. May, J C, Goodwin, C R, Lareau, N M, Leaptrot, K L, Morris, C B, Kurulugama, R T, Mordehai, A, Klein, C, Barry, W, Darland, E, Overney, G, Imatani, K, Stafford, G C, Fjeldsted, J C, and McLean, J A. Conformational Ordering of Biomolecules in the Gas Phase: Nitrogen Collision Cross Sections Measured on a Prototype High Resolution Drift Tube Ion Mobility-Mass Spectrometer. Anal. Chem., 86:2107-2116. 2014. PMCID: PMC3931330.
62. Kim, H S, Waqued, S C, Nodurft, D T, Devarenne, T P, Yakovlev, V V, and Han, A. Raman spectroscopy compatible PDMS droplet microfluidic culture and analysis platform towards on-chip lipidomics. Analyst, 142:1054-1060. 2017.
63. Jahn, I J, Zukovskaja, O, Zheng, X S, Weber, K, Bocklitz, T W, Cialla-May, D, and Popp, J. Surface-enhanced Raman spectroscopy and microfluidic platforms: challenges, solutions and potential applications. Analyst, 142:1022-1047. 2017.
64. Abu-Absi, N R, Kenty, B M, Cuellar, M E, Borys, M C, Sakhamuri, S, Strachan, D J, Hausladen, M C, and Li, Z J. Real Time Monitoring of Multiple Parameters in Mammalian Cell Culture Bioreactors Using an In-Line Raman Spectroscopy Probe. Biotechnol. Bioeng., 108:1215-1221. 2011.
65. Whelan, J, Craven, S, and Glennon, B. In situ Raman spectroscopy for simultaneous monitoring of multiple process parameters in mammalian cell culture bioreactors. Biotechnol. Prog., 28:1355-1362. 2012.
66. Rafferty, C, O'Mahony, J, Burgoyne, B, Rea, R, Balss, K M, and Latshaw, D C. Raman spectroscopy as a method to replace off-line pH during mammalian cell culture processes. Biotechnol. Bioeng., 117:146-156. 2020.
67. Iversen, J A, Berg, R W, and Ahring, B K. Quantitative monitoring of yeast fermentation using Raman spectroscopy. Anal. Bioanal. Chem., 406:4911-4919. 2014.
68. Markov, D A, Lillie, E M, Garbett, S P, and McCawley, L J. Variation in diffusion of gases through PDMS due to plasma surface treatment and storage conditions. Biomed. Microdevices, 16:91-96. 2014. PMCID: PMC3945670.
69. Eklund, S E, Cliffel, D E, Kozlov, E, Prokop, A, Wikswo, J P, Jr., and Baudenbacher, F J. Modification of the Cytosensor TM Microphysiometer to Simultaneously Measure Extracellular Acidification and Oxygen Consumption Rates. Anal. Chim. Acta, 496:93-101. 2003.
70. Velkovsky, M, Cliffel, D, Eklund, S, Eluvathingal, S, Stremler, M A, and Wikswo, J P. Extracting Metabolic Fluxes from Measurements with a Multianalyte Micro-Physiometer. Biophysical Society 49th Annual Meeting, Long Beach, C A, 2005,
71. Eklund, S E, Snider, R M, Wikswo, J, Baudenbacher, F, Prokop, A, and Cliffel, D E. Multianalyte microphysiometry as a tool in metabolomics and systems biology. J. Electroanal. Chem., 587:333-339. 2006.
72. Eklund, S E, Thompson, R G, Snider, R M, Carney, C K, Wright, D W, Wikswo, J, and Cliffel, D E. Metabolic discrimination of select list agents by monitoring cellular responses in a multianalyte microphysiometer. Sensors, 9:2117-2133. 2009. PMCID: PMC3345856.
73. Snider, R M, McKenzie, J R, Kraft, L, Kozlov, E, Wikswo, J P, and Cliffel, D E. The effects of Cholera Toxin on cellular energy metabolism. Toxins (Basel), 2:632-648. 2010.
74. Velkovsky, M, Snider, R, Cliffel, D E, and Wikswo, J P. Modeling the measurements of cellular fluxes in microbioreactor devices using thin enzyme electrodes. Journal of Mathematical Chemistry, 49:251-275. 2011. PMCID: PMC3768171.
75. Lima, E A, Snider, R M, Reiserer, R S, McKenzie, J R, Kimmel, D W, Eklund, S E, Wikswo, J P, and Cliffel, D E. Multichamber multipotentiostat system for cellular microphysiometry. Sensors and Actuators B-Chemical, 204:536-543. 2014. PMCID: PMC4167374.
76. McKenzie, J R, Cognata, A C, Davis, A N, Wikswo, J P, and Cliffel, D E. Real-Time Monitoring of Cellular Bio- 77. "Integrated organ-on-chip systems and applications of the same," Wikswo, J P, Cliffel, D E, Markov, D A, McLean, J A, McCawley, L J, Samson, P C, Reiserer, R S, Block, F E, and McKenzie, J R, U.S. Pat. No. 10,078, 075 B2 (Sep. 18, 2018)

78. Kwon, T, Prentice, H, De Oliveira, J, Madziva, N, Warkiani, M E, Hamel, J F P, and Han, J. Microfluidic Cell Retention Device for Perfusion of Mammalian Suspension Culture. Sci. Rep., 7: 6703. 2017.

79. Sonmez, U, Jaber, S, and Trabzon, L. Super-enhanced particle focusing in a novel microchannel geometry using inertial microfluidics. J. Micromech. Microeng., 27: 065003. 2017.

80. Warkiani, M E, Tay, A K P, Guan, G F, and Han, J. Membrane-less microfiltration using inertial microfluidics. Sci. Rep., 5: 11018. 2015.

81. Warkiani, M E, Guan, G F, Luan, K B, Lee, W C, Bhagat, A A S, Chaudhuri, P K, Tan, D S W, Lim, W T, Lee, S C, Chen, P C Y, Lim, C T, and Han, J. Slanted spiral microfluidics for the ultra-fast, label-free isolation of circulating tumor cells. Lab Chip, 14:128-137. 2014.

82. Bosco, B, Paillet, C, Amadeo, I, Mauro, L, Orti, E, and Forno, G. Alternating Flow Filtration as an Alternative to Internal Spin Filter Based Perfusion Process: Impact on Productivity and Product Quality. Biotechnol. Prog., 33:1010-1014. 2017.

83. Clincke, M-F, Mölleryd, C, Zhang, Y, Lindskog, E, Walsh, K, and Chotteau, V. Study of a recombinant CHO cell line producing a monoclonal antibody by ATF or TFF external filter perfusion in a WAVE Bioreactor™. BMC Proc., 5: P105. 2011.

84. Karst, D J, Serra, E, Villiger, T K, Soos, M, and Morbidelli, M. Characterization and comparison of ATF and TFF in stirred bioreactors for continuous mammalian cell culture processes. Biochem. Eng. J., 110:17-26. 2016.

85. Wang, S, Godfrey, S, Ravikrishnan, J, Lin, H, Vogel, J, and Coffman, J. Shear contributions to cell culture performance and product recovery in ATF and TFF perfusion systems. J. Biotechnol., 246:52-60. 2017.

86. Gorkov, L P. On the Forces Acting on a Small Particle in an Acoustic Field Within an Ideal Fluid. Soviet Physics.Doklady, 6:773-775. 1962.

87. Goddard, G, Martin, J C, Graves, S W, and Kaduchak, G. Ultrasonic particle-concentration for sheathless focusing of particles for analysis in a flow cytometer. Cytometry Part A, 69A:66-74. 2006.

88. Gencturk, E, Ulgen, K O, and Mutlu, S. Thermoplastic microfluidic bioreactors with integrated electrodes to study tumor treating fields on yeast cells. Biomicrofluidics, 14: 034104. 2020.

89. Bugeja, C. The printable motor. The trick is to use circuit board traces for coils. IEEE Spectr., 55:18-19. 2018.

90. Greene, J F, Preger, Y, Stahl, S S, and Root, T W. PTFE-Membrane Flow Reactor for Aerobic Oxidation Reactions and Its Application to Alcohol Oxidation. Org. Process Res. Dev., 19:858-864. 2015.

91. Ramirez, L A, Perez, E L, Diaz, C G, Luengas, D A C, Ratkovich, N, and Reyes, L H. CFD and Experimental Characterization of a Bioreactor: Analysis via Power Curve, Flow Patterns and k(L)a. Processes, 8: 878. 2020.

92. Unger, M A, Chou, H P, Thorsen, T, Scherer, A, and Quake, S R. Monolithic microfabricated valves and pumps by multilayer soft lithography. Science, 288:113-116. 2000.

93. Thorsen, T, Maerkl, S J, and Quake, S R. Microfluidic Large-Scale Integration. Science, 298:580-584. 2002.

94. McKenzie, J R, Cliffel, D E, and Wikswo, J P. Electrochemical monitoring of cellular metabolism. In: Encyclopedia of Applied Electrochemistry. R. Savinell, K. Ota and G. Kreysa, eds. Springer Science+Business Media, New York. pp 522-528. 2014.

95. Marasco, C C, Enders, J R, Seale, K T, McLean, J A, and Wikswo, J P. Real-time Cellular Exometabolome Analysis with a Microfluidic-mass Spectrometry Platform. PLoS One, 10: e0117685. 2015. PMCID: PMC4344306.

96. Brown, J A, Pensabene, V, Markov, D A, Allwardt, V, Neely, M D, Shi, M, Britt, C M, Hoilett, O S, Yang, Q, Brewer, B M, Samson, P C, McCawley, L J M, James M., Webb, D J, Li, D, Bowman, A B, Reiserer, R S, and Wikswo, J P. Recreating blood-brain barrier physiology and structure on chip: A novel neurovascular microfluidic bioreactor. Biomicrofluidics, 9: 054124. 2015. PMCID: PMC4627929.

97. Brown, J A, Codreanu, S G, Shi, M, Sherrod, S D, Markov, D A, Neely, M D, Britt, C M, Hoilett, O S, Reiserer, R S, Samson, P C, McCawley, L J, Webb, D J, Bowman, A B, McLean, J A, and Wikswo, J P. Metabolic consequences of inflammatory disruption of the blood-brain barrier in an organ-on-chip model of the human neurovascular unit. J. Neuroinflammation, 13: 306. 2016. PMCID: PMC5153753.

98. Brown, J A, Faley, S L, Shi, Y, Hillgren, K M, Sawada, G A, Baker, T K, Wikswo, J P, and Lippmann, E S. Advances in blood-brain barrier modeling in microphysiological systems highlight critical differences in opioid transport due to cortisol exposure. Fluids Barriers CNS, 17: 38. 2020. PMCID: PMC7269003.

99. May, J C, and McLean, J A. Advanced Multidimensional Separations in Mass Spectrometry: Navigating the Big Data Deluge. Annu. Rev. Anal. Chem., 9:387-409. 2016.

100. Enders, J R, Marasco, C C, Kole, A, Nguyen, B, Sundarapandian, S, Seale, K T, Wikswo, J P, and McLean, J A. Towards monitoring real-time cellular response using an integrated microfluidics-MALDINESI-ion mobility-mass spectrometry platform. IET Syst. Biol., 4:416-427. 2010.

101. Gutierrez, D B, Gant-Branum, R L, Romer, C E, Farrow, M A, Allen, J L, Dahal, N, Nei, Y W, Codreanu, S G, Jordan, A T, Palmer, L D, Sherrod, S D, McLean, J A, Skaar, E P, Norris, J L, and Caprioli, R M. An Integrated, High-Throughput Strategy for Multiomic Systems Level Analysis. J. Proteome Res., 17:3396-3408. 2018.

102. Rafferty, C, Johnson, K, O'Mahony, J, Burgoyne, B, Rea, R, and Balss, K M. Analysis of chemometric models applied to Raman spectroscopy for monitoring key metabolites of cell culture. Biotechnol. Prog., 36: e2977. 2020.

103. Short, K W, Carpenter, S, Freyer, J P, and Mourant, J R. Raman spectroscopy detects biochemical changes due to proliferation in mammalian cell cultures. Biophys. J., 88:4274-4288. 2005.

104. Ali, A, Abouleila, Y, and Germond, A. An Integrated Raman Spectroscopy and Mass Spectrometry Platform to Study Single-Cell Drug Uptake, Metabolism, and Effects. J. Vis. Exp.: e60449. 2020.

105. Wolff, A, Perch-Nielsen, I R, Larsen, U D, Friis, P, Goranovic, G, Poulsen, C R, Kutter, J P, and Telleman, P. Integrating advanced functionality in a microfabricated high-throughput fluorescent-activated cell sorter. Lab Chip, 3:22-27. 2003.

106. Hui, W C, Yobas, L, Samper, V D, Heng, C K, Liw, S, Ji, H, Chen, Y, Cong, L, Li, J, and Lim, T M. Microfluidic systems for extracting nucleic acids for DNA and RNA analysis. Sensors and Actuators A, 133:335-339. 2007.
107. Gao, J, Yin, X F, and Fang, Z L. Integration of single cell injection, cell lysis, separation and detection of intracellular constituents on a microfluidic chip. Lab Chip, 4:47-52. 2004.
108. Wikipedia contributors. Single-responsibility principle: Wikipedia, The Free Encyclopedia; [updated 28 May 2021 01:57 UTC. https://en.wikipedia.org/w/index.php?title=Single-responsibility_principie&oldid=1025521437 (accessed 12 Jan. 2022 15:48 UTC)
109. Martin, R C, Agile software development: principles, patterns, and practices. Prentice Hall. 2003.

What is claimed is:

1. A continuous automated perfusion culture analysis system (CAPCAS), comprising:
   one or more fluidic systems configured to operate large numbers of biodevices in parallel,
      wherein each fluidic system comprises an array of biodevice perfusion systems and a media delivering means fluidically coupled to the array of biodevices,
      wherein the media delivering means comprises a multichannel input selector valve fluidically coupled to input vials, an input pump fluidically coupled to the multichannel input selector valve, and a multichannel input director valve fluidically coupled to the input pump, configured such that the multichannel input selector valve operably selects media and/or drugs from the input vials, and the input director valve allows the input pump to deliver individually the selected media and/or drugs to each biodevice,
      wherein the multichannel output collector valve has a connection to pressurized air or other gas to insert one or more bubbles between each sample.

2. The CAPCAS of claim 1, wherein each fluidic system further comprises a media collecting means, wherein the array of biodevice perfusion systems is fluidically coupled between the media delivering means and the media collecting means.

3. The CAPCAS of claim 2, wherein the media collecting means comprises a multichannel output collector valve fluidically coupled to the array of biodevices, an output pump fluidically coupled to the multichannel output collector valve, and a multichannel output director valve fluidically coupled to the output pump, configured to remove media from each biodevice and deliver it to waste, a Turbidimeter, a microclinical analyzer, or a holding reservoir.

4. The CAPCAS of claim 3, wherein the multichannel output collector valve has a connection to back-flush vials, and/or pressurized air or other gas to insert one or more bubbles between each sample.

5. The CAPCAS of claim 3, further comprising a multichannel reservoir collection valve coupled to the holding reservoir of each fluidic system and configured to analyze media from any single biodevice in any of the one or more fluidic systems.

6. The CAPCAS of claim 5, further comprising a low-pressure pump fluidically coupled to the multichannel reservoir collection valve for operably withdrawing the media from the holding reservoir that transiently retains the media and cells withdrawn from the desired biodevice or bioreactor well.

7. The CAPCAS of claim 6, further comprising a bubble detector fluidically coupled to the low pressure pump for operably identifying where one sample ends and another starts, when the low-pressure pump delivers the samples to a mass spectrometer.

8. The CAPCAS of claim 7, further comprising a calibration valve fluidically coupled to the bubble detector for operably removing air through one port (A), sending leading portions of any sample to waste (W), and injecting either a reagent (R) or a calibration solution (C) into the mass spectrometer.

* * * * *

UNITED STATES PATENT AND TRADEMARK OFFICE
CERTIFICATE OF CORRECTION

PATENT NO. : 11,939,563 B2
APPLICATION NO. : 17/947302
DATED : March 26, 2024
INVENTOR(S) : Ronald S. Reiserer et al.

Page 1 of 1

It is certified that error appears in the above-identified patent and that said Letters Patent is hereby corrected as shown below:

In the Specification

Column 1, Lines 33-50: reading:
"This invention was made with government support under Grant No. UH3TR002097 awarded by the National Institutes of Health (NIH) National Center for Advancing Translational Sciences (NCATS), National Institute of Neurological Disorders and Stroke (NINDS), and Eunice Kennedy Shriver National Institute of Child Health and Human Development (NICHD); Grant No. U01TR002383 and (through Vanderbilt University Medical Center) UL1TR002243 awarded by NCATS; Grant No. U01CA202229ſ̓ awarded by the National Cancer Institute (NCI), and Grant No. HHSN271201 700044C (through CFD Research Corporation) awarded by NCATS; by the National Science Foundation (NSF) under Grant No. CBET-1706155 and Grant No. 2117782; and by the National Aeronautics and Space Administration (NASA) under Grant No. 80NSSC20K0108. The government has certain rights in the invention. ſ̓"

Should read as follows:
-- This invention was made with government support under Contract No. HHSN2712017000044C, and Grant Nos. TR002383, TR002243, TR002097, and CA202229, awarded by the National Institutes of Health, Grant Nos. CBET1706155 and 2117782, awarded by the National Science Foundation, and Grant No. 80NSSC20K0108, awarded by the National Aeronautics and Space Administration. The government has certain rights in the invention. --

Signed and Sealed this
Eighth Day of October, 2024

Katherine Kelly Vidal
*Director of the United States Patent and Trademark Office*